United States Patent
Morrow et al.

(10) Patent No.: US 10,960,088 B2
(45) Date of Patent: Mar. 30, 2021

(54) MACROCYCLES, COBALT AND IRON COMPLEXES OF SAME, AND METHODS OF MAKING AND USING SAME

(71) Applicants: The Research Foundation for The State University of New York, Amherst, NY (US); Health Research, Inc., Buffalo, NY (US)

(72) Inventors: Janet R. Morrow, Williamsville, NY (US); Pavel B. Tsitovich, Amherst, NY (US); Sarina J. Dorazio, Elba, NY (US); Abiola O. Olatunde, Chelsea, MA (US); Joseph A. Spernyak, West Seneca, NY (US); Patrick Burns, Germantown, NY (US); Eric M. Snyder, Williamsville, NY (US); Christopher J. Bond, Fairport, NY (US)

(73) Assignees: The Research Foundation for The State University of New York, Amherst, NY (US); Health Research, Inc., Buffalo, NY (US)

( * ) Notice: Subject to any disclaimer, the term of this patent is extended or adjusted under 35 U.S.C. 154(b) by 531 days.

(21) Appl. No.: 15/021,626

(22) PCT Filed: Sep. 12, 2014

(86) PCT No.: PCT/US2014/055468
§ 371 (c)(1),
(2) Date: Mar. 11, 2016

(87) PCT Pub. No.: WO2015/038943
PCT Pub. Date: Mar. 19, 2015

(65) Prior Publication Data
US 2016/0228581 A1    Aug. 11, 2016

Related U.S. Application Data

(60) Provisional application No. 61/877,028, filed on Sep. 12, 2013, provisional application No. 61/898,812, filed on Nov. 1, 2013.

(51) Int. Cl.
*A61B 5/055*    (2006.01)
*A61K 49/10*    (2006.01)
*C07D 255/02*   (2006.01)

(52) U.S. Cl.
CPC .......... *A61K 49/106* (2013.01); *C07D 255/02* (2013.01)

(58) Field of Classification Search
None
See application file for complete search history.

(56) References Cited

U.S. PATENT DOCUMENTS

| 6,646,122 B1 | 11/2003 | Nuhlen |
| 8,344,102 B2 | 1/2013 | Wang et al. |
| 2014/0193344 A1* | 7/2014 | Morrow ............... C07D 213/74 424/9.363 |

FOREIGN PATENT DOCUMENTS

| WO | 9935133 A2 | 7/1999 |
| WO | 2013/109927 A2 | 7/2013 |

OTHER PUBLICATIONS

Li et al. (Inorg. Chim. Acta 2005, 358, 504-512).*
Variana et al. (Inorg. Chem. 2007, 46, 8271-8282).*
Bu et al. (Polyhedron 2012, 31, 402-412).*
Majzoub et al. (Inorg. Chim. Acta 2009, 362, 1169-1178).*
Dorazio et al. (J. Am. Chem. Soc. 2011, 133, 14154-14156).*
Dorazio et al. (J. Inorg. Biochem. 2012, 212, 212-219).*
de Martino Norante et al. (Inorg. Chem. 1990, 29, 2822-2829).*
Regueiro-Figueroa et al. (Eur. J. Inorg. Chem. 2007, 2198-2207).*
Rodriguez-Rodriguez et al. (Polyhedron 2012, 31, 402-412).*
El Hajj et al. (Inorg. Chem. 2009, 48, 10416-10423).*
Viola-Villegas et al. (Coord. Chem. Rev. 2009, 253, 1906-1925).*
Bartholoma (Inorg. Chemica Acta 2012, 389, 36-51).*
Woods et al. (Dalton Trans. 2011, 40, 6759).*
Candia et al. (Acta Cryst. Section C Crystal Structure Comm. 2012, 68, m121-6).*
Vaira et al. (J. Chem. Soc., Dalton Trans. 1996, 2679-2684).*
Di Vaira et al., Co-ordination of 1,4,7-tris(pyrazol-3-ylmethyl)-1,4,7-triaz acyclononane with Iron(III), Nickel(II) and Zinc(II) . . . , Journal of the Chemical Society, pp. 3739-3743. Jan. 1, 1994.
Hubin, T.J., et al., New Iron(II) and Manganese(II) Complexes of Two Ultra-Rigid, Cross-Bridged Tetraazamacrocycles for Catalysis and Biomimicry, Journal of the American Chemical Society, 2000, vol. 122, No. 11, pp. 2512-2522.
Gahan et al, Branched Cyclonane Macrocycles with Pentaamine and Tetraamine-Thioether Donors. Preparation and Base Hydrolysis of Chlorocobalt (III) complexes, Australian Journal of Chemistry, Jan. 14, 1982 , pp. 1119-1131, vol. 35.
Di Vaira et al., A New General Route to the Synthesis of Polyazamacrocyclic Ligands with Pendant Biomimetic Imidazole Groups, J. Chem. Soc., Chem. Commun., 1989, vol. 2, pp. 126-127.
Di Vaira et al., Synthesis and crystal structure of the iron(II)-iron(III) complex [FeL][FeCl4]Cl [L = 1,4,7-tris(pyrazol-3-ylmethyl)-1,4,7-triazacyclononane], J. Che. Soc., Dalton Trans., 1997, vol. 8, pp. 1375-1379.

\* cited by examiner

*Primary Examiner* — Michael G. Hartley
*Assistant Examiner* — Melissa J Perreira
(74) *Attorney, Agent, or Firm* — Hodgson Russ LLP

(57) ABSTRACT

Provided are macrocyclic compounds and iron or cobalt coordinated macrocyclic compounds. The compounds can be used as MRI contrast agents. Certain compounds are redox active and can be used to assess the biological redox status of a sample.

13 Claims, 71 Drawing Sheets or first step can include: [epoxide] [TsN aziridine] [TsN aziridine]

PG = protecting group if any, X is any leaving group second step is removal of PG which may include acid, base, or Pd/C hydrogenation

MACROCYCLES, COBALT AND IRON COMPLEXES OF SAME, AND METHODS OF MAKING AND USING SAME

CROSS-REFERENCE TO RELATED APPLICATIONS

This application claims priority to PCT/US2014/055468, filed Sep. 12, 2014, which claims priority to to U.S. provisional patent application Nos. 61/877,028, filed Sep. 12, 2013, and 61/898,812, filed Nov. 1, 2013, the disclosures of which are incorporated herein by reference.

STATEMENT REGARDING FEDERALLY SPONSORED RESEARCH

This invention was made with government support through the National Institutes of Health under Grant No. CA0173309. The government has certain rights in this invention.

FIELD OF THE DISCLOSURE

This disclosure relates generally to macrocyclic compounds and their use as MRI contrast agents.

BACKGROUND OF THE DISCLOSURE

An intriguing approach in magnetic resonance imaging (MRI) is the development of contrast agents that utilize endogenous metal ions. Contrast agents containing such ions would provide an alternative to Ln(III) contrast agents that are problematic for patients with compromised kidney function. In addition, contrast agents based on transition metal ions may have new applications as responsive or smart contrast agents that register pH, temperature, cations or anions in the biological environment.

The use of biologically relevant paramagnetic transition metal ions to create diagnostic probes for magnetic resonance imaging (MRI) is an emerging area of interest. Paramagnetic metal ion complexes may be used as chemical exchange saturation transfer (paraCEST) MRI contrast agents.

Many disease states including cancer and cardiac disease involve changes in both intracellular and extracellular redox status. In tumors these changes are triggered, in part, by extremely low oxygen partial pressures arising from poor vascularization. Such hypoxia or low oxygen pressure induces changes in the concentrations of small molecule or macromolecular components in cells that buffer redox state. This affects both intra and extracellular redox potential; both of which may modulate cellular redox signaling and interactions with the microenvironment. The development of improved methods for imaging of oxygen levels and/or redox state may enable better therapeutic treatment of diseases such as cancer.

Magnetic resonance imaging (MRI) is the method of choice for high resolution mapping of tissue, but MRI methods for mapping hypoxia or redox status are currently limited. Blood-oxygenation level-dependent MRI (BOLD-MRI) is used to report changes in $T_2$ relaxation rates as a result of stimulus-mediated increases in the ratio of oxyhemoglobin to deoxyhemoglobin, but extrapolating results of BOLD imaging to resting-state $pO_2$ levels remains problematic due to BOLD's intrinsic dependence on flow rates and volumes. MRI methods have also been developed that rely on the oxygen dependence of the $^{19}F$ signal in fluorinated hydrocarbon contrast agents. Nitroxide spin labels have been used for imaging redox environment by EPR or by MRI. While these methods show promise, all have drawbacks including inherently low sensitivity of detection and lack of accessible instrumentation such as clinical EPR or $^{19}F$ MRI scanners. An alternative approach is the development of MRI contrast agents containing metal ion or ligand redox switches that report on hypoxic states or redox imbalances. For example, Mn(II)/Mn(III) MRI contrast agents that produce changes in $T_1$ relaxivity in response to oxygen pressure or other biological redox couples and Ln(III) complexes containing ligand-based redox switches have been reported.

SUMMARY OF THE DISCLOSURE

In an aspect, disclosed is a macrocyclic compound having a macrocyclic core comprising from 9 to 15 atoms, wherein at least one of the atoms in the macrocyclic core is a N atom, at least two carbon atoms separate a heteroatom selected from the group consisting of: N atom, O atom, or S atom, and one or more (e.g., 1, 2, 3, or 4) pendant groups are substituents on the macrocyclic core. In an embodiment, at least one of the one or more pendant groups is covalently bound to a N on the macrocyclic core. In an embodiment, the macrocyclic compound has at least one exchangeable proton. In an embodiment, at least one of the pendant groups is substituted at a benzylic position or any carbon the alkyl group leading to the heteroatom of the pendant group. In an embodiment, the macrocyclic core is a Cyclen moiety, a Cyclam moiety, TACN moiety, or N2O3 moiety. In an embodiment, the macrocyclic compound is one of a plurality of the macrocyclic compounds tethered together via a polymer, dendrimer, protein, or peptide. In an embodiment, a Co(II) cation is complexed to the macrocyclic core and/or at least one pendant group substituent of the macrocyclic compound.

In another aspect, disclosed is a macrocyclic compound having a macrocyclic core comprising from 9 to 15 atoms, wherein at least one of the atoms in the macrocyclic core is a N atom, at least two carbon atoms separate a heteroatom selected from the group consisting of: N atom, O atom, or S atom, and one or more (e.g., 1, 2, 3, or 4) pendant groups as substituents on the macrocyclic core. In an embodiment, the macrocyclic compound has at least one exchangeable proton or associated water molecule. The macrocyclic compound exhibits reversible oxidation to Co(III) or Fe(III), respectively. In an embodiment, at least one of the one or more pendant groups is covalently bound to a N on the macrocyclic core. In an embodiment, at least one of the pendant groups is substituted at a benzylic position or any carbon the alkyl group leading to the heteroatom of the pendant group. In an embodiment, the macrocyclic core is a Cyclen moiety, Cyclam moiety, or TACN moiety. In an embodiment, the macrocyclic compound is one of a plurality of the macrocyclic compounds tethered together via a polymer, dendrimer, protein, or peptide. In an embodiment, a Co(II) or Fe(II) cation is complexed to the macrocyclic core and/or at least one pendant group substituent of the macrocyclic compound.

In an aspect, disclosed is a composition comprising a macrocyclic compound and a pharmaceutically acceptable carrier.

In an aspect, disclosed are imaging methods using the macrocyclic compounds. In an embodiment, a method to obtain an image of at least a portion of a cell, organ, vasculature or tissue comprises contacting the cell, organ, vasculature, or tissue with a macrocyclic compound, and imaging at least a portion of the cell, organ, vasculature, or tissue to obtain an image of the portion of a cell, organ, vasculature, or tissue. The image is obtained by using magnetic resonance. In an embodiment, the cell, organ, vasculature, or tissue is part of an individual. In an embodiment, the image is obtained using magnetic resonance imaging (MRI). In an embodiment, the image is obtained using chemical exchange saturation transfer (CEST). In an embodiment, the image is obtained using paramagnetic chemical exchange saturation transfer (paraCEST). In an embodiment, the image is obtained using magnetic resonance spectroscopy imaging (MRSI).

In an embodiment, the cell, organ, vasculature, or tissue is contacted with a redox-active Co(II) or Fe(II) coordinated macrocyclic compound and the image is indicative of the redox status of (e.g, the concentration of redox active species in) the cell, organ, vasculature, or tissue.

BRIEF DESCRIPTION OF THE FIGURES

For a fuller understanding of the nature and objects of the disclosure, reference should be made to the following detailed description taken in conjunction with the accompanying figures, in which:

FIG. 26. Scheme for the synthesis of di and tetrasubstituted 1,4,7,10-tetraazacyclododecane. This orthogonal protection strategy using both Cbz and Boc protecting groups allows for synthesizing a completely protected intermediate of macrocycle (Cyclen) without secondary amines. This tetra-carbomate intermediate is easily purified by column chromatography. Removal of Cbz groups using Pd/C-catalyzed hydrogenation allows to produce di-Boc-protected intermediate, with could be further used for alkylation/modification with the substituents, which are not compatible with hydrogenation reaction conditions. More labile Boc groups could be easily deprotected under acidic conditions together with other acid-labile protecting groups (PG) on the pendent groups. Each $R_1$ may independently be any of the pendent groups;

FIG. 27. Scheme for the addition of pendent groups to tetraaza, pentaaza macrocycles or macrocycles with both aza and ether donor groups. Each $R_1$ is independently any of the pendent groups. Each $R_3$ is independently an alkyl group, preferably methyl. BOC and CBz are standard carbamate protecting groups;

FIG. 28. Scheme for the synthesis of MPT and AMPT and their complexes with Co(II). Reagents and conditions: (a) NBS, AIBN, carbon tetrachloride, 50° C. to reflux, Ar, 8 hours; (b) DIPEA, acetonitrile, 50° C., 24 hours; (c) hydrogen, 10% Pd/C, methanol, 8 hours, (d) CoCl$_2$(H$_2$O)$_6$, acetonitrile, room temperature, Ar, 8 hours;

FIG. 71. Synthetic scheme for the synthesis of macrocyclic ligands containing mixed triazole, or imidazole pendent groups. Reagents and conditions: (a) 2-(Benzyloxycarbonyloxyimino)-2-phenylacetonitrile, chloroform, room temperature, Ar, 8 hours; (b) DIPEA, acetonitrile, 65° C., Ar, 24 hours; (c) hydrogen, 10% Pd/C, methanol, room temperature, 12 hours; (d) K$_2$CO$_3$, 18-crown-6, acetonitrile, 65° C., Ar, 24 hours; (e) CuSO$_4$, TBTA, L-ascorbic acid, methanol, 60° C., Ar, 12 hours; (f) TFA, methylene chloride, room temperature, 3 hours; (g) sodium triacetoxyborohydride, 1,2-dichloroethane, room temperature, Ar, 24 hours;

FIG. 73. (Scheme 1) Scheme for redox switching between Co(II)/Co(III) complexes of TPT by biological oxidants and reductants;

FIG. 80. Synthesis of ligand TAPC and complex Co(TAPC). Reagents and conditions: (a) phthalic anhydride, 190° C., 1 h; (b) NBS, AIBN, benzene, reflux, 5 hours; (c) Cyclen, DIPEA, ACN, reflux, Ar, 3 hours; (d) $NH_2NH_2*H_2O$, EtOH, reflux, 3 hours; (e) $CoCl_2*6H_2O$, methanol-water (1:1, v/v), pH 7.0, room temperature, 1 hour;

DETAILED DESCRIPTION OF THE DISCLOSURE

Figure 1:
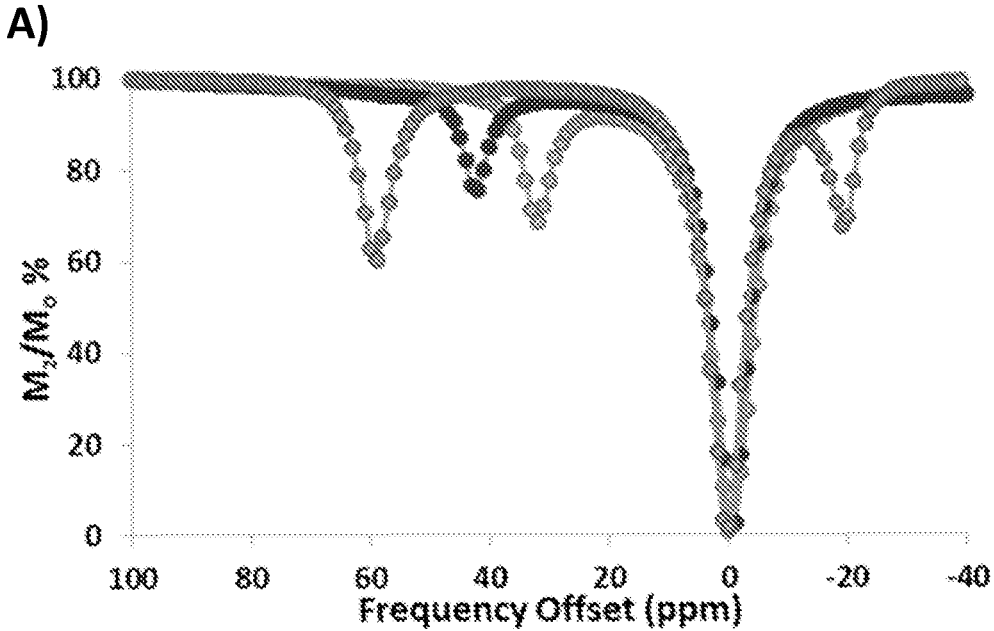
FIG. 1. Overlaid CEST spectra of 10 mM Co(II) complex 20 mM HEPES, 100 mM NaCl, pH 7.4, $B_1=24$ µT for 2 s at 37° C. (A): $[Co(NOPE)]^{2+}$ has two highly separated CEST peaks at 59 and −19 ppm. $Co(TCMT)]^{2+}$ and $[Co(TCMC)]^{2+}$ have CEST peaks at 32 and 45 ppm, respectively. (B): $[Co(CCRM)]^{2+}$ exhibits four CEST peaks (112, 95, 54, and 45 ppm). (C) Ratiometric plot of 10 mM $[Co(CCRM)]^{2+}$, 20 mM Buffer, 100 mM NaCl, $B_1=24$ µT for 2 s at 37° C. pH varied (6.8-7.8). The y-axis "Ratio" represents the ratio of $[(M_o/M_z)-1]$ at 112 ppm to $[(M_o/M_z)-1]$ at 95 ppm at various pH values.
Figure 1:
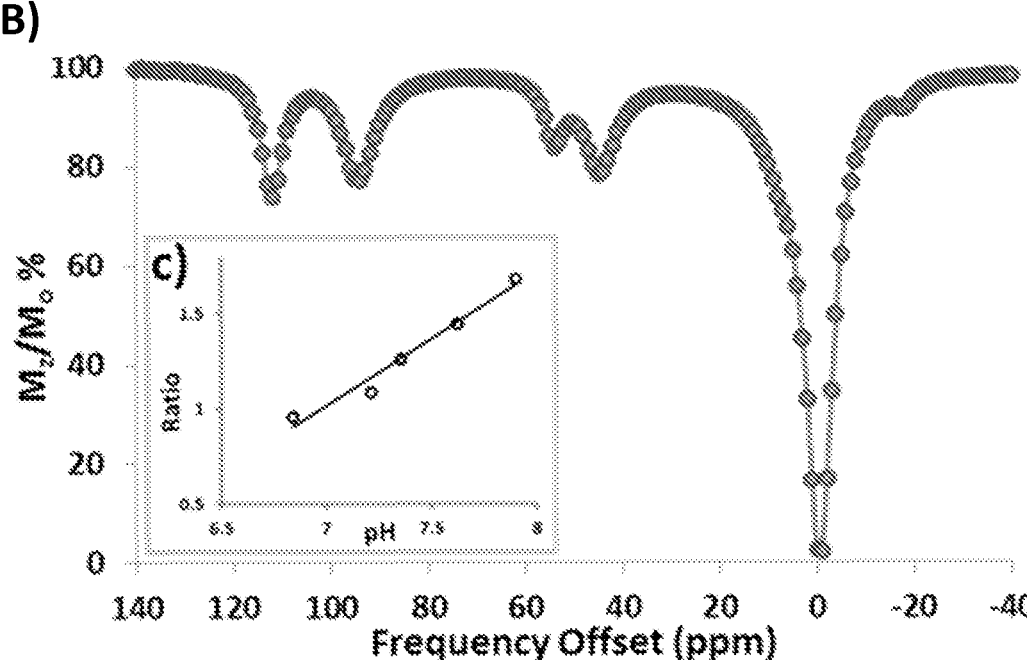

The present disclosure provides macrocycles and cobalt and iron macrocyclic complexes, compositions of the same, and methods of making and using the same. Also provided are redox-activated macrocycle compositions and methods of using the same.

This disclosure describes, for example, paramagnetic Co(II) complexes that act as either paramagnetic chemical exchange saturation transfer (paraCEST) MRI contrast agents or as magnetic resonance shift (MRS) agents. The disclosure also describes, for example, tuning the oxidation potential of a Co(II)/Co(III) or Fe(II)/Fe(III) couple to a biologically relevant redox range in order to form redox activated contrast agents or shift agents.

In an aspect, macrocyclic compounds have a variety of core structures and a variety of substituents on the macrocyclic core. Most typically, donor groups contain amides, alcohols or heterocycles. In an embodiment, the macrocyclic compounds are complexed to Co(II) to provide a stabilized divalent state ($E_o > 0.6$ mV versus NHE). The Co(II) macrocycle compounds produce narrow proton resonances and highly shifted exchangeable proton resonances.

In an embodiment, disclosed are $Co^{II}$ complexes for use as paraCEST or paraCSI (paramagnetic chemical shift imaging) MRI contrast agents. $Co^{II}$ has highly favorable magnetic properties that give rise to large hyperfine proton shifts that are suitable for paraCEST MRI contrast. In an embodiment, the Co(II) macrocyclic compound is a paramagnetic, high-spin complex.

As a component of the vitamin $B_{12}$ complex, cobalt is required for human growth and development, in which it cycles catalytically between $Co^{III}$, $Co^{II}$, and $Co^{I}$ to ensure normal neurologic function and erythrocyte formation.

The paramagnetic high spin $Co^{II}$ macrocyclic complexes contain either exchangeable amide (NH) protons, alcohol (OH) protons or heterocyclic (NH) protons for paraCEST MRI contrast agents.

An intriguing approach in the development of magnetic resonance imaging (MRI) contrast agents (CAs) is the utilization of transition metal ion complexes that have two alternate oxidation states which are influenced by the redox status of the tissue. The two metal ion oxidation states have different magnetic properties so that the MRI contrast agent is turned on or off as a function of the different oxidation state of the metal ion complex. Different oxidation states of the metal ion complex have different numbers of unpaired electrons, and this influences the magnetic properties and hence MRI contrast properties of the complex. The redox status of the tissue (both intra and extracellular) is controlled by the concentration and ratio of different redox buffers including glutathione/glutathione disulfide, cysteine/cystine and oxygen/superoxide or oxygen/peroxide.

Our approach focuses on the development of paramagnetic metal ion complexes as chemical exchange saturation transfer (paraCEST or CEST) MRI contrast agents. Thus, the subject disclosure provides complexes and processes of using these complexes as MRI contrast agents. ParaCEST agents require a paramagnetic metal center which produces a large chemical shift of the exchangeable protons (NH, OH, or bound-$H_2O$) within the complex. The selective irradiation of these labile protons partially saturates the proton spins which are chemically exchanging with bulk water protons on the slow-to-intermediate NMR time regime. This magnetization transfer gives rise to a decrease in the water signal for "on demand" MRI contrast. In choosing a paramagnetic metal ion, it is desirable to have poor proton relaxation enhancement (low relaxivity) and significant paramagnetic induced proton shifts in order to reduce background interference from endogenous magnetization transfer in tissue.

In certain embodiments, the macrocycles have the following structure:

-continued

[macrocycle structure diagram]

In the above, $X_1$, $X_2$, $X_3$, $X_4$ and $X_5$ are each independently N, O or S, $Y_1$, $Y_2$, $Y_3$, $Y_4$, $Y_5$ are each independently nitrogen, sulfur or oxygen atoms in the pendent groups described in this aspect, $m_1$, $m_2$, $m_3$, $m_4$ and $m_5$ are each independently 0, 1 or 2, $n_1$, $n_2$, $n_3$, $n_4$ and $n_5$ are each independently 1 or 2, provided that if X is O or S, then $m_1$ is 0 and $Y_1$ is H. In an embodiment, $Y_1$, $Y_2$, $Y_3$, $Y_4$, $Y_5$ are each independently a pendent group described in this aspect. Any of these macrocycles may be a Co(II) complex (i.e., a macrocycle Co(II) complex.

In general, paraCEST agents require a paramagnetic metal center which produces a large chemical shift of exchangeable ligand protons (NH, OH, or bound-$H_2O$) within the complex. The selective irradiation of these labile protons partially saturates the proton spins which are chemically exchanging with bulk water protons on the slow-to-intermediate NMR time regime. This magnetization transfer gives rise to a decrease in the water signal for "on demand" MRI contrast. In choosing a paramagnetic metal ion, it is desirable to have poor proton relaxation enhancement (low relaxivity) and significant paramagnetic induced proton shifts in order to reduce background interference from endogenous magnetization transfer in tissue. For paramagnetic transition metal ions, the paramagnetic induced proton shifts are a result of varying degrees of contact (through-bond) and pseudocontact (through-space) interactions of the unpaired electrons in the d orbitals.

There are advantages of using Co(II) complexes for paraCEST or for paraCSI. Co(II) produces narrow, highly shifted ligand proton resonances due to short electronic relaxation time constants. In addition, hyperfine shifted proton resonances of Co(II) complexes are a result of substantial dipolar (through space) and contact (through bond) hyperfine coupling. Co(II) is a biologically relevant metal ion in that it is an essential element necessary to maintain health of the human body. In order to produce imaging agents it is desirable to control one or more of the following: 1) oxidation state of the metal ion, 2) spin state of the metal ion, 3) dynamics of the macrocyclic complex, 4) reactivity towards dissociation and 5) reactivity towards biologically relevant compounds present in high concentration, especially carbonate and phosphate. These design elements are elaborated on below.

The oxidation state of the cobalt as expressed by redox potential may be controlled by coordination sphere including the number and type of donor atoms and their geometric arrangement in space. The choice of macrocyclic ligand is thus important for the stabilization of one oxidation state over the other. For example, amide donor groups stabilize the divalent state including Co(II) complexes of NOPE, TCMC, TCMT and CCRM, alcohol groups such as found in LOCO, TACO and STHP stabilize Co(II), and pyridine containing groups such as found in MPT and TMPC also stabilize Co(II).

Control of the spin state is important in order to produce paramagnetic, high spin complexes of Co(II). In certain cases, strong donor ligands, such as pyridine pendants, in the TACN framework should be avoided. For strong donor groups, increasing the Co—N bond length by addition of substituents, such as in MPT or TMPC, generally results in stabilization of the high spin state over the low spin state. For Co(II), macrocyclic ligands of TACN (1,4,7-triazacyclononane), Cyclen (1,4,7,10-tetraazacyclododecane), $N_2O_3$ (1,4,10-trioxa-7,13-diazacyclopentadecane) and Cyclam (1,4,8,11-tetraazacyclododecane) with amide or alcohol pendents generally produce high spin (S=3/2) complexes.

Further challenges include limiting dynamic processes of the macrocyclic complexes that would influence the number of resonances and their peak width. Macrocycles with TACN and Cyclen in particular have two different diastereomeric forms that may interconvert on the NMR time scale, resulting in broadening of the proton resonances. This is especially problematic for MRS (paraCSI) imaging which requires sharp resonances and may also influence the depth of the CEST peak for exchangeable protons. In an embodiment, the macrocycle and/or Co(II) macrocycle complex does not have two or more diasteteromeric forms. Heterocyclic pendent groups or ones with chiral alcohol pendents (STHP) are more likely to form rigid macrocyclic complexes for optimal paraCEST and paraCSI agents.

It is desirable that the macrocyclic complexes be encapsulated to prevent reaction with anions or biologically relevant ligands, which would change the paramagnetic shifts and give new spectra and CEST peaks.

Finally, it is desirable that the macrocyclic complexes be kinetically inert to metal ion release. The complexes should not release metal ions in the presence of carbonate, phosphate or other biologically relevant ligands. Other metal ions including Ca(II), Mg(II) and Zn(II) should not displace the Co(II) from the complexes.

In an embodiment, the macrocyclic compound has at least one heteroatom and at least one pendant donor as a substituent of the macrocyclic core. Any of these macrocyclic compounds can be a Co(II) complex. In an embodiment, the macrocyclic compound having a macrocyclic core having from 9 to 15 atoms where at least one of the atoms in the macrocyclic core is a N atom. In another embodiment, at least two carbon atoms separate a heteroatom selected from the group consisting of: N atom, O atom, or S atom. The compound has at least one substituent (i.e., pendant group) on the macrocyclic core. In various embodiments, the compound has 2, 3, or 4 pendant groups.

The pendant group has at least one pendant donor (e.g., a nitrogen atom, oxygen atom, or sulfur atom). For example, the pendant group can have the following structure:

[chemical structures of pendant groups: —$NHR_4$, C(O)—$NHR_4$, and pyridyl]

where R⁴ is H, C₁ to C₁₂ alkyl groups of linear or branched structure, PEG group (—CH₂CH₂O—)$_n$ (n=1-12), thioether group (—CH₂CH₂S—)$_n$, or CH₂CO₂R⁸, R⁵ is H, C₁ to C₁₂ alkyl groups of linear or branched structure, PEG group (—CH₂CH₂O—)$_n$ (n=1-12), thioether group (—CH₂CH₂S—)$_n$, CH₂CO₂R⁸, or OCH₃, R⁶ is H or OCH₃, R⁷ is H, OCH₃, or CO₂H, and each R⁸ and R⁹ are each independently selected from H, C₁ to C₁₂ alkyl groups, PEG groups, and thioether groups, each R¹⁰ and R¹¹ is a C₁ to C₁₂ alkyl group, or CH₂OH, CH₂NH₂, and R¹¹ is a methyl, ethyl, or CH₂-aromatic group (e.g., a benzyl group). Optionally, the one or more pendant groups are bonded to the macrocyclic core via a methylene group. In an embodiment, the macrocyclic compound has at least one exchangeable proton of water molecule. In certain embodiments, a Co(II) cation is complexed to the macrocyclic compound. In another embodiment, a Co(II) cation is not complexed to certain macrocyclic compounds in this aspect. The pendant substituents can be further substituted at the benzylic position (e.g., etc.), or any part of the alkyl group leading to the heteroatom (e.g.,

).

The pendant groups are covalently attached to a macrocyclic core (e.g. at a nitrogen) such as, for example, Cyclen, Cyclam, TACN, $N_2O_3$. In an embodiment, the macrocyclic core is a Cyclen moiety, Cyclam moiety, TACN moiety, $N_2O_3$ moiety, or substituted analog thereof.

It may be desirable for the macrocyclic compound or Co(II) coordinated macrocyclic compound to have one or more exchangeable protons. In an embodiment, the macrocyclic compound has at least one exchangeable proton. In an embodiment, the macrocyclic compound is a PARASHIFT MRS agent and does not have at least one exchangeable proton.

The macrocyclic core is part of the macrocyclic compound. The macrocyclic core has a ring structure comprising carbon atoms and at least one heteroatom (e.g. N atom, O atom, or S atom). In various examples, the macrocyclic core can have 1, 2, 3, 4 or 5 nitrogen atoms, 1, 2, 3 or 4 oxygen atoms and/or 1, 2, 3 or 4 sulfur atoms. For example, the macrocyclic core can have 6, 7, 8, 9 or 10 carbons. For example, the macrocyclic core has from 9 to 15 atoms wherein at least one of the atoms in the macrocyclic core is a N atom. In various examples, there are 2, 3, 4 or 5 carbon atoms separating the heteroatoms in the macrocyclic core. The one or more carbons in the macrocyclic core can be unsubstituted (e.g., —$CH_2$—) or can be substituted (e.g., —CHR—, or —$CR^2$—). For example, they can be substituted with the substituents disclosed in this aspect.

Examples of suitable macrocyclic compounds include:

-continued

VIII

IX

In these structures, R₁ is one of the pendent groups listed above and R₃ is an alkyl group such as, for example, a methyl group. All of the chiralities shown may independently be replaced by the opposite chiralities. There is a covalent bond between all R-groups and the macrocylic core shown above, whether or not visible in the above representation.

In an embodiment, the macrocycle is TACN or a Co(II) coordinated analog thereof with two pendents or three pendents chosen from any combination of the following:

In an embodiment, the macrocycle is Cyclen or a Co(II) coordinated analog thereof with four pendents chosen from any combination of the following:

In an embodiment, the macrocycle is Cyclen or a Co(II) coordinated analog thereof with two pendents chosen from any combination of the following:

In an embodiment, the macrocycle is Cyclam, a 1,4-substituted Cyclam, or a Co(II) coordinated analog thereof with four pendents chosen from any combination of the following:

In an embodiment, the macrocycle is N2O3 or a Co(II) coordinated analog thereof with two of any pendents (the same or different pendants) chosen from the following:

In an embodiment, the macrocycle is N2O2 (1,7-dioxa-4,10-diazacyclododecane-4,10) or a Co(II) coordinated analog thereof with two of any of the following pendents:

As used in this aspect, "macrocycle donor" refers to a heteroatom with an available lone pair of electrons to donate to the Co(II) center which is present in the macrocyclic core of the compound. For example, the macrocycle donor can be a nitrogen atom (e.g. a tertiary amine, a secondary amine), an oxygen atom (e.g., an ether), or sulfur atom (e.g., sulfane).

As used in this aspect, "pendant donor" refers to a heteroatom with an available lone pair of electrons to donate to the Co(II) center which is present in the substituents on the macrocyclic core of the compound. For example, the pendant donor can be a nitrogen atom (e.g., pyridine nitrogen, amide nitrogen, benzimidazole nitrogen, imidazole nitrogen, amino nitrogen, imidamide nitrogen, aniline nitrogen, pyrazine nitrogen, triazine nitrogen, triazole nitrogen, pyrimidine nitrogen, benzotriazole nitrogen, triazinedione nitrogen, and the like), an oxygen atom (e.g., ketone oxygen, ester oxygen, alcohol oxygen, carboxylic acid oxygen, and the like), or a sulfur atom (e.g., thiol sulfur).

Coordination chemistry of Co(II) is dependent on the coordination number. The macrocyclic compounds have donor groups that can be part of the macrocyclic core, also referred to as macrocycle donors, and donor groups that can be part of the substituents on the macrocyclic core, also referred to as pendant donors. When Co(II) is complexed to the macrocycle, 5 to 8 donors are complexed to the metal ion center. In an embodiment, the macrocyclic core can have from 2 to 5 donors and from 2 to 6 pendant donors. In various embodiments, there are 2 macrocycle donors and 3 pendant donors, 2 macrocycle donors and 4 pendant donors, 2 macrocycle donors and 5 pendant donors, 2 macrocycle donors and 6 pendant donors, 3 macrocycle donors and 2 pendant donors, 3 macrocycle donors and 3 pendant donors, 3 macrocycle donors and 4 pendant donors, 3 macrocycle donors and 5 pendant donors, 3 macrocycle donors and 6 pendant donors, 4 macrocycle donors and 2 pendant donors, 4 macrocycle donors and 3 pendant donors, 4 macrocycle donors and 4 pendant donors, 5 macrocycle donors and 2 pendant donors, and 5 macrocycle donors and 3 pendant donors.

Examples of suitable macrocycle compounds include:

TCMT

TCMC

CCRM

NOPE

TACO

MPT, X = CH$_3$, Y = H
APT, X = NH$_2$, Y = H
AMPT, X = CH$_3$, Y = NH$_2$

STHP

TMPC, X = CH₃
TAPC, X = NH₂

BMPC, X = CH₃
BAPC, X = NH₂

TOPE

LOCO

BzCY

NODA

In an embodiment, the Co(II) macrocyclic compounds can have more than one macrocyclic core tethered together via a polymer, dendrimer, protein, or peptide.

For tumor uptake and retention, the size of the molecule containing the contrast agent can be important. In addition, given that the magnitude of the CEST signal increases proportionally with the number of exchangeable protons, the use of multiple tethered macrocyclic complexes is expected to increase contrast. For example, the compound can have

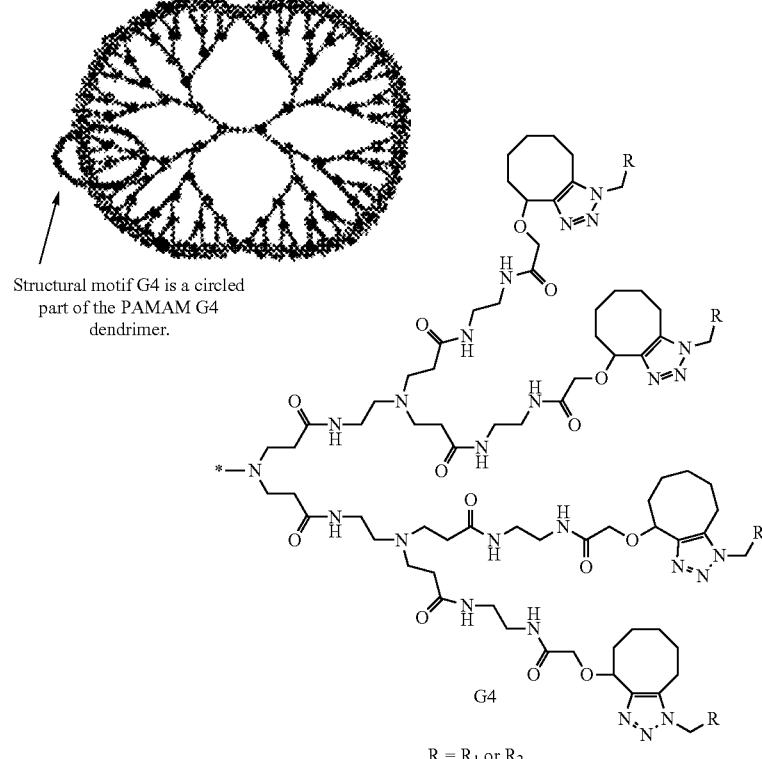

Structural motif G4 is a circled part of the PAMAM G4 dendrimer.

G4

R = R₁ or R₂ the following structure:

In an embodiment, the macrocyclic compound is complexed to a Co(II) cation. Examples of such complexed macrocyclic compounds include:

[Co(TCMT)]$^{2+}$

[Co(TCMC)]$^{2+}$

[Co(CCRM)]$^{2+}$

[Co(NOPE)]$^{2+}$

[Co(TACO)]$^{2+}$

X = CH₃, Y = H, [Co(MPT)]²⁺
X = NH₂, Y = H, [Co(APT)]²⁺
X = CH₃, Y = NH₂, [Co(AMPT)]²⁺

[Co(STHP)]²⁺

X = CH₃, [Co(TMPC)]²⁺
X = NH₂, [Co(TAPC)]²⁺

X = CH₃, [Co(BMPC)]²⁺
X = NH₂, [Co(BAPC)]²⁺

[Co(TOPE)]²⁺

[Co(LOCO)]²⁺

[Co(BzCY)]²⁺

[Co(NODA)]²⁺

In various embodiments, the macrocyclic compound or the Co(II) macrocyclic compound is a salt, a partial salt, a hydrate, a polymorph, a stereoisomer or a mixture thereof. For example, the compound can be present as a racemic mixture, a single enantiomer, a single diastereomer, or mixture of diastereomers. In certain embodiments, after complexation of the metal, the compounds are present as mixtures of diastereomers and/or conformers which can be determined by NMR. The diastereomers arise from the conformation of the macrocyclic core and the directionality of the substituents on the macrocyclic core.

The compounds may have one or more exchangeable protons. In an embodiment the compounds have from 1 to 12 exchangeable protons. For example, the compounds can have from 1 to 12 exchangeable protons per Co(II) complex. This may give hundreds to thousands of exchangeable protons if there are 10-100 Co(II) complexes incorporated into, for example, a liposome or polymer. In various embodiments, the compounds have 1, 2, 3, 4, 5, 6, 7, 8, 9, 10, 11, or 12 exchangeable protons. As used herein, "exchangeable proton(s)" are generally those on N, O, and S atoms (e.g., —OH, —NH, —SH) and in some cases can be —CH if the hydrogen atom is acidic enough (i.e., has a pKa<15). The $pK_a$ of the exchangeable proton is from 6 to 15 and all $pK_a$ ranges there between. Rate constants for exchangeable protons are generally in the range of from 100 to 10,000 s⁻¹. The optimal rate constant is ($k_{CE}$) is as large as possible as long as the ¹H NMR spectrum is in slow to intermediate exchange (i.e., the rate constant (units s⁻¹ or Hz) may not be larger than the separation between the bulk water protons and the exchangeable protons (Δω in Hz) as in Eq. 1.

$$\Delta\omega \geq k_{CE} \qquad \text{Eq. 1}$$

The macrocyclic compounds are thermodynamically stable and/or kinetically inert towards dissociation. In an embodiment, the compounds are thermodynamically stable and kinetically inert towards dissociation. In an embodiment, the kinetic inertness of the macrocyclic compounds of this aspect can be described using a rate constant for dissociation. In an embodiment, the macrocyclic donors and pendant donors don't dissociate appreciably from the metal center for up to 12 hours at neutral pH in the presence of 1) 25 mM carbonate, 0.40 mM phosphate, 100 mM NaCl, pH 7.5; 2) pH 4, 100 mM NaCl; 3) with 5-fold excess $ZnCl_2$, or $CuCl_2$, 100 mM NaCl, pH 7.5.

In an embodiment, the Co(II) is high spin (i.e., paramagnetic). For paraCEST, a paramagnetic spin state is needed. In order to keep Co(II) in the high spin state, the ligand (or crystal) field splitting must not be too large. If the crystal field splitting is larger than the pairing energy, a diamagnetic low spin state will result. Co(II) is readily maintained in a high spin paramagnetic state with a range of ligand donor groups, because low spin Co(II) is quite rare.

The paramagnetic induced proton shifts of the Co(II) complexes are dependent on a number of factors. Paramagnetic induced proton shifts (PIPS) arise from contact (through-bond) and pseudocontact (through-space, dipolar) contributions. These contributions are in addition to inductive diamagnetic effects which are inherent within the compounds of this aspect but are relatively small (Eq. 2):

$$\delta_{PIPS} = \delta_{cont} + \delta_{pseudo} + \delta_{dia} \quad \text{Eq. 2}$$

Transition metal ions with moderately large anisotropic magnetic moments have strong dipolar contributions to PIPS. However, potentially larger contact shifts are anticipated with transition metal ions due to the larger degree of covalency in their metal-ligand bonds. In an example, the large chemical shift difference of 60 ppm between the two amide protons for the Co(II) complexes that contain amide pendent groups of the compounds disclosed is mediated by the multiple-bond character of the N—C bond through contact shift contributions as determined by theoretical calculations. Dipolar shift contributions are a result of through space interactions between the unpaired electrons and the nucleus. They are dependent on the distance of the proton from the metal ion center, the magnitude of the magnetic anisotropy tensor and the angle of the proton with respect to the principal axis of the magnetic susceptibility tensor. Large dipolar shifts are generally observed for protons that are 2-3 bonds away from the metal ion center. Contact shifts are proportional to the unpaired spin density at the proton. Spin density arises from a combination of direct delocalization and spin polarization. Contact shifts are dependent on the hyperfine coupling constant and the spin expectation value as transmitted through bonds. Contact shifts may have an impact on PIPS over relatively long distances, especially in conjugated systems. In an embodiment, primarily contact shifts occur over 3 to 5 bonds from the Co(II) center. In an example, the dipolar and contact shift contributions of paramagnetic Co(II) complexes make it feasible to use donor groups with (proximal) exchangeable protons such as the NH of amides as well as more remotely located groups connected through a ligand pi system such as amino-pyridines or pyrazoles.

Figure 15:
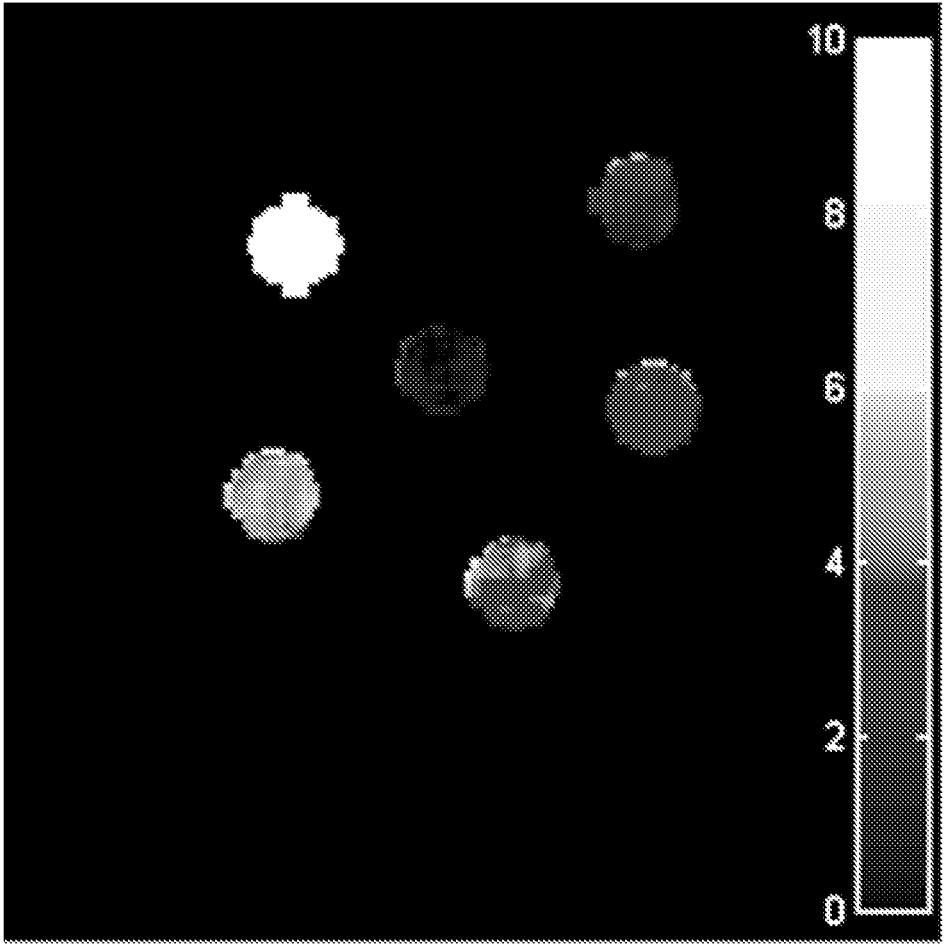
FIG. 15. CEST images of phantoms on a MRI 4.7 T scanner with a pulse train comprised of five Gauss pulses at 12 µT for 1 second each, interpulse delay of 200 is applied symmetrically about the bulk water resonance (+/−59 ppm) for $[Co(NOPE)]^{2+}$ at 0.25, 0.50, 0.75, 1, 4 mM, 20 mM HEPES buffer, 100 mM NaCl, pH 7.4, 37° C. Samples arranged in increasing concentration from the "one o'clock" position, clockwise. Center contains buffer and NaCl only.

Co(II) complexes that produce relatively narrow proton resonances which are highly dispersed over a wide chemical shift range are suitable candidates for magnetic resonance spectroscopy imaging (MRSI) as paraCSI agents. These paraCSI agents do not require exchangeable protons. Instead, the proton resonances of the nonexchangeable protons are monitored in the imaging experiment. The proton NMR spectrum of several Co(II) complexes are indeed highly dispersed as shown in FIGS. 2, 3, 4, 5, 21, 22, 23, 25, 74, and 79. Several of these Co(II) complexes also show promising CEST spectra (FIGS. 1, 14, 16, 18, 19, 20) with CEST peaks that are highly shifted from the bulk water peak. The complexes that show promising CEST spectra have exchangeable NH or OH protons in Co(II) complex. Once the CEST spectra for the Co(II) complexes have been taken, this information is used to form a CEST image on a MRI scanner as shown in FIG. 15. This experiment shows images of phantoms, or solutions containing the Co(II) paraCEST MRI contrast agent.

In another aspect, the present disclosure provides macrocyclic compounds having a variety of core structures and a variety of substituents on the macrocyclic core. The macrocyclic compounds may be complexed to a redox active metal ion such as Co(II) or Fe(II). The Co(II) or Fe(II) complexes cycle between Co(II) and Co(III) or Fe(II) and Fe(III) based on redox potential of the metal complex and biological redox status. Co(II) produces relatively narrow proton resonances that have a large chemical shift dispersion due to interaction of the protons with the paramagnetic metal ion. In contrast, Co(III) is diamagnetic and not a paraCEST agent. However, Co(III) complexes as diaCEST agents may produce CEST peaks that are not highly shifted from the bulk water. Fe(II) produces highly shifted and sharp proton resonances whereas high spin Fe(III) efficiently relaxes protons to give extremely broadened proton resonances which are not suitable for CEST contrast. High spin Fe(III) is an effective $T_1$ MRI contrast agent. However, low spin Fe(III) produces narrow shifted proton resonances and has low relaxivity. These properties make Fe(III) suitable for paraCEST contrast. The complexes are the first paraCEST MRI contrast agents that switch on/off with changes in redox potential. Redox potential is mediated by molecules that act as redox buffers such as glutathione/glutathione disulfide or cysteine/cystine or oxygen/superoxide or oxygen/peroxide. Redox-switched paramagnetic chemical shift imaging is another application of these cobalt or iron complexes. In an embodiment, the Fe(II) macrocyclic complex is not an iron bound to TACN with three benzimidizole pendants.

In an embodiment, disclosed are Co(II)/Co(III) complexes and Fe(II)/Fe(III) complexes for use as paraCEST or paraCSI (paramagnetic chemical shift imaging) MRI contrast agents. These contrast agents switch oxidation states in response to biological redox buffers and biological environment. The divalent (+2) versus trivalent (+3) oxidation states have different magnetic properties and hence have distinct MRI contrast properties. High spin Co(II), low spin Co(II), high spin Fe(II) and low spin Fe(III) give large hyperfine-shifted proton resonance that are suitable for paraCEST or paraCSI agents. Low spin Co(III) complexes are diamagnetic and may be used as diaCEST (diamagnetic chemical exchange saturation transfer) agents. Any of the Co(II) complexes or Fe(II) complexes can be oxidized to provide corresponding Co(III) complexes or Fe(III) complexes. In an embodiment, the macrocyclic compound is a Co(III) complex or Fe(III) complex.

The iron or cobalt macrocyclic complexes contain either exchangeable NH or OH protons for paraCEST MRI contrast agents. By contrast, paraCSI agents do not require exchangeable protons, but should have large highly dispersed proton resonances (>±50 ppm) that are relatively sharp (100-300 Hz).

In certain embodiments, the macrocycles have the following structure:

In the above, $X_1$, $X_2$, $X_3$, $X_4$ and $X_5$ are each independently N, O or S, $X_6$ or $X_7$ are each independently C or N and $Y_1$, $Y_2$, $Y_3$, $Y_4$, $Y_5$ are each independently nitrogen, sulfur or oxygen atoms in the pendent groups described in this aspect, $Y_6$ and $Y_7$ are each independently halides (F, Cl, Br, I) or amines ($NH_2$ or NHR, $NR_2$ or $NR_3$ where R is an alkyl group) or $NO_2$ group, $m_1$, $m_2$, $m_3$, $m_4$ and $m_5$ are each independently 0, 1 or 2 and $n_1$, $n_2$, $n_3$, $n_4$ and $n_5$ are each independently 1 or 2, provided that if X is O or S, then $m_1$ is 0 and $Y_1$ is H. In an embodiment, $Y_1$, $Y_2$, $Y_3$, $Y_4$, $Y_5$ are each independently a pendent group described in this aspect. Any of these macrocycles may be a Co(II) complex (i.e., a macrocycle Co(II) complex or Fe(II) complex (i.e., a macrocycle Fe(II) complex.

In general, paraCEST agents require a paramagnetic metal center which produces a large chemical shift of exchangeable ligand protons (NH, OH, or bound-$H_2O$) within the complex. The selective irradiation of these labile protons partially saturates the proton spins which are chemically exchanging with bulk water protons on the slow-to-intermediate NMR time regime. This magnetization transfer gives rise to a decrease in the water signal for "on demand" MRI contrast. In choosing a paramagnetic metal ion, it is desirable to have poor proton relaxation enhancement (low relaxivity) and significant paramagnetic induced proton shifts in order to reduce background interference from endogenous magnetization transfer in tissue. For paramagnetic transition metal ions, the paramagnetic induced proton shifts are a result of varying degrees of contact (through-bond) and pseudocontact (through-space) interactions of the unpaired electrons in the d orbitals.

There are advantages of using high spin (HS) Co(II) or Fe(II) complexes for paraCEST or for paraCSI. Both metal ions produce narrow, highly shifted ligand proton resonances due to short electronic relaxation time constants. In addition, hyperfine shifted proton resonances of Co(II) and Fe(II) complexes are a result of substantial dipolar (through space) and contact (through bond) hyperfine coupling. Both Fe(II) and Co(II) are biologically relevant metal ions that are essential elements necessary to maintain health of the human body. In order to produce imaging agents the following must be controlled: 1) oxidation state of the metal ion, 2) spin state of the metal ion, 3) dynamics of the macrocyclic complex, 4) reactivity towards dissociation and 5) reactivity towards biologically relevant compounds present in high concentration, especially carbonate and phosphate. These design elements are elaborated on below.

The oxidation state of the iron or cobalt complex as expressed by redox potential is controlled by coordination sphere including the number and type of donor atoms and their geometric arrangement in space. The choice of macrocyclic ligand is thus crucial for the stabilization of one oxidation state over the other. Amine, heterocyclic amine and carboxylate donor groups tune the Co(II)/Co(III) or Fe(II)/Fe(III) redox couple to the biological range such as shown here for the Co(II) complex of TPT. $[Co(TPT)]^{2+}$, $[Fe(TPT)]^{2+}$, $[Co(BZT)]^{2+}$ and [Co(BAC)] all readily oxidize to complexes containing the trivalent metal ion.

Control of the spin state is important in order to produce paramagnetic, high spin (HS) complexes of Fe(II) and Co(II). For Fe(II) especially, ligands that produce a strong crystal field such as pendent pyridine groups in the TACN framework must be avoided because a low spin (LS) complex may be produced. However, substituents on the pyridine may be added that increase the Fe—N bond length with a corresponding decrease in ligand field strength to give the HS complex. Pendent groups containing five-membered heterocyclic rings such as pyrazole, imidazole and benzimidazole are especially useful because they give HS Fe(II) and HS Co(II) complexes in both trizaa (TACN) or tetraaza (Cyclen and Cyclam) macrocycles. Macrocyclic ligands of Cyclen, and Cyclam with most pendent groups produce HS Fe(II) and HS Co(II), (S=4 or S=3/2, respectively) complexes.

Further challenges include limiting dynamic processes of the macrocyclic complexes that would influence the number of resonances and their peak width. Macrocycles with TACN and Cyclen in particular have two different diastereomeric forms that may interconvert on the NMR time scale, resulting in broadening of the proton resonances. This is especially problematic for MRSI imaging which requires paraCSI agents that have sharp resonances. Line broadening due to exchange processes may also influence the magnitude of the CEST peak for exchangeable protons. Heterocyclic pendent groups or groups with chiral amine or carboxylate pendents are more likely to form rigid macrocyclic complexes for optimal paraCEST and paraCSI agents.

The macrocyclic complexes are typically encapsulated to prevent reaction with anions or biologically relevant ligands.

Encapsulation is accomplished by creating a coordinatively saturated complex with no available coordination sites for binding other ligands. This may be important because interaction with ligands in the biological environment would change the paramagnetic shifts and change CEST contrast. The cobalt cage complexes are good examples of encapsulated complexes [Co(SAR)]$^{2+}$. Alternatively, complexes that have a bound water ligand for paraCEST must have an available coordination site. The coordination sphere may be modified so that water binds to the exclusion of most biologically available ligands.

In addition, it is desirable that the macrocyclic complexes be kinetically inert to metal ion release. The complexes must not release metal ions in the presence of carbonate, phosphate or other biologically relevant ligands. Other metal ions including Ca(II), Mg(II) and Zn(II) should not displace Co(II), Fe(II), Co(III) or Fe(III) from the complexes.

There are challenges to overcome in the synthesis of transition metal ion redox-activated PARACEST MRI probes. An important challenge is controlling redox potential. For example, if the redox potential is too high (>500 mV versus NHE), the paraCEST agent will be stable in the divalent form and will be active and not responsive to redox status (Scheme 1). If the redox potential is too negative (<−500 mV versus NHE), the trivalent state will be stabilized and the agent will not demonstrate optimal paraCEST contrast properties. For example, if the trivalent state is stabilized, LS and diamagnetic Co(III) may produce CEST peaks that are very close to bulk water from protons that are not paramagnetically shifted. For LS Fe(III), less highly paramagnetically shifted CEST peaks may be observed. High spin Fe(III) typically has good relaxivity and will not be a paraCEST contrast agent. Optimally, the MRI probe redox potential will be in the range of +100 mV to −300 mV so that the probe can be switched on or off by biologically abundant redox buffers. To modulate the redox potential of the Co(II)/Co(III) or Fe(II)/Fe(III) complexes, the number and type of donor atoms must be varied. In an embodiment, the macrocyclic compound has a redox potential less than 500 mV vs. NHE and greater than −500 mV vs. NHE. In an embodiment, the macrocyclic compound has a redox potential of −50 mV vs. NHE to −350 mV vs. NHE.

Figure 40:
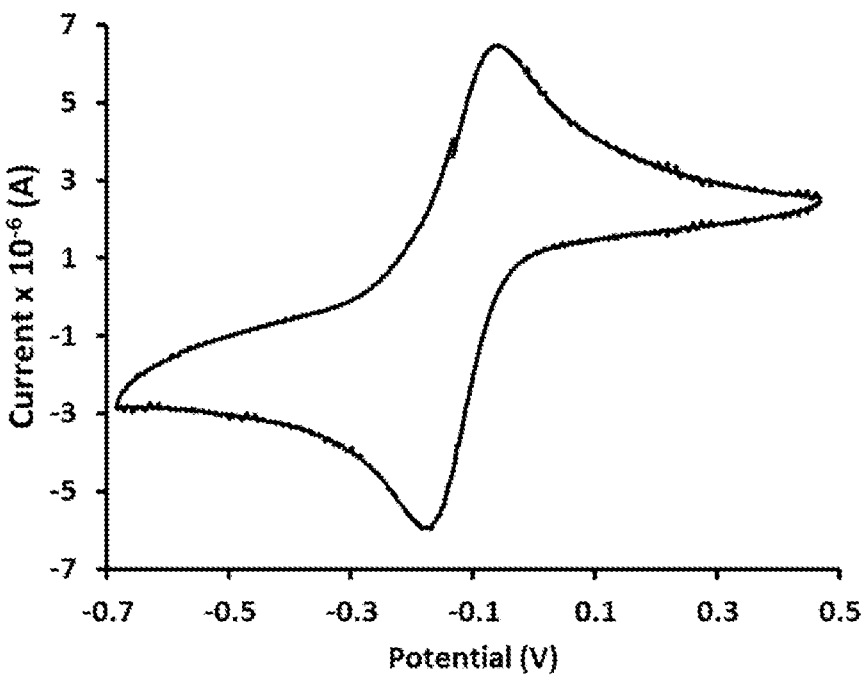
FIG. 40. Cyclic voltammogram of argon-saturated aqueous solution of 1.7 mM [Co(TPT)]Cl$_2$ containing 1 M KCl, pH 6.0. A scan rate of 50 mV/s was used.
Figure 58:
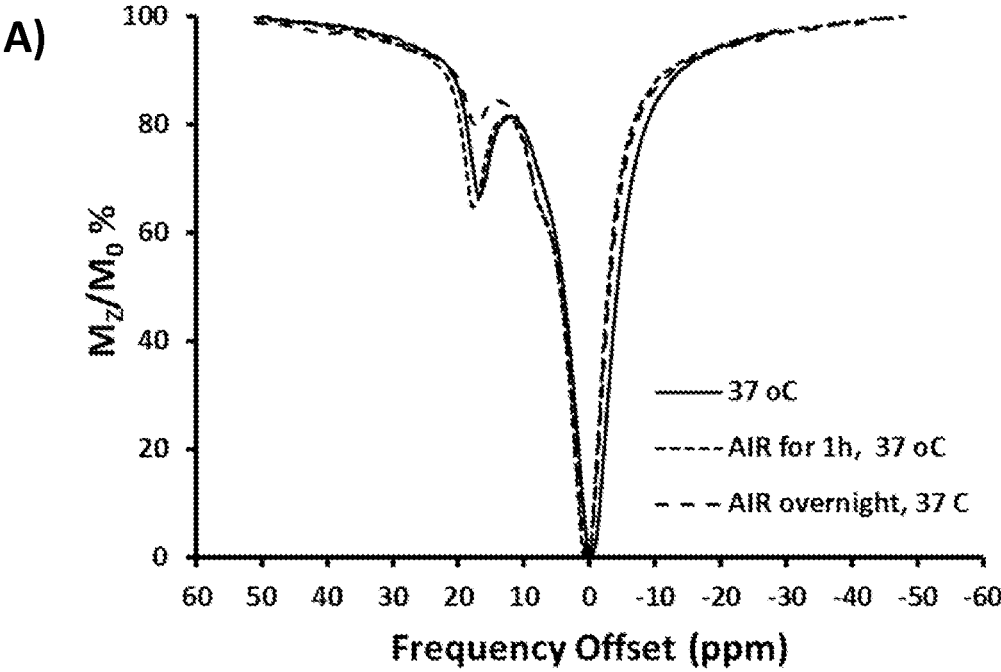
FIG. 58. CEST spectra recorded at 11.7 T of a solution containing 8 mM [Fe(TPT)]$^{2+}$, 100 mM NaCl, 20 mM HEPES pH 6.5, 37° C. RF presaturation applied for 3 seconds, B$_1$=24 μT at 37° C. Spectra show (A) the effect of air as an oxidant and (B) Na$_2$S$_2$O$_4$ as reductant.
Figure 58:
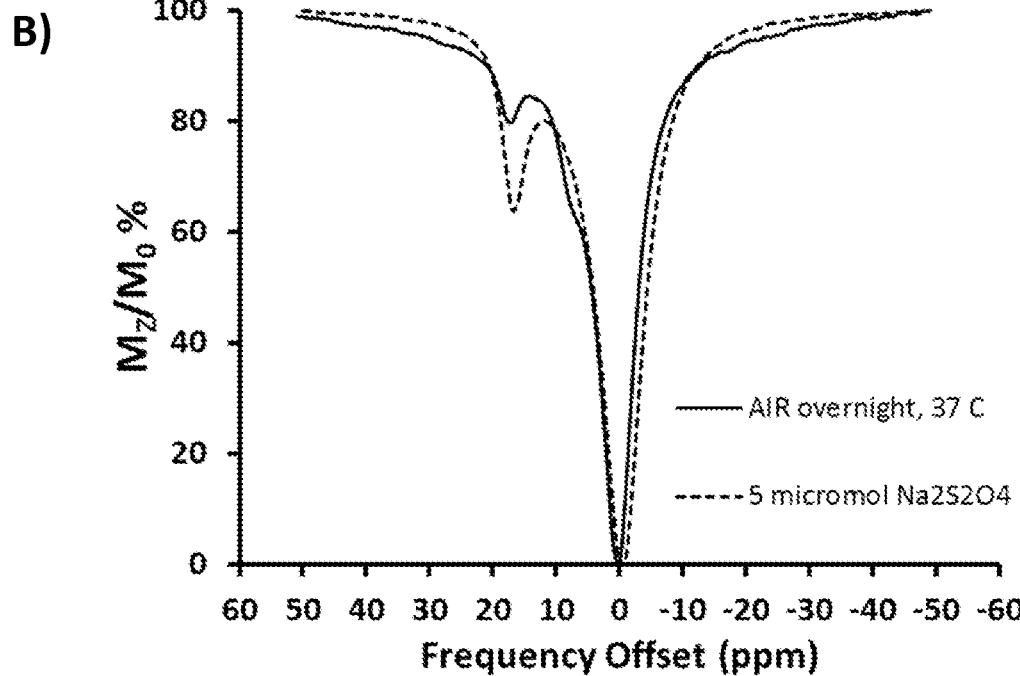
Figure 59:
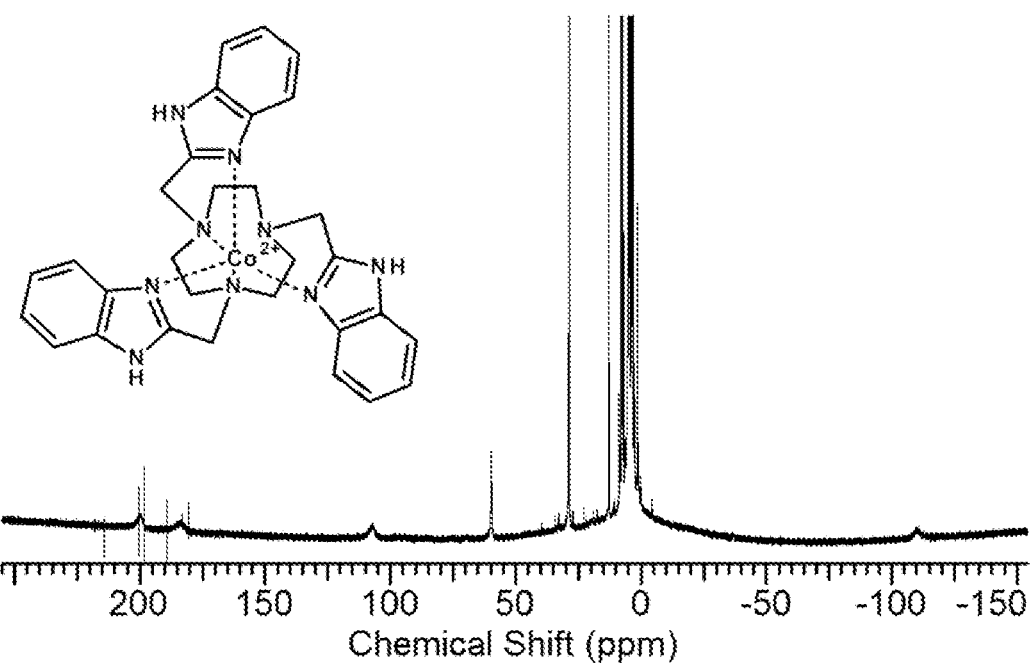
FIG. 59. $^1$H NMR spectrum of [Co(BZT)]$^{2+}$.
Figure 61:
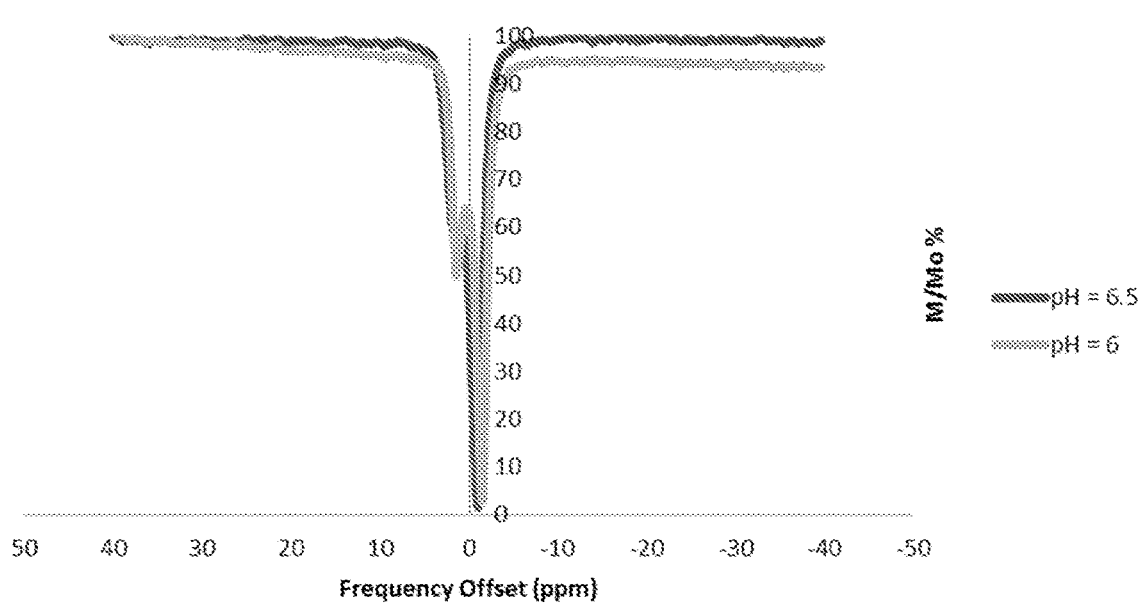
FIG. 61. CEST spectrum of [Co(SAR)]$^{3+}$ at pH 6 and 6.5.
Figure 62:
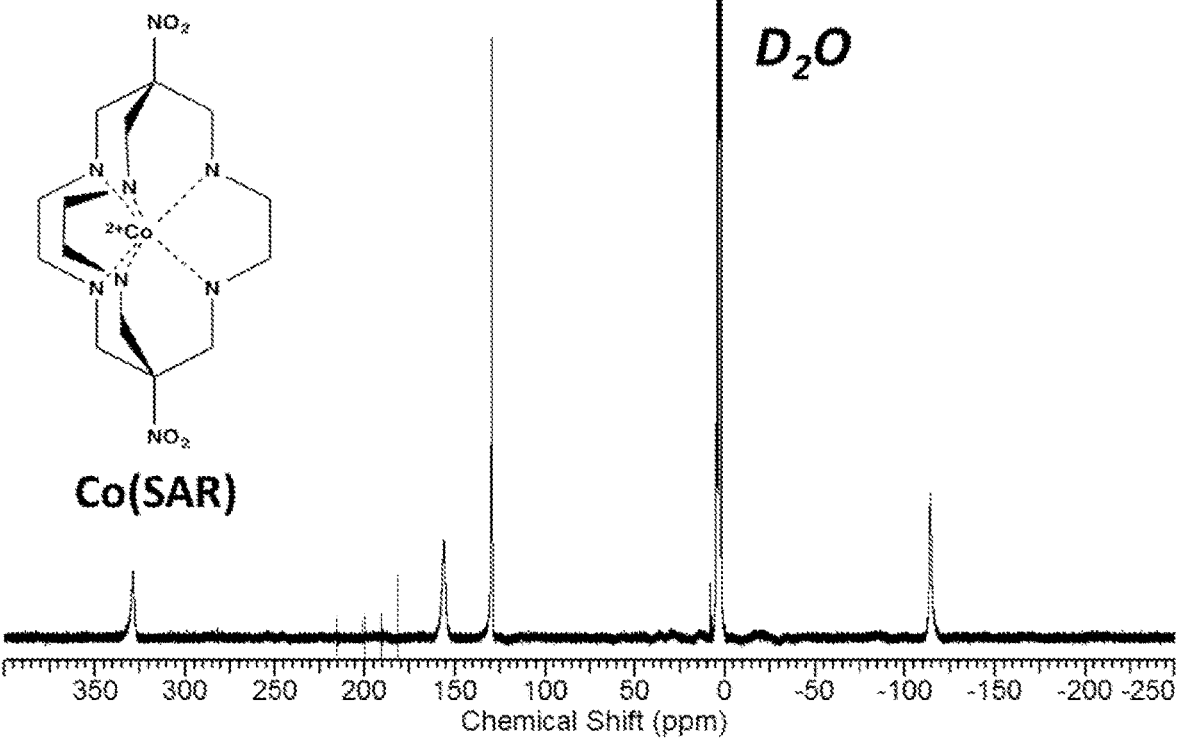
FIG. 62. $^1$H NMR spectrum of [Co(SAR)]$^{3+}$ in D$_2$O.

The redox potential of the Fe(II)/Fe(III) and Co(II)/Co(III) couples can be tuned to a potential that would be influenced by biological environment by choice of pendents and macrocycle backbone. For pendents, one desirable choice is anionic oxygen groups such as carboxylates or phenolates. For example, switching from three neutral amide pendents attached to TACN (TCMT=tris(carbamoylmethyl)-1,4,7-triazacyclononane) to three carboxylate pendents attached to TACN (NOTA=tris(acetato)-1,4,7-triazacyclononane) gives iron complexes with redox potentials of 860 mV for [Fe(TCMT)]$^{2+}$ and 195 mV for Fe(NOTA). The lower potential of Fe(NOTA) is closer to that required for biological response than that of [Fe(TCMT)]$^{2+}$, in part because it contains anionic oxygen donor groups. Pendent groups that contain five-membered heterocyclic rings such as pyrazole, imidazole or benzimidazole are also beneficial for tuning the redox potential to a favorable value. For example, [Co(TPT)]$^{2+}$ has a negative redox potential (−107 mV) (FIG. 40). Another example is shown for [Co(BZT)]$^{2+}$ and [Fe(TPT)]$^{2+}$ which are both are oxidized in air (FIGS. 58-59). Amine donor groups such as found in caged complexes including [Co(SAR)]$^{3+}$ also tune the metal ion center to favorable redox potentials by favoring the trivalent state (FIGS. 61, 62).

The macrocyclic backbone is also an important choice in tuning redox potential. For example, TACN with three pendent arms is a desirable choice because it forms stable six-coordinate complexes with the metal ion in the trivalent state. Fe(III) and Co(III) have small ionic radii (69 pm for LS Fe(III), 77 pm for HS Fe(III), 69 pm LS Co(III)) compared to Fe(II) and Co(II) (92 pm HS Fe(II), 89 pm HS Co(II)), thus ligands that favor smaller ions in a six-coordinate environment are beneficial for lowering the redox potential. Cyclam-based ligands are also good choices for lowering the oxidation potential into a biologically relevant range (Cyclam=1,4,8,11-tetraazacyclotetradecane).

In an embodiment, the macrocyclic compound has at least one heteroatom and at least one pendant donor as a substituent of the macrocyclic core. Any of the macrocyclic compounds in this aspect may be Fe(II) or Co(II) complexes. In an embodiment, the macrocyclic compound has a macrocyclic core having from 9 to 14 atoms where at least one of the atoms in the macrocyclic core is a N atom. In another embodiment, at least two carbon atoms separate a heteroatom selected from the group consisting of: N atom, O atom, or S atom. The compound has at least one substituent (i.e., pendant group) on the macrocyclic core. In various embodiments, the compound has 2, 3, or 4 pendant groups.

The pendant group has at least one pendant donor. For example, the pendant group has the following structure:

To modulate the redox potential of the Co/II)/Co(III) or Fe(II)/Fe(III) complexes, the number and type of donor atoms must be varied. Six or seven donor atoms are preferable. Complexes of 1,4,7-triazacyclononane (TACN) with two or three pendent groups may be optimal. The use of six nitrogen donors in a TACN framework such as in the ligand TPT works especially well for tuning the redox potential of the Co(II) or Fe(II) center to this range.

In another embodiment, the macrocycle has a cage structure. For example, cage structures include structures IX and X in this aspect and $[Co(SAR)]^{2+}$. Cages do not contain pendent groups but may be functionalized through the cap for attachment to macromolecules, for targeting certain to cell receptors that are unique to tumors, as an example, or to change solubility.

The macrocyclic core is part of the macrocyclic compound. The macrocyclic core has a ring structure comprising carbon atoms and at least one heteroatom (e.g. N atom, O atom, or S atom). In various examples, the macrocyclic core can have 1, 2, 3, 4, or 5 nitrogen atoms, 1, 2, 3, or 4 oxygen atoms, and/or 1, 2, 3, or 4 sulfur atoms. For example, the macrocyclic core can have 6, 7, 8, 9, or 10 carbons. For example, the macrocyclic core has from 9 to 15 atoms where at least one of the atoms in the macrocyclic core is a N atom. In various examples, there are two carbon atoms separating the heteroatoms in the macrocyclic core, there are three carbon atoms separating the heteroatoms in the macrocyclic core. The one or more carbons in the macrocyclic core can be unsubstituted (e.g., —$CH_2$—) or can be substituted (e.g., —CHR—, or —$CR_2$—). For example, they can be substituted with the substituents disclosed herein.

Examples of suitable macrocyclic compounds include:

where $R^1$ is H, $C_1$ to $C_{12}$ alkyl groups of linear or branched structure (e.g., a methyl group), PEG group (—$CH_2CH_2O$—)$_n$ (n=1-12), thioether group (—$CH_2CH_2S$—)$_n$ (n=1-12), or $CH_2CO_2R'$, $R^2$ is H, $C_1$ to $C_{12}$ alkyl groups of linear or branched structure, PEG group (—$CH_2CH_2O$—)$_n$ (n=1-12), thioether group (—$CH_2CH_2S$—)$_n$ (n=1-12), $CH_2CO_2R$, or $OCH_3$. $R^3$ is H, $C_1$ to $C_{12}$ alkyl groups of linear or branched structure, PEG group (—$CH_2CH_2O$—)$_n$ (n=1-12), thioether group (—$CH_2CH_2S$—)$_n$ (n=1-12), or $CH_2CO_2R'$. R' is an alkyl group (e.g., a $C_1$ to $C_{12}$ alkyl groups of linear or branched structure). The macrocyclic compound has at least one exchangeable proton or water molecule for paraCEST agents. In certain embodiments, a Co(II), Co(III), Fe(II), or Fe(III) cation is complexed to the macrocyclic compound. In another embodiment, a Co(II), Co(III), Fe(II), or Fe(III) cation is not complexed to certain compounds of this aspect. In an embodiment, an amide pendant is present only with another pendant.

These pendant groups are covalently attached to a macrocyclic core (e.g., at a nitrogen) such as, for example, Cyclen, Cyclam, or TACN. In an embodiment, the macrocyclic core is a Cyclen moiety, Cyclam moiety, or TACN moiety, or substituted analog thereof.

where $R_4$ and $R_5$ are one of the pendent groups listed above and $R_6$ is an alkyl group, especially a methyl group. All of the chiralities shown may independently be replaced by the opposite chiralities. There is a covalent bond between all R-groups and the macrocylic core shown above, whether or not visible in the above representation. $R_7$ and $R_8$ may be amine groups ($NH_2$, NHR, $NR_2$, $NR_3^+$), nitro group ($NO_2$), or halides.

In an embodiment, the macrocycle is TACN or a Co(II), Co(II), Fe(II), or Fe(III) coordinated analog thereof with three pendents chosen from any combination of the following:

where $R_1$ or $R_2$ is an alkyl group (e.g., a methyl group).

In an embodiment, the macrocycle is Cyclam, a 1,4-, or 1,8-substituted Cyclam, or a Co(II), Co(II), Fe(II), or Fe(III) coordinated analog thereof with four pendents chosen from any combination of the following:

In an embodiment, the macrocycle is Cyclen (or an alkyl substituted Cyclen (e.g., R1=methyl) or a Co(II), Co(II), Fe(II), or Fe(III) coordinated analog thereof with two or four pendants chosen from any combination of the following:

where R₁ or R₂ is an alkyl group (e.g., a methyl group). In this embodiment, if there are two pendants, the pendants are substituted in the 1 and 10 positions of the Cyclen.

As used in this aspect, "macrocycle donor" refers to a heteroatom with an available lone pair of electrons to donate to the Fe(II) or Co(II) center which is present in the macrocyclic core of the compound. For example, the macrocycle donor can be a nitrogen atom (e.g. a tertiary amine, a secondary amine), an oxygen atom (e.g., an ether), or sulfur atom (e.g., sulfane).

As used in this aspect, "pendant donor" refers to a heteroatom with an available lone pair of electrons to donate to the Fe(II) or Co(II) center which is present in the substituents on the macrocyclic core of the compound. For example, the pendant donor can be a nitrogen atom (e.g., pyridine nitrogen, amide nitrogen, benzimidazole nitrogen, imidazole nitrogen, amino nitrogen, pyrazole nitrogen, imidamide nitrogen, aniline nitrogen, pyrazine nitrogen, triazine nitrogen, triazole nitrogen, pyrimidine nitrogen, benzotriazole nitrogen, triazinedione nitrogen, and the like), an oxygen atom (e.g carboxylic acid oxygen, and the like), or a sulfur atom (e.g., thiol sulfur).

Coordination chemistry of Fe(II) and Co(II) are dependent on the coordination number. The compounds of this aspect have donor groups that can be part of the macrocyclic core, also referred to as macrocycle donors, and donor groups can be part of the substituents on the macrocyclic core, also referred to as pendant donors. When Fe(II) or Co(II) is complexed to the compound of this aspect, 5 to 8 donors are complexed to the metal ion center. In an embodiment, the macrocyclic core can have from 2 to 5 donors and from 2 to 6 pendant donors. In various embodiments, there are 2 macrocycle donors and 3 pendant donors, 2 macrocycle donors and 4 pendant donors, 2 macrocycle donors and 5 pendant donors, 2 macrocycle donors and 6 pendant donors, 3 macrocycle donors and 2 pendant donors, 3 macrocycle donors and 3 pendant donors, 3 macrocycle donors and 4 pendant donors, 3 macrocycle donors and 5 pendant donors, 3 macrocycle donors and 6 pendant donors, 4 macrocycle donors and 2 pendant donors, 4 macrocycle donors and 3 pendant donors, 4 macrocycle donors and 4 pendant donors.

Examples of suitable macrocycle compounds include:

-continued

TPC

BBzC

BAC

BzTODA

PTODA

BBzCy

TMIT is also referred to herein as MIM.

In an embodiment, the macrocyclic compound is complexed to a Co(II) or a Fe(II) cation. Examples of such complexed macrocyclic compounds include:

[M(TPT)]$^{2+}$
M = Co, Fe

[M(BZT)]$^{2+}$
M = Co, Fe

[Fe(TMIT)]$^{2+}$

[Co(BAC)]

[Co(Bn-TTT)]²⁺

[M(BPC)]²⁺
M = Co, Fe

[M(TPC)]²⁺
M = Fe, Co

[M(BBzC)]²⁺
M = Co, Fe

[M(BzTODA)]²⁺
M = Co, Fe

[Co(PTODA)]²⁺

[Co(BBzCy)]²⁺

[Co(SAR)]²⁺

In an embodiment, the compounds or Co(II) or Fe(II) coordinated compounds can have more than one macrocyclic core tethered together via a polymer, dendrimer, protein, or peptide. For tumor uptake and retention, the size of the molecule containing the contrast agent is important. In addition, given that the magnitude of the CEST signal increases proportionally with the number of exchangeable protons, the use of multiple tethered macrocyclic complexes should increase contrast. For example, the compound can have the following structure:

In an embodiment the compound is complexed to an Fe(II) or Co(II) cation.

In various embodiments, the macrocycle or Co(II) or Fe(II) coordinated macrocycle or is a salt, a partial salt, a hydrate, a polymorph, a stereoisomer or a mixture thereof. For example, the compound can be present as a racemic mixture, a single enantiomer, a single diastereomer, or a mixture of diastereomers. In certain embodiments, after complexation of the metal the compounds are present as mixtures of diastereomers and/or conformers which can be determined by NMR. The diastereomers arise from the conformation of the macrocyclic core and the directionality of the substituents on the macrocyclic core.

The macrocycle or Co(II) or Fe(II) coordinated macrocycle compounds may have exchangeable protons. In an embodiment the compounds have from 1 to 12 exchangeable protons. For example, the compounds can have from 1 to 12 exchangeable protons per Fe(II) or Co(II) complex. This may give hundreds to thousands of exchangeable protons if there are 10-100 Fe(II) complexes incorporated into, for example, a liposome or polymer. In various embodiments, the compounds have 1, 2, 3, 4, 5, 6, 7, 8, 9, 10, 11, or 12 exchangeable protons. As used herein, "exchangeable proton(s)" are generally those on N, O, and S atoms (e.g., —OH, —NH, —SH) and in some cases can be —CH if the hydrogen atom is acidic enough (i.e., has a $pK_a$<15). The $pK_a$ of the exchangeable proton is from 6 to 15 and all $pK_a$ ranges there between. Rate constants for exchangeable protons are generally in the range of from 100 to 10,000 $s^{-1}$.

The optimal rate constant is ($k_{CE}$) is as large as possible as long as the $^1$H NMR spectrum is in slow to intermediate exchange (i.e., the rate constant (units s$^{-1}$ or Hz) may not be larger than the separation between the bulk water protons and the exchangeable protons ($\Delta\omega$ in Hz) as in Eq. 3.

$$\Delta\omega \geq k_{CE} \qquad \text{Eq. 3}$$

The compounds of this aspect are thermodynamically stable and/or kinetically inert towards dissociation. In an embodiment, the compounds are thermodynamically stable and kinetically inert towards dissociation. In an embodiment, the kinetic inertness of the compounds of this aspect can be described using a rate constant for dissociation. In an embodiment, the macrocyclic donors and pendant donors don't dissociate appreciably from the metal center for up to 12 hours at neutral pH in the presence of 1) 25 mM carbonate, 0.40 mM phosphate, 100 mM NaCl, pH 7.5; 2) pH 4, 100 mM NaCl; 3) with 5-fold excess $ZnCl_2$, 100 mM NaCl, pH 7.5. Thermodynamic stability is also high. The logarithm of the equilibrium constant for binding of the macrocycle to the metal ion (log K) is between 7 and 20 in the presence of 100 mM NaCl.

In an embodiment, the Fe(II) or Co(II) is high spin (HS) (i.e., paramagnetic). For paraCEST, a paramagnetic spin state is needed. In order to keep Fe(II) in the high spin state, the ligand (or crystal) field splitting must not be too large. If the crystal field splitting is larger than the pairing energy, a diamagnetic low spin (LS) state will result.

The paramagnetic induced proton shifts of the Fe(II) and Co(II) complexes are dependent on a number of factors. Paramagnetic induced proton shifts (PIPS) arise from contact (through-bond) and pseudocontact (through-space, dipolar) contributions. These contributions are in addition to inductive diamagnetic effects which are inherent within the compounds of this aspect but are relatively small (Eq. 4):

$$\delta_{PIPS} = \delta_{cont} + \delta_{pseudo} + \delta_{dia} \qquad \text{Eq. 4}$$

Transition metal ions with moderately large anisotropic magnetic moments have strong dipolar contributions to PIPS. However, potentially larger contact shifts are anticipated with transition metal ions due to the larger degree of covalency in their metal-ligand bonds. In an example, the large chemical shift difference of 50 to 70 ppm between the two amide protons in the Fe(II) complexes or 70 ppm for the Co(II) complexes that contain amide pendent groups of the compounds disclosed is mediated by the multiple-bond character of the N—C bond through contact shift contributions as determined by theoretical calculations. Dipolar shift contributions are a result of through space interactions between the unpaired electrons and the nucleus. They are dependent on the distance of the proton from the metal ion center, the magnitude of the magnetic anisotropy tensor and the angle of the proton with respect to the principal axis of the magnetic susceptibility tensor. Large dipolar shifts are generally observed for protons that are 2-3 bonds away from the metal ion center. Contact shifts are proportional to the unpaired spin density at the proton. Spin density arises from a combination of direct delocalization and spin polarization. Contact shifts are dependent on the hyperfine coupling constant and the spin expectation value as transmitted through bonds. Contact shifts may have an impact on PIPS over relatively long distances, especially in conjugated systems. In an embodiment, primarily contact shifts occur over 3 to 5 bonds from the Fe(II) or Co(II) center. In an example, the dipolar and contact shift contributions of paramagnetic Fe(II) complexes make it feasible to use donor groups with (proximal) exchangeable protons such as the OH of alcohols as well as more remotely located groups connected through a ligand pi system such as amino-pyridines.

In an embodiment, the stability in an oxidative environment can be related to the reduction potential of the complex. In an embodiment, the compounds of this aspect have a reduction potential between 200 and −500 mV vs. NHE (Normal Hydrogen Electrode), including all integer mV values and ranges therebetween.

For use in the disclosure, the compounds described herein can be administered as pharmaceutical preparations. Thus, they can be provided in a variety of solutions of various compositions, and can be combined with one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art may be used to introduce the compositions of the disclosure to an individual. These methods include but are not limited to intravenous, intramuscular, intracranial, intrathecal, intradermal, subcutaneous, and oral routes. In one embodiment, the composition is administered intravenously. The composition can be provided as a liquid, a solution, or a solid, and may be provided in combination with any suitable delivery form or vehicle, examples of which include but are not limited to caplets, capsules, tablets, an inhalant or aerosol, etc.

The necessary solubility of the complexes depends on their effectiveness in producing contrast. For paraCEST contrast agents that have CEST peaks shifted greater than 100 ppm from the proton resonance of bulk water, it is desirable that the complexes have 20 to 100 µM (micromolar) solubility. For paraCEST complexes that have peaks of less than 100 ppm, it is desirable that the solubility be at least in the low milimolar range. For Co(II) complexes used for paraCSI, complexes should have solubilities of 1-20 mM. Solubility is generally measured in aqueous solution at near neutral pH (6.5 to 7.5) in 100 mM NaCl with 25 mM carbonate and 0.4 mM phosphate. The dose of the composition to be used will necessarily be dependent upon the needs of the individual to whom the composition of the disclosure is to be administered. These factors include but are not necessarily limited to the weight, age, sex, and medical history of the individual.

The necessary solubility of the complexes depends on their effectiveness in producing contrast. For paraCEST contrast agents that have CEST peaks shifted greater than 90 ppm from the proton resonance of bulk water, the complexes need approximately 200 µM (micromolar) solubility. For paraCEST complexes that have peaks of less than 90 ppm, solubility must be in the low milimolar range. For Fe(II) and Co(II) complexes used for MRSI, complexes should have solubilities of 1-20 mM. Solubility is generally measured in aqueous solution at near neutral pH (6.5 to 7.5) in 100 mM NaCl with 25 mM carbonate and 0.4 mM phosphate. The dose of the composition to be used will necessarily be dependent upon the needs of the individual to whom the composition of the disclosure is to be administered. These factors include but are not necessarily limited to the weight, age, sex, and medical history of the individual.

In yet another aspect, the present disclosure provides imaging methods using the macrocyclic compounds described herein. The imaging methods use magnetic resonance imaging methods. Examples of such methods include, Magnetic Resonance Imaging (MRI) and Magnetic Resonance Spectroscopic Imaging (MRSI).

Specifically, the macrocyclic compounds of the present disclosure, which are complexed to Co(II) can be used as paraCEST MRI contrast agents or as paramagnetic complexes for magnetic resonance spectroscopy. These complexes may have properties that change with alterations in pH. Such properties make these complexes useful for mapping pH to enable better therapeutic treatment of diseases such as cancer, stroke and heart disease.

Specifically, the macrocyclic compounds of the present disclosure which are complexed to Co(II) or Fe(II), can be used as paraCEST MRI contrast agents or as paramagnetic complexes for magnetic resonance spectroscopy (paraCSI) agents. These complexes may have properties that change with alterations in redox potential and oxygen level. Such properties make these complexes useful for mapping hypoxia and redox state to enable better therapeutic treatment of diseases such as cancer, stroke and heart disease.

The imaging methods of the present disclosure can be used to image a cell, tissue, organ, vasculature, or a part thereof. The cell, tissue, organ, vasculature can be a part of an individual. By "individual" it is meant a human or animal. In an embodiment, the disclosure provides a method to obtain an image of at least a portion of a cell, tissue, organ, or vasculature comprising the steps of: contacting a cell, tissue, organ, or vasculature with the compounds of the present disclosure, and imaging at least a portion of the cell, tissue, organ, or vasculature to obtain an image of the portion of cell, tissue, organ, or vasculature. The at least part of a cell, tissue, or organ can be alive or dead. Likewise, the individual can also be alive or deceased.

In an embodiment, the imaging technique can use MRSI. MRSI is used to measure the levels of different metabolites in body tissues. The MR signal produces a spectrum of resonances that correspond to different molecular arrangements of the isotope being "excited". In an embodiment, the compounds can be used in MRSI (Magnetic resonance spectroscopy imaging). MRSI combines both spectroscopic and imaging methods to produce spatially localized spectra for each voxel from within the sample or patient. The spatial resolution is much lower (limited by the available signal to noise ratio and memory availability for data storage), but the spectra in each voxel contains information about metabolites.

Preliminary experiments involved taking the proton NMR spectrum of the complexes in solutions containing 100 mM NaCl, 25 mM carbonate, 0.4 mM phosphate as a function of temperature on a high field NMR spectrometer (300-500 MHz). The spectra were acquired and averaged for about 10 minutes and a proton NMR spectrum was obtained. Future experiments will involve taking the proton NMR spectrum in blood plasma taken from a laboratory mouse and in vivo on a MRI scanner. The spectrum will be created by using multi-voxel spectroscopic techniques and water suppression.

Figure 11:
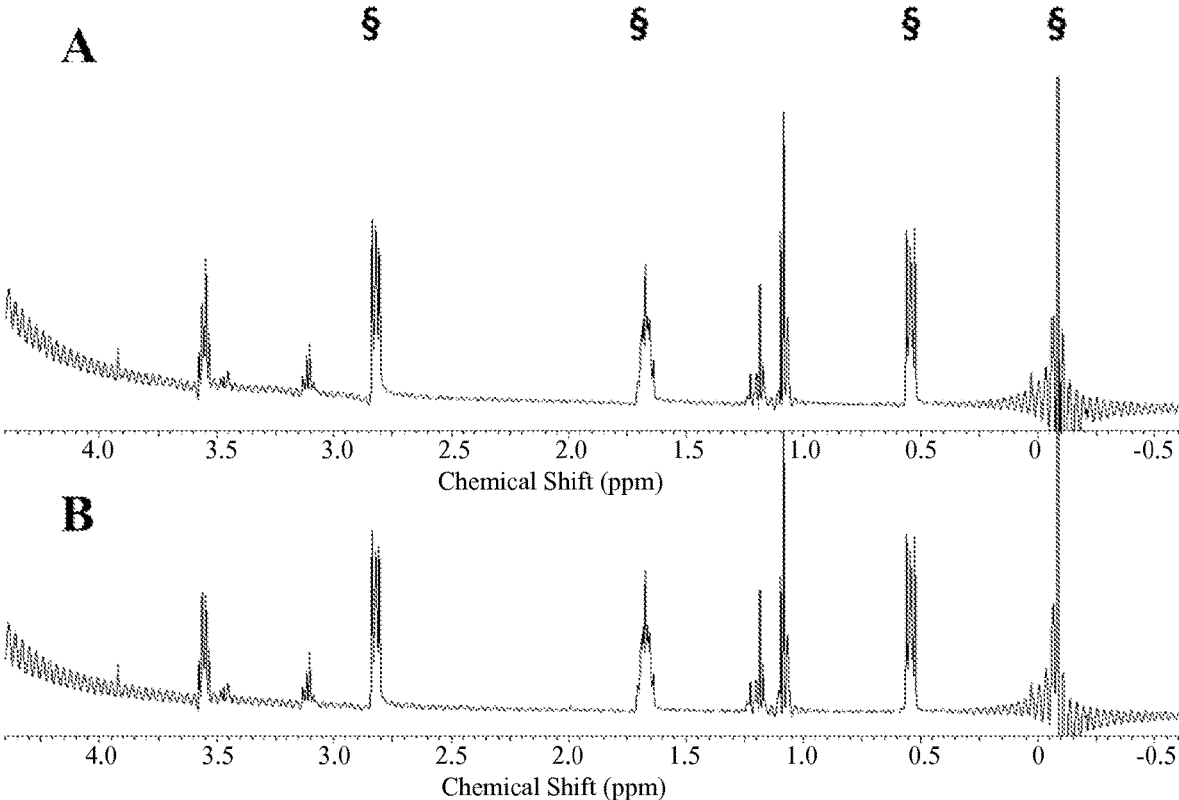
FIG. 11. Diamagnetic region $^1$H NMR spectra of 10 mM $[Co(TCMC)]^{2+}$, 100 mM NaCl, in $D_2O$, pD 3.5 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.
Figure 12:
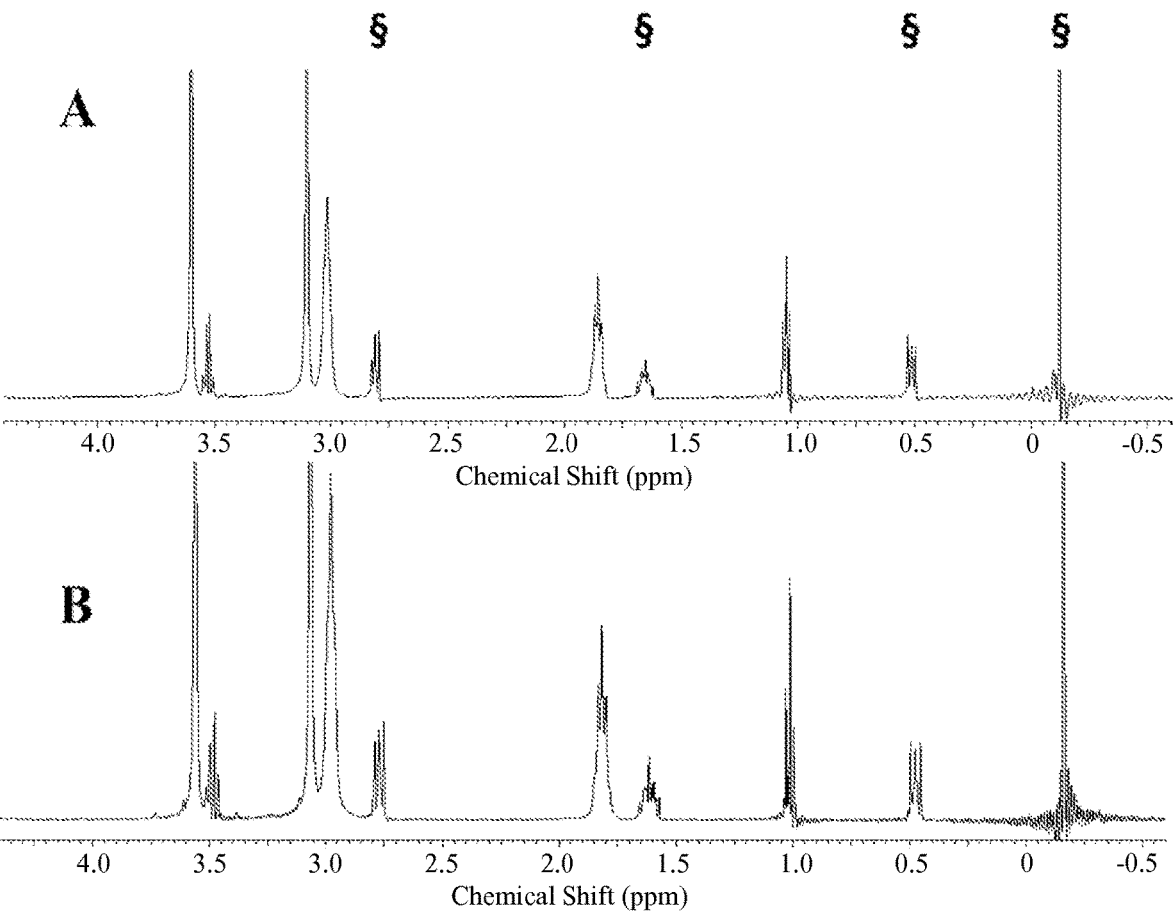
FIG. 12. Diamagnetic region $^1$H NMR spectra of 10 mM $[Co(CCRM)]^{2+}$, 100 mM NaCl, in $D_2O$, pD 3.9 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.
Figure 13:
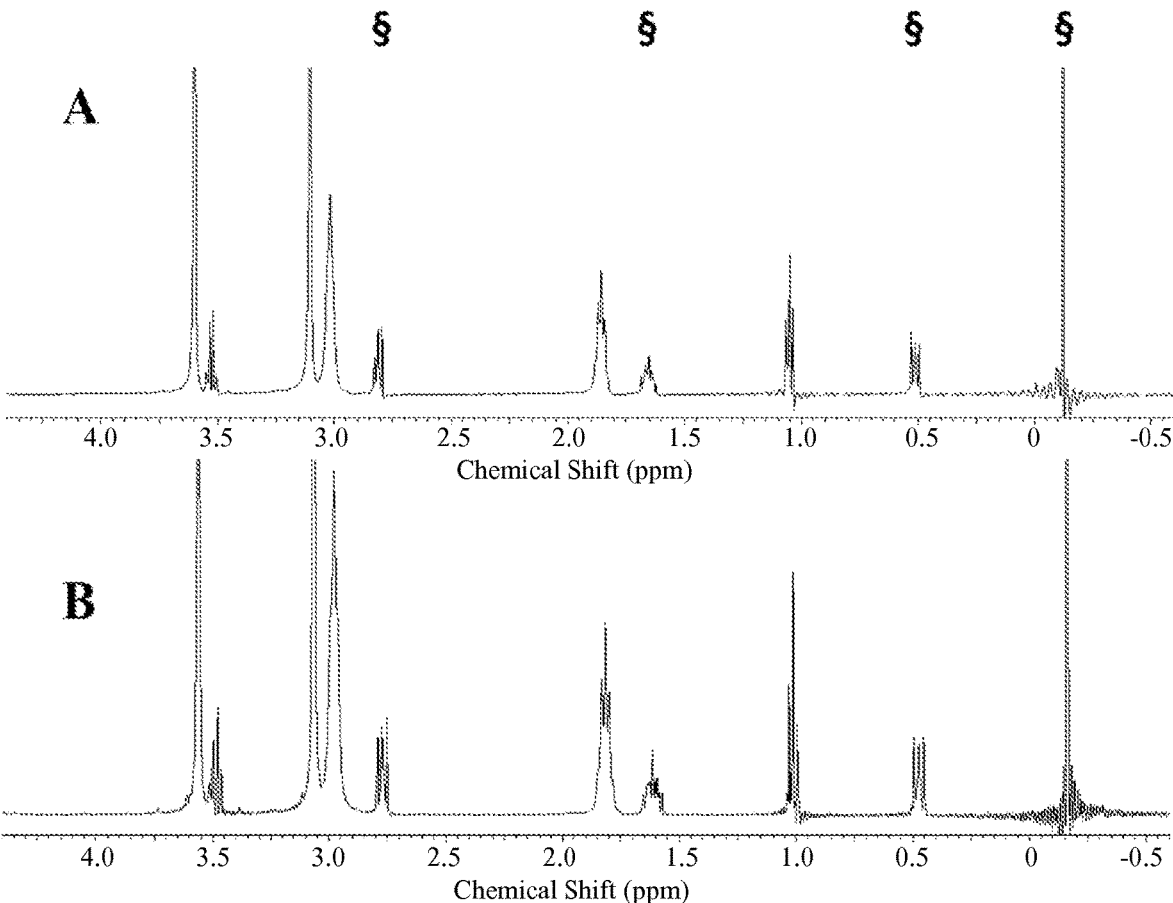
FIG. 13. Diamagnetic region $^1$H NMR spectra of 10 mM $[Co(NOPE)]^{2+}$, 100 mM NaCl, in $D_2O$, pD 3.9 at 37° C. (A) at 1 hr (B) at 4 hrs after incubation at 37° C. Contains 5 mM 3-(trimethylsilyl)-1-propanesulfonic acid standard, indicated by §. This data shows that the complex doesn't dissociate under these conditions.
Figure 14A:
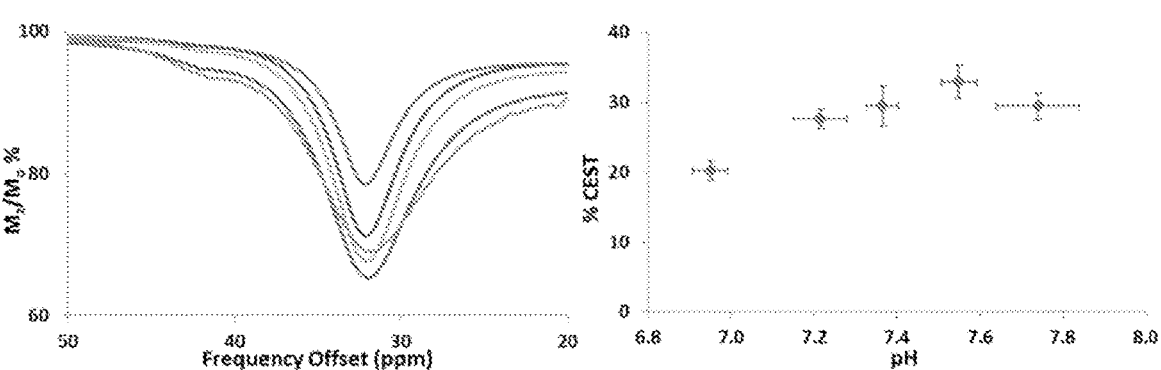
FIG. 14. CEST recorded at 11.7 T of (A) 10 mM $[Co(TCMT)]^{2+}$; (B) 10 mM $[Co(TCMC)]^{2+}$; (C) 10 mM $[Co(CCRM)]^{2+}$; (D) 10 mM $[Co(NOPE)]^{2+}$; All solutions contained 20 mM buffer (pH 6.6 to 7.8) and 100 mM NaCl. RF presaturation pulse ($B_1=24$ µT) was applied for 2 s at 37° C. Plot on the left shows the CEST peak shape in the region of exchange and plot on the right shows the maximum % CEST (depth of peak) over the pH range of pH 6.6 to 7.8.
Figure 14B:
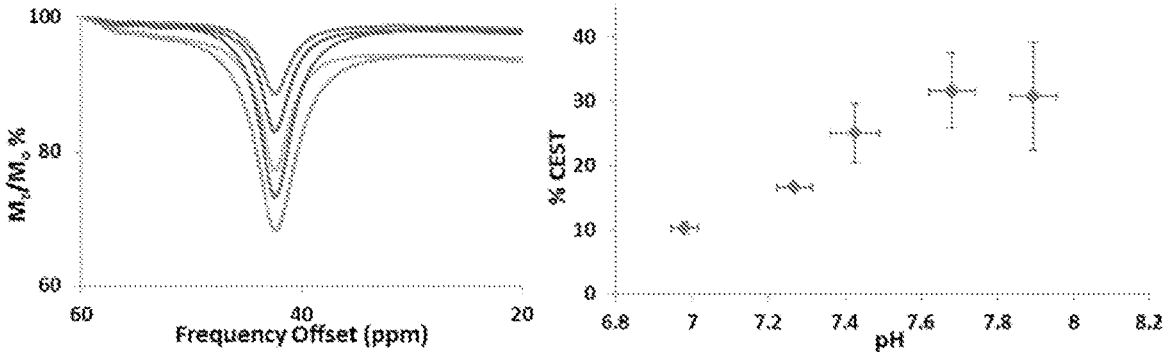
Figure 14C:
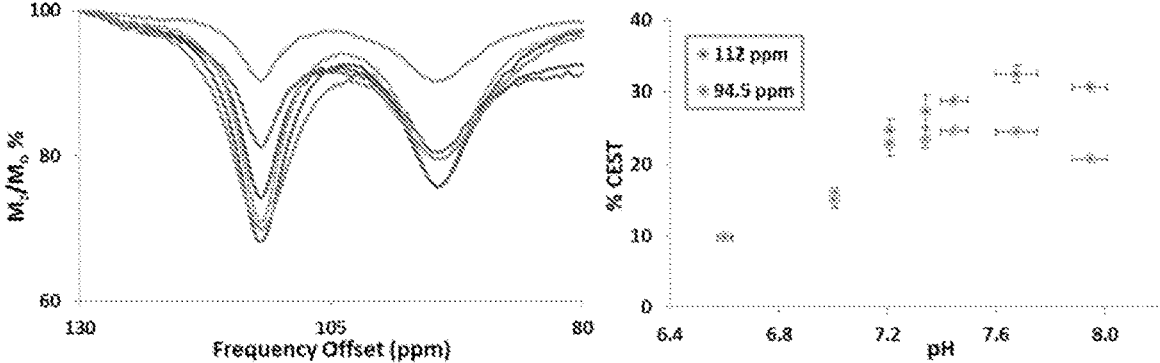
Figure 14D:
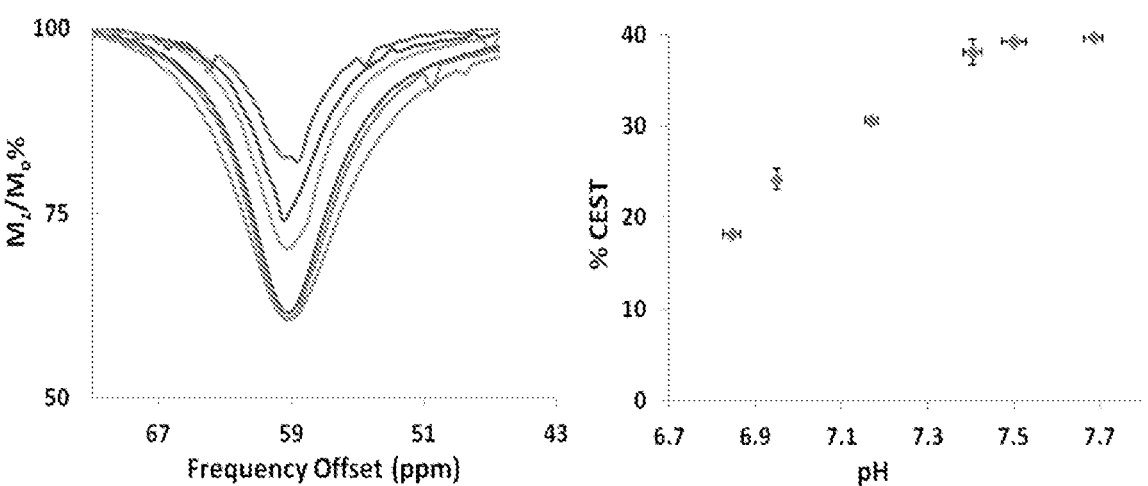

Preliminary experiments involved taking the proton NMR spectrum of the complexes in solutions containing 100 mM NaCl, 25 mM carbonate, 0.4 mM phosphate as a function of temperature (see FIG. 1) on a high field NMR spectrometer (300-500 MHz). The spectra were acquired and averaged for about 10 minutes and a proton NMR spectrum was obtained. CEST spectra are also taken in rat serum (FIG. 11). Future experiments will involve taking the proton NMR spectrum in blood plasma taken from a laboratory mouse and in vivo on a MRI scanner. The spectrum will be created by using multi-voxel spectroscopic techniques and water suppression.

In an embodiment, the macrocyclic compound of the method can be a Chemical Exchange Saturation Transfer (CEST) agent. CEST exploits the ability of Nuclear Magnetic Resonance (NMR) to resolve different signals arising from protons on different molecules. By selectively saturating a particular proton resonance of the compounds of the present disclosure that is in exchange with the surrounding water molecules, the MRI signal from the surrounding bulk water is also attenuated. A requirement for off-resonance saturation is that chemical exchange of the proton between contrast agent and water must be in the intermediate regime where exchange is fast enough to efficiently saturate the bulk water signal but slow enough on the NMR timescale to retain two proton resonances. In other words, there is a chemical shift difference between the exchangeable proton and the bulk water proton resonances. Paramagnetic metal ions (such as iron) shift the proton ($^1$H) resonances of substituents that bind to them. Design of a paraCEST agent involves incorporation of at least one exchangeable proton into the compound. The exchangeable proton should be placed such that its $^1$H resonance is shifted substantially by interaction with the cobalt(II). Application of a frequency selective presaturation pulse at the resonance of the exchangeable proton prior to the NMR spectroscopy experiment gives rise to the paraCEST spectrum which maps the water proton intensity as a function of presaturation pulse frequency. In an embodiment, the difference between the bulk water signal and the exchangeable proton is from 20 to 250 ppm, from the proton resonance of bulk water. It is important to produce exchangeable proton resonances that are sufficiently shifted from bulk water to avoid the endogenous macromolecule magnetization transfer (MT) effect. Obtaining the highly shifted proton resonance (large $\Delta\omega$ from bulk water) that would avoid sensitivity loss in vivo due to endogenous MT has been a difficult hurdle to overcome. Shifting the exchangeable proton resonance by >100 ppm away from the bulk water resonance will lead to more sensitive contrast agents that will enable their development for pH and temperature sensing by avoiding MT effects.

The detection sensitivity of CEST agents depends on several factors including the rate constant for proton exchange, the number of exchangeable protons, the concentration of the contrast agent, the value of $T_1$ for water protons in the presence of the agent and the pulse power and duration. Eq. 5 is derived from the assumption that the magnetization of the exchangeable proton is saturated and defines the CEST effect as the net reduction in the water magnetization ($M_z/M_o$).

$$\frac{M_Z}{M_0} = \frac{1}{1+k_1 T_1} \qquad \text{Eq. 5}$$

$$k_1 = n[\text{agent}]k_{CE}$$

where $k_{CE}$ is the single site exchange rate, n is the number of exchangeable protons/molecule, and $T_1$ is the water spin-lattice relaxation time in the presence of the saturating pulse. A large n is accomplished by incorporating symmetry into the macrocyclic compound.

In an embodiment, the macrocyclic compound of the method can be a paraCEST agent. This novel contrast mechanism (paraCEST) is important during in vivo imaging due to the complex biological environment. The complexes are high spin Co(II) under biologically reducing conditions and contain multiple protons for exchange with bulk water.

In an embodiment, the macrocyclic compound can be a paraCEST agent. paraCEST is a novel contrast mechanism that is important during in vivo imaging due to the complex biological environment. The complexes are stable as high spin Fe(II) and Co(II) under physiologically relevant conditions and contain multiple protons for exchange with bulk water.

In an embodiment, a method to obtain an image of at least a portion of a cell, organ, vasculature or tissue comprises contacting the cell, organ, vasculature, or tissue with a redox-active Co(II) or Fe(II) macrocyclic compound, and imaging at least a portion of the cell, organ, vasculature, or tissue to obtain an image of the portion of a cell, organ, vasculature, or tissue. The image is obtained by using magnetic resonance. The image is indicative of the redox status of the cell, organ, vasculature, or tissue. The redox status in tissue is controlled by the concentration and type of biological molecules that act as redox buffers.

The macrocyclic compounds of the present disclosure can be prepared, for example, as described in the Examples and in FIGS. 26-30, 56, 71-73, and 81-82. Modifications of these methods to provide modified compounds is within the purview of one having skill in the art.

The following examples are presented to illustrate the present disclosure. They are not intended to be limiting in any manner. Those skilled in the art will recognize that routine modifications to these embodiments can be made which are intended to be within the scope of the disclosure.

Example 1

Example of Co(II) macrocyclic compounds having amide pendant groups as paraCEST MRI contrast agents.

Described are the first air stable $Co^{II}$ paraCEST (Co-CEST) MRI contrast agents. The rich coordination chemistry of $Co^{II}$ with azamacrocyclic ligands supports the formation of complexes that are stable in aqueous solution. Amide pendent groups were attached to several different azamacrocycles bind $Co^{II}$ to give CoCEST agents with unique MRI contrast properties.

$Co^{II}$ complexes of four different macrocycles with pendent amide groups were prepared, depicted below.

[Co(TCMT)]$^{2+}$

[Co(TCMC))]$^{2+}$

[Co(NOPE)]$^{2+}$

[Co(CCRM)]$^{2+}$

To characterize their solution chemistry, magnetic moments were determined from magnetic susceptibility measurements using a previously described method. [Co(TCMT)]$^{2+}$, [Co(TCMC)]$^{2+}$, [Co(CCRM)]$^{2+}$, and [Co(NOPE)]$^{2+}$ have magnetic moments of 5.2, 4.5, 4.6, and 4.1 μB, respectively, at 25° C. in $D_2O$, suggestive of high spin (HS) $Co^{II}$ (S=3/2). The larger value for [Co(TCMT)]$^{2+}$ also lies within the range for HS $Co^{III}$ (S=2), yet similarly large values are observed for [Co(TCMT)](ClO$_4$)$_2$ in the solid state, as characterized through SQUID magnetometry (4.9 μB at 17° C.). The constancy of these magnetic moments over 72 hours incubation at 37° C. is consistent with the stability of these complexes as discussed further below.

Figure 2:
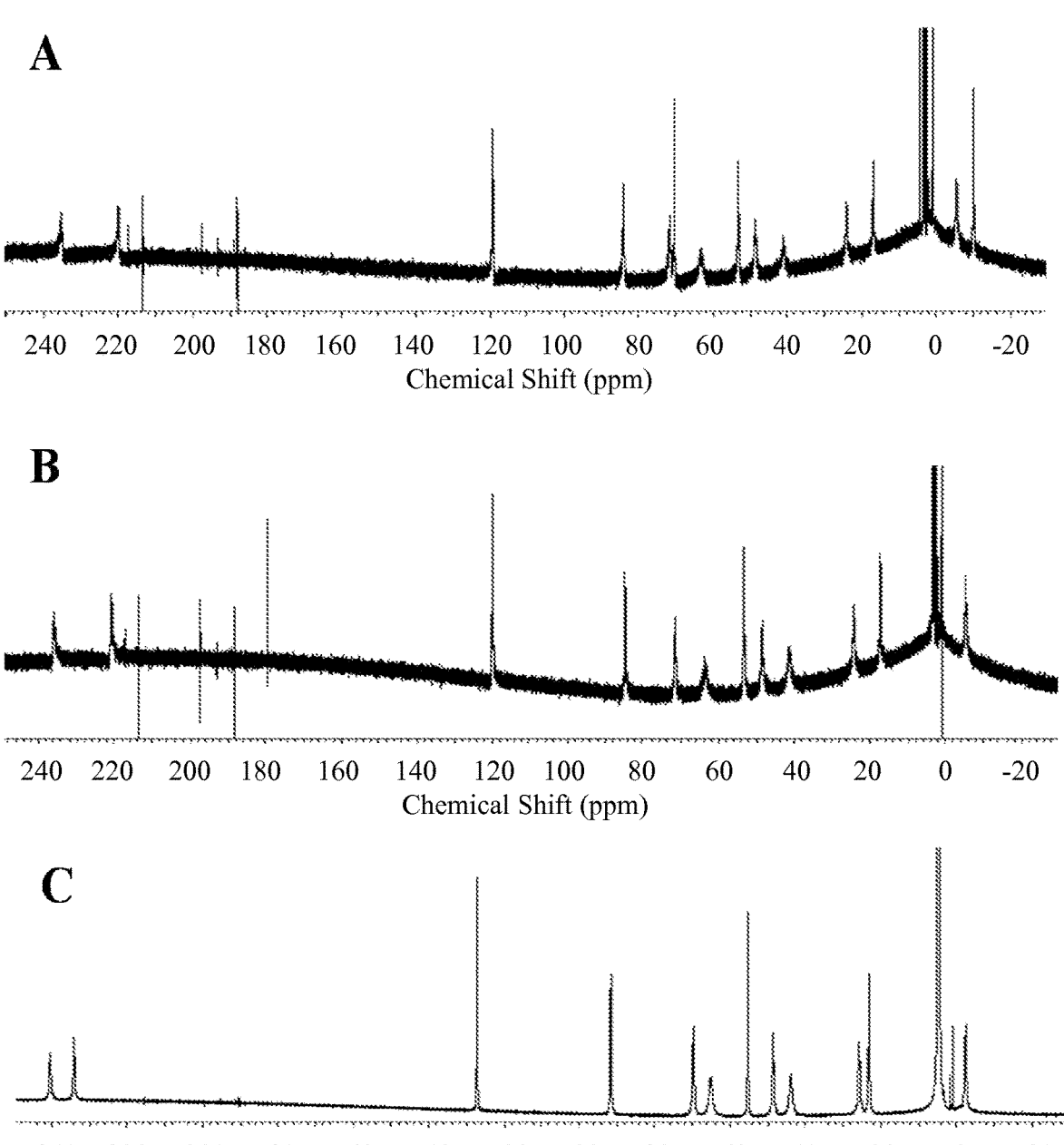
FIG. 2. $^1$H NMR spectra of $[Co(NOPE)]^{2+}$ in (A) $d_6$-DMSO, (B) $d_6$-DMSO+$D_2O$ (C) $D_2O$. Amide protons are identified at 70 ppm in $d_6$-DMSO solution versus TMS as a standard.

In the absence of dynamic processes, the $Co^{II}$ complexes have fairly narrow proton resonances at full width half maximum (FWHM), corresponding to the relatively short electronic longitudinal relaxation time (T1e) of HS $Co^{II}$. Large proton chemical shifts of up to 280 ppm are observed for CoCEST agents. The 12 distinct narrow (FWHM=70-350 Hz) peaks of [Co(NOPE)]$^{2+}$ in $D_2O$ correspond to the number of expected peaks for a 7-coordinate complex with two coordinated pendent amides and $C_2$ symmetry (FIG. 2).

Figure 3:
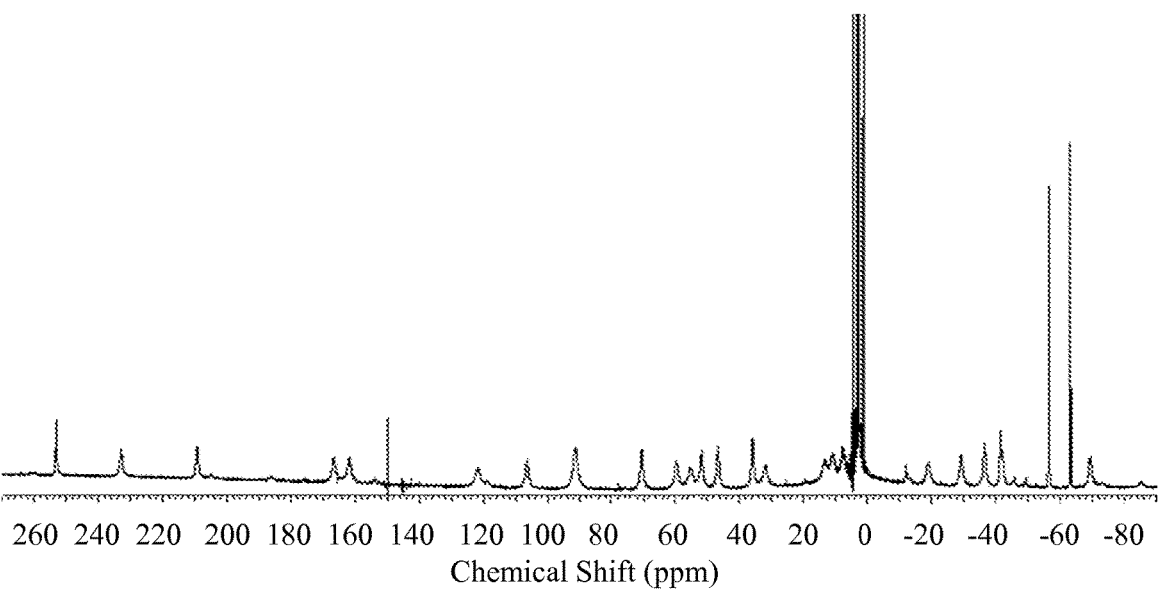
FIG. 3. $^1$H NMR spectrum of $[Co(CCRM)]^{2+}$ in $D_2O$.
Figure 4:
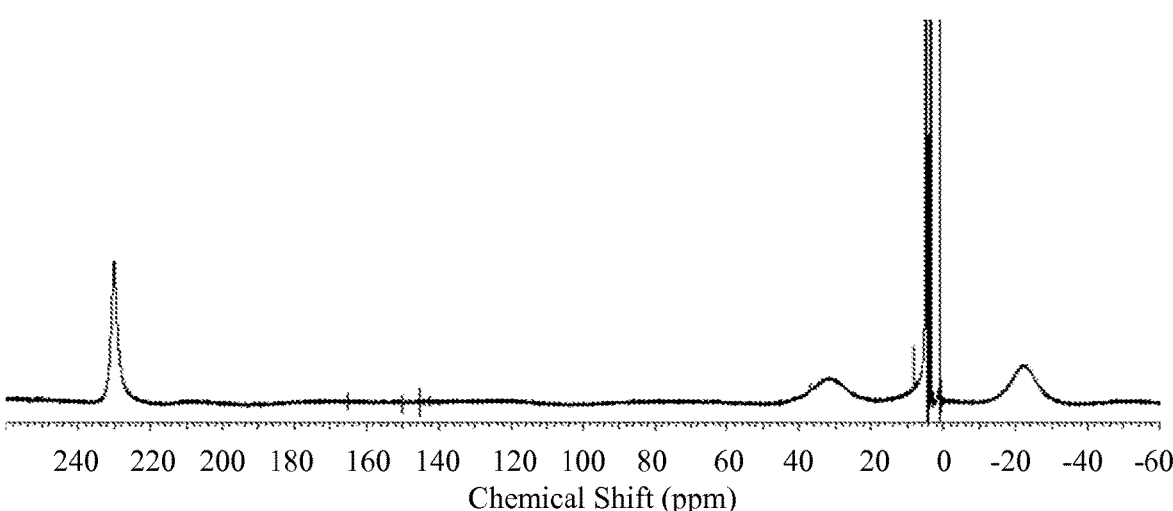
FIG. 4. $^1$H NMR spectrum of $[Co(TCMT)]^{2+}$ in $D_2O$.
Figure 5:
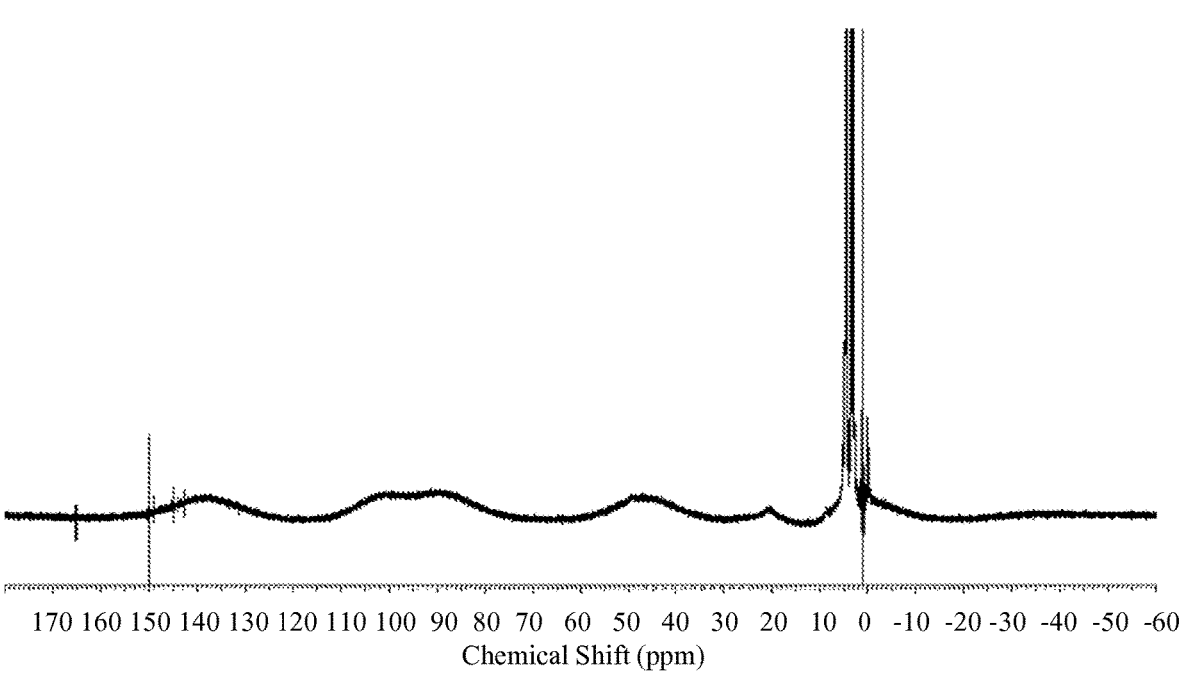
FIG. 5. $^1$H NMR spectrum of $[Co(TCMC)]^{2+}$ in $D_2O$.

Exchangeable protons were identified for [Co(NOPE)]$^{2+}$ by comparison of the $^1$H NMR spectra of the complex in the presence of H/D exchange (D$_2$O) and absence of exchange (d$_6$-DMSO). [Co(CCRM)]$^{2+}$ also displays relatively narrow $^1$H peaks (FWHM=70-500 Hz), although the spectrum is complicated by a small percentage of a minor isomer (~4%) (FIG. 3). This corresponds to the fact that several different conformations may be adopted by transition metal ion complexes of tetrasubstituted Cyclam derivatives including isomers that have pendent groups bound either trans or cis with respect to each other. The large number of proton resonances for the major isomer of [Co(CCRM)]$^{2+}$ suggests a lack of symmetry in the complex. A conformation consistent with the NMR spectrum has two bound amide pendent groups in the 1,8-Cyclam ring positions that are bound cis, similar to a related Co$^{II}$ complex. Broad and fairly indistinguishable resonances are observed for [Co(TCMT)]$^{2+}$ and [Co(TCMC)]$^{2+}$ (FIGS. 4 and 5). Analogous complexes of Fe$^{II}$ are fluxional on the NMR time-scale, also exhibiting broad macrocyclic CH$_2$ resonances. [Co(TCMT)]$^{2+}$ is proposed to be 6-coordinate, consistent with IR data supporting coordination through the carbonyl oxygen. The coordination geometry of [Co(TCMC)]$^{2+}$ is most likely 8-coordinate given that the similar-sized HS Mn$^{II}$ complex of TCMC is 8-coordinate as shown by crystallography.

To gauge the feasibility of studying these compounds in vivo, the degree of dissociation of the Co$^{II}$ complexes was monitored by using $^1$H NMR spectroscopy. The diamagnetic region of the NMR spectra was monitored in the presence of a standard after 12 hours incubation at 37° C. In the presence of physiologically relevant concentrations of phosphate (0.40 mM) and carbonate (25 mM) at near-neutral pD, dissociation of all complexes was minimal (Table 1 and FIGS. 6-9). Acidic conditions (pD 3.5-3.9) gave more variable results. At the two extremes, dissociation of [Co(TCMT)]$^{2+}$ was insignificant at only 1% over 12 hours, while [Co(CCRM)]$^{2+}$ dissociated 95% within the first hour. [Co(TCMC)]$^{2+}$ and [Co(NOPE)]$^{2+}$ were moderately inert at 7% and 16% dissociation, respectively (Table 1 and FIGS. 10-13). Dissociation of the complexes was also studied by addition of a 10-fold excess of Cu$^{II}$ as a competing metal ion and monitoring the formation of the Cu$^{II}$ complex through UV-vis spectroscopy. While [Co(TCMC)]$^{2+}$ is inert to dissociation, [Co(TCMT)]$^{2+}$ dissociates ~15% over 4 hours. [Co(CCRM)]$^{2+}$ and [Co(NOPE)]$^{2+}$ are significantly more labile, dissociating completely within one hour.

TABLE 1

Effective magnetic moment and dissociation of Co$^{II}$ complexes in D$_2$O solutions at 37° C.

| Complex | $\mu_{eff}$[a] ($\mu_s$) | % Dissociation[b] Acidic | % Dissociation[c] Anions |
|---|---|---|---|
| [Co(TCMT)]$^{2+}$ | 5.2 | 1 | 5 |
| [Co(TCMC)]$^{2+}$ | 4.5 | 7 | 2 |
| [Co(CCRM)]$^{2+}$ | 4.6 | 95 | 5 |
| [Co(NOPE)]$^{2+}$ | 4.1 | 16 | <1 |

[a]5 mM Co$^{II}$ complex in D$_2$O.
[b]Samples contained 10 mM Co$^{II}$ complex, pD 3.5-3.9, 100 mM NaCl, 5 mM 3-(trimethylsilyl)-1-propanesulfonic acid standard, monitored at 12 hours after incubation at 37° C.
[c]Samples contained 10 mM Co$^{II}$ complex, 0.40 mM Na$_2$HPO$_4$, 25 mM K$_2$CO$_3$, 100 mM NaCl, pD 7.5-7.9, 5 mM 3-(trimethylsilyl)-1-propanesulfonic acid standard, monitored at 12 hours after incubation at 37° C.

CEST NMR spectra were produced using an 11.7 T NMR spectrometer through a presaturation experiment plotted as normalized water signal intensity (M$_z$/M$_o$%) against frequency offset (ppm). Restricted C—N bond rotation of the amide groups in these complexes yields two magnetically inequivalent NH protons for each amide group. For example, [Co(NOPE)]$^{2+}$ has two highly separated CEST peaks at 59 and −19 ppm assigned to two magnetically inequivalent amide protons arising from two symmetry-related pendent groups (FIG. 1a). The single observed CEST peaks for [Co(TCMT)]$^{2+}$ or [Co(TCMC)]$^{2+}$ are shifted away from bulk water at 32 and 45 ppm, respectively (FIG. 1a). The second amide proton resonance is presumably not sufficiently shifted to distinguish it from the water peak. [Co(CCRM)]$^{2+}$ exhibits four CEST peaks (112, 95, 54, and 45 ppm) of similar intensity and a smaller CEST peak at −15 ppm from bulk water (FIG. 1b). The appearance of four major CEST peaks is consistent with two bound amides in a cis-configuration to give four magnetically inequivalent amide protons. [Co(CCRM)]$^{2+}$ produces the most highly shifted CEST peaks of the four complexes.

Figure 17:
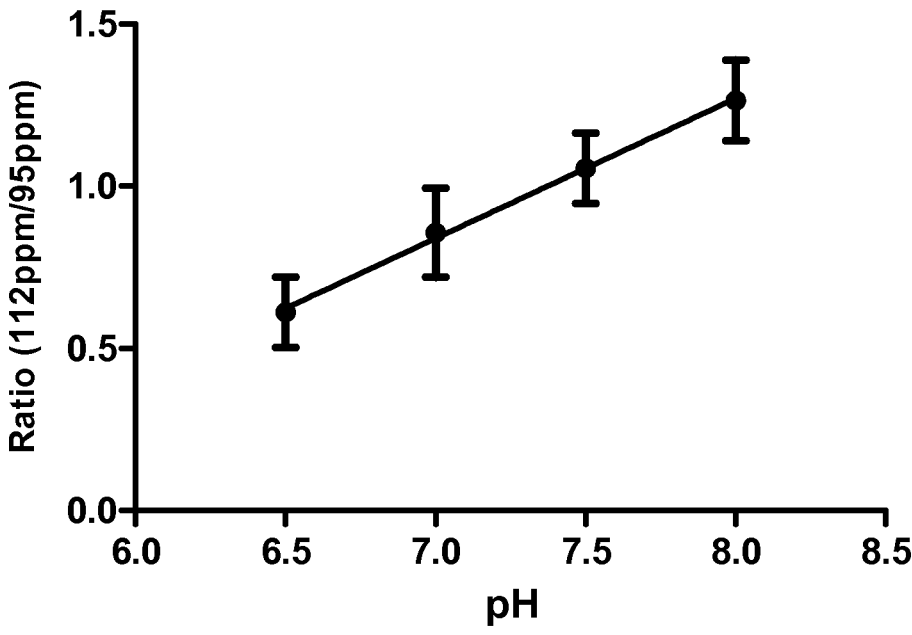
FIG. 17. 4 mM samples of $[Co(CCRM)]^{2+}$ containing 20 mM buffer (MES or HEPES), 100 mM NaCl, at pH 6.5-8.0, plotted ratiometrically as % CEST at 112 ppm: % CEST at 95 ppm. Recorded at 37° C. using a CEST-FISP acquisition with a 5×1 second, 12 µT pulse train on a 4.7T MRI scanner.

The CEST peak intensity of the complexes increased over the pH range of 6.5-7.5, consistent with base-catalyzed amide exchange (FIG. 14). All four complexes have maximal CEST effects at pH 7.5-7.7. Interestingly, the two most highly shifted peaks of [Co(CCRM)]$^{2+}$ at 112 and 95 ppm have a different pH dependence. A ratiometric plot of the CEST effect of these two peaks versus pH shows that this agent might be used for concentration-independent ratiometric analysis of pH (FIG. 17).

Figure 16:
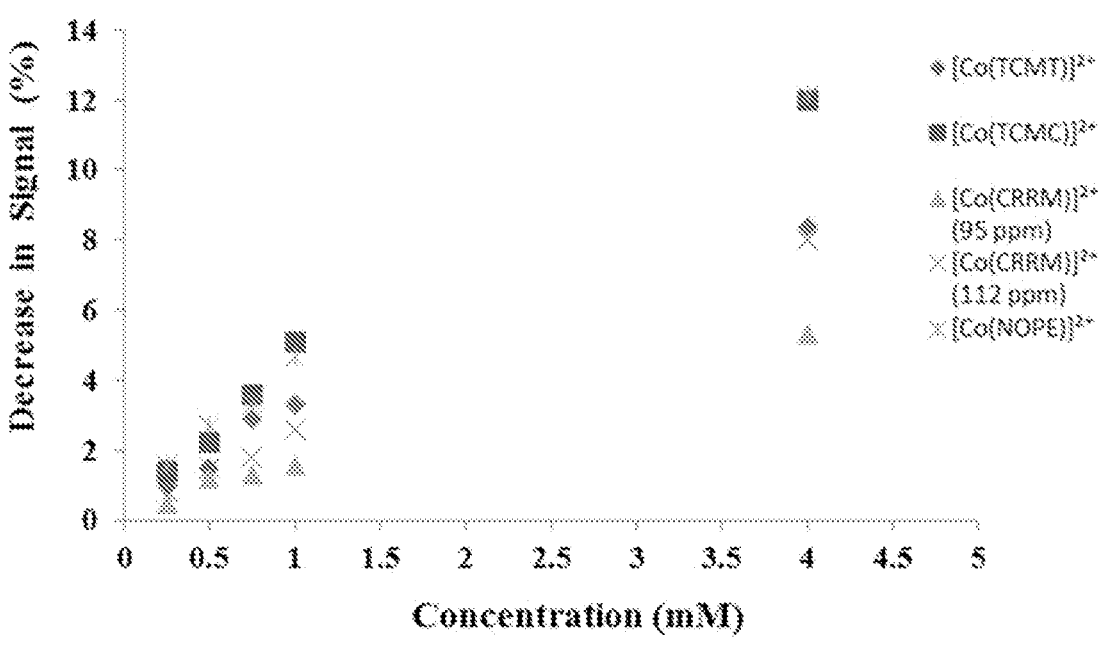
FIG. 16. Plot of the decrease in CEST (corresponding to an increase in the CEST contrast) with $B_1=12$ µT on 4.7 T MRI scanner of a solution containing 0.25 mM-4.00 mM $Co^{II}$ complexes, 100 mM NaCl, and 20 mM HEPES pH 7.4-7.5 at 37° C.

CEST MR phantom images were acquired on a 4.7 T scanner using a phantom array containing solutions of 0.25, 0.50, 0.75, 1.0 or 4.0 mM Co$^{II}$ complex, 100 mM NaCl, 20 mM buffer pH 7.4 at 37° C. (FIG. 15). A pair of gradient echo images was acquired with a presaturation pulse either on-resonance or off-resonance of the exchangeable protons (59/−59 ppm for [Co(NOPE)]$^{2+}$, 45/−45 ppm for [Co(TCMC)]$^{2+}$, 32/−32 ppm for [Co(TCMT)]$^{2+}$ and either 112/−95 ppm or 95/−95 ppm for [Co(CCRM)]$^{2+}$. The ratio between these two images is subtracted from 100% to generate a CEST image. The phantoms show that the CEST effect increases with the concentration of the Co$^{II}$ complex over the range 0.25 to 4.0 mM (FIG. 16). CEST contrast typically increases with number of magnetically equivalent exchangeable protons, increasing concentration of agent, increasing rate constant for proton exchange (kex) in the absence of exchange broadening, and with long T$_1$ time constant of water protons (low T$_1$ relaxivity) in the presence of agent. Increasing the saturation pulse power also leads to an increase in CEST, but there are limitations for power deposition in tissue and on kex. All CoCEST agents produce CEST phantom images at 4 mM agent (5-12%), with the most intense CEST effect belonging to [Co(NOPE)]$^{2+}$ and [Co(TCMC)]$^{2+}$. The CEST effect for these two complexes is similar, despite the fact that there are half the number of amide NH protons for [Co(NOPE)]$^{2+}$ as for [Co(TCMC)]$^{2+}$ and both have similar kex. Notably, the T$_1$ relaxivity for both [Co(NOPE)]$^{2+}$ and [Co(CCRM)]$^{2+}$ is favorably low, and this may contribute to an enhanced CEST effect (Table 2).

TABLE 2

Exchange Rate Constants, Relaxivity and CEST effect of CoCEST agents.

| Complex | k$_{ex}$[a] (s$^{-1}$) | T$_1$ Relaxivity[b] (mM$^{-1}$ · s$^{-1}$) | T$_2$ Relaxivity[c] (mM$^{-1}$ · s$^{-1}$) | % CEST[d] |
|---|---|---|---|---|
| [Co(TCMT)]$^{2+}$ | 890 | 0.125 | 0.297 | 8 |
| [Co(TCMC)]$^{2+}$ | 300 | 0.096 | 0.213 | 12 |

TABLE 2-continued

Exchange Rate Constants, Relaxivity and CEST effect of CoCEST agents.

| Complex | $k_{ex}^{[a]}$ (s$^{-1}$) | $T_1$ Relaxivity[b] (mM$^{-1}$·s$^{-1}$) | $T_2$ Relaxivity[c] (mM$^{-1}$·s$^{-1}$) | % CEST[d] |
|---|---|---|---|---|
| [Co(CCRM)]$^{2+}$ | 510[e], 910[f] | 0.008 | 0.127 | 8[e], 5[f] |
| [Co(NOPE)]$^{2+}$ | 240 | 0.038 | 0.119 | 12 |

[a]Average proton exchange rate constant ($k_{ex}$) obtained on 11.7 T spectrometer using the omega plot method of 10 mM CoCEST complex, 20 mM HEPES pH 7.4, 100 mM NaCl, with $B_1$ varied between 8 and 24 µT, presat 4 s, 37° C.
[b,c]$T_1$ and $T_2$ relaxivities, respectively, acquired at 4.7 Telsa, 37° C. for 0.25-4 mM CoCEST complex, 20 mM HEPES, 100 mM NaCl, pH 7.4-7.5 using an inversion-recovery TrueFISP relaxometry protocol ($T_1$) and a Carr-Purcell-Meiboom-Gill multi-echo echo sequence ($T_2$)
[d]% CEST of 4 mM CoCEST complex, 20 mM HEPES, 100 mM NaCl, pH 7.4-7.5, 37° C, on a 4.7 T MRI scanner.
[e]% CEST for peak at 112 ppm
[f]peak at 95 ppm.

CEST MR phantom images of [Co(CCRM)]$^{2+}$ were obtained as a function of pH for the furthest shifted CEST peaks (112 ppm and 95 ppm) to further validate ratiometric pH contrast properties (FIG. 17). In order to shorten the acquisition time in order to improve data precision by averaging multiple data points, images were obtained by using CEST FISP (FISP=fast imaging with steady-state free precession) protocol. As FISP imaging allows for the acquisition of the entire MR image after the CEST saturation pulse, we are able to acquire 20 CEST image data points in under 2 minutes, greatly shortening experimental data collection time. Performing linear regression on the ratio of CEST signal (112:95 ppm) vs. pH yields a slope of 0.4313, analogous to the CEST NMR experiments (FIG. 1c).

X-ray diffraction data for [Co(NOPE)]$^{2+}$ complex cation shows that the cobalt(II) complex is seven-coordinate complexes with all nitrogen and oxygen donor atoms of the 1,10-diaza-15-crown-5 macrocycle and amide pendent groups bound to the metal ion. The Co(II) ion binds the carbonyl oxygen of the amide pendent in axial position with the five macrocyclic backbone donors in a planar arrangement to produce a distorted pentagonal bipyramidal geometry. This geometry is consistent with the two CEST peaks observed for this complex, one for each set of amide protons.

X-ray diffraction data for [Co(CCRM)]$^{2+}$ complex cation shows a six coordinate complex with donor groups consisting of the carbonyl oxygens of the 1-, 4-pendent groups and the four nitrogen donor atoms of the tetraazamacrocycle. This highly asymmetric structure is consistent with the CEST spectrum which shows four major CEST peaks. The complex cation of [Co(TCMC)]$^{2+}$ features a seven-coordinate Co$^{II}$ bound to three pendent carbonyl oxygens and four nitrogen donors. The CEST spectrum shows a single peak, suggesting that the complex is fluxional in solution.

Figure 18:
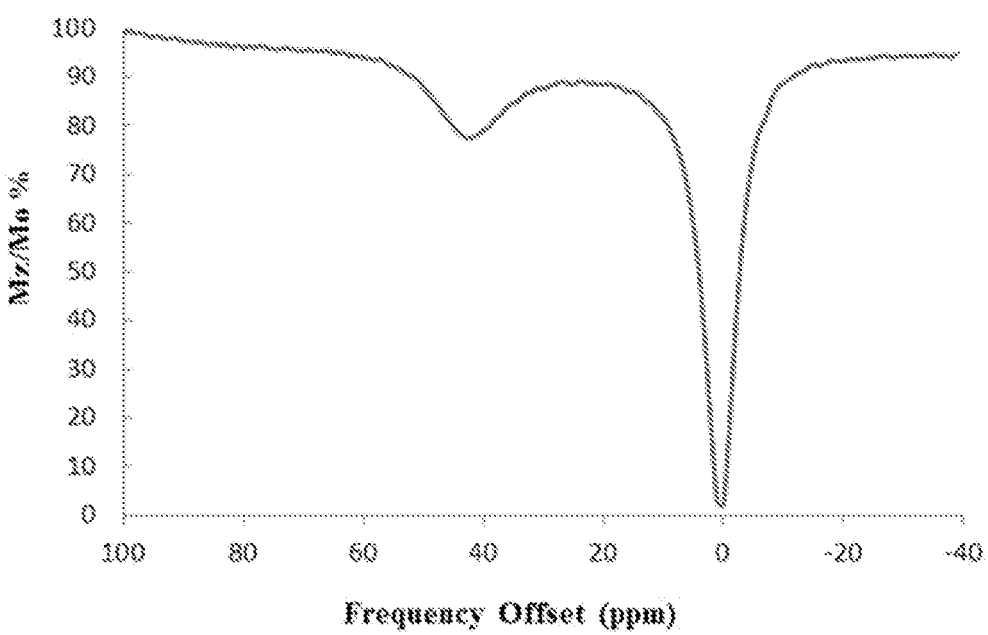
FIG. 18. CEST spectra recorded at 11.7 T of a solution containing 10 mM $[Co(STHP)]^{2+}$ complex, 100 mM NaCl, 20 mM MES RF presaturation pulse applied for 2 seconds $B_1=24$ µT at 37° C. The CEST peak is shifted 43 ppm away from bulk water.
Figure 19:
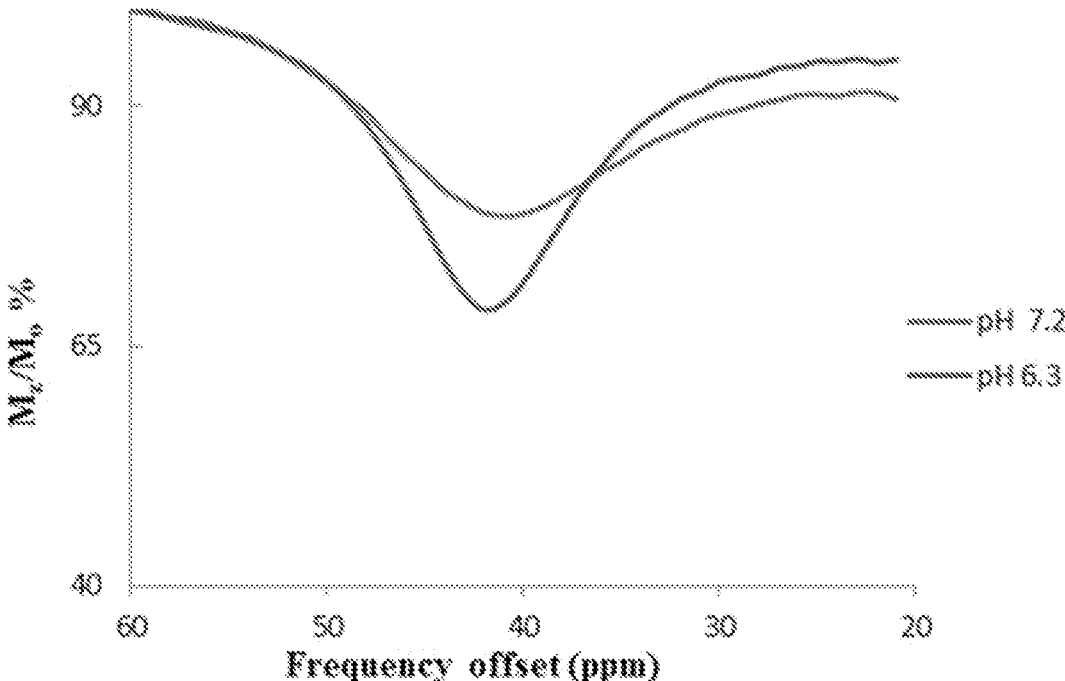
FIG. 19. CEST spectra recorded at 11.7 T of solutions containing 10 mM $[Co(STHP)]^{2+}$, 20 mM buffer (pH 6.5 and 7.2), and 100 mM NaCl, RF-presaturation pulse applied for 2 seconds $B_1=24$ µT at 37° C.
Figure 20:
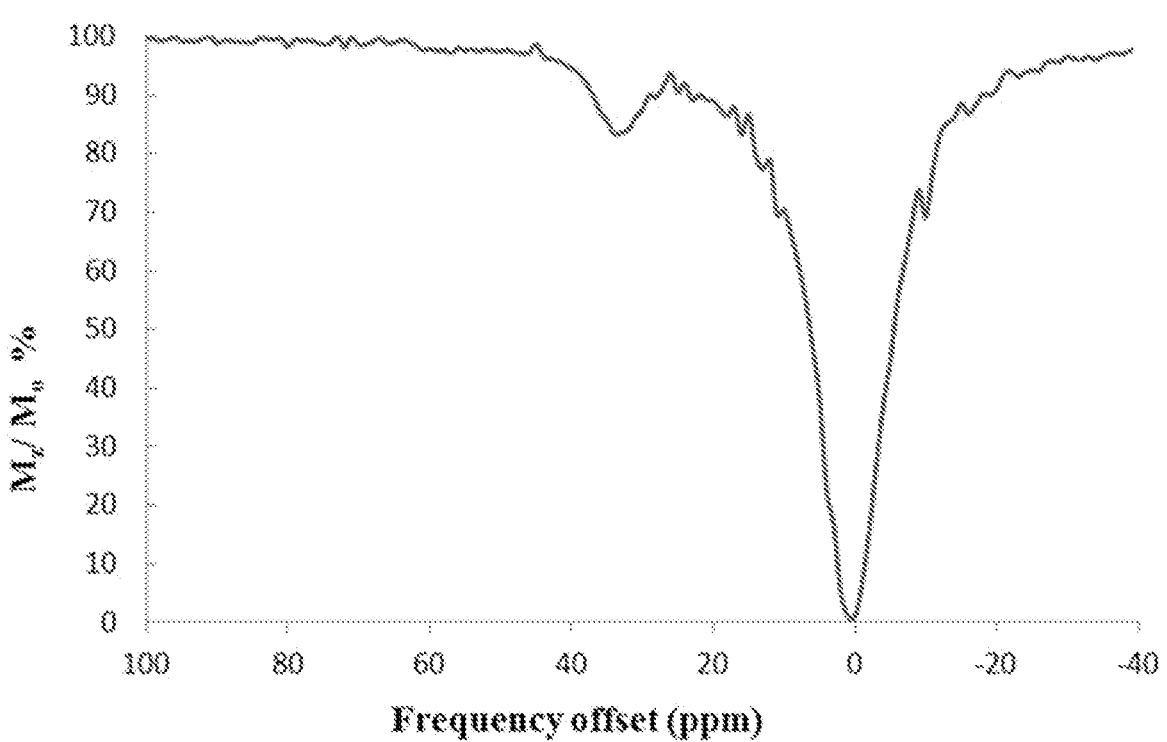
FIG. 20. CEST spectra recorded at 11.7 T of a solution containing 10 mM $[Co(LOCO)]^{2+}$, 100 mM NaCl, 20 mM MES pH 7.0, RF presaturation pulse applied for 2 seconds $B_1$=24 µT at 37° C. The CEST peak is shifted 33 ppm away from bulk water.
Figure 21:
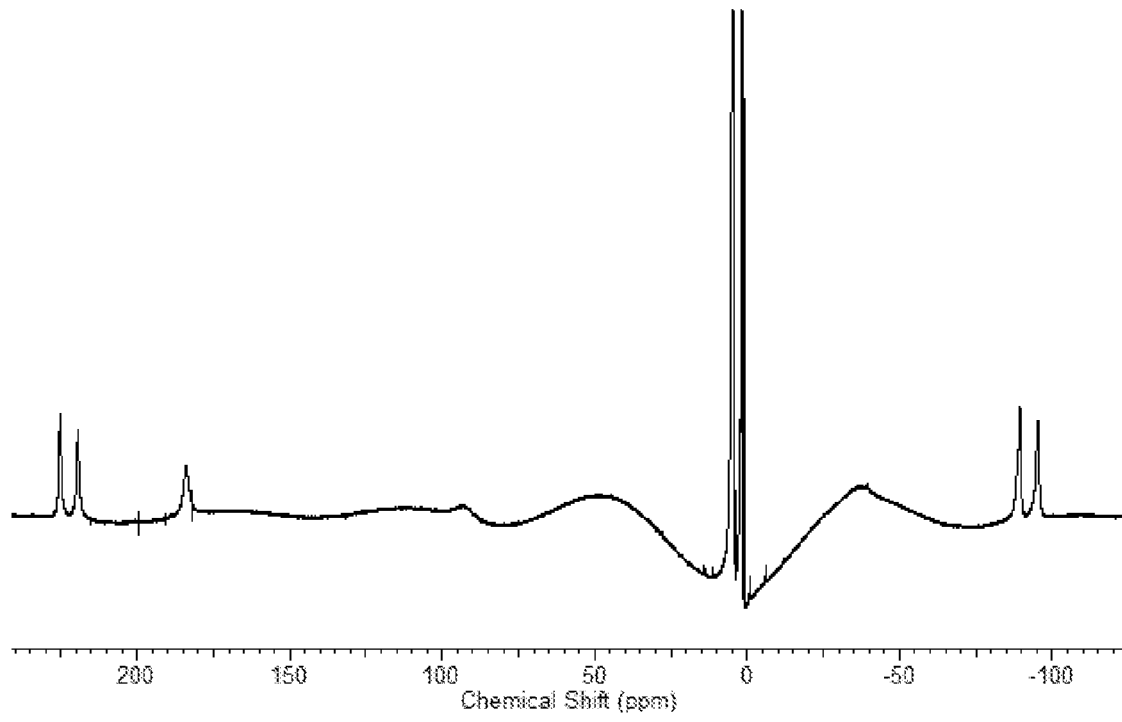
FIG. 21. $^1$H NMR spectrum of [Co(TACO)]$^{2+}$ in $D_2O$.
Figure 22:
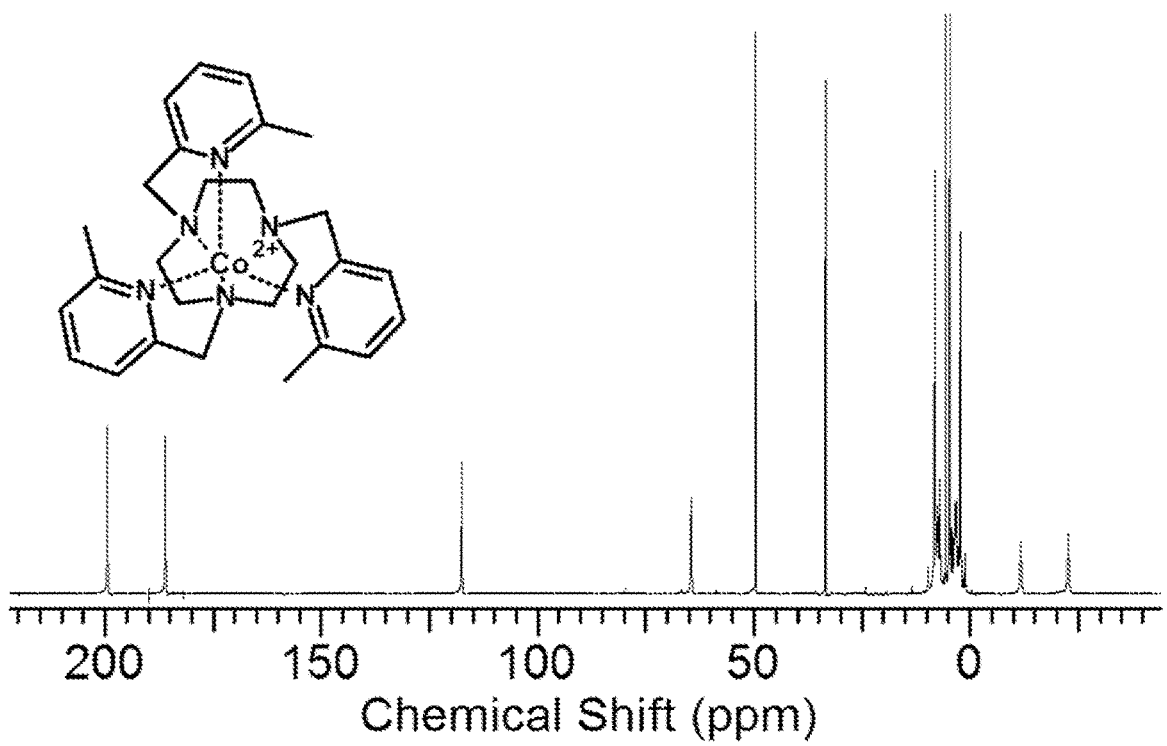
FIG. 22. $^1$H NMR spectrum of [Co(MPT)]$^{2+}$ in $D_2O$, pD 7.1, at 25° C.
Figure 23:
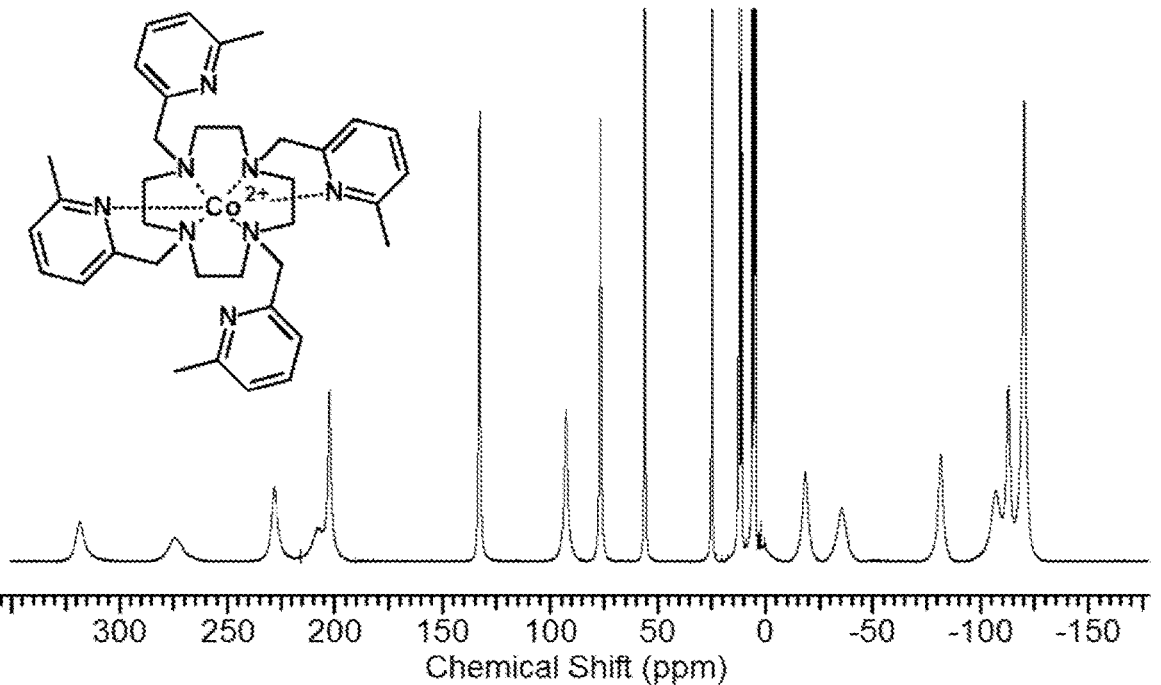
FIG. 23. $^1$H NMR spectrum of [Co(TMPC)]$^{2+}$ in $D_2O$, pD 7.2.
Figure 24:
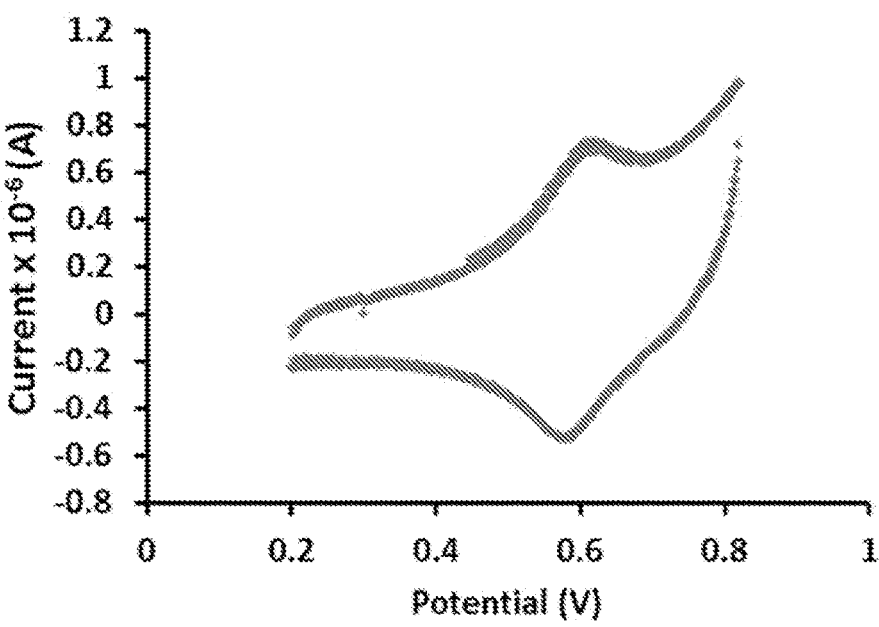
FIG. 24. Cyclic voltammogram of argon-saturated aqueous solution of 1.0 mM [Co(TMPC)]Cl$_2$ containing 1.00 M KCl, pH 6.8. A scan rate of 100 mV/s was used.
Figure 25:
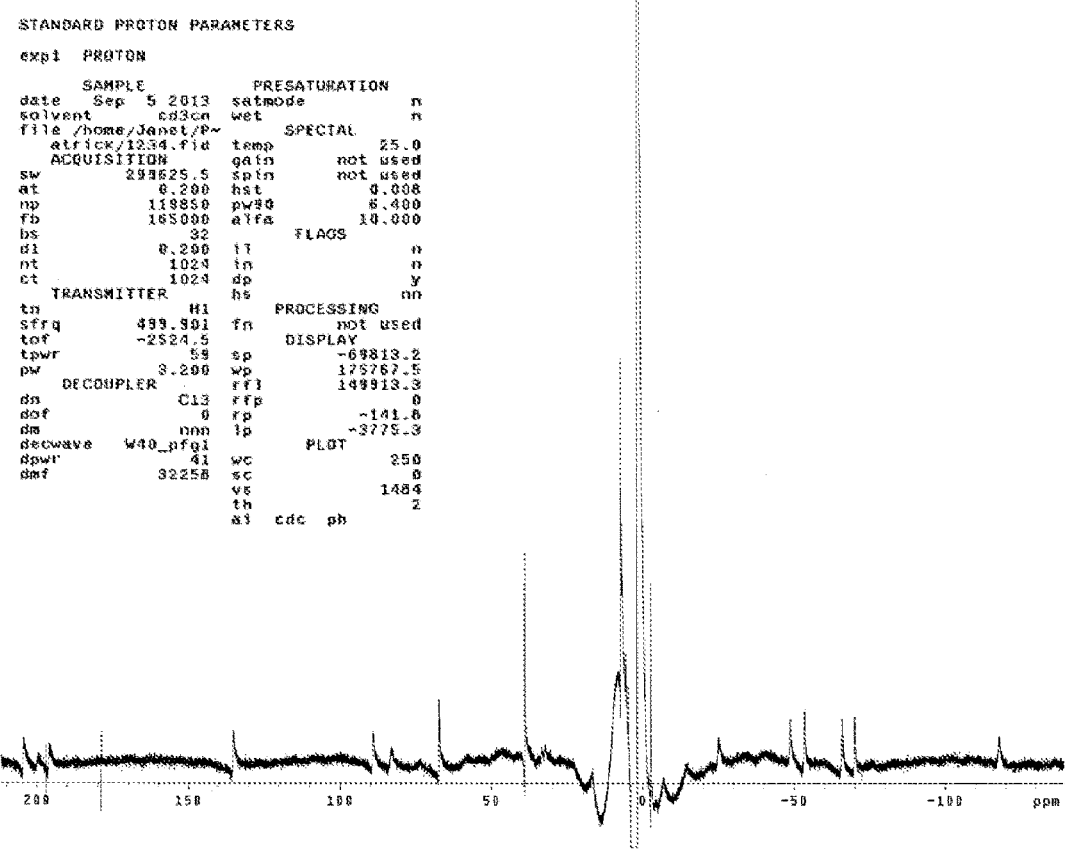
FIG. 25. $^1$H NMR spectrum of [Co(BzCY)]$^{2+}$ in $D_2O$.
Figure 29:
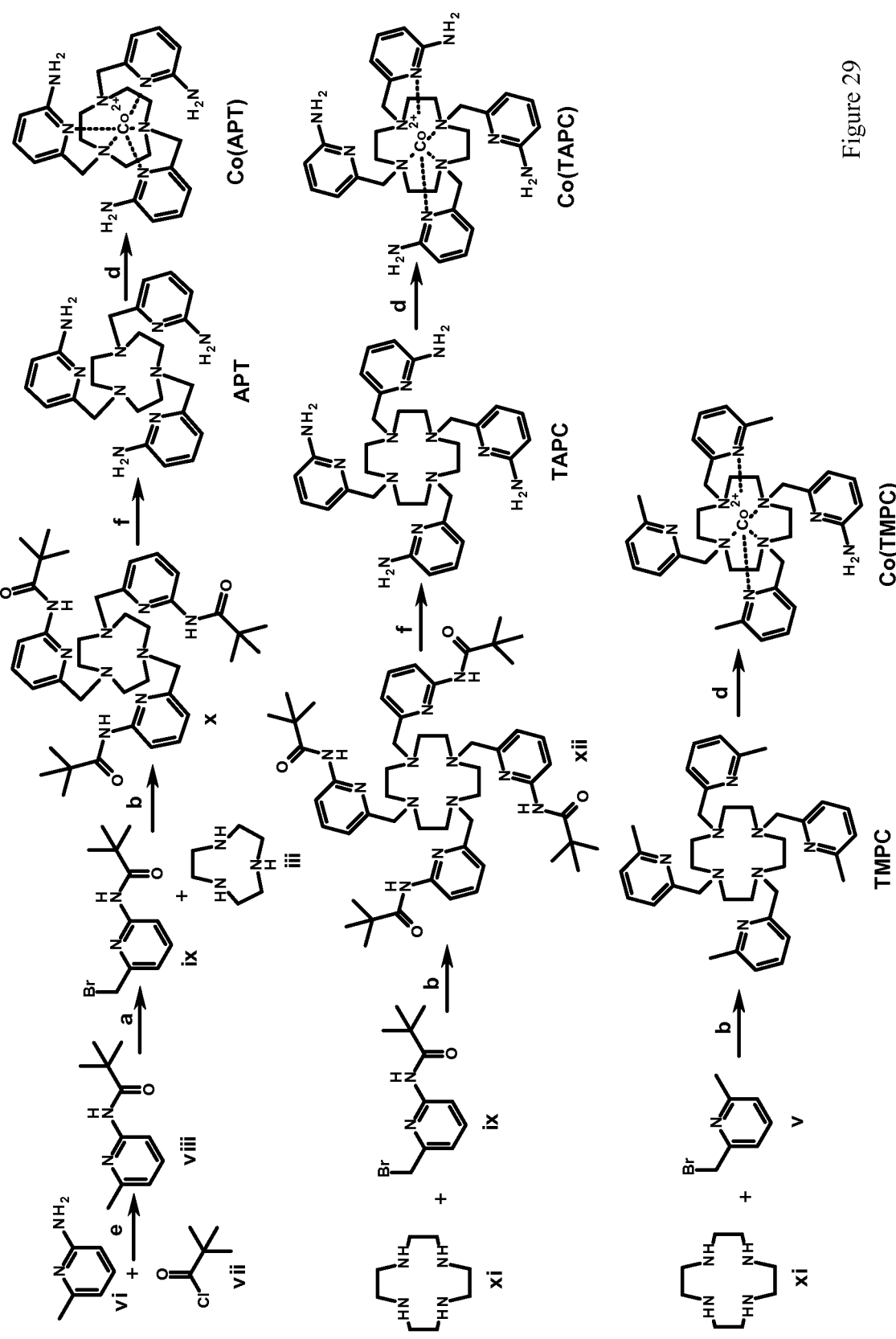
FIG. 29. Scheme for the synthesis of APT, TAPC, and TMPC and their complexes with Co(II). Reagents and conditions: (a) AIBN, carbon tetrachloride, 50° C. to reflux, Ar, 8 hours; (b) DIPEA, acetonitrile, 50° C., 24 hours; (d) CoCl$_2$(H$_2$O)$_6$, acetonitrile, room temperature, Ar, 8 hours; (e) methylene chloride, TEA, room temperature, 3 hours; (f) KOH, methanol, water, 60° C., Ar, 4 days.
Figure 30:
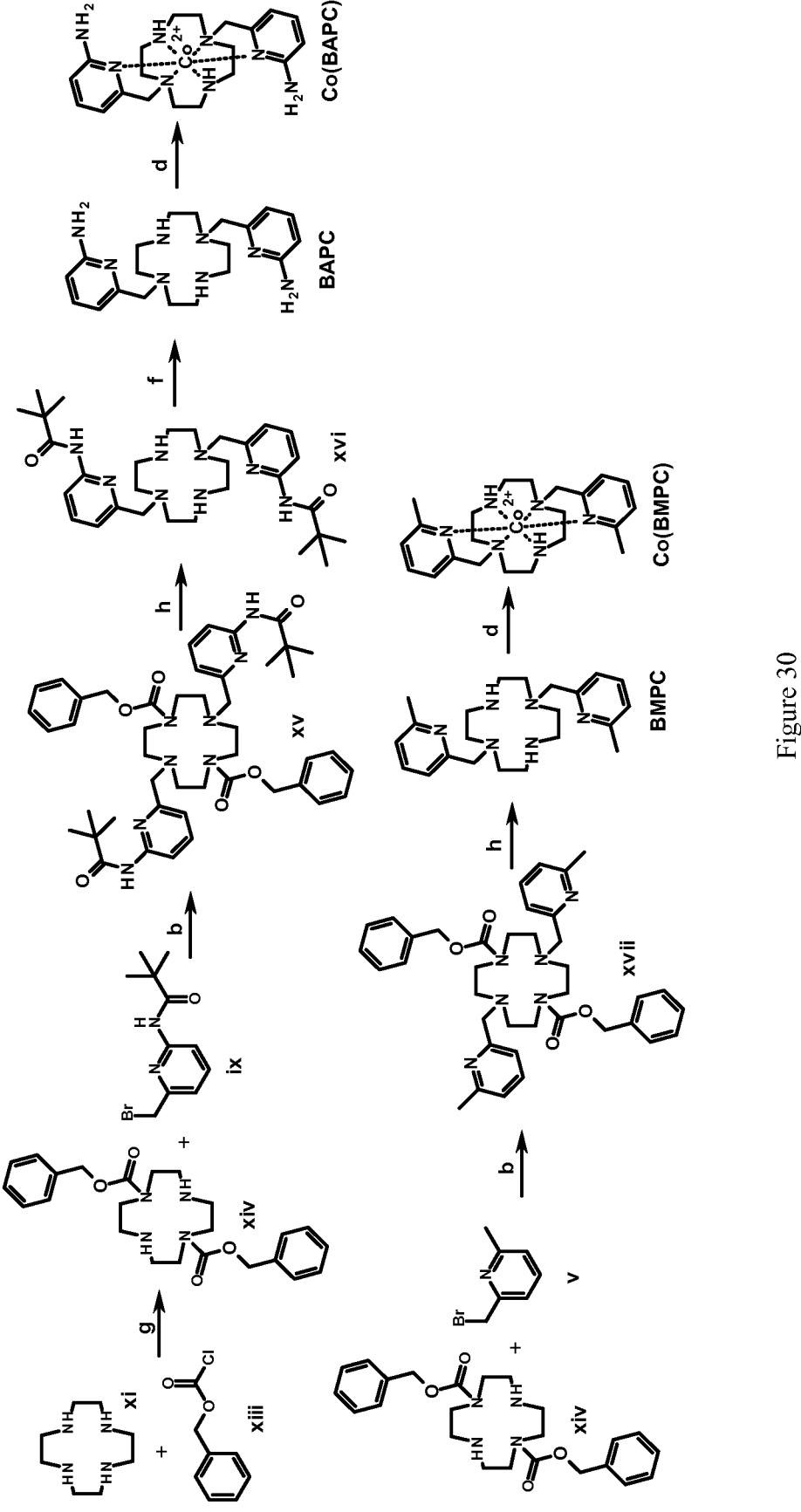
FIG. 30. Scheme for synthesis of BAPC, BMPC, and their complexes with Co(II). Reagents and conditions: (b) DIPEA, acetonitrile, 50° C., 24 hours; (d) CoCl$_2$(H$_2$O)$_6$, acetonitrile, room temperature, Ar, 8 hours; (f) KOH, methanol, water, 60° C., Ar, 4 days; (g) dioxane-water (50:50, v/v), pH 3.0-4.0, room temperature, 16 hours; (h) hydrogen, 10% Pd/C, methanol, 12 hours.

In FIG. 18-20 are shown CEST spectra of the Co(II) macrocyclic complexes containing alcohol pendents including LOCO and STHP. In FIG. 21 is shown the proton NMR of the Co(II) complex of TACO. FIGS. 22 and 23 show two Co(II) complexes that show sharp proton NMR spectra for use in MRS. One of these complexes, [Co(TMPC)Cl2 shows a reversible cyclic voltammogram (FIG. 24). The relatively high potential of approximately 0.55 V is consistent with the resistance of the Co(II) complex towards oxidation. FIG. 25 shows the proton NMR of the Co(II) complex of BZCY.

Figure 31:
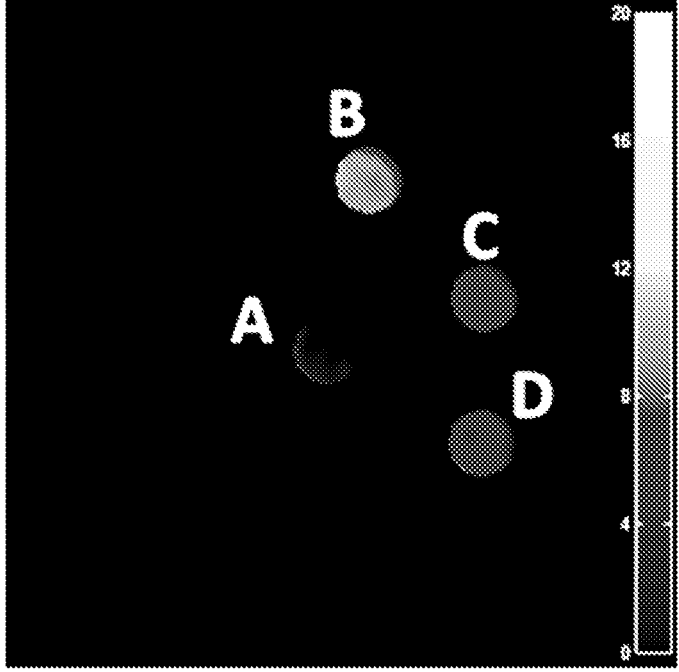
FIG. 31. CEST images of phantoms on a MRI 4.7 T scanner with a pulse train comprised of five Gauss pulses at 12 µT for 1 second each, interpulse delay of 200 µs applied symmetrically about the bulk water resonance (±59 ppm). Sample A consisted of 20 mM HEPES pH 7.4 and 100 mM NaCl. All other solutions contained 4 mM [Co(NOPE)]$^{2+}$ in B) 20 mM HEPES pH 7.4 and 100 mM NaCl, C) rabbit serum, D) 20 mM HEPES pH 7.4 and 100 mM NaCl in 4% agarose gel (w/w) pH 7.3-7.4 at 37° C.
Figure 32:
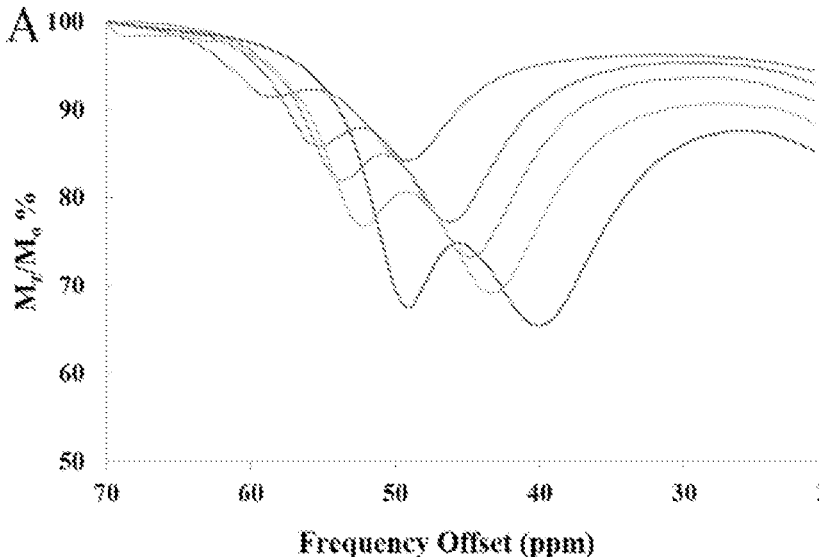
FIG. 32. Overlaid CEST spectra at varying temperatures of (A) the two nearest CEST peaks and (B) the two furthest CEST peaks of 10 mM [Co(CCRM)]$^{2+}$, 20 mM HEPES, 100 mM NaCl, pH 7.4, B1=24 µT for 2 seconds.
Figure 32:
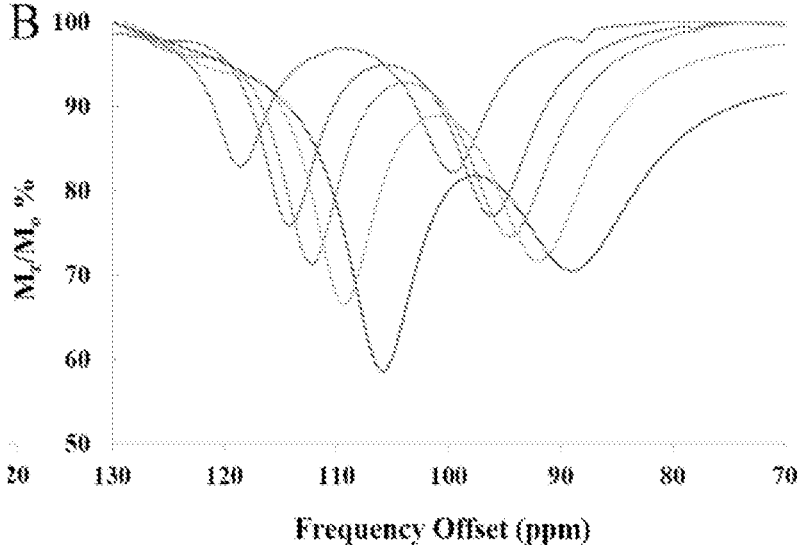
Figure 33:
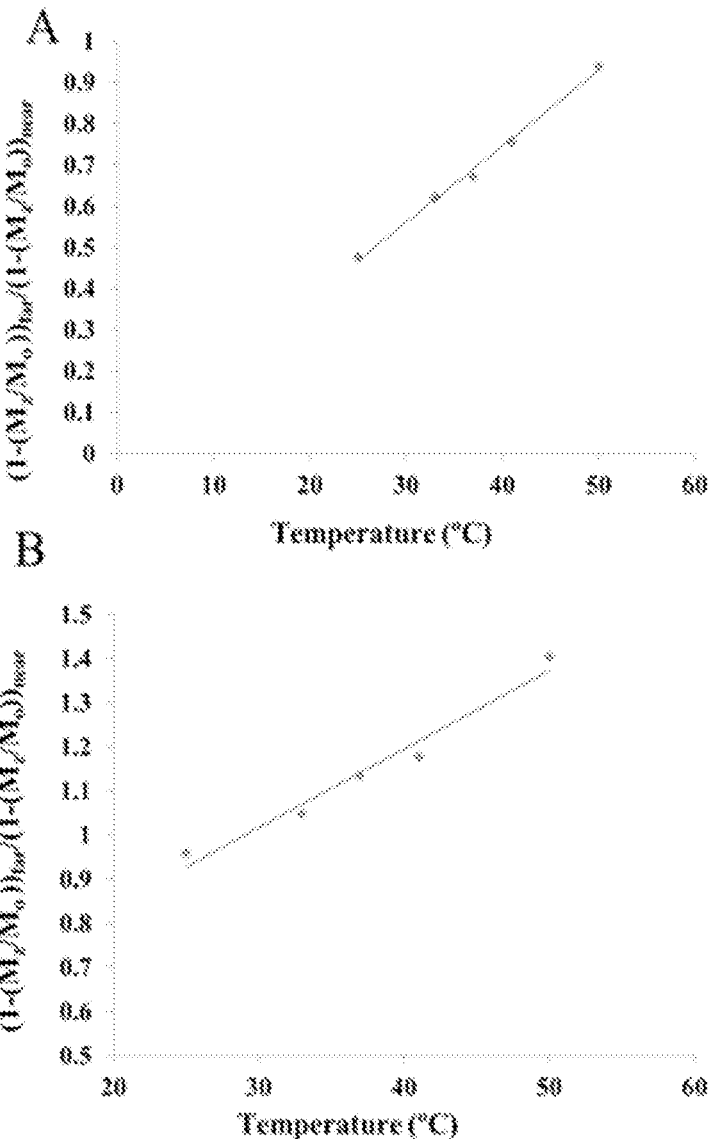
FIG. 33. The ratiometric plot of the (A) nearest CEST peaks (30-60 ppm) and (B) furthest shifted CEST peaks (90-120 ppm) of a solution containing 10 mM [Co(CCRM)]$^{2+}$, 20 mM HEPES, 100 mM NaCl, pH 7.4 at varying temperatures.
Figure 34:
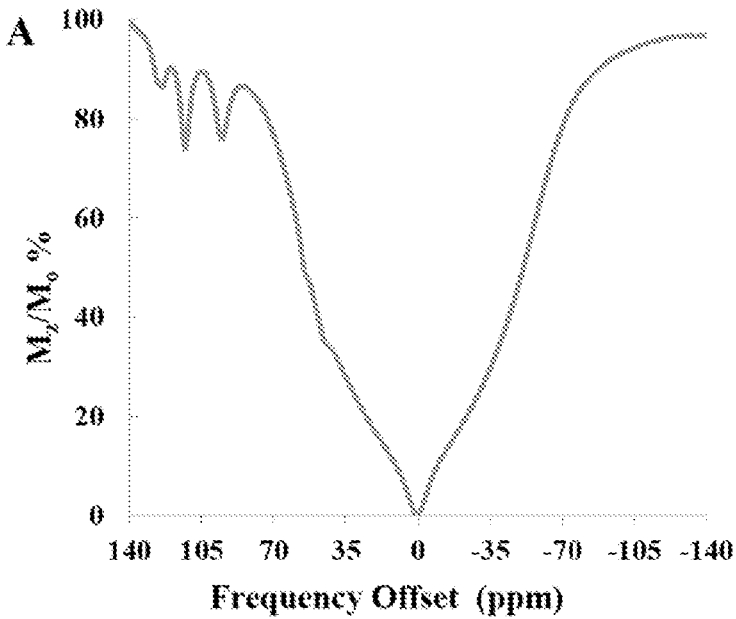
FIG. 34. CEST spectra recorded at 11.7 T of a solution containing (A) 10 mM [Co(CCRM)]$^{2+}$, 100 mM NaCl, 20 mM HEPES in 4% agarose gel (w/w) and (B) 10 mM [Co(CCRM)]$^{2+}$ in rabbit serum. RF presaturation pulse applied for 2 seconds B1=24 µT at 37° C.
Figure 34:
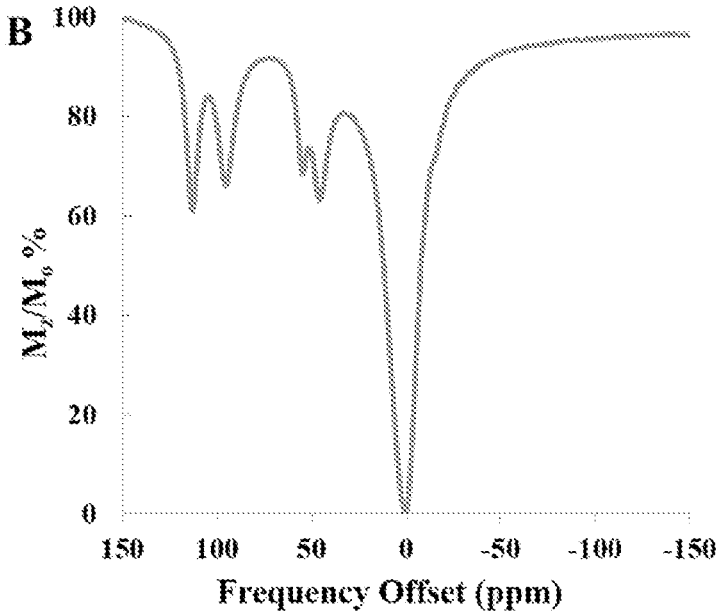

In FIG. 31 is shown phantom images of [Co(NOPE)]$^{2+}$ in buffered solution, serum and in agarose to demonstrate that CEST contrast is visualized even under physiologically relevant conditions. In FIG. 32 is shown the temperature dependence of the CEST peaks of [Co(CCRM)]$^{2+}$ and in FIG. 33 is shown a plot of these CEST peak intensity ratios. This shows how the complex might be useful to monitor the temperature of samples by MRI. Furthermore, FIG. 34 shows that [Co(CCRM)]$^{2+}$ gives a CEST spectrum even in agarose.

This example illustrates the first series of air stable CoCEST agents formed from azamacrocycles containing pendent amide groups. All complexes are moderately stable in the presence of biologically relevant anions, while TCMC and TCMT give the most stable Co$^{II}$ complexes under acidic conditions or with competing transition metal ions. The diverse coordination chemistry of Co$^{II}$ leads to the production of one, two or four CEST peaks with shifts ranging from −19 ppm to 112 ppm. Notably, the multiple CEST peaks produced by [Co(CCRM)]$^{2+}$ facilitate the development of ratiometric agents by using the distinct pH dependence of two different protons. This simplifies the synthesis of ratiometric paraCEST agents because it eliminates the need to add different pendent groups. These examples show that CoCEST agents are a valuable addition to the growing repertoire of paramagnetic divalent transition metal ion contrast agents.

Materials & Methods. Materials. All reagents were used without further purification. CoCl$_2$.6H$_2$O was purchased from Alfa Aesar. TACN was purchased from TCI America. Cyclen and Cyclam were purchased from Strem Chemicals.

Synthesis of Macrocycles.

Syntheses were similar to previously published procedure for the syntheses of ligands TCMT, TCMC, CCRM, and NOPE.

The procedure for the synthesis of the macrocyclic ligand 1,4,7,10-tetrakis(carbamoylmethyl)-1,4,7,10-tetraazacyclododecane (TCMC) follows. To a 100 mL round bottom flask fitted with a reflux condenser and stir bar was added 1.4696 g Cyclen (8.5 mmol). 5.4411 g of 2-bromoacetamide (39.4 mmol, 4.6 eq) was added with 4.5748 g triethylamine (44.9 mmol, 5.3 eq) in 30 mL absolute ethanol. The contents were refluxed for 4 hours at −80° C., after which time a white precipitate formed in the flask. After cooling to room temperature, the precipitate was decanted and placed in a 250 mL round bottom flask, then dissolved in 200 mL of hot 80% ethanol/20% water. The volume was reduced by approximately 30% on a roto-evaporator, then placed in the refrigerator overnight to produce white crystals. The remaining solvent was removed by filtration and the crystals were transferred to a 50 mL round bottom flask to dry on a Schlenk line under vacuum for several hours (66% yield). ESI-MS: m/z=401.3 (100%), 402.3 (15%) [M+H]+; 423.4 (25%), 424.4 (<10%) [M+Na]+. 1H NMR (500 MHz, D2O), ppm: 3.02 (s, amide pendent CH2 8H), 2.57 (s, Cyclen ring 16H). 13C NMR (125 MHz, D2O), ppm: 174.07 (carbonyl C), 55.86 (amide CH2), 50.42 (ring CH2).

The ligand 1,4,7-tris(carbamoylmethyl)-1,4,7-triazacyclononane (TCMT), was synthesized as follows. To a 25 mL round bottom flask was added 157.5 mg (1.219 mmol) TACN (1,4,7-triazacyclononane), 3.4 equivalents of 2-bromoacetamide (565.7 mg, 4.100 mmol), and 12 mL ethanol. 3.5 mL triethylamine was added dropwise over several minutes until the solution turned cloudy and persisted, then the mixture was refluxed for 3 hours. After cooling, the mixture was decanted to remove most of the liquid, then 20 mL of warm 80% ethanol/20% water was added to yield a slightly opaque white solution resembling nonfat milk. The volume was slightly reduced under vacuum on a Schlenk line, then placed in the freezer for 3 days to recrystallize. After allowing white crystals to form, the solvent was removed by decanting and further dried under vacuum on the Schlenk line (90% yield). ESI-MS: m/z=301.3 (100%), 302.3 (20%) [M+H]+; 323.3 (25%) [M+Na]+. 500 MHz $^1$H NMR spectrum, $D_2O$+DCl: ppm=3.96 (s, 6H, amide CH2); 3.44 (s, 12H, ring CH2). 75 MHz 13C NMR spectrum, $D_2O$: ppm=173.64 (amide CO), 56.75 (amide $CH_2$), 49.30 (ring $CH_2$).

The ligand 1,4,8,11-tetrakis(carbamoylmethyl)-1,4,8,11-tetraazacyclotetradecane (CCRM) was prepared according to a slightly modified literature procedure. In a typical preparation, 1,4,8,11-tetraazacyclotetradecane (Cyclam) (0.44 g, 2.20 mmol) was added to a round bottom flask. Water (4 mL) and 2 M NaOH (0.5 mL) were added to dissolve the Cyclam. 2-Bromoacetamide (1.39 g, 10.1 mmol) was added and additional 2 M NaOH was added to maintain pH 10-11. Upon reaction, the solution became opaque white. The solution was stirred for 15 minutes at 80° C., and then stirred for an additional 4 hours at room temperature. The precipitate was isolated by filtration and rinsed with 0.20 M NaOH, then rinsed with acetone. The precipitate was dried under vacuum. Yield: 76%. ESI-MS m/z: 215.3 (100%), 216.1 (<10%) [M/2]+; 429.4 (70%), 430.4 (10%) [M+H]+; 451.4 (100%), 452.4 (20%) [M+Na+]. $^1$H NMR (300 MHz, $D_2O$+DCl): 3.39 (s, 8H, pendent $CH_2$), 2.90 (s, 8H, ring $CH_2$[NCH2CH2N]), 2.82 (s, 8H, ring CH2 [NCH2CH2N]), 1.73 (t, 4H, ring CH2 [NCH2CH2N], J=7). $^{13}$C NMR (75 MHz, $D_2O$+DCl): 173.34, 55.22, 52.13, 51.35, 22.56.

The following procedure was used for the synthesis of 1,4,10-trioxa-7,13-diazacyclopentadecane-7,13-diacetamide (NOPE). The synthesis of NOPE is similar to a previously reported procedure with slight modifications. In a round bottom flask, 4,10-diaza-15-crown-5-ether (0.12 g, 0.56 mmol), 2-bromoacetamide (0.17 g, 1.23 mmol), and N-ethyldiisopropylamine (0.38 mL, 2.18 mmol) were heated to reflux in acetonitrile (2 mL) for 30 minutes. The solution was filtered and the white precipitate was dried under vacuum. Yield: 38%. ESI-MS m/z: 333.3 (M+H$^+$). $^1$H NMR (400 MHz, DMSO-$d_6$): δ=7.39 (s, 2H, NH), 7.04 (s, 2H, NH), 3.49 (s, 4H, ring $CH_2[OCH_2CH_2O]$), 3.45-3.40 (q, 8H, ring $CH_2[NCH_2CH_2O]$), 2.95 (s, 4H, pendent $CH_2$), 2.65-2.61 (m, 8H, ring $CH_2[NCH_2CH_2O]$). $^{13}$C NMR (75 MHz, DMSO-$d_6$): δ=173.79, 70.12, 69.09, 68.84, 59.65, 55.68.

Formation of the Co(II) Complexes.

In a typical preparation, the ligand was mixed with equimolar amounts of $CoCl_2.6H_2O$ in ethanol at room temperature and stirred for 1 hour. The complexes were isolated by precipitation and dried under vacuum to produce [Co(TCMT)]$Cl_2$, [Co(NOPE)]$Cl_2$, [Co(TCMC)]$Cl_2$, and [Co(CCRM)]$Cl_2$. [Co(TCMT)]$Cl_2$ was obtained as a pastel blue to periwinkle powder. Yield: 71% ESI-MS: m/z=179.8 (86%) [M/2]$^+$, 358.2 (100%) [M−H]$^+$, 394.0 (20%) [M+Cl]$^+$. [Co(NOPE)]$Cl_2$ was obtained as a light purple powder. Yield: 80% ESI-MS: m/z=195.8 (100%) [M/2]$^+$, 390.2 (57%) [M−H]$^+$, 426.0 (54%) [M+Cl]$^+$. [Co(TCMC)]$Cl_2$ was obtained as a pastel blue powder. Yield: 91% ESI-MS: m/z=229.8 (100%) [M/2]$^+$, 458.3 (72%) [M−H]$^+$. [Co(CCRM)]$Cl_2$ was obtained as a pale pink to lavender powder. Yield: 90% ESI-MS: m/z=243.8 (100%) [M/2]$^+$, 486.3 (56%) [M−H]$^+$.

Example 2

Additional example of Co(II) macrocyclic compounds having amide pendent groups as paraCEST MRI contrast agents.

Several additional complexes were synthesized and studied that have pendent groups which are not amides including: [Co(MPT)]$^{2+}$, [Co(BzCY)]$^{2+}$, [Co(STHP)]$^{2+}$, [Co(LOCO)]$^{2+}$, [Co(TACO)]$^{2+}$, [Co(APT)]$^{2+}$, [Co(AMPT)]$^{2+}$. Examples of proton NMR spectra are shown in FIGS. 21, 22, 13, 25. Examples of CEST spectra are show in FIGS. 18, 19, 20. FIGS. 26, 27, 28, 29, 30 are schematics that show the synthetic routes undertaken for these macrocycles.

Synthesis of Macrocycles.

Syntheses were similar to previously published procedure for the syntheses of ligands MPT, BzCY, TACO, STHP, and LOCO.

The procedure for the synthesis of (1S,4S,7S,10S)-1,4,7,10-tetrakis(2-hydroxypropyl)-1,4,7,10-tetraazacyclododecane (STHP) was as follows. To a 25 mL round bottom flask with gas inlet and stir bar was added 1.0053 g Cyclen (5.835 mmol) and 3.0837 g S-propylene oxide (53.094 mmol, 9.1 eq). The volume was reduced after stirring for three days under Ar at room temperature and crystals formed over time (days to weeks) of STHP. The contents were isolated and dried on a Schlenk line under vacuum to obtain white crystals (42% yield). ESI-MS: m/z=203.3 (35%) [M/2]+; 405.3 (100%), 406.3 (20%) [M+H]+; 427.4 (10%) [M+Na]+. $^1$H NMR, 500 MHz (CDCl3, ppm): 5.20 (s, 4H, OH); 3.94 (m, 4H, CH, J=4.0, 5.8, 6.0); 2.97 (m, 8H, pendent CH2, J=4.0, 8.5, 10.5); 2.40 (m, 4H, ring CH2, J=8.5, 10.0); 2.08 (m, 12H, ring CH2, J=8.0, 10.0, 12.5); 1.09 (d, 12H, CH3, J=6). 13C NMR, 75 MHz (CDCl3, ppm): 63.69 (CH), 62.75 (pendent CH2), 51.29 (ring CH2), 20.01 (CH3). A similar synthesis was used to obtain (1R,4R,7,10R)-1,4,7,10-tetrakis(2-hydroxypropyl)-1,4,7,10-tetraazacyclododecane (RTHP) by using R-propylene oxide instead of S-propylene oxide.

The macrocyclic ligand TACO was prepared by treatment of 1,4,7-triazacyclononane in 50% excess of S-propylene oxide in ethanol at room temperature for two days. The ethanol was removed in vacuo to yield a sticky white solid and the product was obtained as a colorless oil in quantitative yield. $^{13}$C NMR (CDCl$_3$) δ (ppm)=66.8, 63.2, 52.8, 20.1.

Preparation of 1,4,8,11-tetra(2-hydroxypropyl)-1,4,8,11-tetraazacyclotetradecane (LOCO) was carried out by treatment of Cyclam with 50% excess of S-propylene oxide and stirring the solution in ethanol for 20 hours. The solvent volume was reduced by rotary evaporation and the solution was cooled to induce crystallization. Clear colorless crystals formed and were washed with ice-cold water (2 mL) and dried under vacuum. Yield: 68%. $^{13}$C NMR spectrum ($D_2O$): δ=60.9, 53.1, 52.8, 51.3, 23.1, 22.9, ESI/MS: m/z=433.

BzCY was prepared from 1,4,8,11-Tetraazatricyclo [9.3.1.14,8]hexadecane. A solution of Cyclam in dichloromethane (1 g, 5 mmol in 100 ml) was added to an aqueous solution of sodium hydroxide (30 g in 100 ml). After refluxing the mixture for 36 hours, the two phases were separated and the aqueous phase extracted with dichloromethane. The organic phases were concentrated to give a yellowish product which was recrystallized from THF/water to give colourless crystals. The resulting 1,4,8,11-Tetraazatricyclo[9.3.1.14,8]hexadecane was stirred with 2.2 equivalents of 2-chloromethyl benzimidazole in acetonitrile for two weeks. The solid was isolated from solution by filtration and dissolved in 3M NaOH. This solution was extracted with chloroform and the solvent was evaporated to give a white solid. ESI-MS=461.4 (M+H)$^+$, 483.4 (M+Na)$^+$.

The procedure for the synthesis of 6-(bromomethyl)-2-methyl-3-nitropyridine follows. 3-Nitro-2,6-lutidine (2.50 g, 16.5 mmol, 1 equiv.) was dissolved in 200 mL of argon-purged carbon tetrachloride. The reaction mixture was heated to 50° C. under argon. AIBN (0.14 g, 0.83 mmol, 5 mol %) was added to the reaction mixture in one portion under constant stirring, followed by the addition of NBS (2.93 g, 16.5 mmol, 1 equiv.) in small portions over a period of 2 hours. The reaction mixture was further refluxed for 8 hours at constant stirring and under light irradiation. Once the reaction was complete, solvent was removed in vacuo producing a brownish residue. This residue was suspended in a mixture of methanol-dichloromethane, in which non-dissolved solids were removed by filtering through a $SiO_2$ plug (ca. 120 mL) using an eluent of methanol-dichloromethane (1:20 v/v). Fractions containing ii were combined and solvent was removed in vacuo. The resultant oil was subject to $SiO_2$ column chromatography using a mixture of ethyl acetate (gradient from 2% to 10%) in hexanes as an eluent. Fractions containing product were concentrated in vacuo producing analytically pure ii. Yield: 0.41 g, 1.78 mmol, 11%. $^1$H NMR, 500 MHz ($CDCl_3$, ppm): δ=8.26 d (1H, Ar, J=9 Hz), 7.47 d (1H, Ar, J=9 Hz), 4.52 s (2H, $CH_2$), 2.83 s (3H, $CH_3$). $^{13}$C NMR, 75 MHz ($CDCl_3$, ppm): δ=160.46, 153.73, 144.66, 133.66, 121.61, 32.07, 23.84. ESI-MS (m/z): $[M+H]^+$, calculated: 231.0. found: 231.0.

The procedure for the synthesis of 1,4,7-tris[(6-methyl-5-nitro-2-pyridyl)methyl]-1,4,7-triazacyclononane follows. 1,4,7-Triazacyclononane (41 mg, 0.32 mmol, 1 equiv.) and 6-(bromomethyl)-2-methyl-3-nitropyridine (258 mg, 1.12 mmol, 3.5 equiv.) were dissolved in 8 mL of dry acetonitrile followed by addition of triethylamine (180 μL, 1.29 mmol, 4 equiv.). The reaction mixture was stirred at 50° C. for 24 hours under argon. Upon completion of the reaction, solvent was removed in vacuo producing a brown oily residue. The crude product was purified by reversed-phase HPLC using a gradient of solvent B from 30% to 70% in solvent A over 40 minutes. ESI-MS analyses of fractions with retention time $t_R$=21 minute confirmed product iv. These fractions were combined and solvent was removed by lyophilization producing iv in the form of TFA salt. Yield: 80 mg, 63 μmol, 20%. $^1$H NMR, 500 MHz ($CD_3OD$, ppm): δ=8.35 d (3H, Ar, J=9 Hz), 7.55 d (3H, Ar, J=9 Hz), 4.32 s (6H, $3CH_2$), 3.23 m (12H, $6CH_2$), 2.78 s (9H, $3CH_3$). $^{13}$C NMR, 75 MHz ($CD_3OD$, ppm): δ=160.60, 154.51, 146.59, 134.91, 123.40, 60.07, 50.74, 23.92. High-resolution ESI-MS (m/z): $[M+H]^+$, calculated: 580.2627. found: 580.2691.

The procedure for the synthesis of 1,4,7-tris[(5-amino-6-methyl-2-pyridyl)methyl]-1,4,7-triazacyclononane (AMPT) follows. The TFA salt of 1,4,7-tris[(6-methyl-5-nitro-2-pyridyl)methyl]-1,4,7-triazacyclononane (80 mg, 63 μmol) was dissolved in 40 mL of methanol containing 21 mg (11 mol %) of 10% Pd/C. Reduction of nitro groups was carried out in a Parr hydrogenation apparatus for 8 hours using hydrogen gas. Once reduction was complete, the reaction mixture was filtered through Celite. The solvent was removed in vacuo producing yellow oil. The crude product was HPLC-purified using a gradient of solvent B (5% to 35%) in solvent A over 30 minutes. ESI-MS analyses of fractions with retention time $t_R$=11 minute confirmed product AMPT. These fractions were combined and solvent was removed by lyophilization producing AMPT in the form of TFA salt. The product was further desalted by passing through 2 mL of Dowex® 1×2-100 strongly basic anion exchange resin. The resulting aqueous solution was concentrated in vacuo producing AMPT. Yield: 12.6 mg, 26 μmol, 41%. $^1$H NMR, 500 MHz ($D_2O$, pH 7.0, ppm): δ=7.10 d (3H, Ar, J=9 Hz), 6.77 d (3H, Ar, J=8 Hz), 3.77 s (6H, $3CH_2$), 2.75-2.95 m (12H, $6CH_2$), 2.35 s (9H, $3CH_3$). High-resolution ESI-MS (m/z): $[M+H]^+$, calculated: 490.3374. found: 490.3385.

The procedure for the synthesis of 1,4,7-tris[(6-methyl-2-pyridyl)methyl]-1,4,7-triazacyclononane (MPT) was as follows. 1,4,7-Triazacyclononane (0.3 g, 2.3 mmol, 1 equiv.) and 2-(bromomethyl)-6-methyl-pyridine (1.3 g, 7.0 mmol, 3 equiv.) were dissolved in 18 mL of methanol followed by addition of triethylamine (1.2 mL, 8.6 mmol, 3.7 equiv.) (FIG. 28). The reaction mixture was refluxed under argon for 1 hour. After cooling to room temperature, the volume of methanol was reduced in vacuo, and diethyl ether was added to the reaction mixture until the formation of white precipitate was completed. The mixture was filtered, and the filtrate was concentrated under reduced pressure, producing a brown oil. The crude product was purified by reversed-phase HPLC using a gradient of solvent B (0.1% trifluoroacetic acid in methanol) from 10% to 40% in solvent A (0.1% trifluoroacetic acid in water) over 30 minutes. These fractions were combined and solvent was removed by lyophilization producing MPT in the form of TFA salt. Yield: 0.54 g, 0.5 mmol, 21%. $^1$H NMR, 500 MHz ($CD_3OD$, ppm): δ=8.19 t (3H, Ar), 7.80 d (3H, Ar), 7.67 d (3H, Ar), 4.40 s (6H, $3CH_2$), 3.17 m (12H, $6CH_2$), 2.76 s (9H, $3CH_3$). $^{13}$C NMR, 75 MHz ($CD_3OD$, ppm): δ=156.11, 151.21, 143.44, 125.80, 123.28, 55.99, 48.72, 19.92. ESI-MS (m/z): $[M+H]^+$, calculated: 445.3. found: 445.2.

Formation of Complexes.

In a typical preparation, the ligand was mixed with equimolar amounts of $CoCl_2.6H_2O$ in ethanol at room temperature and stirred for 1 hour. The complexes were isolated by precipitation and dried under vacuum. In a typical preparation, $[Co(BzCY)]Cl_2$ was isolated as a deep blue powder, ESI-MS: m/z=259.9 (100%) $[M/2]^+$, 518.4 (56%) $[M-H]^+$. In a representative procedure, AMPT or MPT (0.15 mmol) were placed in the tube with 1.1 mL of acetonitrile. After purging the solvent with argon, $CoCl_2$ $(H_2O)_6$ (0.15 mmol) was added. The reaction mixture was sonicated for 20 minutes and then stirred under argon at room temperature After 8 hours the reaction mixture was centrifuged, and the supernatant solution was decanted affording $[Co(AMPT)]Cl_2$, or $[Co(MPT)]Cl_2$.

Instrumentation.

Varian Inova 400 MHz and Inova 500 MHz NMR spectrometers were used to collect 1H NMR spectra. The measurements of magnetic susceptibility and CEST data were acquired on a Varian Inova 500 MHz spectrometer. ThermoFinnigan LCQ Advantage IonTrap LC/MS equipped with a Surveyor HPLC system was used to collect mass spectral data. $Cu^{II}$ displacement assay absorbance measurements were recorded every 60 seconds with a Beckman-Coulter DU 800 UV-vis spectrophotometer connected to a Peltier Temperature Controller. A Thermo Scientific Orion 9826BN NMR micro pH electrode connected to a SympHony SB20 pH meter was used to obtain pH measurements.

Determination of Magnetic Moment.

The effective magnetic moment ($\mu_{eff}$) was calculated by using a previously known method. 5 mM $Co^{II}$ complex and 5% t-butanol by volume was placed in a NMR insert while the outer NMR tube contained 5% by volume t-butanol in $D_2O$. The $\mu_{eff}$ was calculated at 298 K (T) and monitored over a period of 72 hours using the following approach.

The mass susceptibility of solute ($\chi_g$) was calculated by obtaining the observed frequency shift of the reference (Δf) in Hz, the spectrometer frequency (f) in Hz, the mass of the substance per $cm^3$ of solution (m), and the mass susceptibility of solvent $D_2O$ ($\chi_0$=−0.6466×$10^{-6}$ $cm^3$/g). The last term is neglected due to the minimal contribution to mass susceptibility of solute. The molar susceptibility ($\chi_m$) is the product of $\chi_g$ multiplied by the molecular weight of the $Co^{II}$ complex.

Monitoring Dissociation of Complex Over Time.

Dissociation of the $Co^{II}$ complexes was monitored via $^1H$ NMR spectroscopy of samples incubated at 37° C. over a period of 12 hours. To monitor acid dissociation, samples contained 10 mM $Co^{II}$ complex, 100 mM NaCl, and 3-5 mM 3-(trimethylsilyl)-1-propanesulfonic acid sodium salt as a standard at pD 3.5-3.9. To assess the complexes in the presence of biologically relevant anions, solutions contained 10 mM $Co^{II}$ complex, 100 mM NaCl, 0.40 mM $Na_2HPO_4$, 25 mM $K_2CO_3$, and 5 mM 3-(trimethylsilyl)-1-propanesulfonic acid sodium salt as a standard. Generally, 1024 transients were collected for each spectrum.

Displacement by $Cu^{II}$.

The displacement of $Co^{II}$ from the complex by $Cu^{II}$ was monitored over a period of 3 hours at 37° C. by UV-vis. Samples contained 200 μM $Co^{II}$ complex, 10 mM MES buffer pH 5.5 and 1, 4, or 10 equivalents of $CuCl_2$. The formation of the $Cu^{II}$ complexes was monitored at 264 nm, 286 nm, 312 nm and 310 nm for $[Cu(TCMT)]^{2+}$, $[Cu(NOPE)]^{2+}$, $[Cu(TCMC)]^{2+}$, and $[Cu(CCRM)]^{2+}$, respectively. A previously reported procedure was followed.

CEST Spectroscopy.

CEST data were acquired with a presaturation pulse power ($B_1$) of 1000 Hz (24 μT) applied for 2 seconds at 37° C. Data were acquired in 0.5 or 1 ppm increments and plotted as normalized water signal intensity ($M_z/M_o\%$) against frequency offset (ppm) to produce a CEST spectrum. Samples contained 10 mM $Co^{II}$ complex, 20 mM buffer, and 100 mM NaCl in a NMR insert. To lock the sample, $d_6$-DMSO was placed in the outer NMR tube.

Determination of Exchange Rate Constants.

Exchange rate constants were calculated following a previously reported procedure. Measurements of on-resonance ($M_z$) and off-resonance ($M_o$) were acquired at different presaturation pulse powers between 350-1000 Hz (8-24 μT) applied for 4 seconds at 37° C. The exchange rate constant ($k_{ex}$) is calculated from the x-intercept from the plot of $M_z/(M_o-M_z)$ against $1/\omega_1^2$ ($\omega_1$ in rad/s). The rate constant, $k_{ex}$, is converted into units of $s^{-1}$. Samples contained 10 mM $Co^{II}$ complex, 20 mM HEPES pH 7.4, and 100 mM NaCl.

CEST Imaging.

CEST MR images were acquired at 4.7 Tesla preclinical MR scanner using a 35 mm transceiver coil (ParaVision 3.0.2, Bruker Biospin, Billerica, Mass.) as detailed elsewhere. Two spoiled gradient-echo images (TE/TR=2.1/5010 ms, flip angle=90 deg) were acquired at 37° C. after employing a pulse train comprised of five Gauss pulses (12ρT for 1 second each, interpulse delay of 200 μs) applied symmetrically about the bulk water resonance.

Image processing was carried out using in-house software algorithms developed in MATLAB (MathWorks, Natick, Mass.). Each image was normalized to the mean intensity of the buffer/salt phantom, and the mean signal intensity of each compound was sampled. The percent change in signal, or CEST effect (CE), was calculated as: CE=$(1-SI_{on}/SI_{off})$ *100%, where $SI_{on}$ and $SI_{off}$ represent the mean signal intensity of each sample with the pre-saturation pulse applied on- and off-resonance of the exchangeable protons, respectively. CEST images (FIGS. 14, 15) were calculated by determining CE on a pixel-by-pixel basis in MATLAB. To improve visualization of the CEST effect, images were filtered with a spatial averaging filter (kernel size=5×5), background noise was removed using a binary mask of the samples, and a 'hotiron' color lookup table was applied. For determining the ratio of CEST effect at 112 ppm vs. 95 ppm, CEST images were acquired with an identical saturation pulse train as above but image encoding was carried out using an FID-FISP acquisition to reduce acquisition times. Imaging parameters for the FID-FISP acquisition include: matrix=128×128, field of view=3.2×3.2 cm, TE/TR=1.5/3.0 ms, flip angle=90, number of repetitions=20. Processing was carried out as above with the exception that the 20 repetition image datasets were averaged together prior to normalization by the buffer signal intensity. The experiment was repeated with three separate preparations of $[Co(CCRM)]^{2+}$.

$T_1/T_2$ Relaxivity.

Using serial dilutions, $T_1/T_2$ relaxivity values were determined at 4.7 T, 37° C. as previously described. $T_1$ relaxation rates were measured using an inversion-recovery TrueFISP acquisition, while $T_2$ relaxation rates were measured using a multi-echo, Carr-Purcell-Meiboom-Gill spin-echo sequence with a fixed TR of 3000 ms and TE times ranging from 20-1200 ms. Non-linear regression analysis in MATLAB was used to calculate the $T_1$ and $T_2$ relaxation rates and relaxivities were then determined by linear regression fitting of the concentration vs. $T_1/T_2$ rate in Microsoft Excel.

Example 3

Example of Co(II) and Fe(II) macrocyclic compounds having pyrazole pendant groups as CEST and paraCEST MRI contrast agents for measuring redox state and hypoxic conditions ($[Co(TPT)]^{2+}$ and $[Co(TPT)]^{3+}$ or ($[Fe(TPT)]^{2+}$ and $[Fe(TPT)]^{3+}$.

In this example, presented are redox active MRI contrast agents with a metal ion center that switches between paramagnetic and diamagnetic states. Our metal ion complex produces contrast by chemical exchange saturation transfer (CEST) of a paramagnetically shifted proton as a PARACEST agent. Specifically, these Co-based complexes involve macrocycles with pyrazole pendant groups. Saturation of the magnetization of the ex-changeable proton of the contrast agent followed by exchange to bulk water leads to a reduction in water signal. It was shown that Co(II), a desirable metal ion shift agents for paramagnetic NMR spectroscopy, forms a PARACEST MRI contrast or CoCEST agent. The exchangeable pyrazole NH protons of $[Co(TPT)]^{2+}$ give narrow highly shifted resonances that are suitable for PARACEST contrast whereas Co(III) is diamagnetic and silent as a contrast agent. The complexes cycle between Co(II) and Co(III) (FIG. 73) based on the concentration of biologically relevant reductant as well as oxygen pressure.

Figure 35:
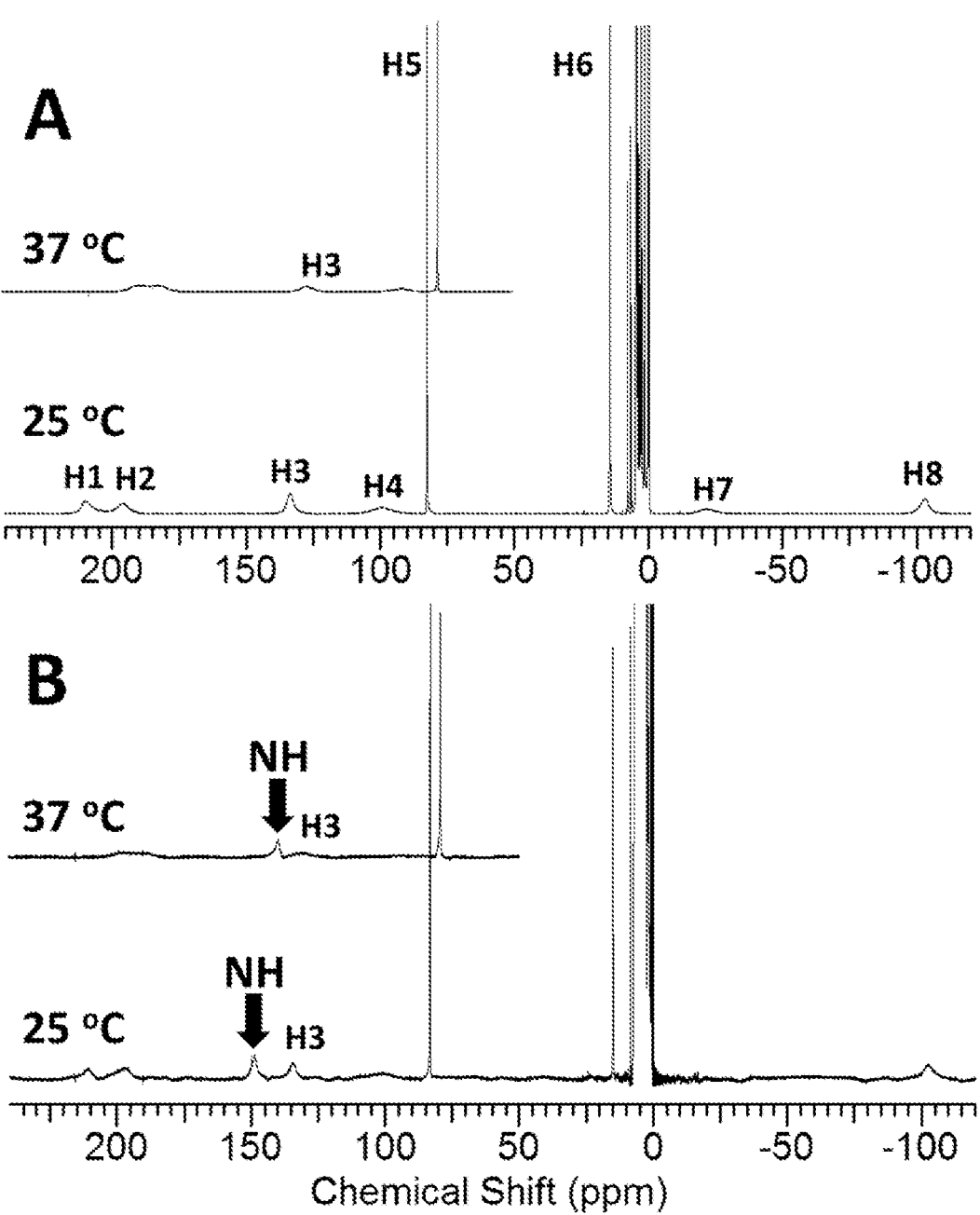
FIG. 35. $^1$H NMR spectra of [Co(TPT)]Cl$_2$ in $D_2O$, 100 mM NaCl, pD 5.2 (A) and in $H_2O$, 100 mM NaCl, pH 5.0 (B) at 25° C. Inserts show regions of the spectra (50-240 ppm) obtained at 37° C. Proton resonances H5 and H6 are tentatively assigned to aromatic CH protons of pyrazole, while signal from the exchangeable protons at 149 ppm, 25° C. (140 ppm, 37° C.) is tentatively assigned to NH protons of pyrazole ring. Diamagnetic region consists of resonances arising from the complex in Co(III) state.
Figure 36:
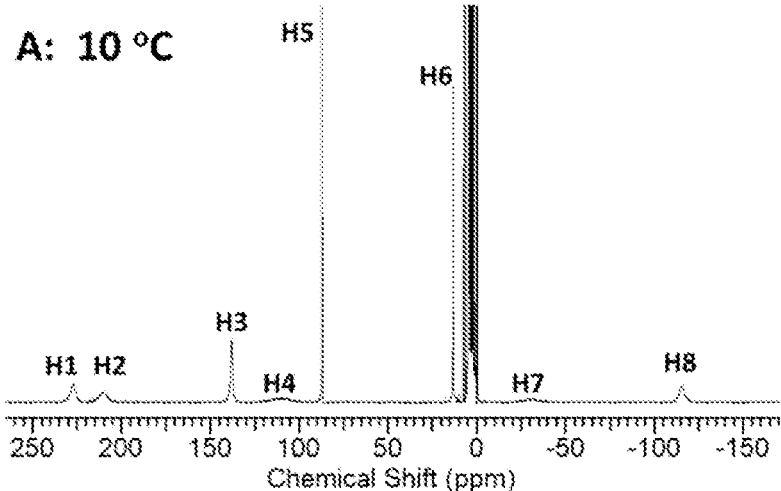
FIG. 36. Temperature dependence (10° C.-55° C.) of $^1$H NMR spectra of [Co(TPT)]Cl$_2$ in $D_2O$, pD 7.30, 100 mM NaCl. At lower temperatures of 10-37° C., eight resonances of non-exchangeable protons H1-H8 are distinguished, as labeled in spectrum A (10° C.). Resonances in the diamagnetic region arise from the Co(III) complex.
Figure 36:
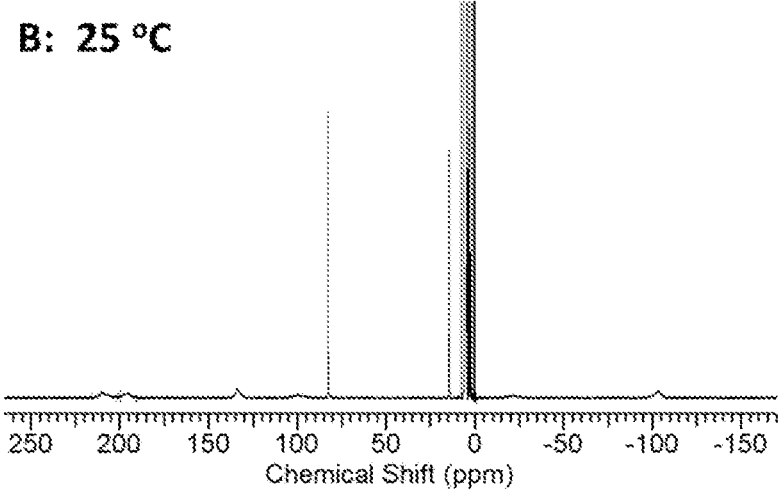
Figure 36:
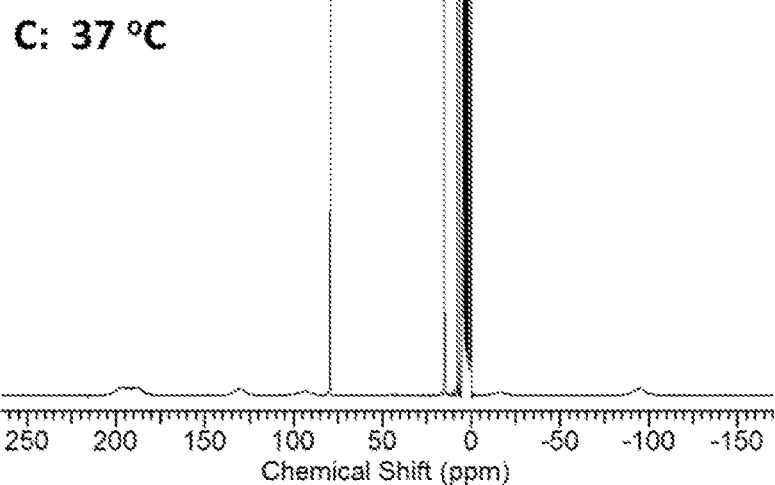
Figure 36:
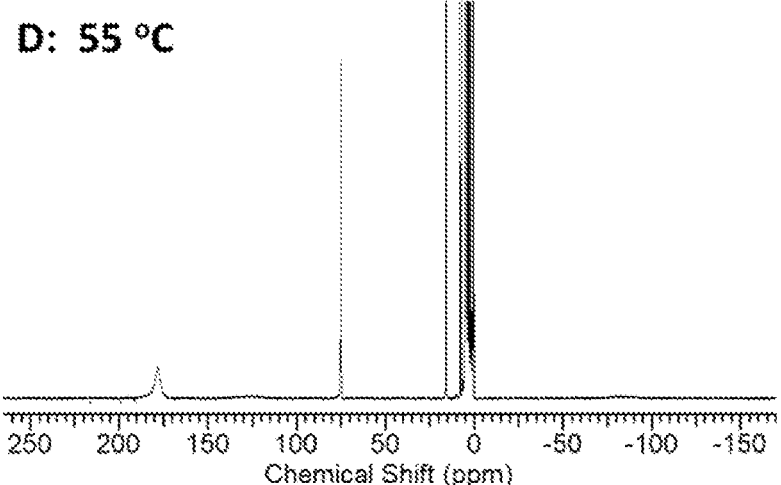
Figure 37:
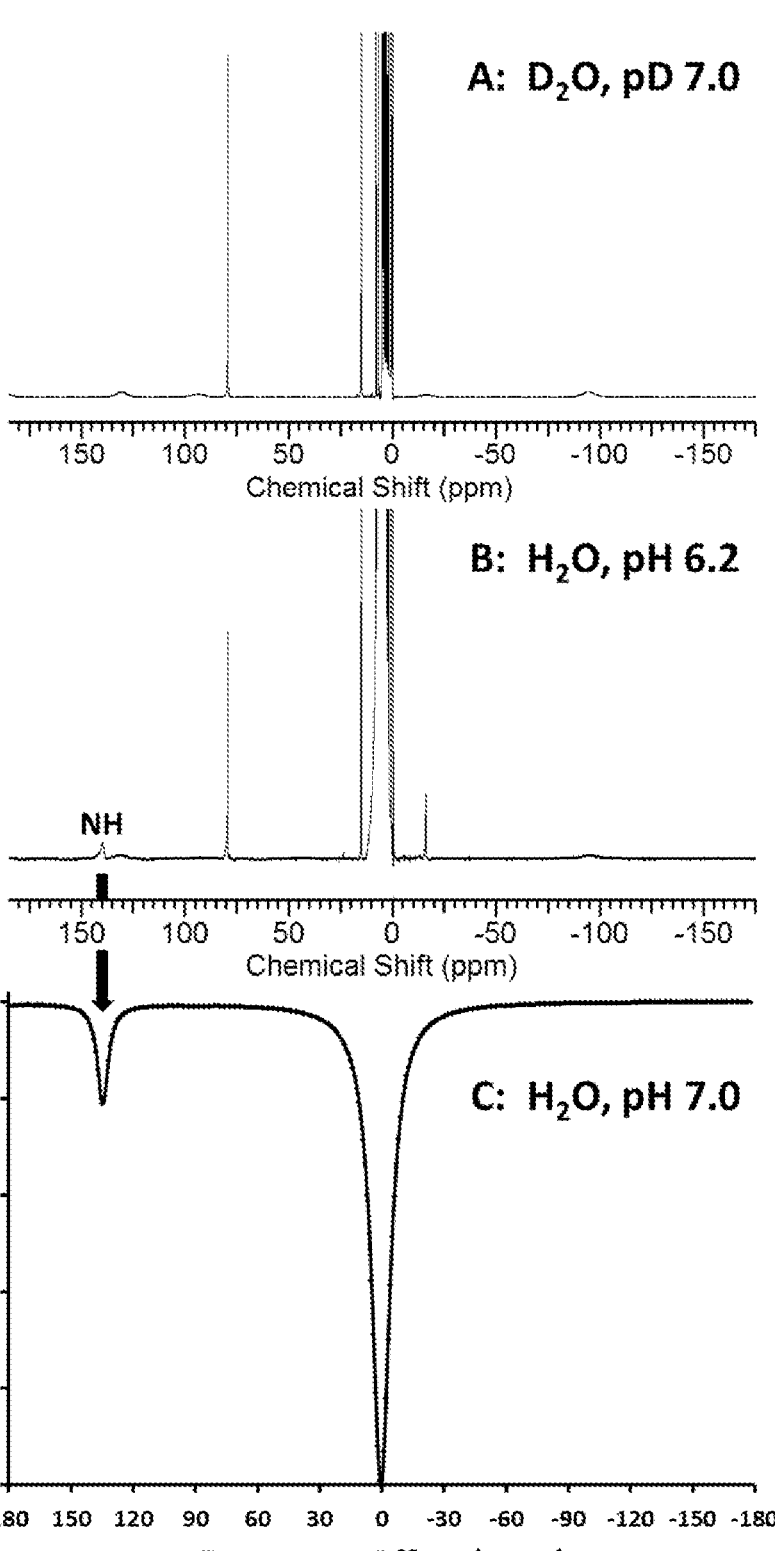
FIG. 37. $^1$H NMR spectra at 37° C. of [Co(TPT)]Cl$_2$ in $D_2O$, 100 mM NaCl, pD 7.0 (A) and in $H_2O$, 100 mM NaCl, pH 6.2 (B) in comparison to CEST spectrum (3 s, $B_1$=24 µT) of 8 mM [Co(TPT)]Cl$_2$ in aqueous solution of 100 mM NaCl, 20 mM HEPES, pH 7.0 at 37° C. (C). Arrow shows that chemical shift of the exchangeable proton resonance corresponds to that of the CEST peak. Note that in the CEST spectrum, the water peak is set to 0 ppm. Exchangeable protons are tentatively assigned to NH of pyrazole rings.
Figure 38:
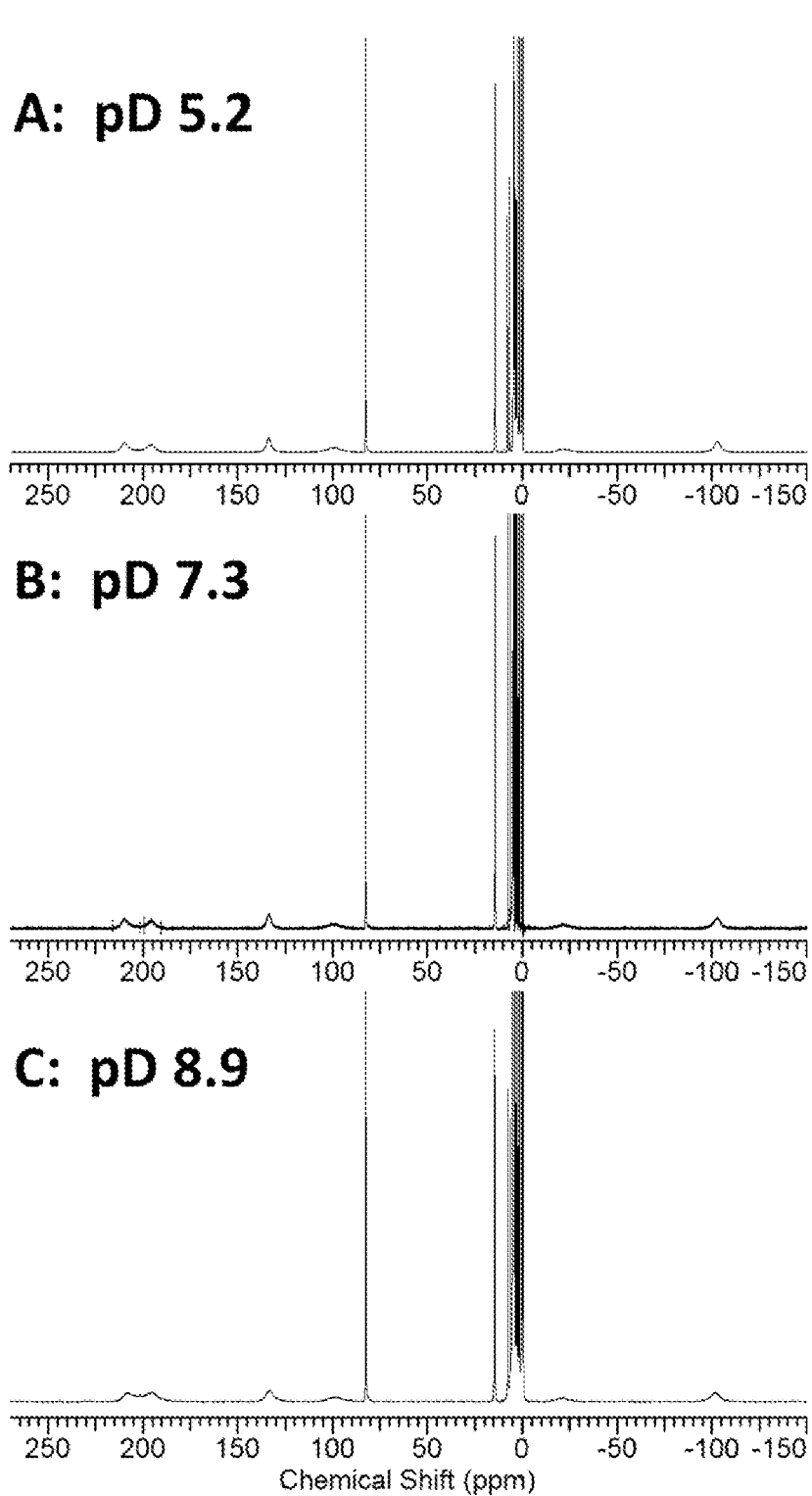
FIG. 38. pH (pD) dependence of $^1$H NMR spectra of [Co(TPT)]Cl$_2$ at 25° C. in $D_2O$ containing 100 mM NaCl at pD 5.2 (A), pD 7.3 (B), and pD 8.9 (C). Resonances in the diamagnetic region arise from the complex in the Co(III) state.

The 1,4,7-tris(pyrazol-3-ylmethyl)-1,4,7-triazacyclonone (TPT) complex of $Co^{2+}$ was chosen for study as a PARACEST agent in order to capitalize on the stability and kinetic inertness of a macrocyclic complex. The six nitrogen donors of TPT essentially encapsulate the $Co^{2+}$ ion, based on comparison to analogous complexes. The pyrazole pendent group has protons that are in chemical exchange with water protons and the high symmetry of the complex ensures that all three exchangeable proton resonances fall at a single frequency. The NH protons of the pyrazole group are a new addition to the repertoire of pendent groups with ex-changeable protons for PARACEST agents based on transition metal ions. The air sensitive nature of the Co(II) complex necessitates manipulation under inert atmosphere. The blue complex has an effective magnetic moment of 5.7±0.2 BM in aqueous solution, characteristic of high spin octahedral Co(II). The proton NMR spectrum of $[Co(TPT)]^{2+}$ in $D_2O$ has eight highly dispersed proton resonances, consistent with a C3 symmetric complex with one diastereomeric form at 25° C. (FIG. 35). The proton reso-nances of the pyrazole ring at 14.4 and 82.6 ppm (25° C.) are sharp with FWHM of 54 Hz and 45 Hz, respectively, while the remaining macrocycle proton resonances are relatively broad and range from 820 Hz up to >2000 Hz. Variable temperature $^1$H NMR studies from 10 to 55° C. show further broadening of the macrocycle proton resonances, consistent with a dynamic process (FIG. 36). $^1$H NMR spectra collected in H$_2$O at pH 5.0 show the presence of an additional peak at 149 ppm which is not present in D$_2$O at 25° C. This resonance shifts to 140 ppm at 37° C. due to the strong temperature dependence of the hyperfine shift (FIG. 35 & FIG. 36). Notably, as described below, the CEST peak position matches the chemical shift of the exchangeable protons, and shows the same temperature dependence. Thus, this resonance at 140 ppm (37° C.) is tentatively assigned as the pyrazole protons of [Co(TPT)]$^{2+}$ (FIG. 37). In contrast to temperature, pH does not have any detectible effect on the proton chemical shifts of [Co(TPT)]$^{2+}$ in the pD 5.2-8.9 range (FIG. 38). This suggests that there is a single Co(II) complex species with a single protonation state over this pH range.

Figure 39:
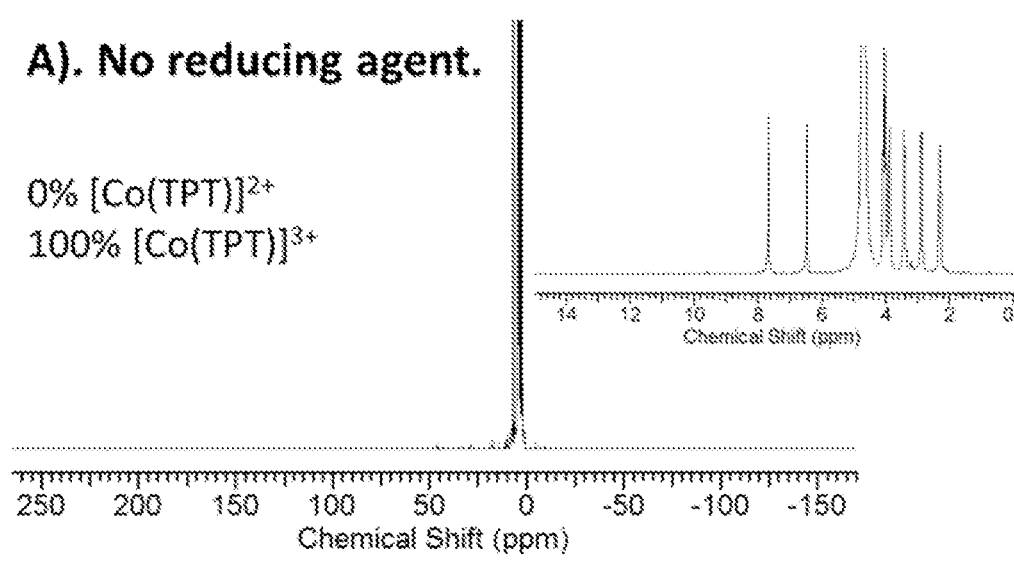
FIG. 39. Reduction of 30 mM [Co(TPT)]$^{3+}$ in $D_2O$ (pD 7.10, 100 mM NaCl) with 0.25, 0.5, and 0.75 equiv. of $Na_2S_2O_4$. Near complete reduction to [Co(TPT)]$^{2+}$ is observed at 0.75 equiv. of $Na_2S_2O_4$. Insert shows diamagnetic region together with paramagnetic peak at δ=14.5 ppm. Intensity of the resonance at 14.5 ppm increases with addition of $Na_2S_2O_4$, while diamagnetic signals disappear.
Figure 39:
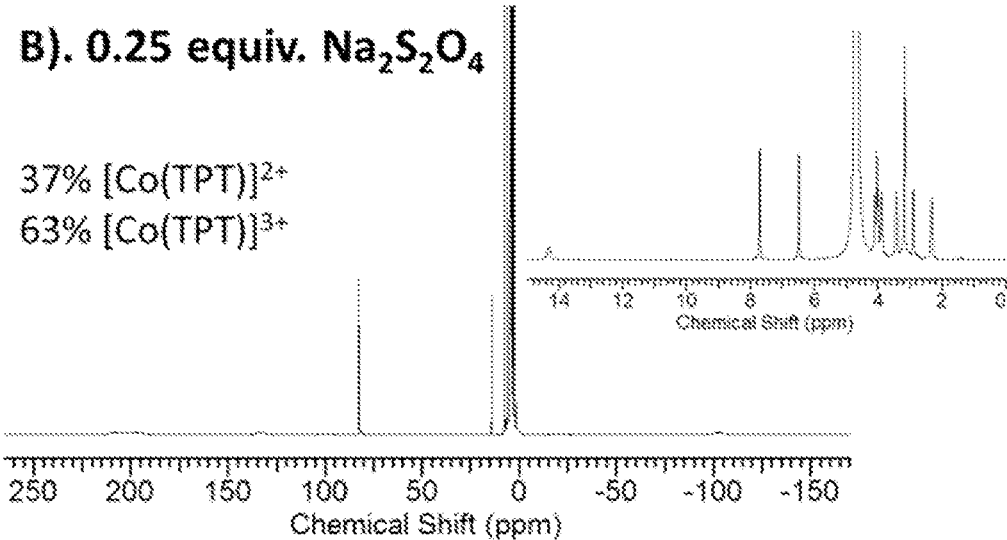
Figure 39:
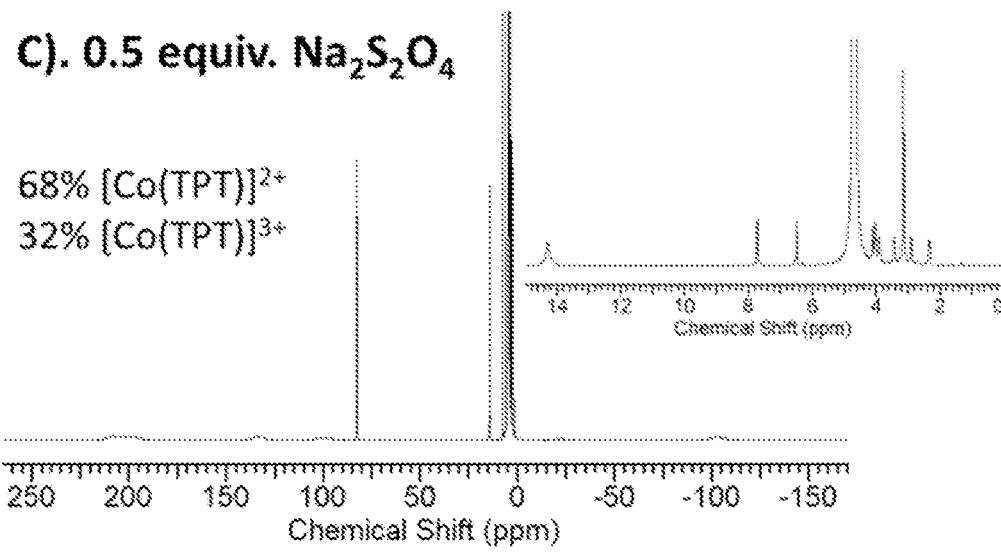
Figure 39:
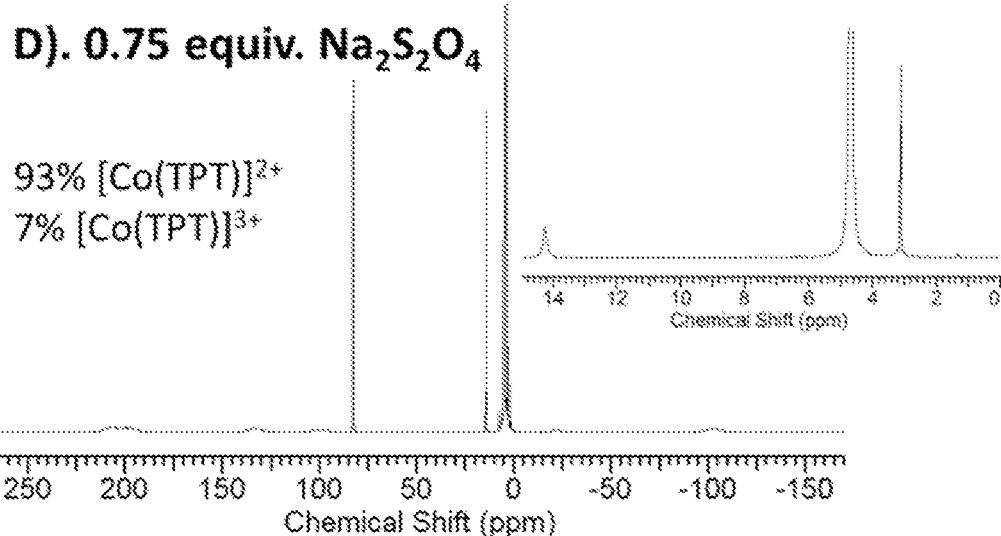
Figure 48:
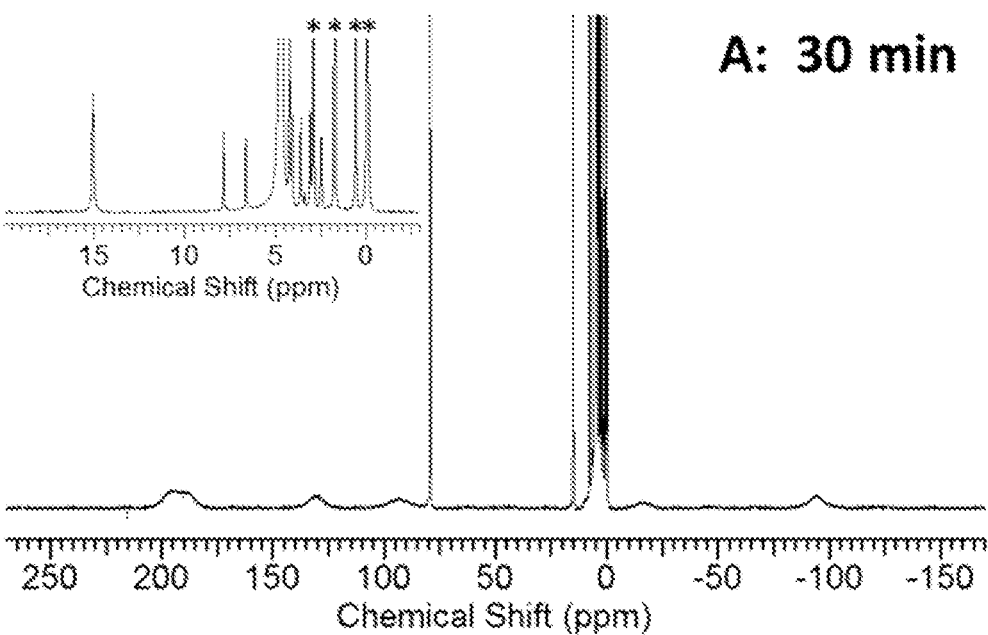
FIG. 48. $^1$H NMR spectra of 8 mM [Co(TPT)]Cl$_2$ incubated at 37° C. in D$_2$O solution containing 0.4 mM K$_3$PO$_4$, 25 mM K$_2$CO$_3$, and 100 mM NaCl, pD 7.5, for 0.5, 12, 18, and 24 hours. Insert shows diamagnetic region with one paramagnetically shifted peak at δ=15 ppm and peaks from the Co(III) complex. Asterisks represent signals from 10 mM TMSP standard.
Figure 48:
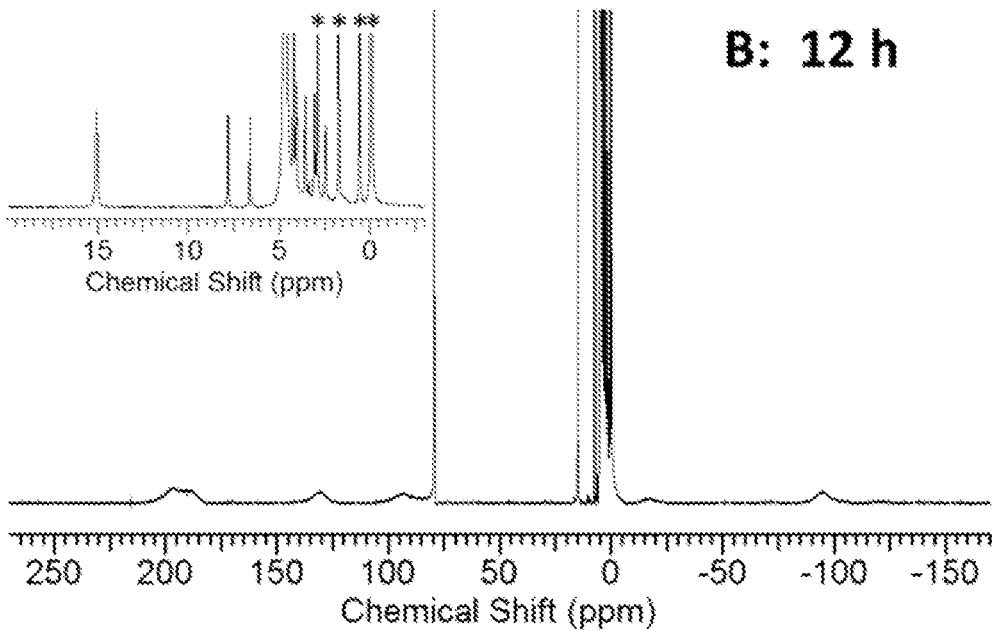
Figure 48:
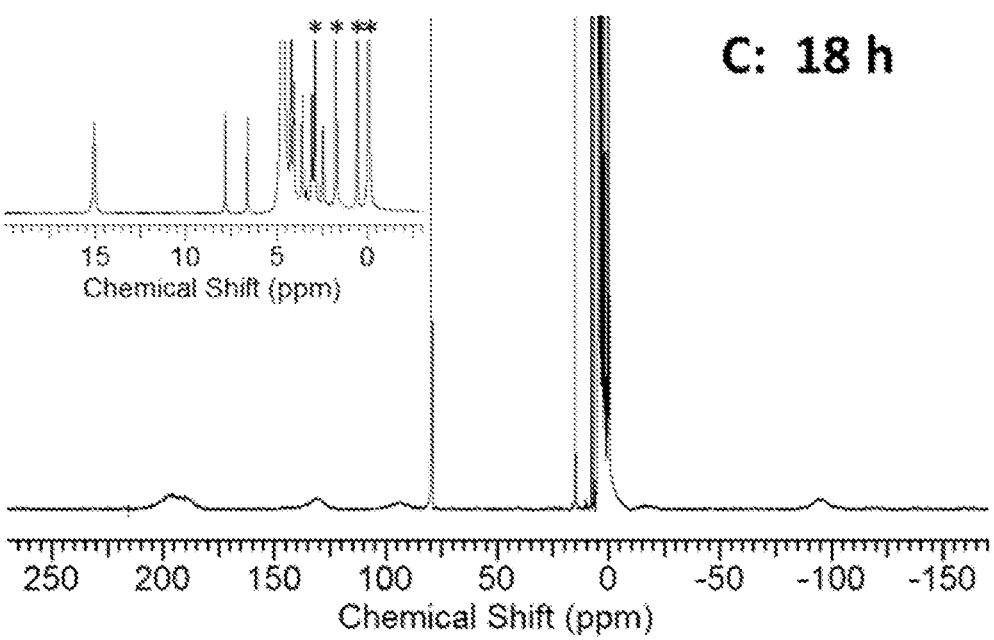
Figure 48:
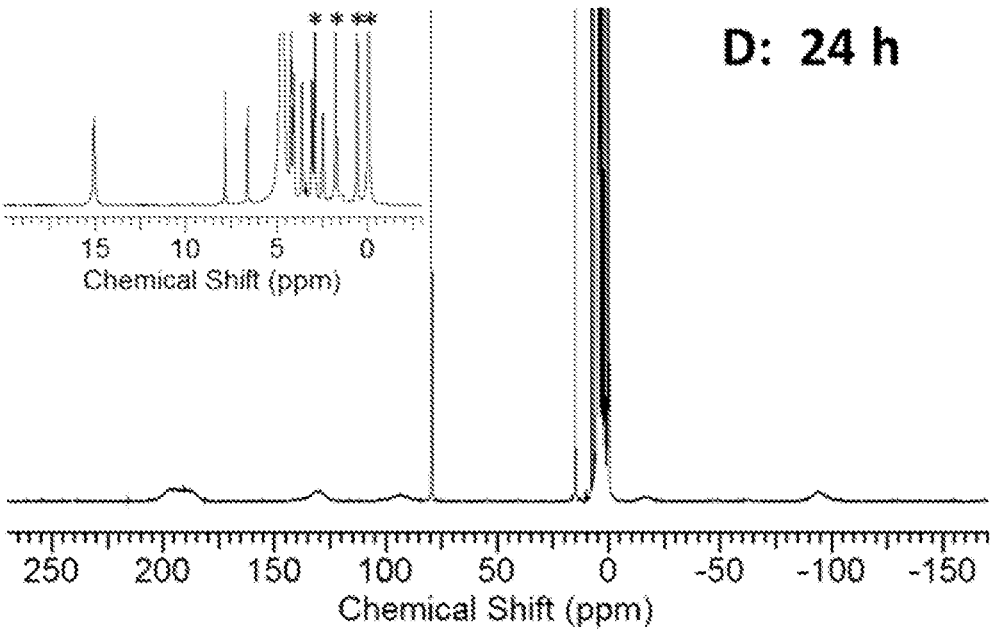
Figure 55:
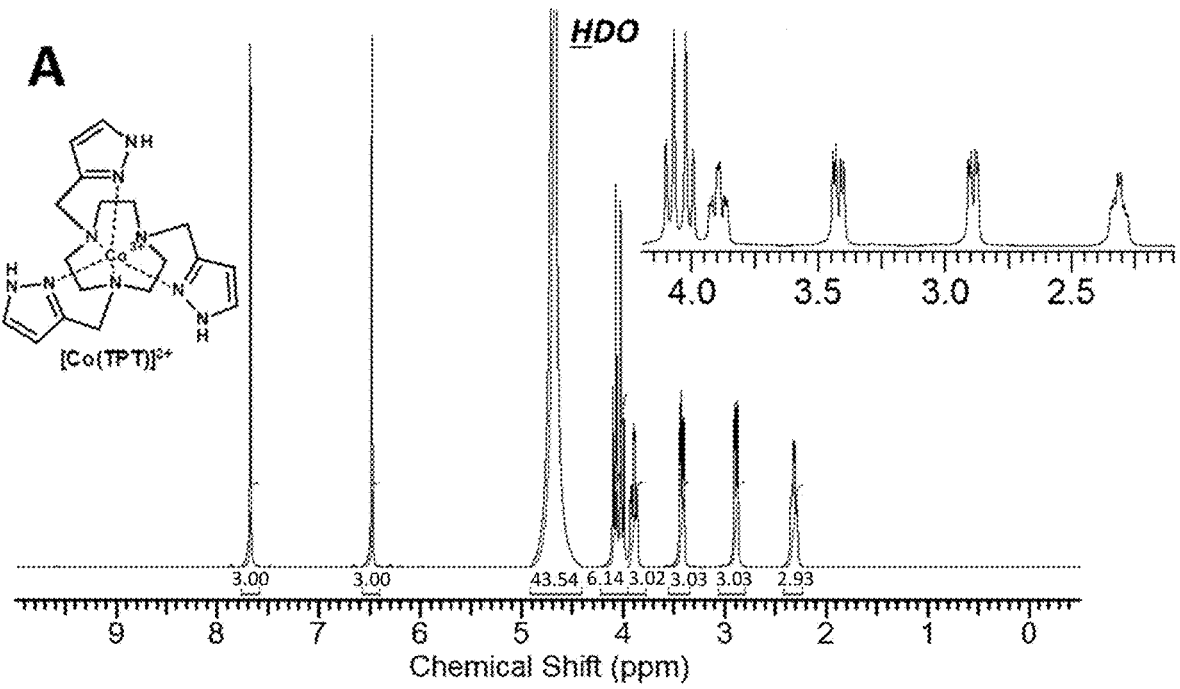
FIG. 55. $^1$H NMR (A) and $^{13}$C NMR (B) spectra of [Co(TPT)]$^{3+}$ in D$_2$O, pD 7.0. Methanol was used for $^{13}$C NMR reference.
Figure 55:
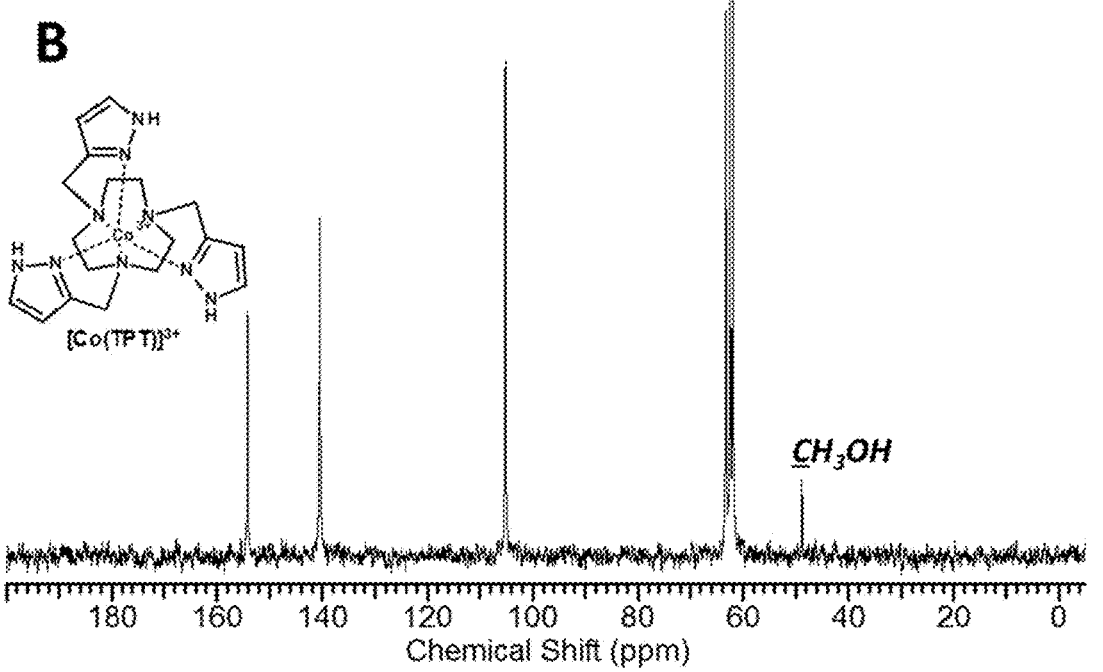
Figure 56:
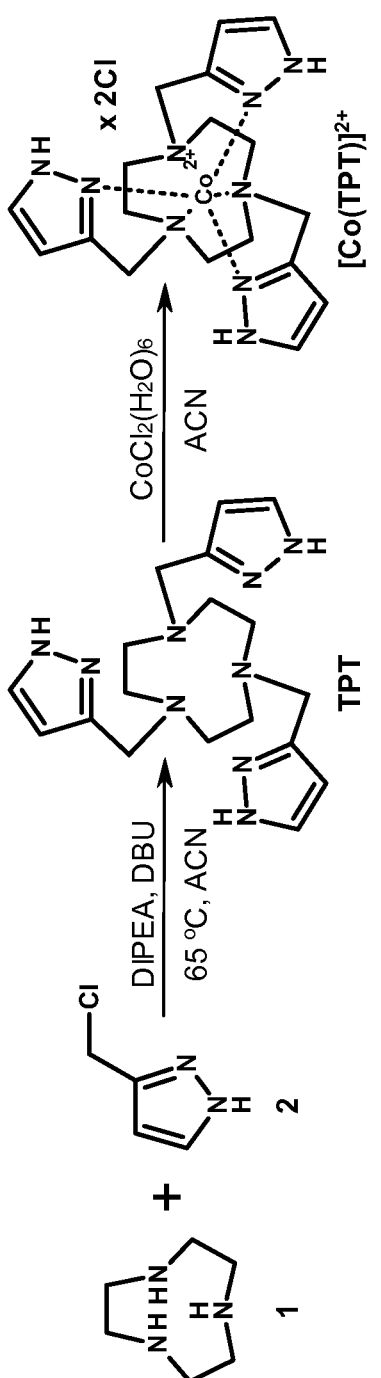
FIG. 56. Synthesis of TPT ligand and [Co(TPT)]$^{2+}$ complex.

The [Co(TPT)]$^{2+}$ complex oxidizes in air to the Co(III) form as shown by proton NMR spectroscopy. The paramagnetically shifted protons disappear and proton resonances in the diamagnetic region of the spectrum appear for the Co(III) complex (FIG. 55). Addition of aliquots of dithionite again restores the proton NMR spectrum characteristic of the Co(II) complex (FIG. 39). Near complete reduction to the Co(II) state (93%) is observed after addition of 0.75 molar equivalent (1.5 reducing equivalents) of dithionite. Both the Co$^{2+}$ and Co$^{3+}$ complexes are kinetically inert towards dissociation under biologically relevant conditions. Proton NMR studies in 0.40 mM phosphate, 25 mM carbonate at pH 7.0, 20 mM Hepes buffer showed resonances only for the divalent Co$^{2+}$ complex and increasing amounts of the trivalent complex upon incubation for 24 hours under argon (FIG. 48). No other proton resonances were detected that could be assigned to either free ligand or decomposed complex.

To determine the reduction potential of the complex, cyclic voltammetry experiments were carried out in water. Under these conditions, [Co(TPT)]$^{2+}$ exhibited a reversible oxidation peak with a reduction potential of −107±11 mV versus NHE (FIG. 40). The moderately negative potential is consistent with the relative ease of oxidation of [Co(TPT)]$^{2+}$ in the presence of dioxygen and the reduction of [Co(TPT)]$^{3+}$ by dithionite. The negative redox potential is in a desirable range for hypoxia probes (−100 to −500 mV vs. NHE) that respond to the redox potential of cells (−170 to −280 mV vs. NHE) through modulation of MRI contrast.

Figure 41:
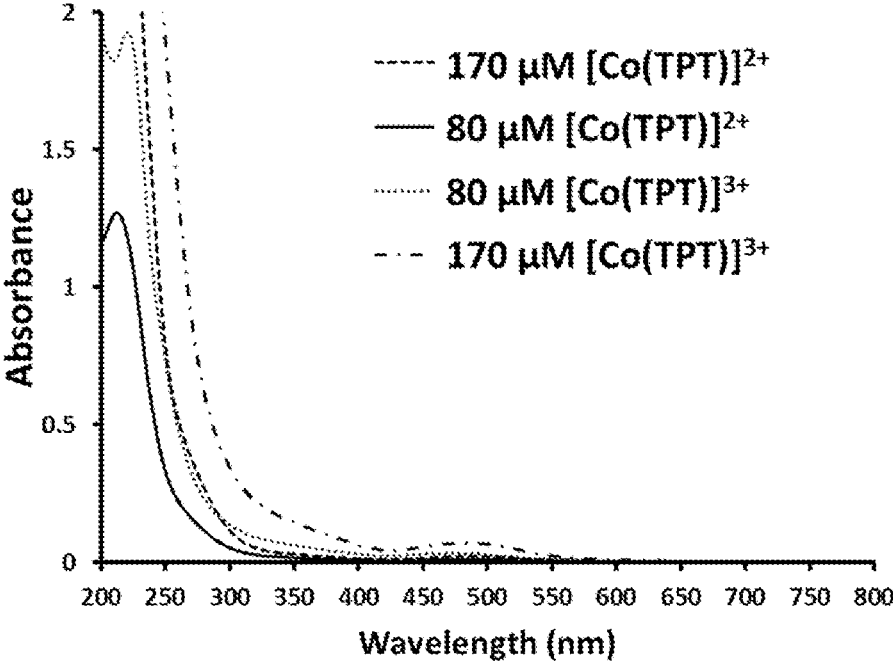
FIG. 41. UV-vis spectra of [Co(TPT)]$^{2+}$ and [Co(TPT)]$^{3+}$ in 100 mM NaCl, 20 mM HEPES, pH 7.0. Spectrum of [Co(TPT)]$^{3+}$ has an additional red-shifted band with the maximum centered at λ=485 nm.
Figure 42:
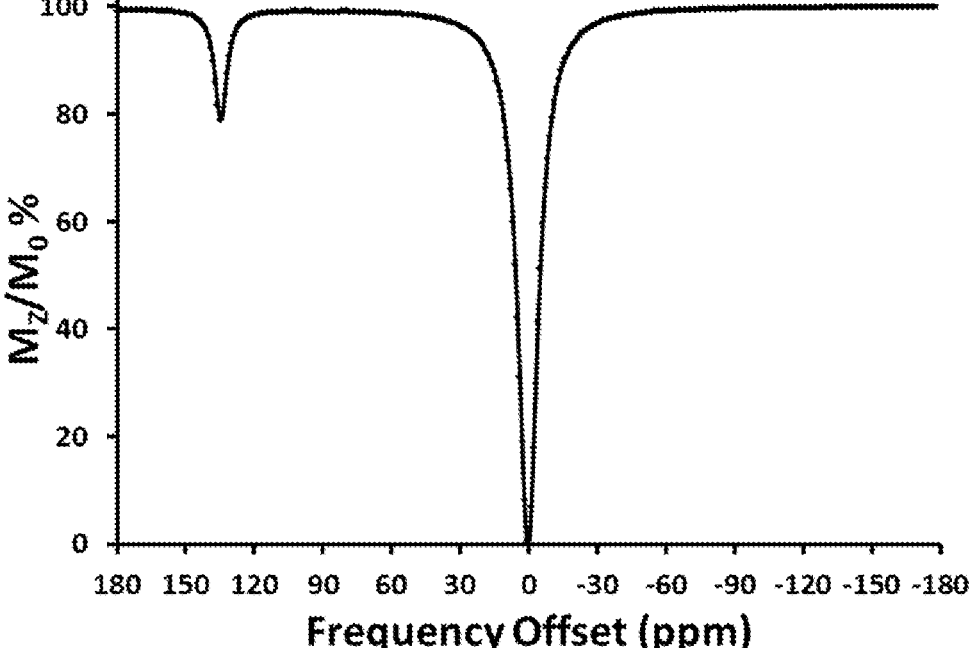
FIG. 42. CEST spectra recorded at 11.7 T of a solution containing 8 mM [Co(TPT)]$^{2+}$, 100 mM NaCl, 20 mM HEPES pH 7.0, 37° C. RF presaturation applied for 3 seconds, $B_1$=24 µT at 37° C. The large peak arises from direct irradiation of water protons, set to 0 ppm.

The redox environment of tissue is set by different redox couples in addition to oxygen with the most important of these being glutathione/glutathione disulfide (E$_o$=−240 mV at pH 7.0) in intracellular space and cysteine/cystine in extracellular space. In order to determine whether our Co(II)/(III) PARACEST probe would respond to the cellular redox environment, the kinetics of the reaction of the [Co(TPT)]$^{2+}$ complex with oxygen and the reduction of [Co(TPT)]$^{3+}$ with dithionate as a thiol containing reductant related to glutathione was studied. The effect of redox agents on the cobalt complexes was further monitored by using UV-vis spectroscopy (FIG. 41). A peak at 480 nm in solutions containing 1.0 mM cobalt complex at pH 7.0, 20 mM buffer and 100 mM NaCl was followed by using UV-visible spectroscopy (FIG. 41). The rate constant for oxidation of the Co(II) complex was 5×10$^{-6}$ s$^{-1}$ at ambient pressures of oxygen. This rate constant decreased to 2×10$^{-6}$ at partial pressures of oxygen of 5%. Introduction of O$_2$ to a solution of [Co(TPT)]$^{2+}$ led to an increase in the 485 nm peak which is characteristic of the Co(III) form of the complex. Addition of reductants such as dithionite resulted in the disappearance of the peak at 485 nm. The rate constant for reduction of Co(III) complex in the presence of excess dithionate was 4×10$^{-5}$ s$^{-1}$. This shows that the oxidation state of the cobalt complex is influenced by the presence of thiol reductants and by oxygen to switch between the divalent and trivalent oxidation states. The concentrations of such cellular reductants as well as oxygen levels in tissue will influence the oxidation state of the cobalt complex.

Figure 49:
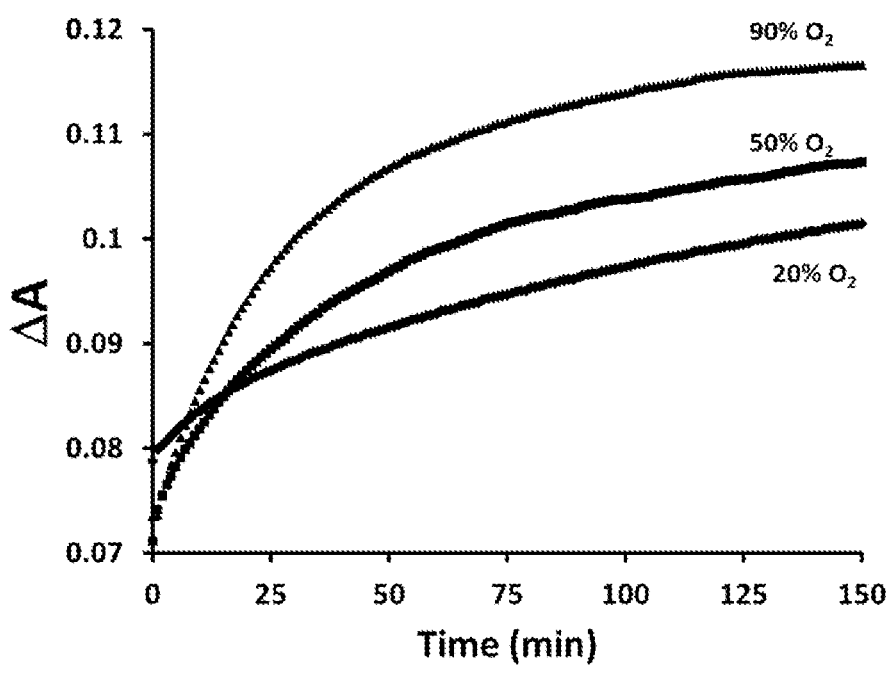
FIG. 49. Single-exponential kinetic traces under pseudo-first order reaction conditions for 70 μM Co(II) oxidized with N$_2$/O$_2$ mixtures containing 20%, 50%, and 90% O$_2$, respectively, at 25° C. Solutions contained 200 mM NaCl and 40 mM HEPES, pH 7.1.
Figure 50:
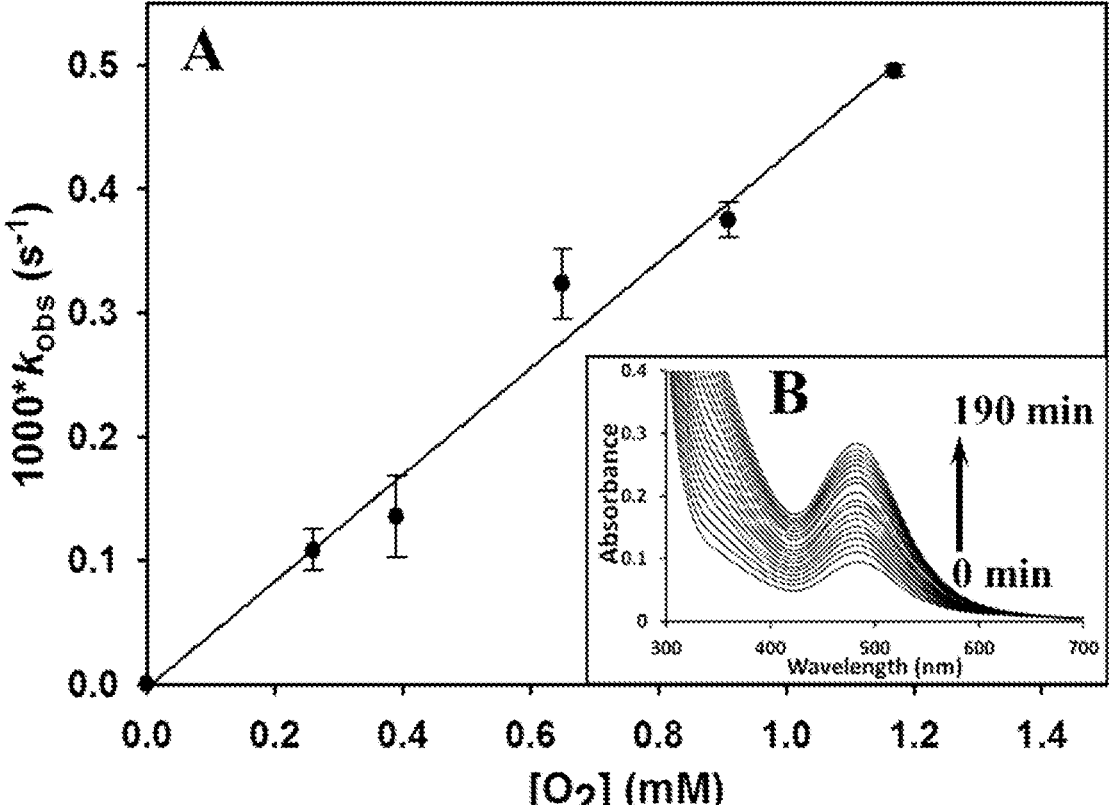
FIG. 50. Plot of pseudo-first order rate constants for the reaction of 70 μM [Co(TPT)]$^{2+}$ with oxygen. Solid line represents a linear fit giving k$_b$; 0.43 M$^{-1}$s$^{-1}$. Insert B: Change in absorbance in aerated solutions were recorded at 10 minute intervals. Conditions: 200 mM NaCl, 40.0 mM HEPES, pH 7.1 at 25° C.
Figure 51:
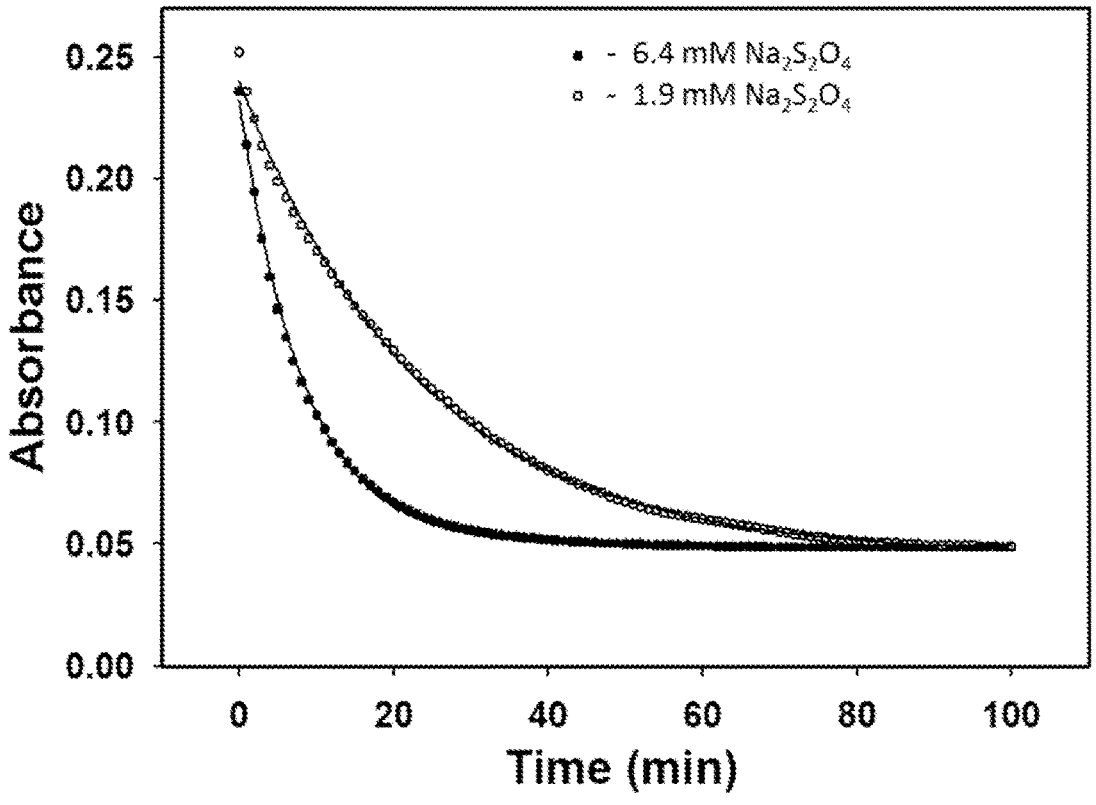
FIG. 51. Determination of the pseudo-first order rate constants following the absorbance decay of 0.6 mM [Co (TPT)]$^{3+}$ in the presence of 1.9 mM and 6.4 mM Na$_2$S$_2$O$_4$ containing 0.2 M NaCl and 40 mM HEPES, pH 7.0. Solutions were purged with argon prior to mixing, and the samples were kept under inert atmosphere. Solid lines represent the fit of the data to a single exponential decay.
Figure 52:
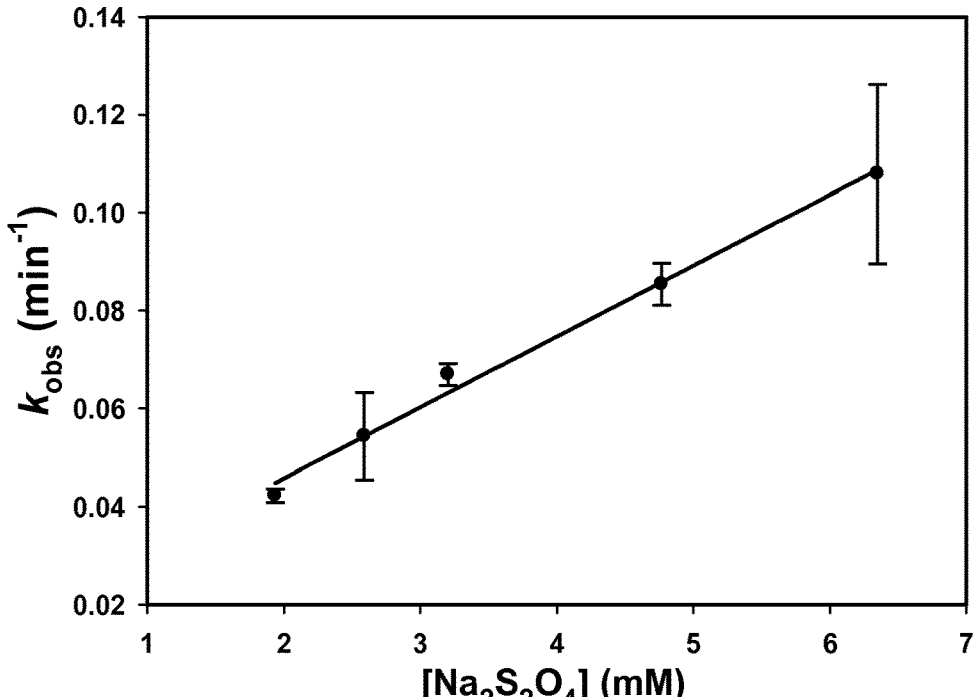
FIG. 52. Dependence of the observed pseudo-first order rate constants for the reduction of 0.6 mM [Co(TPT)]$^{3+}$ on the Na$_2$S$_2$O$_4$ concentration at 200 mM NaCl, 40 mM HEPES, pH 7.0, 37° C. The linear fit of the data (solid line) gives bimolecular rate constant=0.24 M$^{-1}$s$^{-1}$.

The reaction kinetics of the redox-activated MRI probe is also important. UV-vis spectroscopy provided a convenient means of measuring conversion between Co(II) and Co(III) (FIG. 41), by monitoring the increase or decrease of the 485 nm peak characteristic of [Co(TPT)]$^{3+}$. Using this method, pseudo-first order rate constants for reduction of [Co(TPT)]$^{3+}$ by excess dithionite were obtained (FIG. 51). A plot of pseudo-first order rate constant as a function of dithionate gave a second-order rate constant of 0.24 M$^{-1}$s$^{-1}$ (FIG. 52). Reactions were also conducted under pseudo-first order conditions for oxidation of [Co(TPT)]$^{2+}$ by excess oxygen (FIG. 49). A plot of pseudo-first order rate constants as a function of oxygen concentration gave a second-order rate constant of 0.43 M$^{-1}$s$^{-1}$ (FIG. 50). This second-order rate constant is similar to rigid Co(II) cages based on triazacyclononane that react with oxygen through outer-sphere mechanisms. Extrapolation to oxygen levels of 100 mm Hg (0.17 mM O$_2$), representative of arterial blood, gives a rate constant of 7.3×10$^{-5}$ s$^{-1}$ (half-life of 2.6 hours). Very low oxygen levels in hypoxic conditions (10 mm Hg, 17 μM O$_2$) would give a rate constant of 7.3×10$^{-6}$ s$^{-1}$ or a half-life of the complex of 26 hours. Notably, electron self-exchange rate constants for Co(III) complexes vary by nine orders of magnitude, suggesting it is feasible to kinetically tune the redox reactions of our CoCEST agents.

Figure 43:
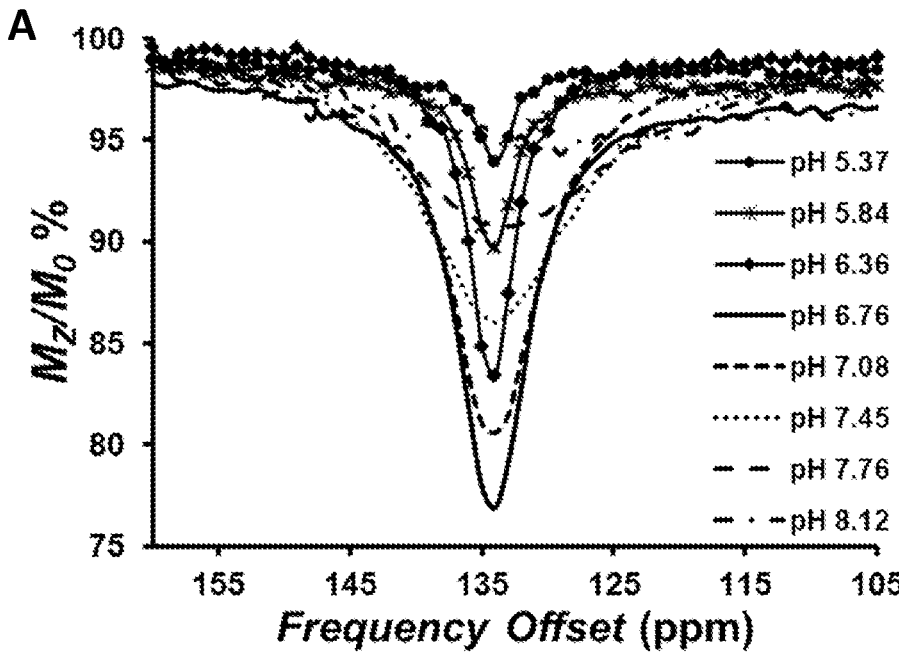
FIG. 43. (A) Top: CEST spectra recorded at 11.7 T of solutions containing 8 mM [Co(TPT)]$^{2+}$ at various pH values, 200 mM NaCl, and 40 mM MES, HEPES, or CHES at 37° C. RF presaturation applied for 3 seconds, $B_1$=24 µT at 37° C. (B) Bottom: Dependence of [Co(TPT)]$^{2+}$ CEST effect intensity at 135 ppm, 37° C., on pH of the solution.
Figure 43:
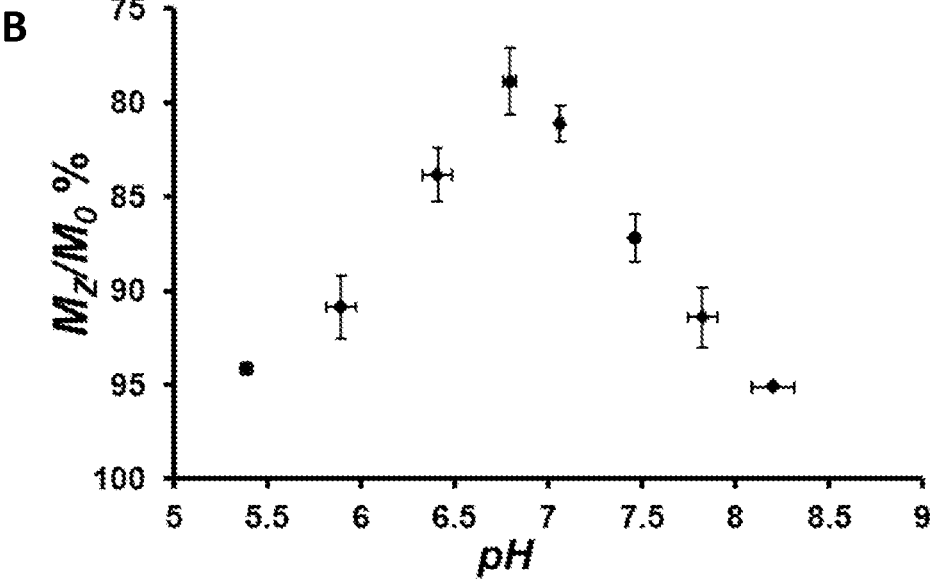
Figure 53:
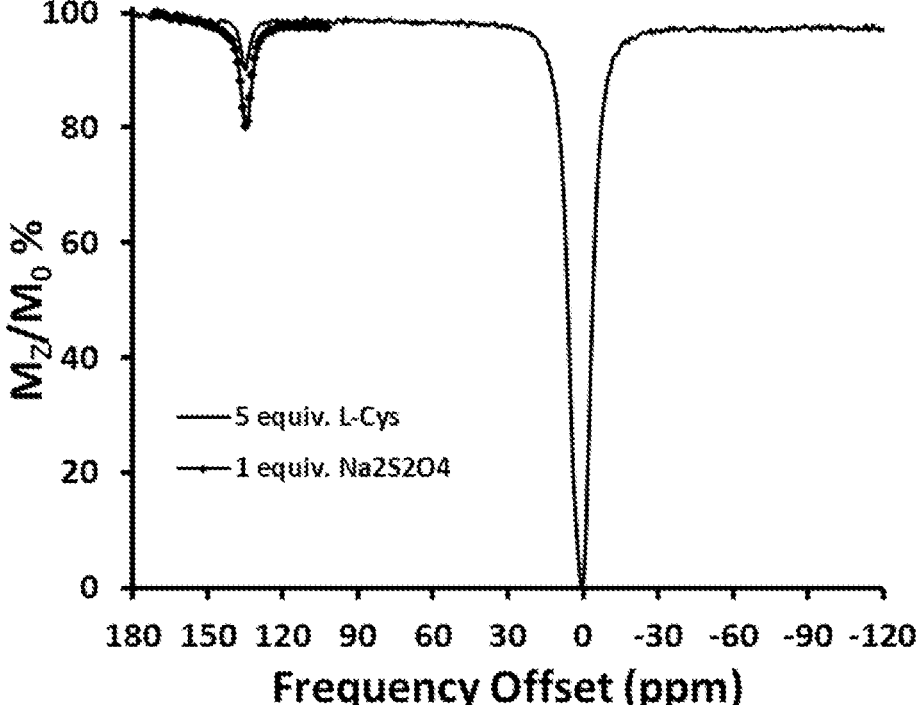
FIG. 53. CEST spectrum upon reduction of 9.0 mM [Co(TPT)]$^{2+}$ with 1.0 equiv. Na$_2$S$_2$O$_4$ and 5.0 equiv. of L-cysteine, respectively. CEST spectra recorded at 11.7 T of a solution containing 200 mM NaCl, 40.0 mM HEPES pH 7.0, 37° C. RF presaturation applied for 3 seconds, B$_1$=24 μT at 37° C.
Figure 54:
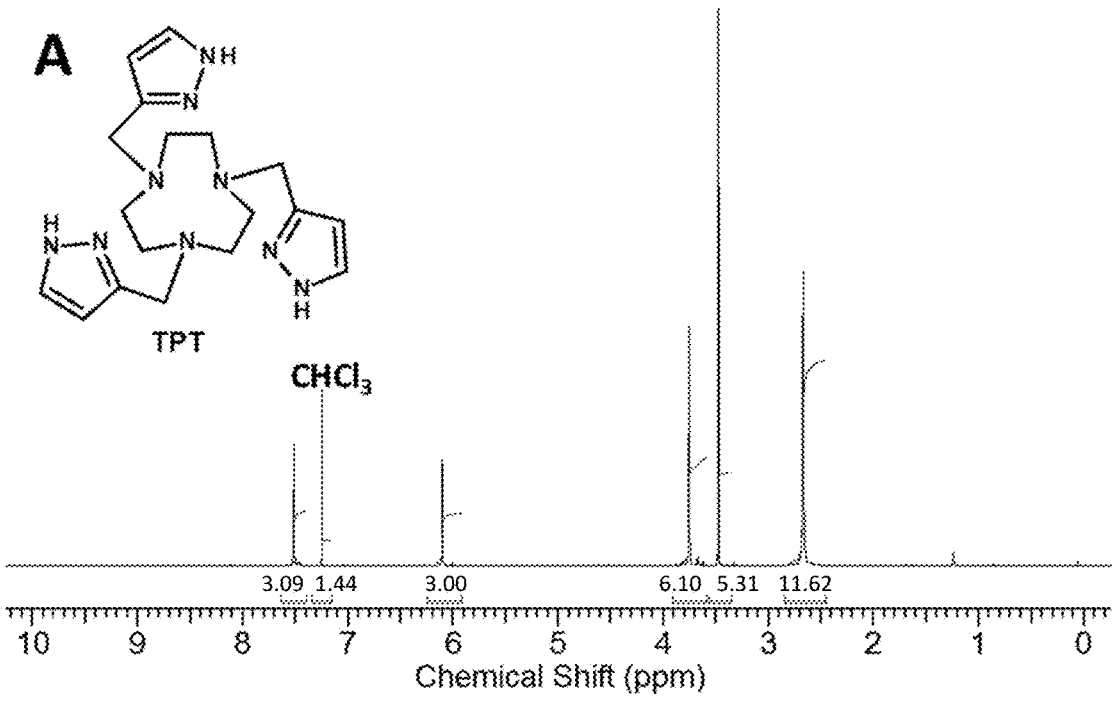
FIG. 54. (A)$^1$H NMR spectrum of TPT ligand in CDCl$_3$ and (B)$^{13}$C NMR spectrum of TPT in CD$_3$OD.
Figure 54:
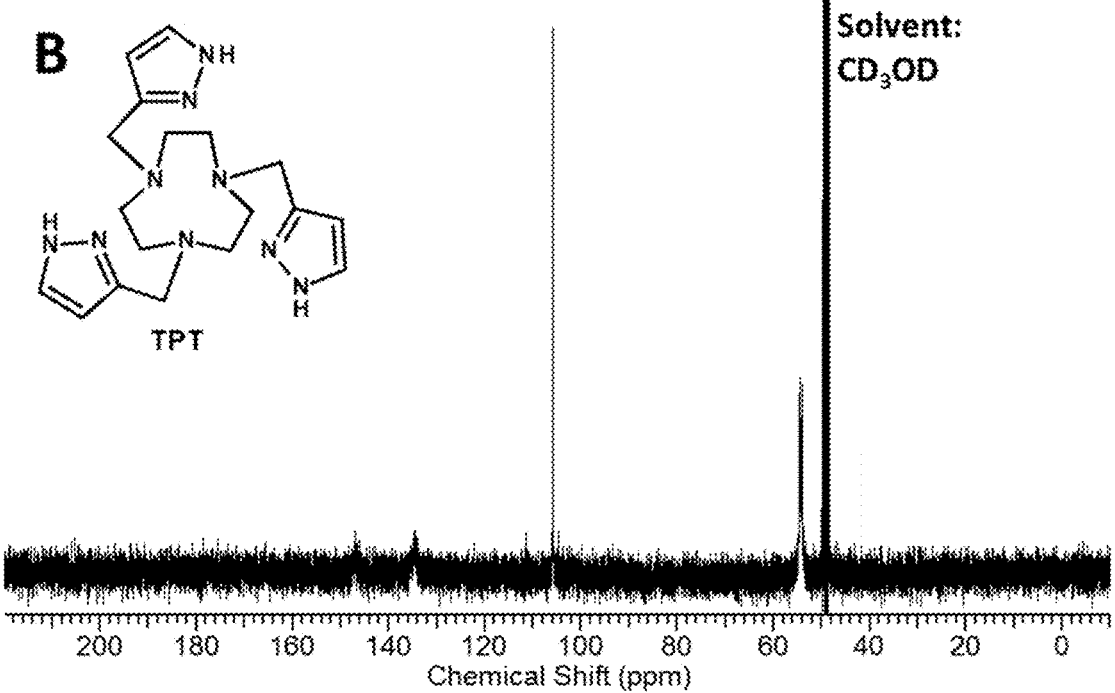

CEST spectra were obtained of [Co(TPT)]$^{2+}$ by applying a presaturation pulse in 1 ppm increments and were plotted as normalized water signal intensity (M$_z$/M$_o$%) against frequency offset (ppm). Spectra were collected at 37° C. in the presence of 20 mM buffer and 100 mM NaCl over a range of pH values (FIG. 43). The CEST peak at 135 ppm (versus the proton resonance of water set at zero) is close to the frequency for the exchangeable proton NMR resonance which is attributed to the NH proton of the pyrazole. Other options such as exchangeable water ligand protons are unlikely given that the [Co(TPT)]$^{2+}$ complex is presumably coordinatively saturated. The CEST peak at 135 ppm is remarkable in that it is highly shifted from the bulk water peak. This will minimize interference from magnetization transfer effects present in tissue and thus may enable higher MRI contrast to noise ratios in vivo. As expected, diamagnetic [Co(TPT)]$^{3+}$ gave no highly shifted CEST peak. Addition of either of the reductants dithionite or cysteine reproduced the 135 ppm CEST peak (FIG. 53).

Figure 44:
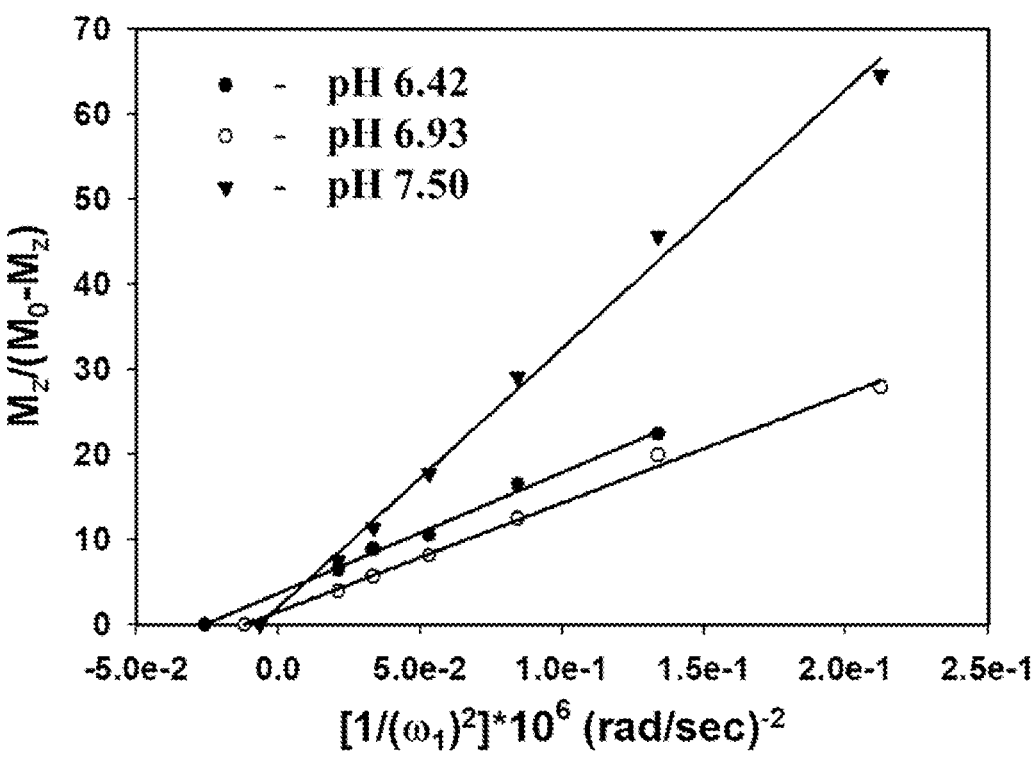
FIG. 44. Determination of the exchange rate constants ($k_b$) at pH 6.42, pH 6.93, and pH 7.50 at 37° C. Data points (except x-intercept points) correspond to the CEST signal intensity at 135 ppm obtained at various pre-saturation pulse powers of 350-1090 Hz applied for 4 seconds. Solid lines represent the linear fit of the data for each sample. The x-intercept values are obtained by extrapolation of linear fits. Samples contained 16 mM [Co(TPT)]Cl$_2$, 200 mM NaCl, and 40 mM MES or HEPES.
Figure 45:
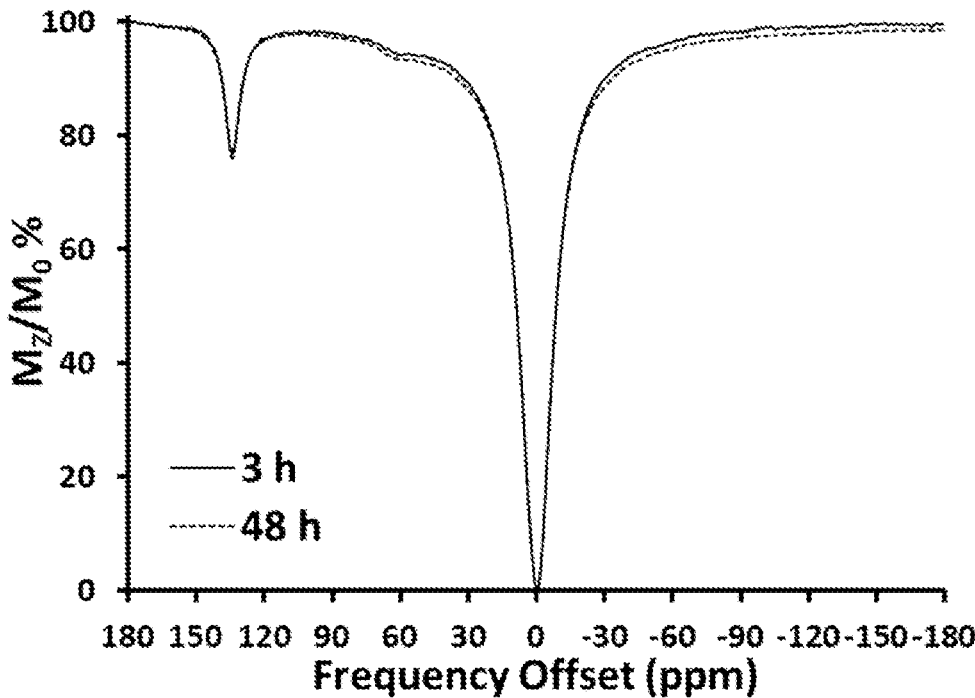
FIG. 45. CEST spectra recorded at 11.7 T of a solution containing 8 mM [Co(TPT)]$^{2+}$, 100 mM NaCl, 20 mM HEPES pH 7.0, 37° C. RF presaturation applied for 3 seconds, B$_1$=24 μT at 37° C. in rat serum.

The CEST effect is pH dependent over the pH range of 6-8 with an optimum at pH 6.9 (FIG. 43). The increase in the rate constants for proton exchange as a function of pH, as determined by using Omega plots, is consistent with base catalyzed proton exchange. Rate constants are 6,200 s$^{-1}$, 9,200 s$^{-1}$ and 12,400 s$^{-1}$ at pH 6.4, 6.9 and 7.5, respectively at 37° C. (FIG. 44). These rate constants led to an increase in the intensity of the CEST peak as pH increases from 6 to 6.9 and then to a decrease in the CEST peak at pH values greater than 6.9 due to rapid proton exchange that leads to CEST peak broadening. [Co(TPT)]$^{2+}$ also gives a CEST spectrum in serum (FIG. 45).

Figure 46:
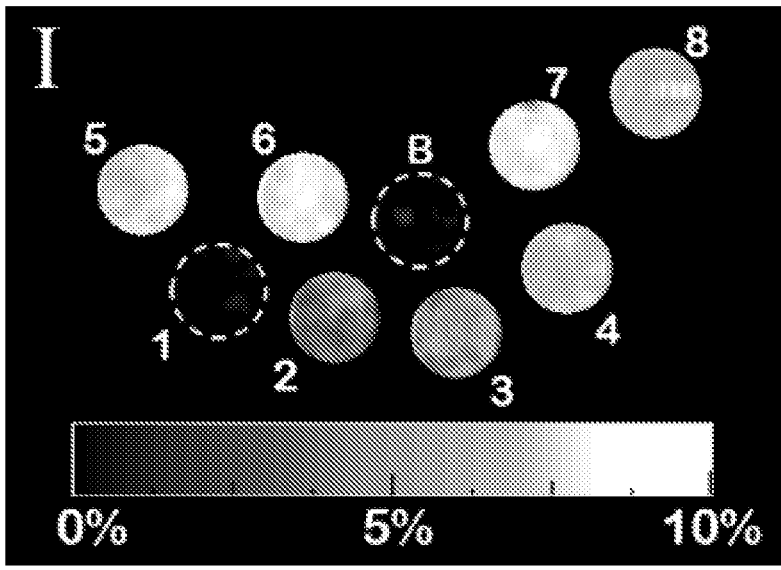
FIG. 46. CEST images of phantoms at 37° C. on a MRI 4.7 T scanner with a pulse train comprised of five Gauss pulses at 12 μT for 1 second each, interpulse delay of 200 μs applied symmetrically about the bulk water resonance (+/− 135 ppm). All solutions contain 40 mM HEPES buffer, pH 7.0, and 200 mM NaCl. Samples containing 8 mM Co(III)/ Co(II) complex were prepared from: 1) [Co(TPT)]$^{3+}$; 2) [Co(TPT)]$^{3+}$ and 0.25 molar eq. Na$_2$S$_2$O$_4$; 3) [Co(TPT)]$^{3+}$ and 0.38 eq Na$_2$S$_2$O$_4$; 4) [Co(TPT)]$^{3+}$ and 0.5 eq Na$_2$S$_2$O$_4$; 5) [Co(TPT)]$^{3+}$ and 0.75 eq Na$_2$S$_2$O$_4$; 6) [Co(TPT)]$^{3+}$ and 1.0 eq Na$_2$S$_2$O$_4$; 7) [Co(TPT)]$^{3+}$ and 1.25 eq Na$_2$S$_2$O$_4$; 8) [Co(TPT)]$^{2+}$ as Co(II) reference. Scale represents the percent loss of signal due to CEST saturation pulse. The chart (bottom) represents phantom image intensities as average of three independent experiments.
Figure 46:
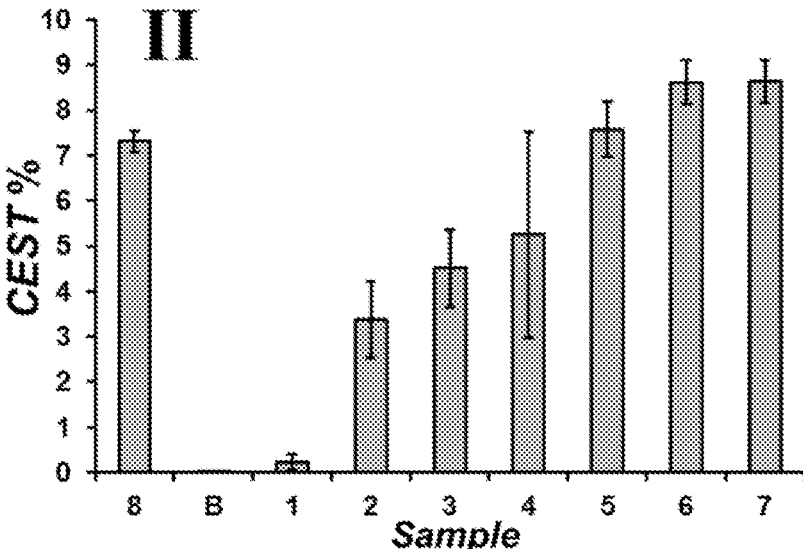

Magnetic resonance imaging experiments showed that the magnitude of CEST contrast correlates with the extent of reduction of [Co(TPT)]$^{3+}$ to the PARACEST active form of the complex, [Co(TPT)]$^{2+}$. CEST images were taken on a 4.7 T scanner using a phantom array. A pair of gradient echo images were acquired with a presaturation pulse either on-resonance or off-resonance of the exchangeable protons (135 ppm or −135 ppm). The ratio between these two images is subtracted from 100% to generate a CEST image. Solutions contained 8 mM cobalt complex, 200 mM NaCl, 40 mM buffer, pH 7.0 at 37° C. with 0 to 1.25 equivalents of dithionate (Na$_2$S$_2$O$_4$). Comparison was made to buffer, oxidized complex and the divalent [Co(TPT)]$^{2+}$ complex isolated under argon. The data show that the CEST image increases linearly as dithionate is added and plateaus at 1.25 molar equivalents (FIG. 46). For solutions containing 8 mM cobalt complex, 100 mM NaCl, 20 mM buffer, pH 7.0 at 37° C. with 0 to 2.5 reducing equivalents of dithionate (Na$_2$S$_2$O$_4$), assuming that dithionate is a two electron reducing agent, the data shows that the CEST image increases linearly as dithionate is added and plateaus at 2 equivalents. This latter set of data corresponds to the highly reducing nature of dithionate which is normally a two electron donor. However, dithionate does not have simple redox chemistry in aqueous solution and this may account for the requirement of two equivalents rather than one. In comparison, the slightly lower CEST effect of [Co(TPT)]$^{2+}$ prepared under anaerobic conditions is consistent with slight oxidation of the Co(II) sample during transport to the MRI scanner.

Figure 47:
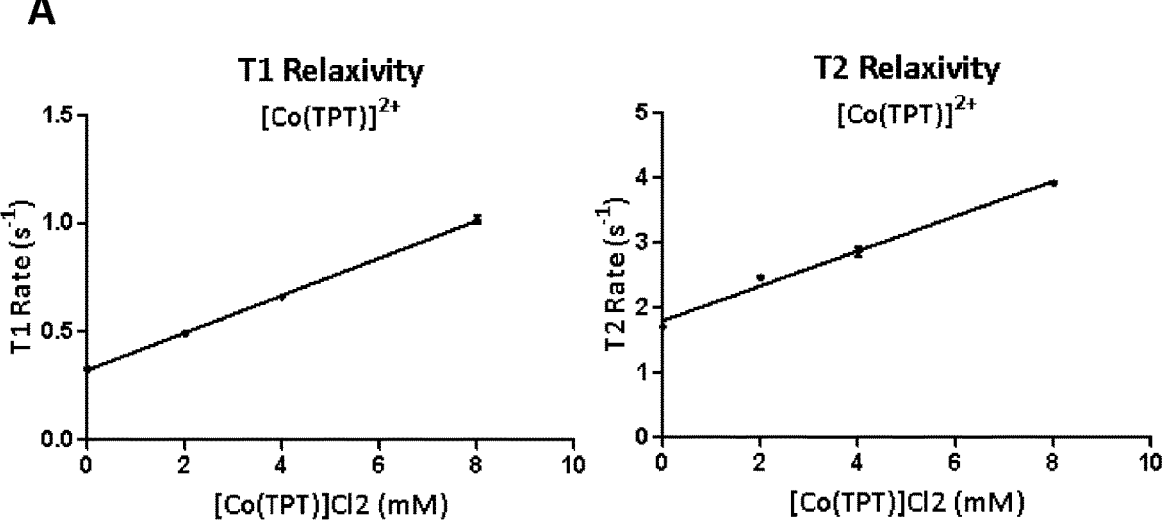
FIG. 47. Linear fits of [Co(TPT)]$^{2+}$ concentration vs. T1 (left) and T2 (right) relaxation rates for (A) in HEPES buffer, at pH 7.2, 37° C. and (B) in serum. T1 and T2 relaxivities were determined from slopes as 0.093 and 0.50 (mM·s)$^{-1}$, respectively. The low relaxivities are advantageous in reducing line broadening and loss of saturation labeling at high [Co(TPT)]$^{2+}$ concentrations.
Figure 47:
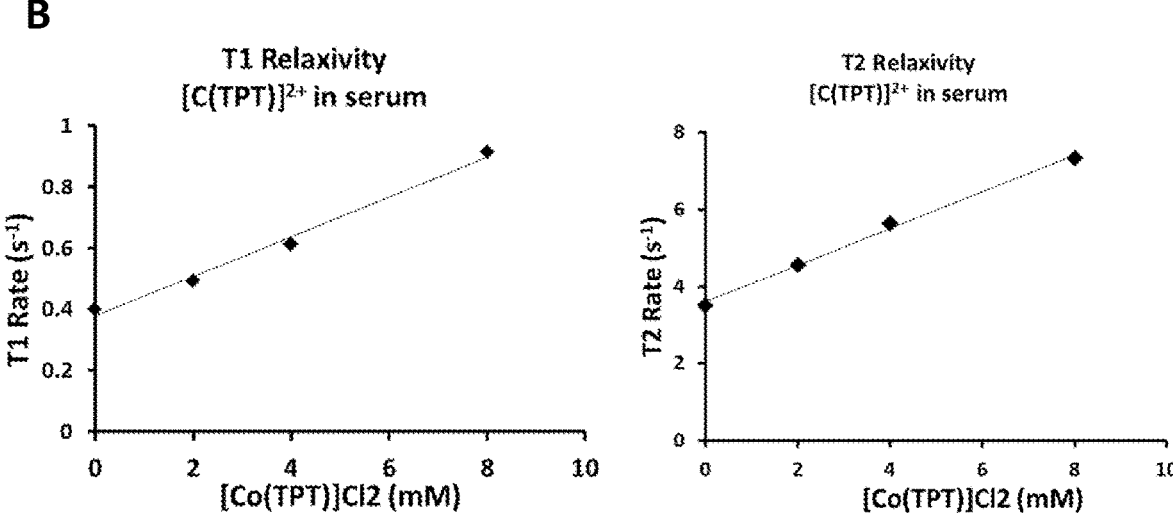

The T1 and T2 relaxivities of [Co(TPT)]$^{2+}$ were 0.093 and 0.50 mM$^{-1}$s$^{-1}$, respectively, as measured on the 4.7 T MRI scanner (FIG. 47). These relatively low relaxivities demonstrate that the paramagnetic properties of Co$^{2+}$ are well-suited for PARACEST.

Both the Co(II) and Co(III) complexes are kinetically inert towards dissociation under biologically relevant conditions. $^1$H NMR studies in 0.40 mM phosphate, 25 mM carbonate at pH 7.0, 20 mM HEPES buffer showed resonances for the divalent Co(II) complex, and slightly increased amounts of the trivalent complex upon incubation for 24 hours under argon (FIG. 48). No other proton resonances were detected that could be assigned to either free ligand or any form of decomposed complex.

The TPT complexes of Co(II)/Co(III) are promising for development as a redox-activated MRI contrast agent. Notably, the Co(II) complex produces large paramagnetic proton shifts and low proton relaxation enhancements suitable for paraCEST agents. The CEST peak at 135 ppm (37° C.) is shifted further than any of those reported for transition metal ion paraCEST agents to date including those containing Ni(II) and Fe(II). A highly shifted CEST peak is an important feature in overcoming background from magnetization transfer (MT) effects. Furthermore, the Co(II)/Co(III) redox couple is readily tunable over the biologically relevant range of −80 to −280 mV.

Figure 57:
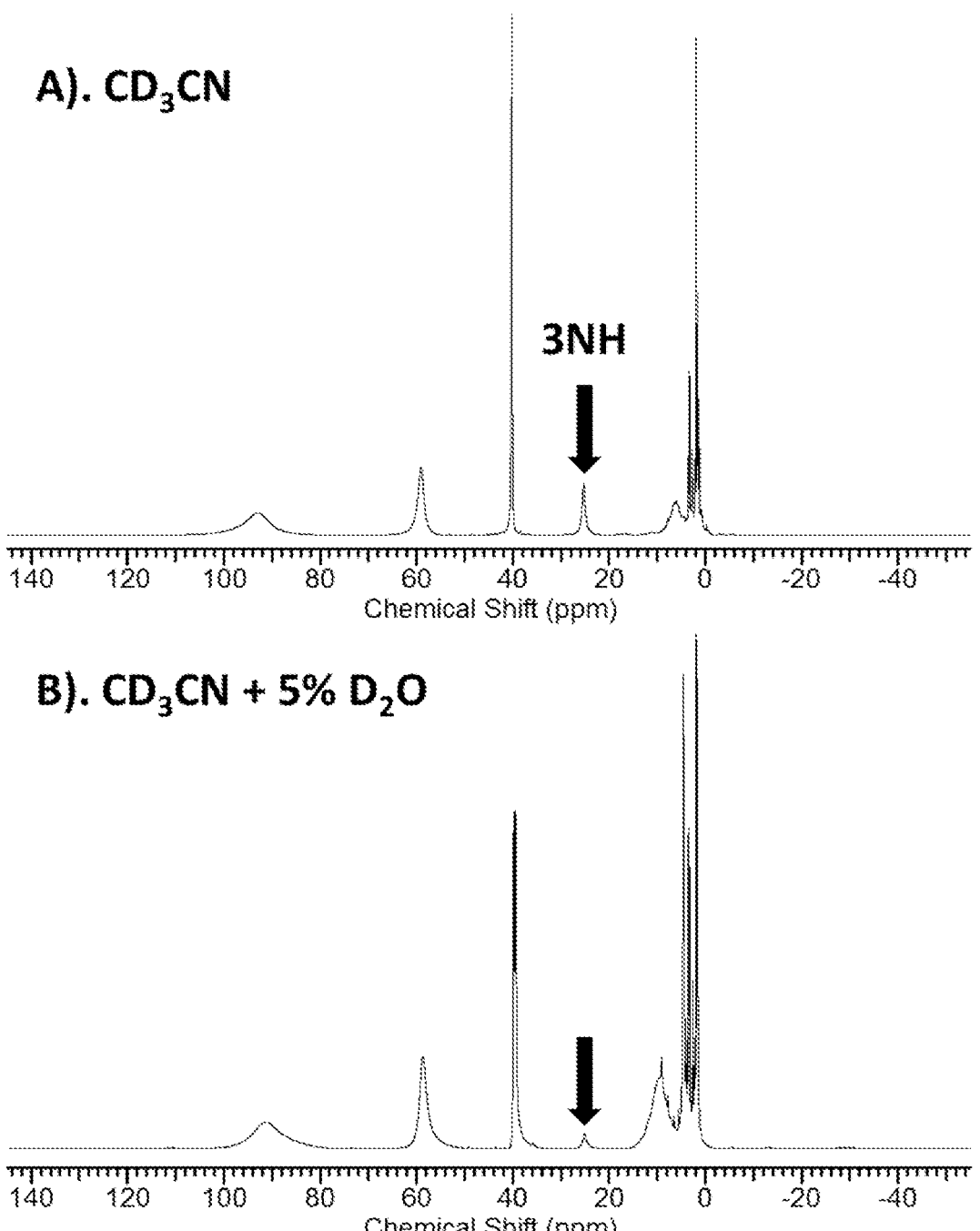
FIG. 57. $^1$H NMR spectra of [Fe(TPT)]$^{2+}$ in CD$_3$CN (A) and CD$_3$CN containing 5% D$_2$O (B)

[Fe(TPT)]$^{2+}$ is a paraCEST agent. The paramagnetically shifted protons of [Fe(TPT)]$^{2+}$ are shown in the proton NMR spectrum of the complex (FIG. 57). The CEST spectrum of the complex shows a peak at 18 ppm, at neutral pH. Upon air oxidation, the complex changes colors and gives a CEST peak at 5 ppm versus the bulk water peak (FIG. 58).

Figure 60:
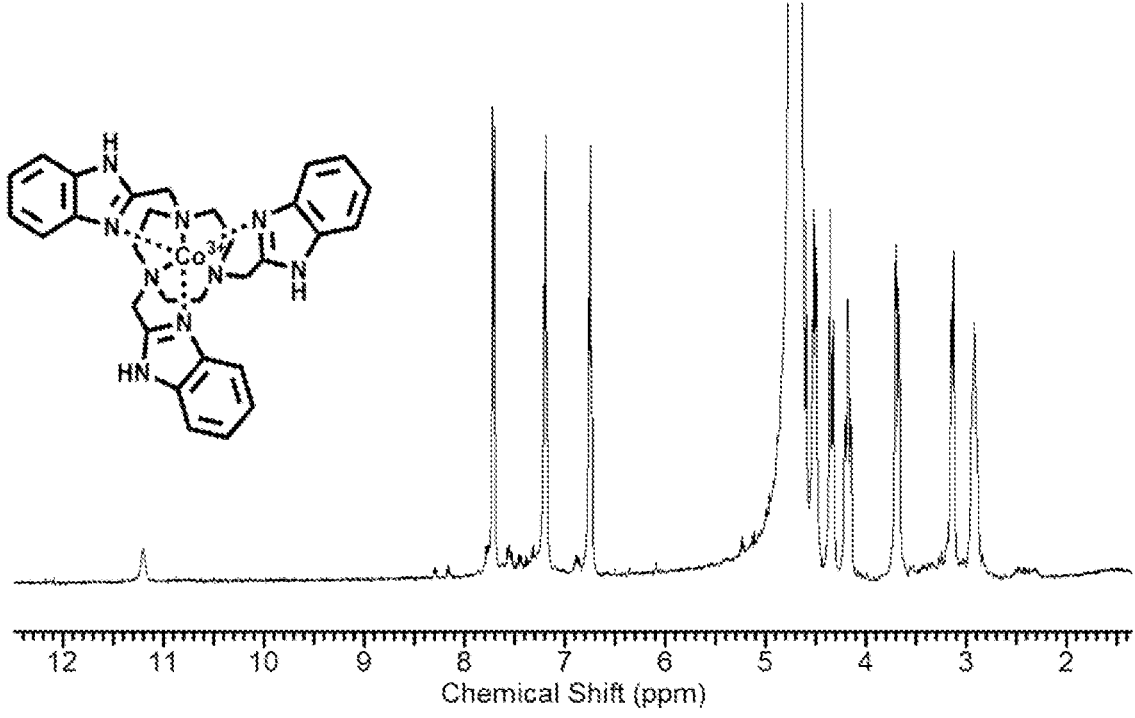
FIG. 60. $^1$H NMR spectrum of [Co(BZT)]$^{3+}$ (diamagnetic). Sample was originally isolated in divalent form [Co(BZT)]$^{2+}$ and further air oxidized.

[Co(BZT)]$^{2+}$ is a redox sensitive complex that cycles between Co(II) and Co(III) states. The proton NMR spectrum of [Co(BZT)]$^{2+}$ shows paramagnetically shifted proton resonances (FIG. 59). Upon oxidation in air, the diamagnetic [Co(BZT)]$^{2+}$ complex is formed (FIG. 60).

[Co(SAR)]$^{2+}$ is prepared by dithionate reduction of the trivalent complex, [Co(SAR)]$^{3+}$. The proton NMR of the paramagnetic complex shows four highly shifted proton resonances (FIG. 62) consistent with C3 symmetry. The CEST spectrum of the oxidized, diamagnetic [Co(SAR)]$^{3+}$ complex shows a CEST peak at 3 ppm versus water (FIG. 61).

Figure 63:
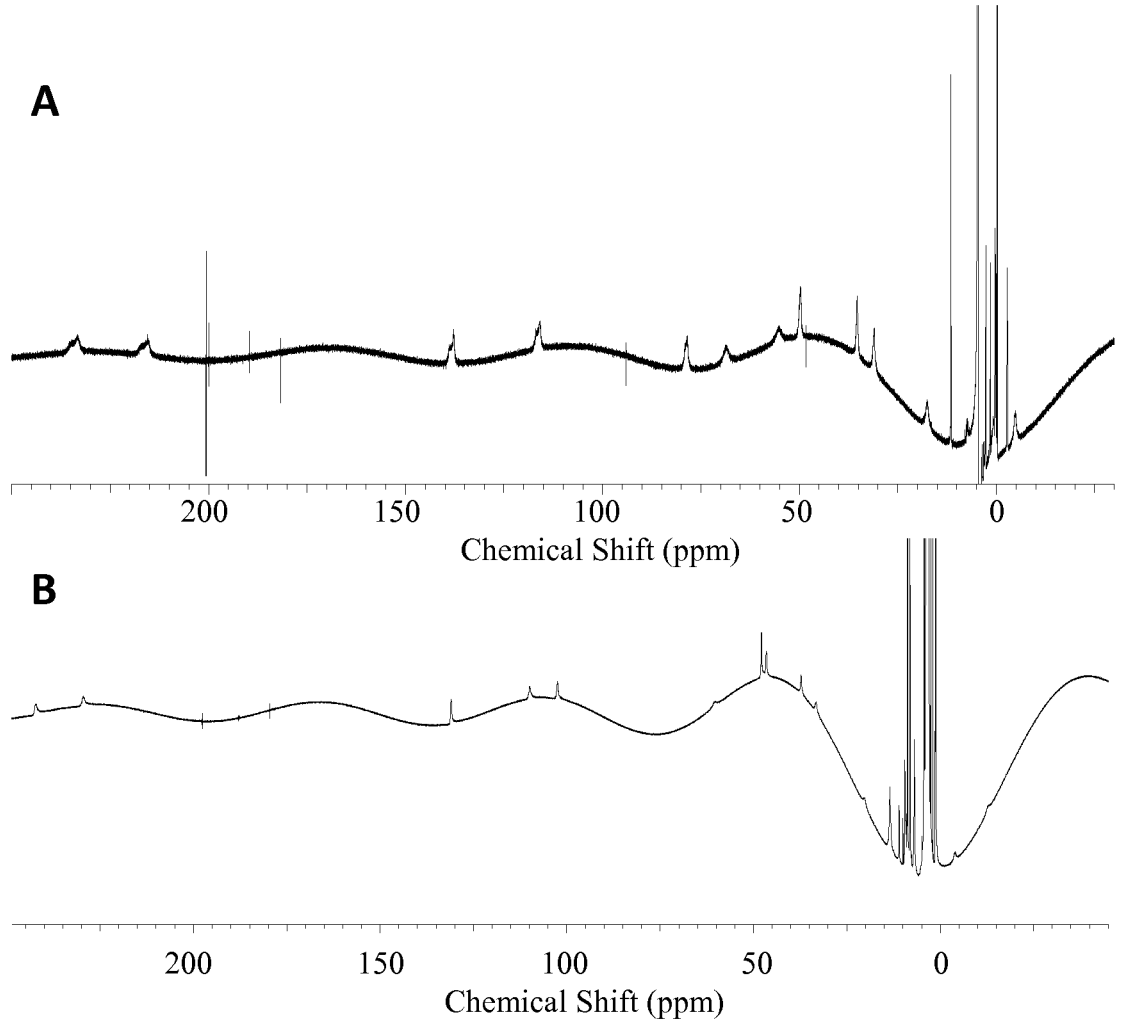
FIG. 63. $^1$H NMR (A) [Co(BzTODA)]$^{2+}$ in D$_2$O and (B) [Co(PTODA)]$^{2+}$ in d$_6$-DMSO.

[Co(BzTODA)]$^{2+}$ and [Co(PTODA)]$^{2+}$ have rigid structures that give rise to relatively sharp proton resonance as shown in their NMR spectra (FIG. 63). [Co(BzTODA)]$^{2+}$ has an exchangeable NH on the benzimidazole group and [Co(PTODA)]$^{2+}$ has an exchangeable pyrazole NH.

Figure 64:
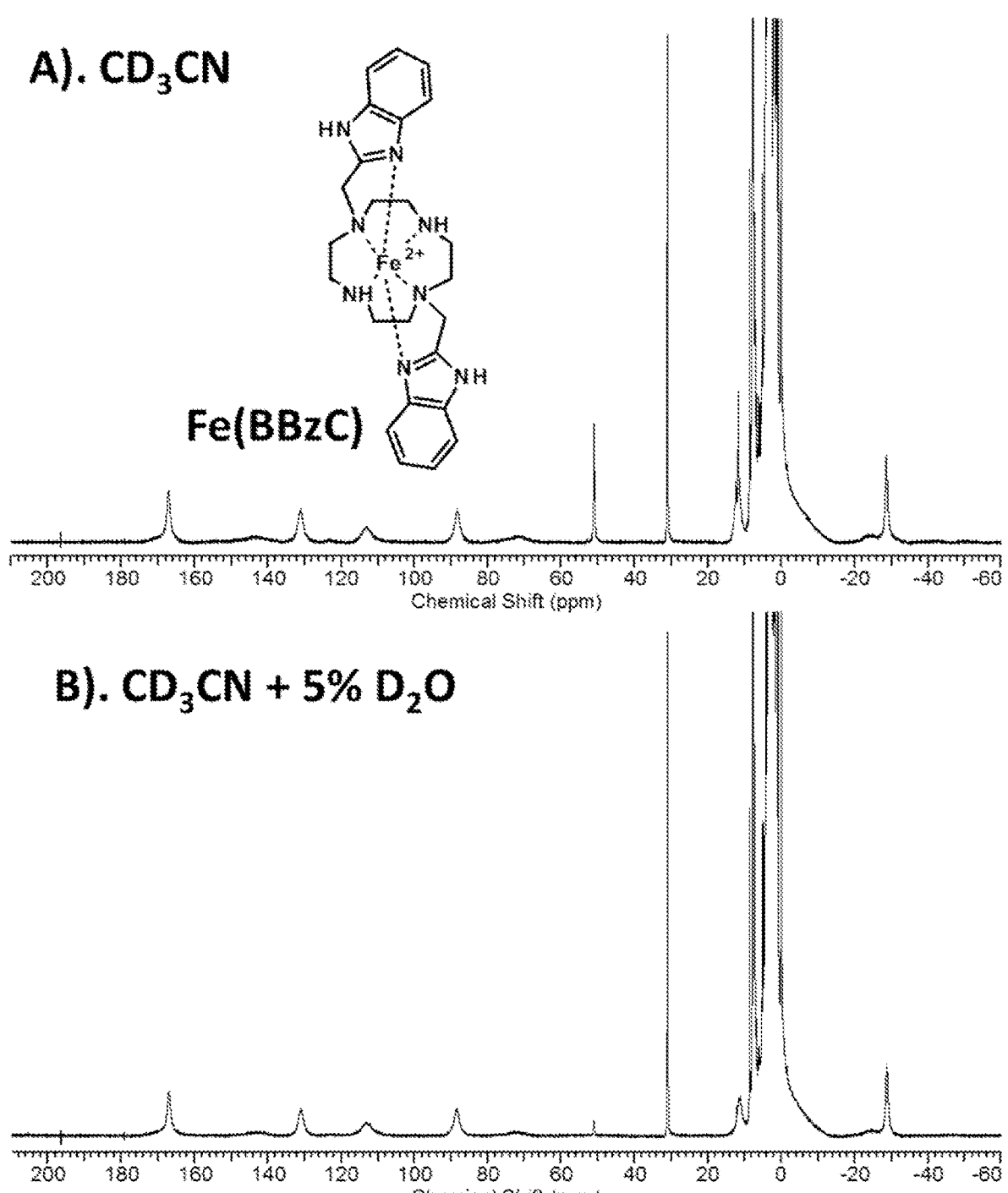
FIG. 64. $^1$H NMR spectrum of [Fe(BBzC)]$^{2+}$ in (A) (top) in CD$_3$CN (B) (bottom) D$_2$O.

[Fe(BBzC)]$^{2+}$ has a dynamic structure on the proton NMR time scale as shown by the broad resonances in FIG. 64.

Figure 65:
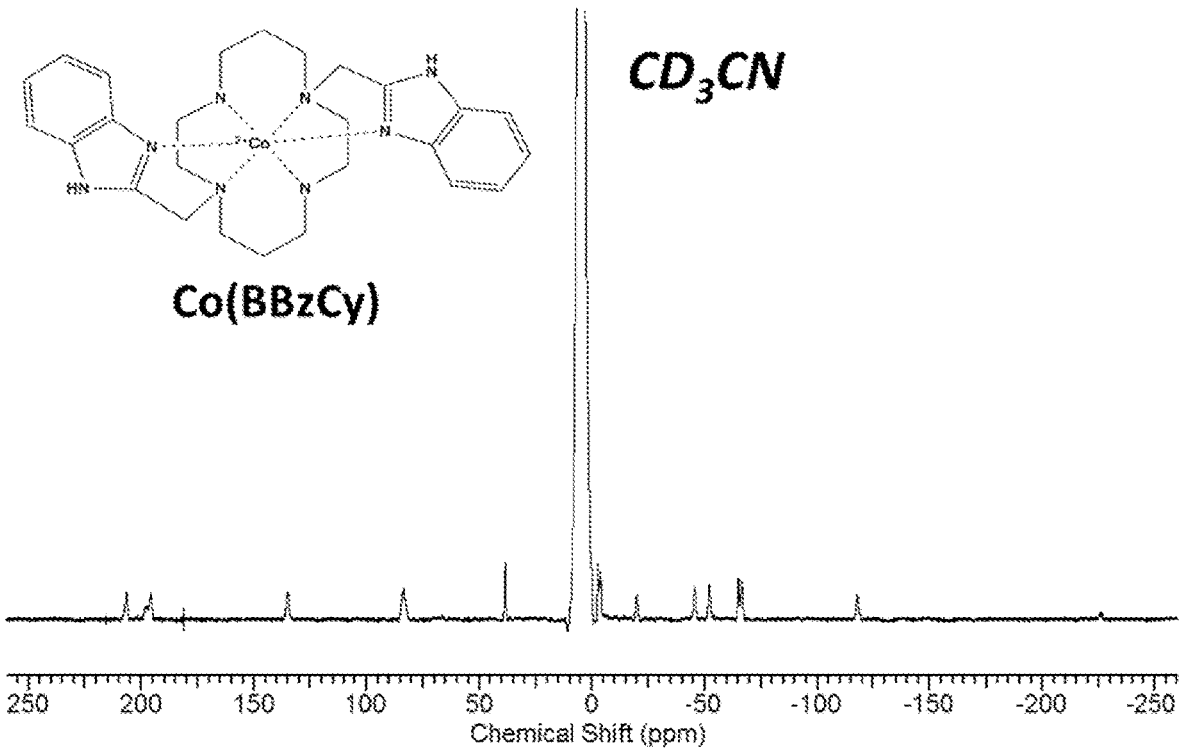
FIG. 65. $^1$H NMR spectrum of [Co(BBzCy)]$^{2+}$ in CD$_3$CN.

[Co(BBzCY)]$^{2+}$ has a relatively rigid structure as shown by the proton NMR spectrum in FIG. 65. A CEST peak at approximately 60 ppm has been observed, corresponding to an exchangeable NH proton of the imidazole. This compound changes color in oxygenated solution, consistent with oxidation to Co(III).

Figure 66:
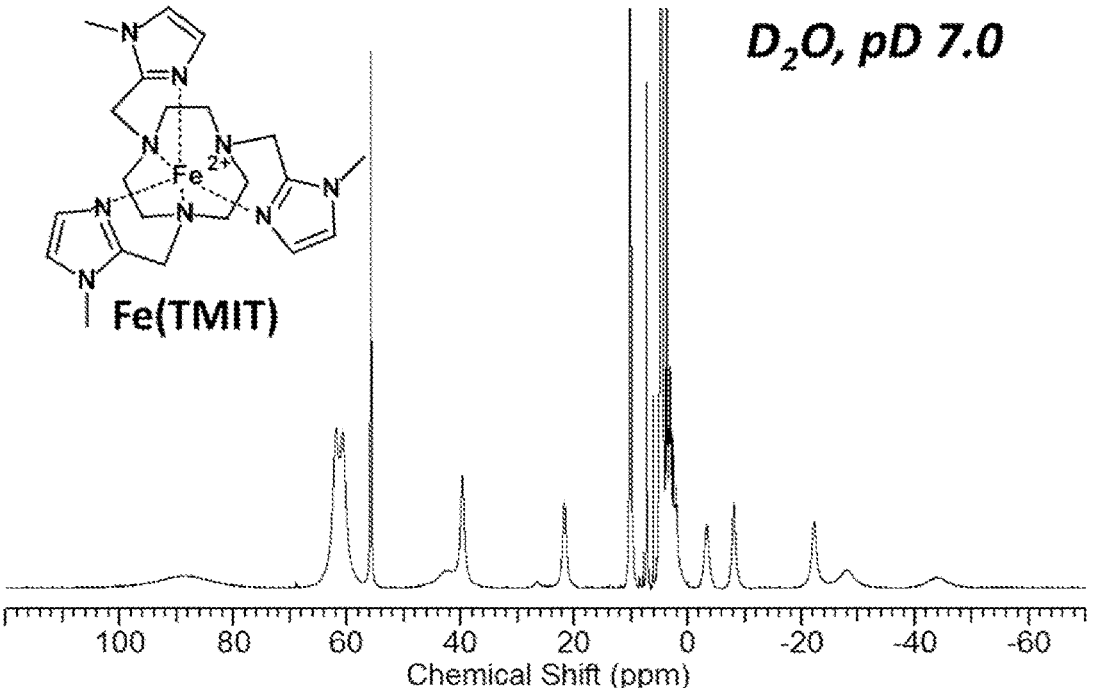
FIG. 66. $^1$H NMR spectrum of [Fe(TMIT)]$^{2+}$ in D$_2$O at pD=7.0.

[Fe(TMIT)]$^{2+}$ shows intense and highly shifted proton resonance for methyl groups that will be useful as a magnetic resonance spectroscopy (MRS) shift agent as shown in FIG. 66.

Figure 67:
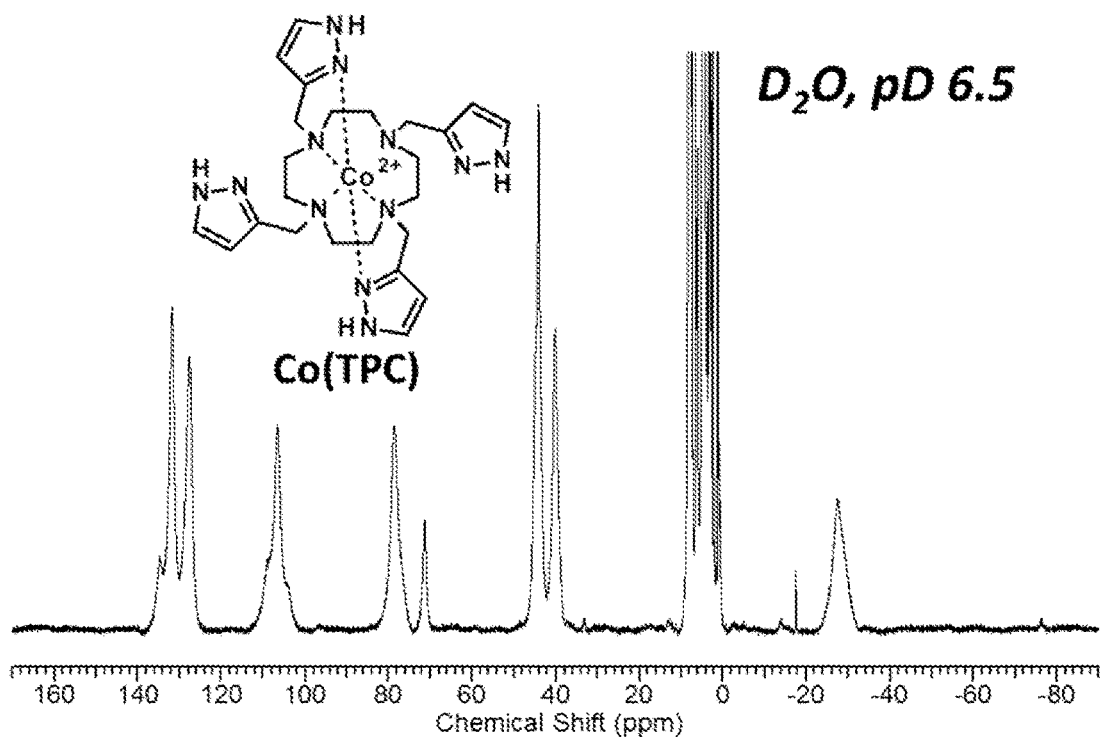
FIG. 67. $^1$H NMR spectrum of [Co(TPC)]$^{2+}$ in D$_2$O at pD=6.5.
Figure 68:
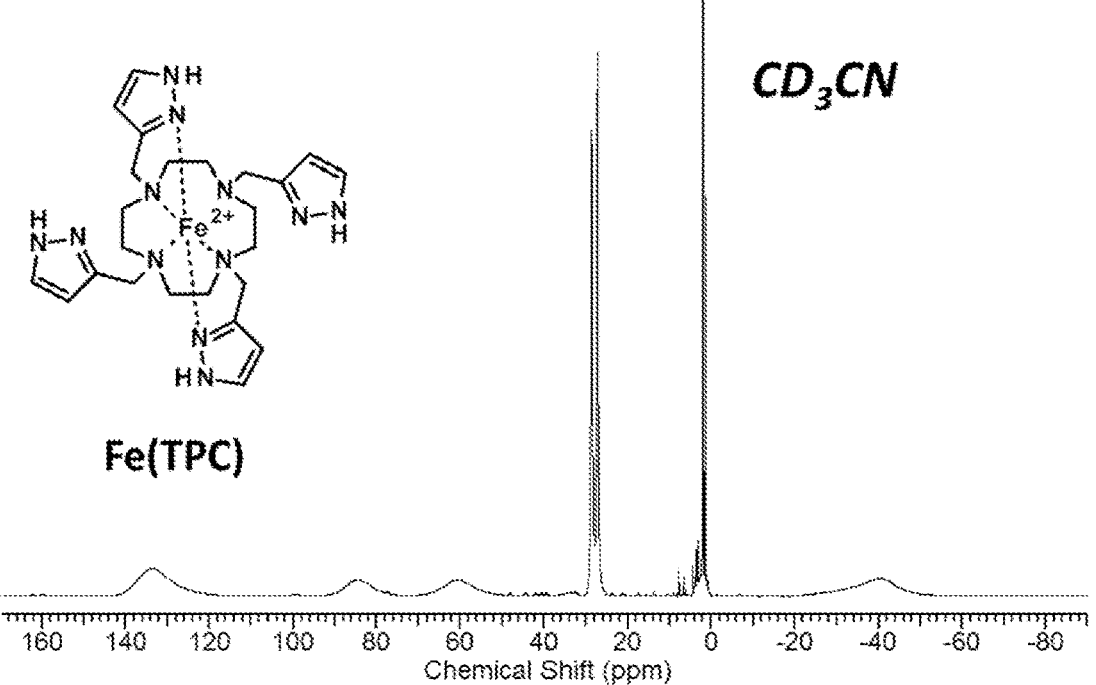
FIG. 68. $^1$H NMR spectrum of [Fe(TPC)]$^{2+}$ in CD$_3$CN.

[Fe(TPC)]$^{2+}$ and [Co(TPC)]$^2$ show relatively sharp proton resonances assigned to the pyrazole protons with broader proton resonances for the remaining macrocyclic CH protons (FIGS. 67 and 68).

Figure 69:
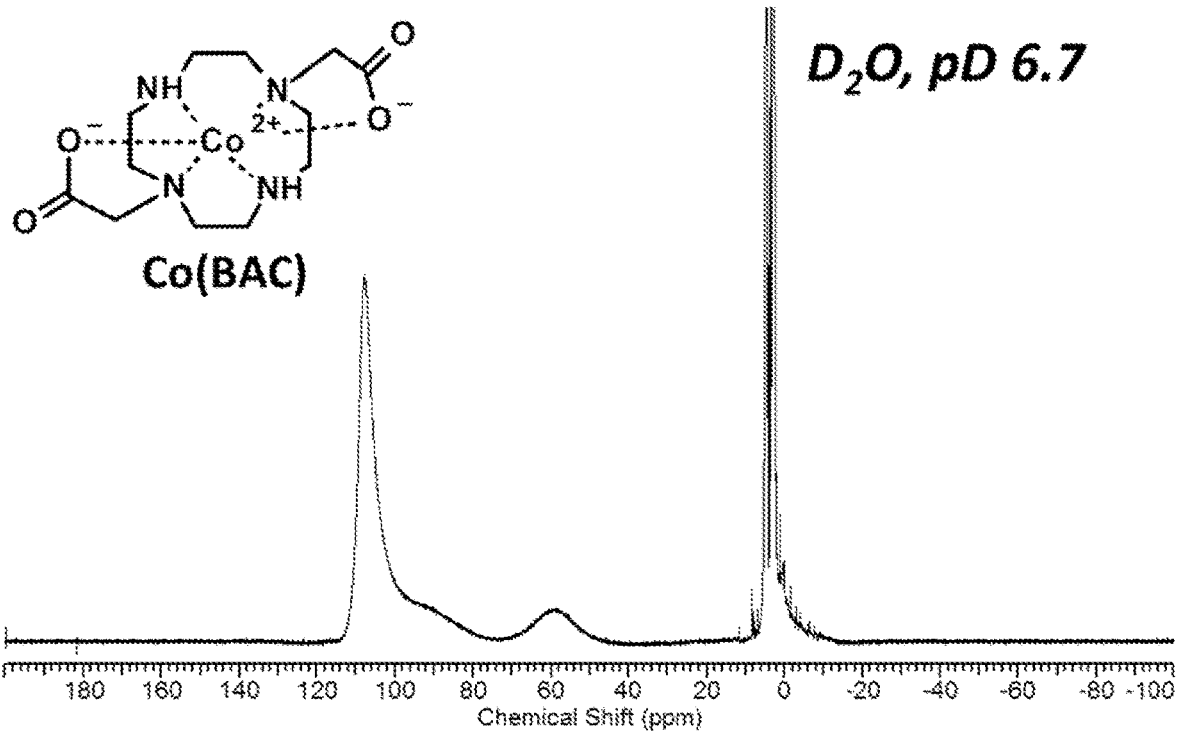
FIG. 69. $^1$H NMR spectrum of [Co(BAC)] in D$_2$O at pD=6.7.

[Co(BAC)] has two carboxylate pendent groups, as an example of a Cyclen derivative that has a readily oxidized Co(II) center. The paramagnetically shifted proton resonances of [Co(BAC)] are shown in FIG. 69. These proton resonances decrease in intensity upon oxidation.

Figure 70:
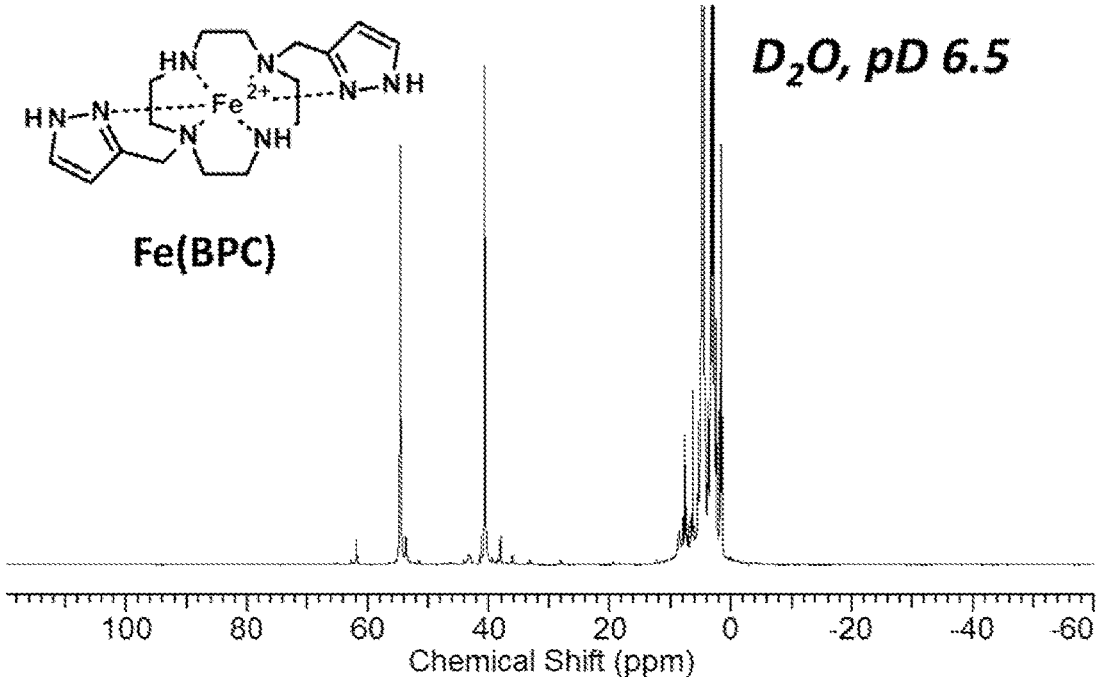
FIG. 70. $^1$H NMR spectrum of [Fe(BPC)]$^{2+}$ in D$_2$O at pD=6.5.

[Fe(BPC)]$^{2+}$ shows two sharp proton resonances assigned to pyrazole pendents and broadened macrocycle proton resonances (FIG. 70).

Figure 74:
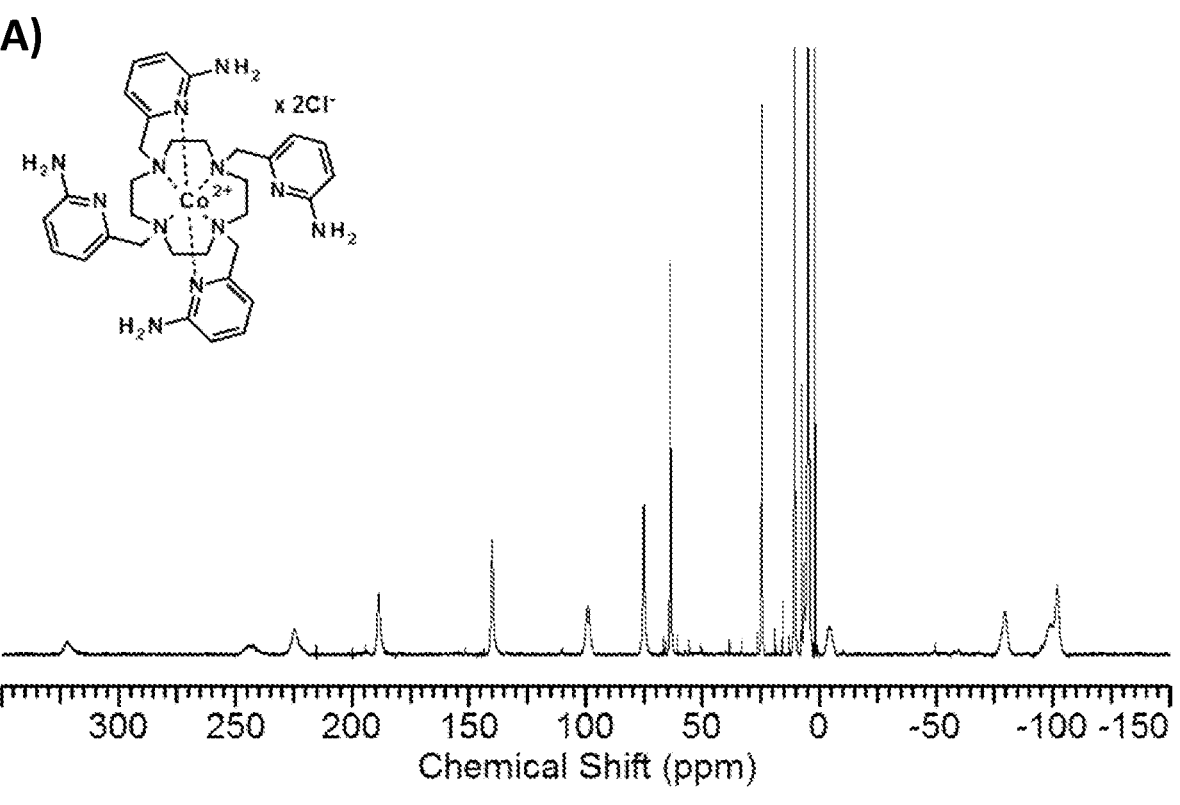
FIG. 74. $^1$H NMR spectra of (A) [Co(TAPC)]$^{2+}$ and (B) [Fe(TAPC)]$^{3+}$ in D$_2$O, pD 7.2.
Figure 74:
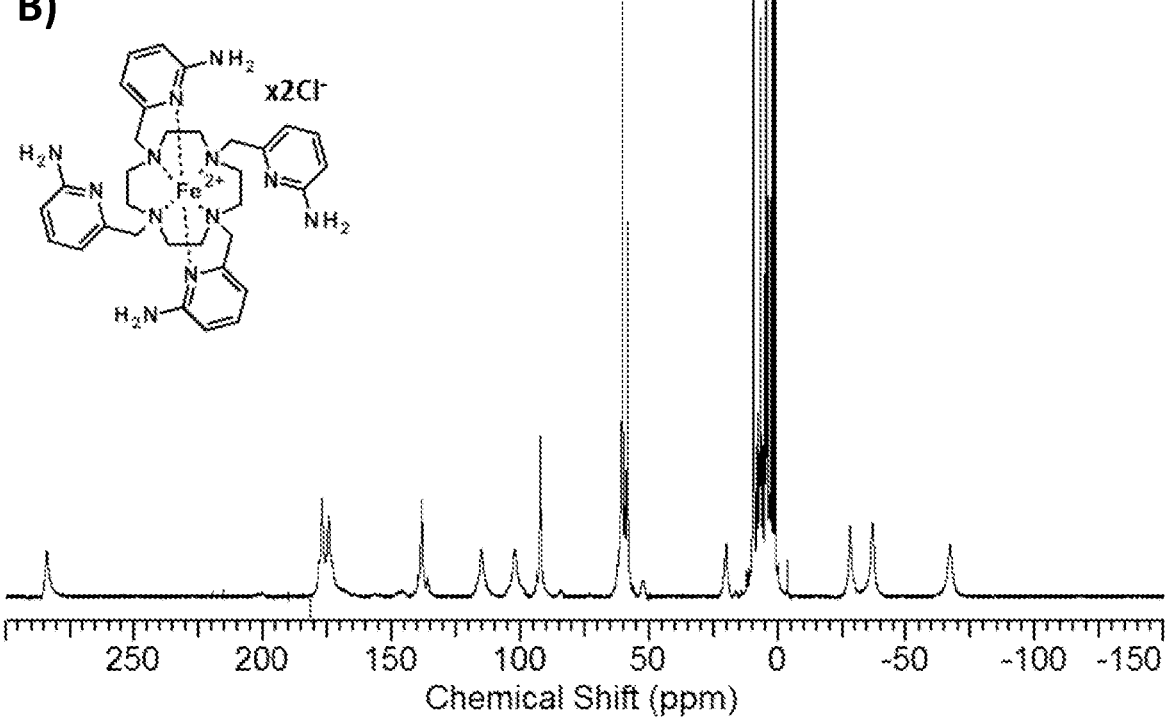

Co(II) and Fe(II) complexes of TAPC give very sharp proton resonances in solution (FIG. 74). The amino group has exchangeable protons that give CEST spectra.

Figure 75:
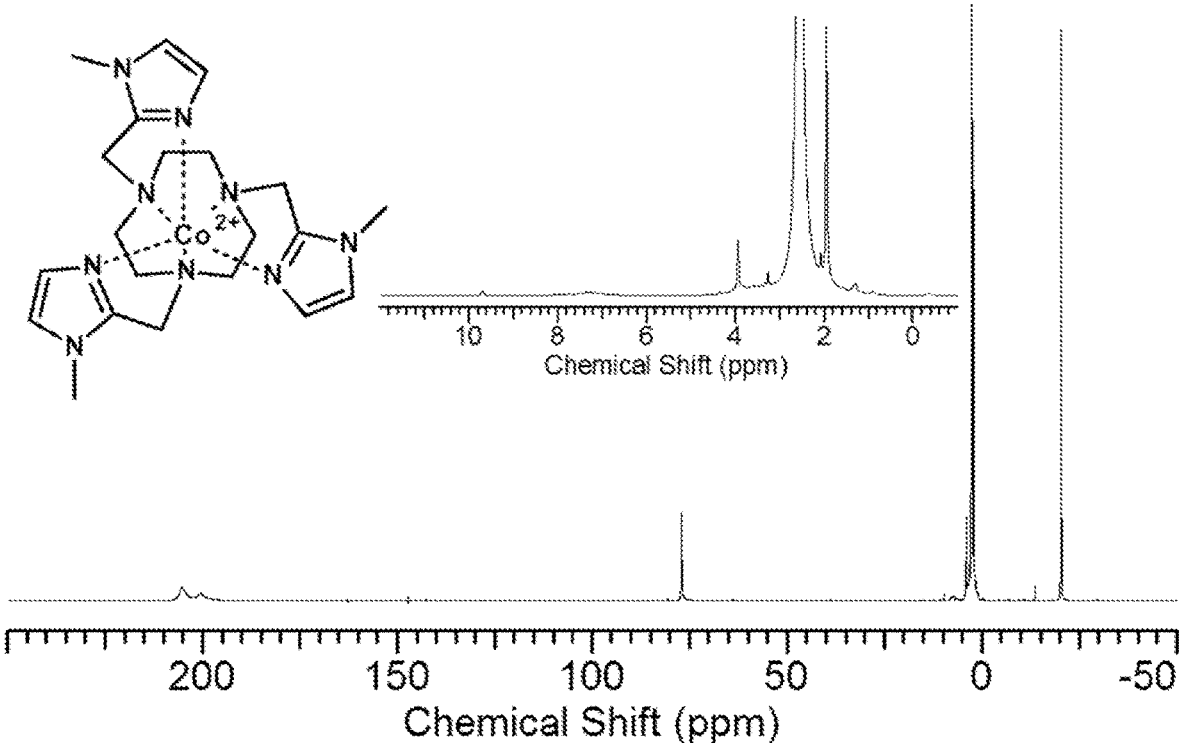
FIG. 75. $^1$H NMR spectrum of [Co(MIM)]$^{2+}$ in CD$_3$CN (MIM is also referred to as TMIT)
Figure 76:
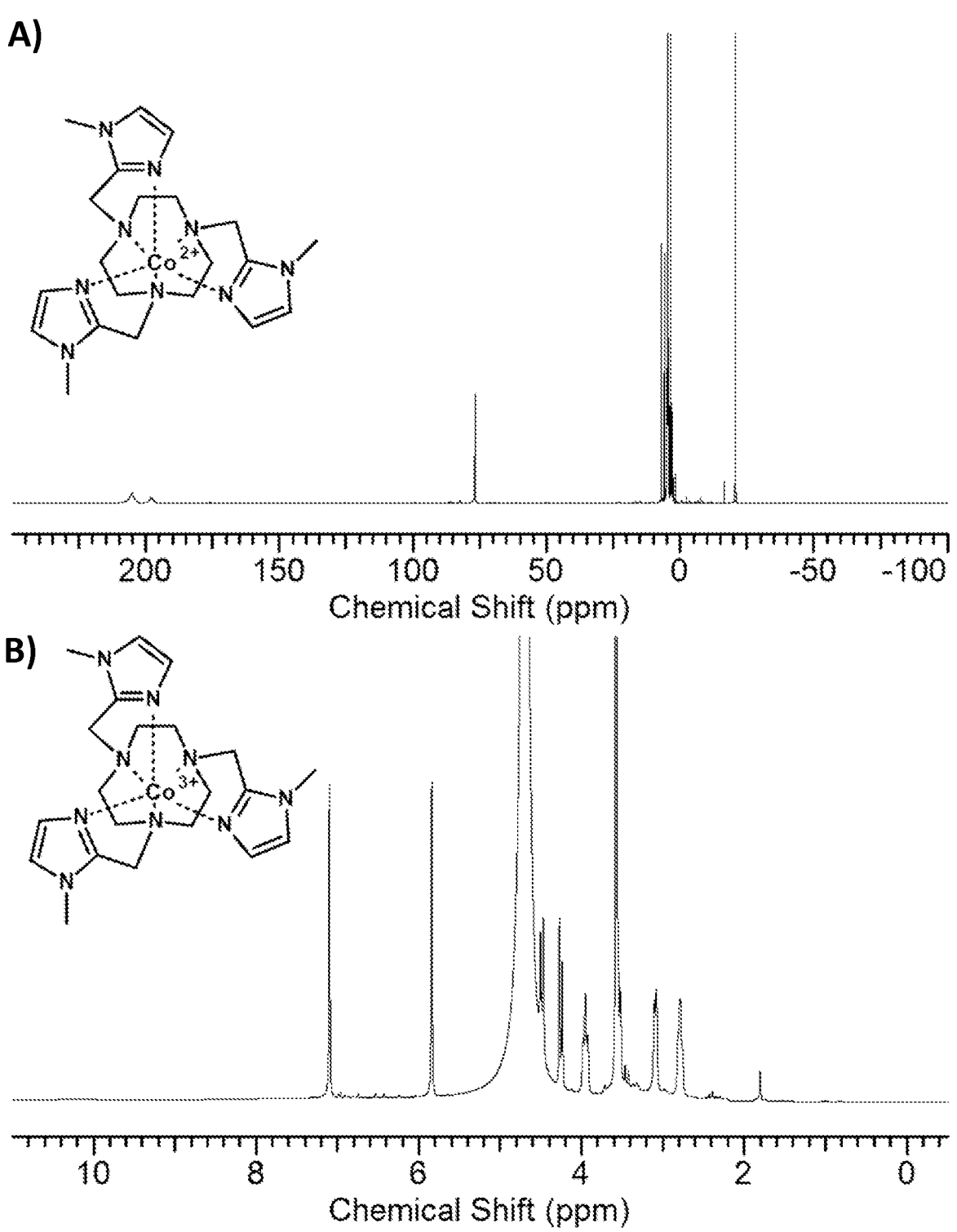
FIG. 76. $^1$H NMR spectra of (A) (top) [Co(MIM)]$^{2+}$ and (B) (bottom) [Co(MIM)]$^{3+}$. [Co(MIM)]$^{3+}$ appears in diamagnetic region.

[Co(TMIT)]$^{2+}$ is very air-sensitive. As shown in FIGS. 75 and 76, the complexes loses its paramagnetically shifted proton resonances as it oxidizes in solution to give the Co(III) complex.

Figure 77:
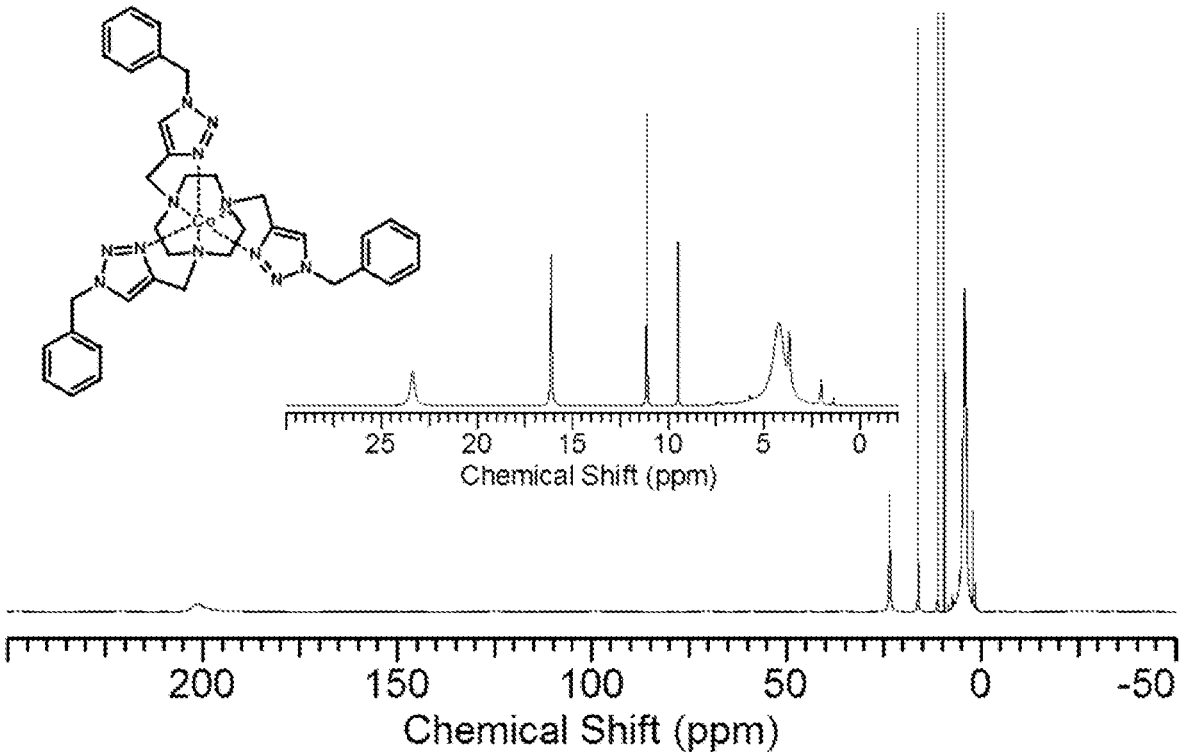
FIG. 77. $^1$H NMR spectra of [Co(Bn-TTT)]$^{2+}$ in CD$_3$CN.
Figure 78:
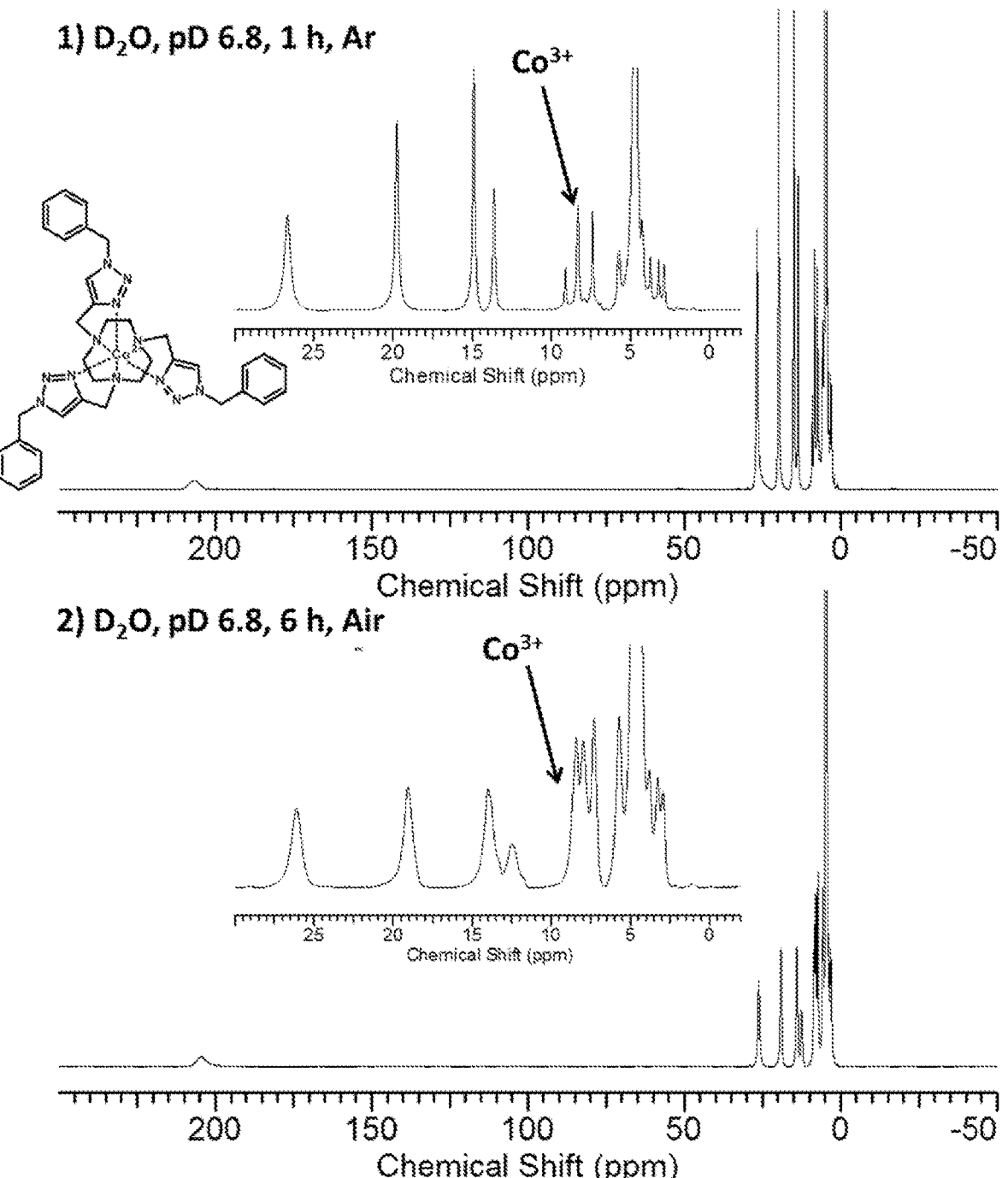
FIG. 78. $^1$H NMR spectra of (1) (top) [Co(Bn-TTT)]$^{2+}$ in D$_2$O, pD 6.8, which contains some oxidized [Co (Bn-TTT)]$^{3+}$. (2) (bottom) More oxidized [Co(Bn-TTT)]$^{3+}$ is formed after 6 hours under air.

Data for another example of an air-sensitive Co(II) complex is shown in FIGS. 77 and 78 for [Co(Bn-TTT)]$^{2+}$. Under air, this complex oxidizes to the Co(III) complex as shown by the proton NMR spectra.

Figure 79:
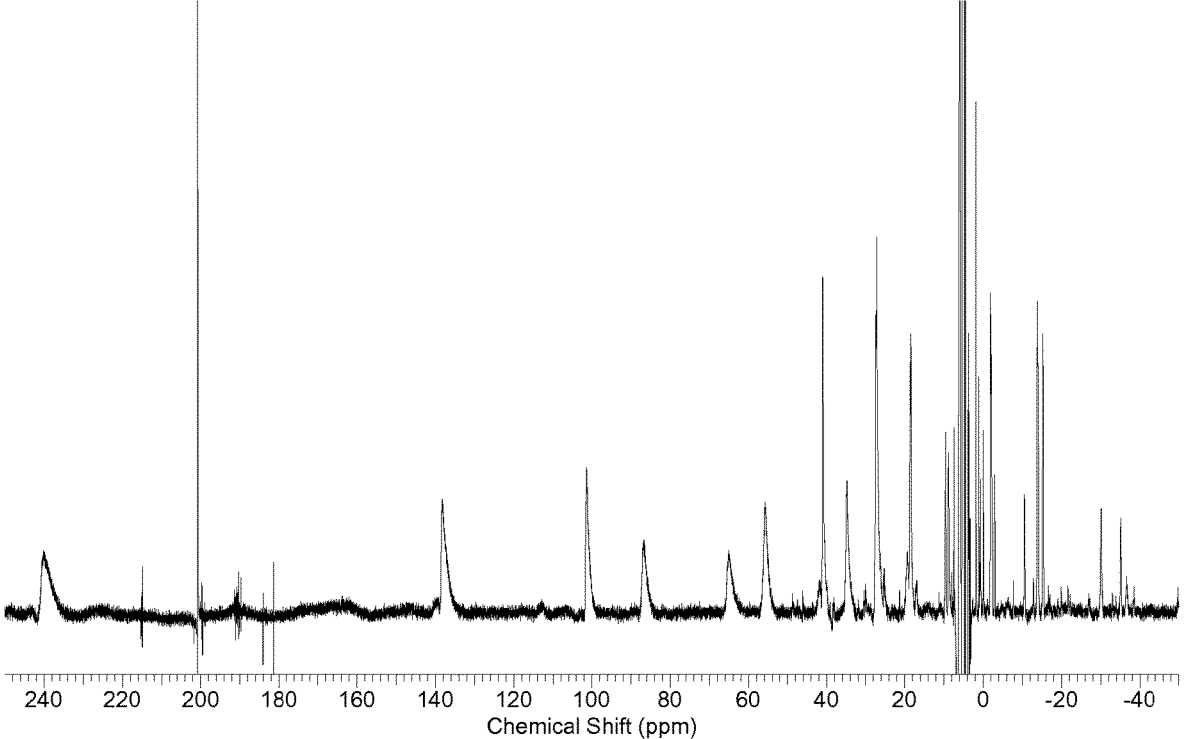
FIG. 79. $^1$H NMR spectra of [Co(TOPE)]$^{2+}$ in D$_2$O.
Figure 81:
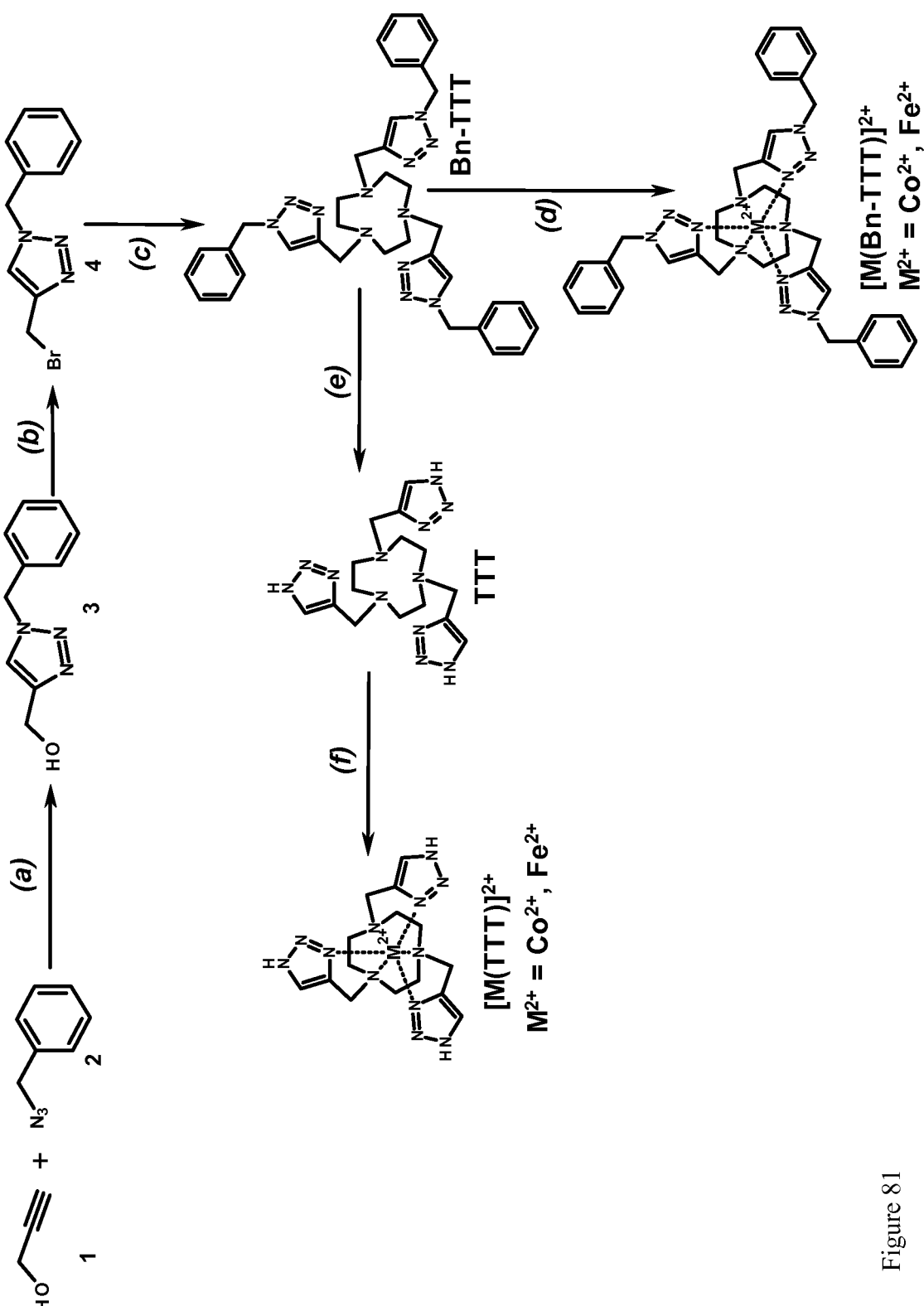
FIG. 81. Scheme for synthesis of TTT, Bn-TTT, $[M(TTT)]^{2+}$, $[M(Bn-TTT)]^{2+}$, where M is $Co^{2+}$ and $Fe^{2+}$. Reagents and conditions: (a) 5 mol % $CuSO_4$, 10 mol % Vitamin C, tert-butanol, Ar, room temperature, 8 hours; (b) $PBr_3$, methylene chloride, Ar, room temperature, 3 hours; (c) TACN, DIPEA, ACN, 65° C., Ar, 12 hours; (d) $MCl_2$, $M^{2+}=Co^{2+}$ or $Fe^{2+}$, methanol-acetonitrile (1:1, v/v), room temperature, 6 hours; (e) 1,4-cyclohexadiene, 10% Pd/C, isopropanol, 70° C., 12 hours; (f) $MCk_2$, $M^{2+}=Co^{2+}$ or $Fe^{2+}$, methanol-water (1:1, v/v), pH 7.0, room temperature, 1 hour.
Figure 82:
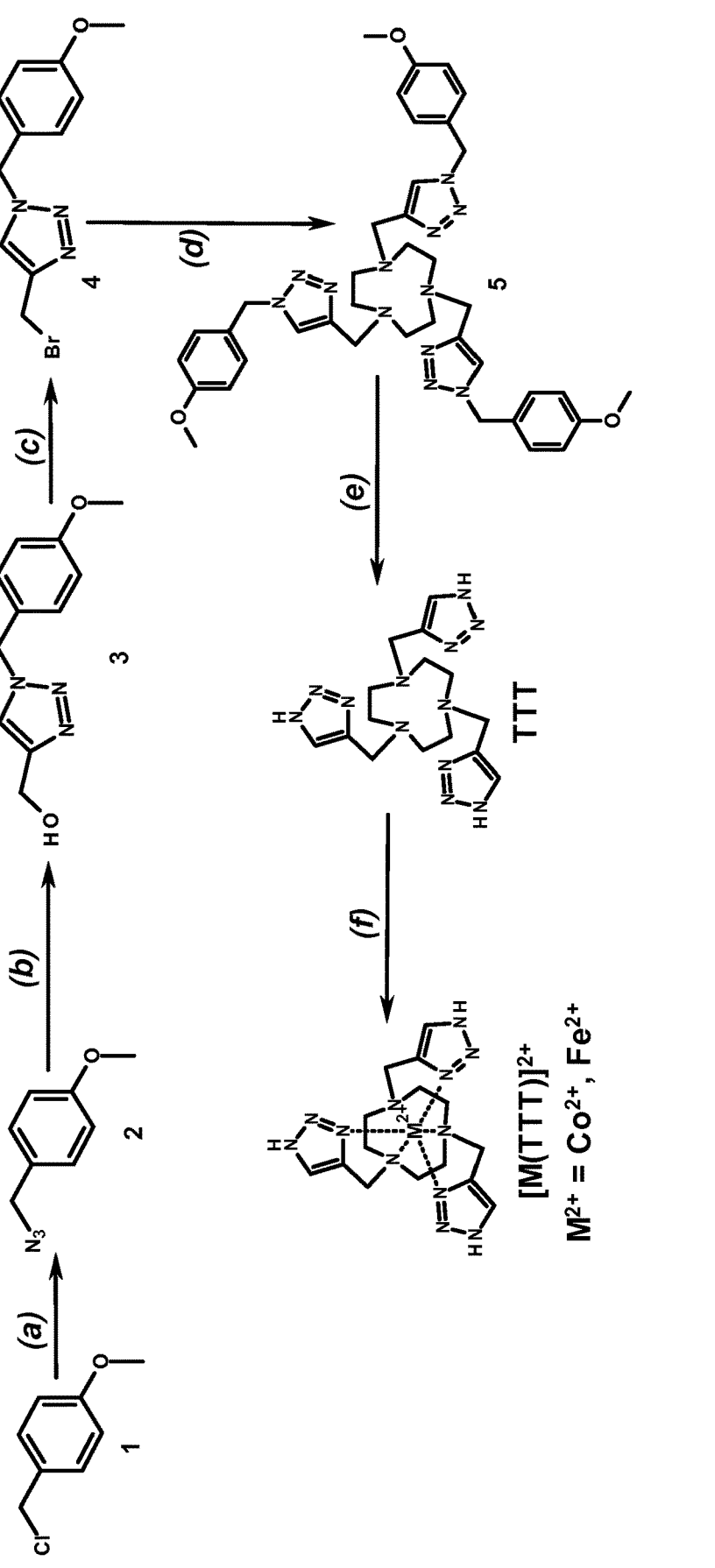
FIG. 82. Scheme for synthesis of TTT and $[M(TTT)]^{2+}$, where M is $Co^{2+}$ and $Fe^{2+}$. Reagents and conditions: (a) sodium azide, DMF, 50° C., Ar, 24 hours; (b) propargyl alcohol, 5 mol % $CuSO_4$, 10 mol % Vitamin C, tert-butanol, Ar, room temperature, 8 hours; (c) $PBr_3$, methylene chloride, Ar, room temperature, 3 hours; (d) TACN, DIPEA, ACN, 65° C., Ar, 12 hours; (e) hydrogen, 10% Pd/C, methanol, 12 hours; (f) $MCl_2$, $M^{2+}=Co^{2+}$ or $Fe^{2+}$, methanol-water (1:1, v/v), pH 7.0, room temperature, 1 hour.

[Co(TOPE)]$^{2+}$ is a stable Co(II) complex with the pendent triazole groups (FIG. 79).

Figure 83:
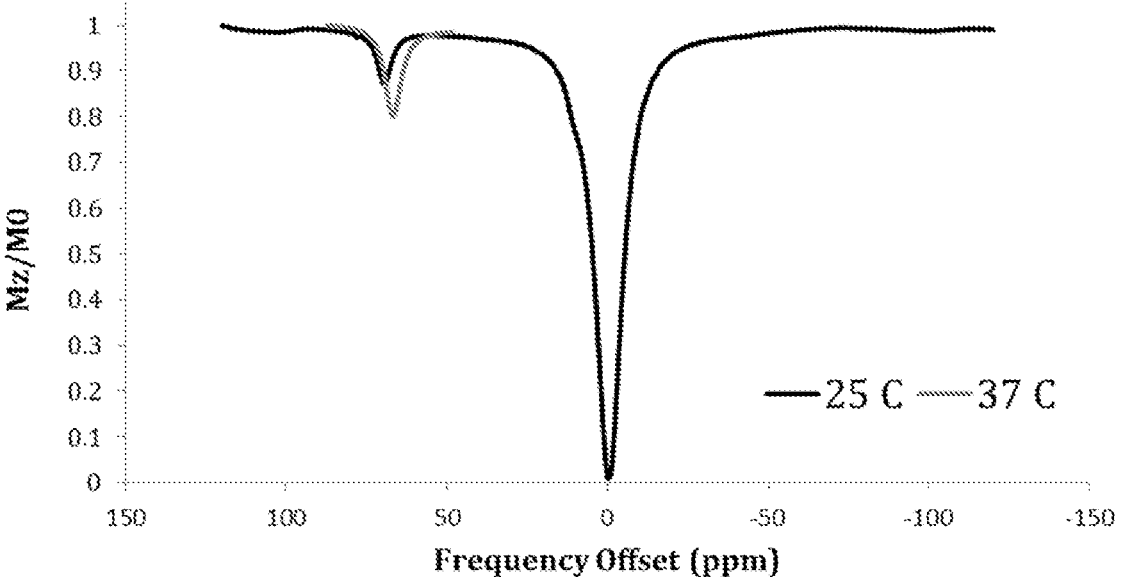
FIG. 83. 10 mM Co(NODA) complex. 20 mM HEPES buffer (pH 7.4), 100 mM NaCl.
Figure 84:
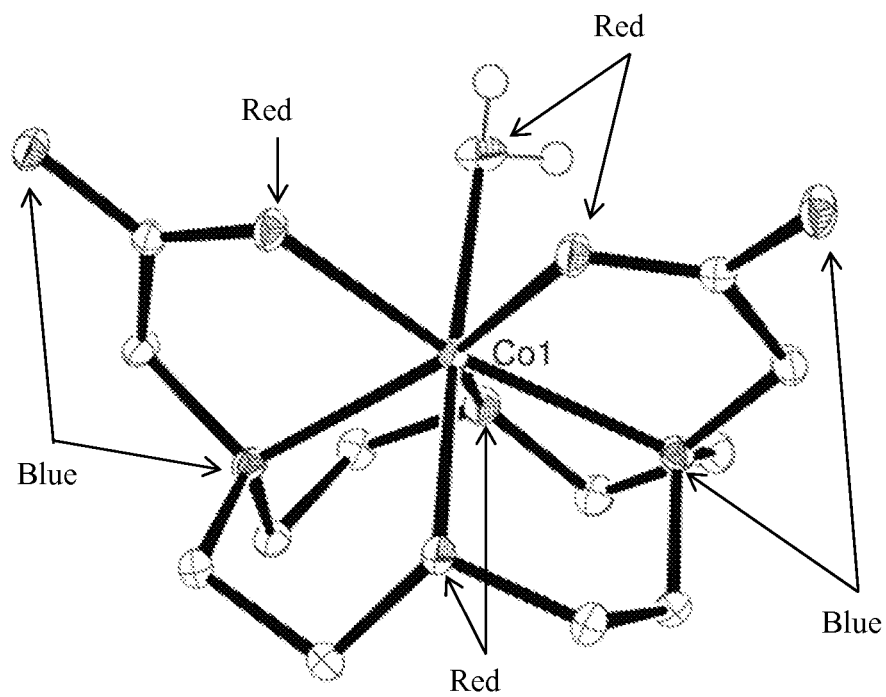
FIG. 84. Complex cation of $[Co(NODA)]Cl_2$ showing bound water ligand. Red indicates a oxygen atom, blue indicates a nitrogen atom.
Figure 85:
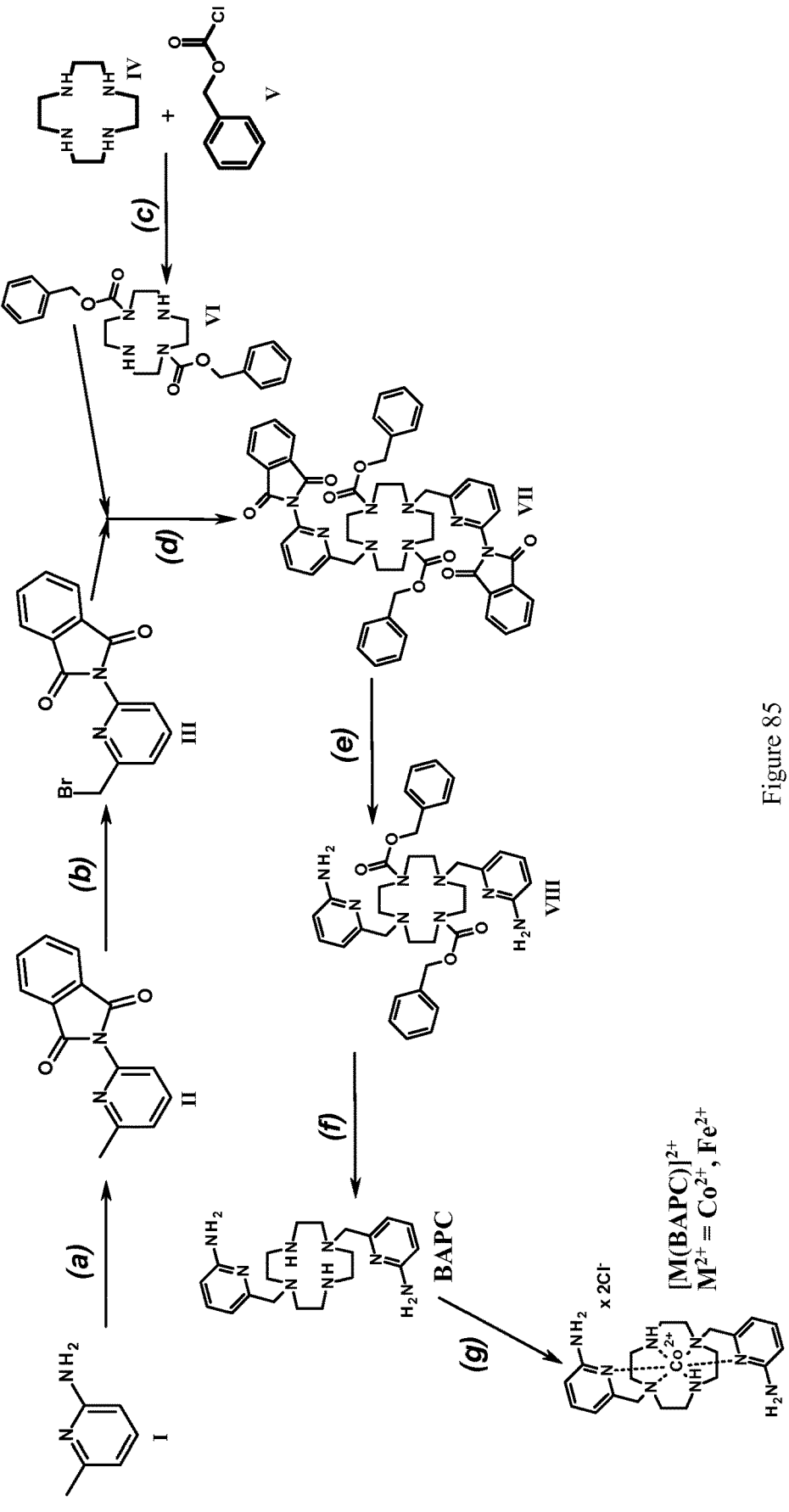
FIG. 85. Synthesis of ligand BAPC and metal complexes Co(BAPC) and Fe(BAPC). Reagents and conditions: (a) phthalic anhydride, 190° C., 1 h; (b) NBS, AIBN, benzene, reflux, 6 hours; (c) dioxane-water (50:50, v/v), pH 3.0-4.0, room temperature, 16 hours; (d) DIPEA, ACN, reflux, Ar, 3 hours; (e) $NH_2NH_2*H_2O$, EtOH, reflux, 3 hours; W hydrogen, 10% Pd/C, methanol, 12 hours; (g) $MCl_2$, $M^{2+}=Co^{2+}$ or $Fe^{2+}$, $CD_3OD-D_2O$ (1:1, v/v), pD 7.0, room temperature, 1 hour.

[Co(NODA)]$^{2+}$ is an air-stable complex that gives a CEST spectrum (FIG. 83). This complex has a bound water molecule as shown in FIG. 84. CEST contrast may be arise from either exchangeable protons on the amide pendents or from the water ligand.

Figure 72:
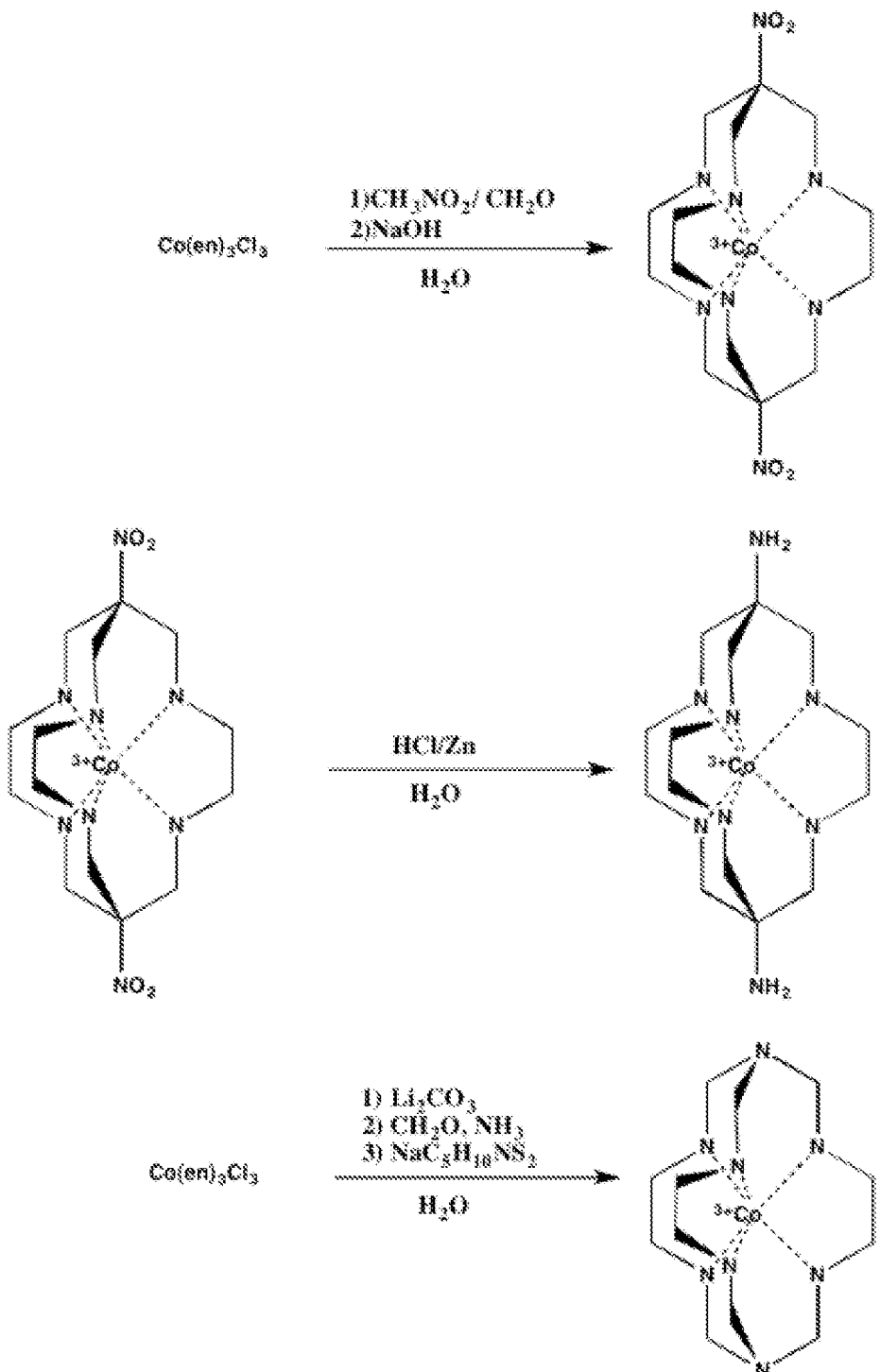
FIG. 72. Synthesis of cobalt cage complexes.

Synthetic methods for the preparation of TACN base macrocycles are shown in FIG. 71. A typical Co(III) cage synthesis is shown in FIG. 72.

Materials and methods. Instrumentation. Varian Inova 400 MHz and Inova 500 MHz NMR spectrometers were used to collect $^1$H NMR spectra. $^{13}$C NMR spectra were acquired using a Varian Mercury 300 MHz NMR spectrometer operating at 75 MHz. The measurements of magnetic susceptibility and CEST data were acquired on Varian Inova 500 MHz NMR spectrometer. Temperature of samples during $^1$H NMR and CEST experiments was controlled with FTS Systems TC-84 Kinetics Air Jet Temperature Controller. A Thermo Scientific Orion 9826BN NMR micro pH electrode connected to a SympHony SB20 pH meter and the Orion 8115BNUWP Ross-ultra semi micro pH electrode connected to a Titrino 702 pH meter were used for pH measurements. ThermoFinnigan LCQ Advantage IonTrap LC/MS equipped with a Surveyor HPLC system was used to collect mass spectral data. Absorbance spectra of [Co(TPT)]$^{2+}$ and [Co(TPT)]$^{3+}$, together with the kinetic experiments for the reduction of Co(III) with L-ascorbic acid or sodium dithionite, and for the oxidation of Co(II) with oxygen or sodium peroxydisulfate were measured with a Beckman-Coulter DU 800 UV-vis Spectrophotometer equipped with a Peltier Temperature Controller. Kinetic experiments for the oxidation of Co(II) complex were performed after equilibration of the solutions with a mixture containing 5%, 10%, and 20% of oxygen in nitrogen followed by addition of [Co(TPT)]$^{2+}$ in the minimal volume of solvent. All experiments for the reduction of Co(II) were performed under an inert atmosphere of argon. Kinetic experiments were carried out at 37° C., and absorbance measurements were recorded every 60 seconds for 120 minutes.

Figure 6:
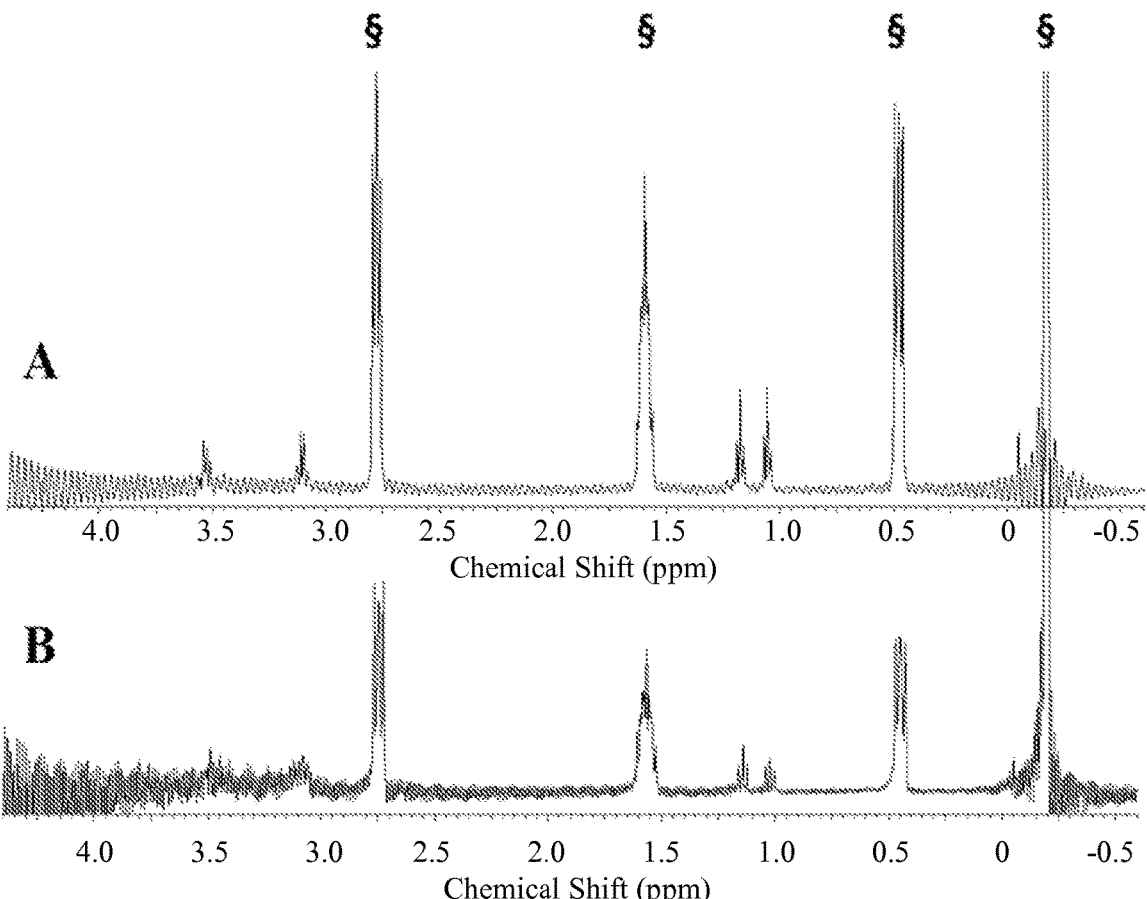
FIG. 6. Diamagnetic region $^1$H NMR spectra of 10 mM $[Co(TCMT)]^{2+}$, 100 mM NaCl, 0.40 mM $Na_2HPO_4$, 25 mM $K_2CO_3$ in $D_2O$, pD 7.5 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.
Figure 7:
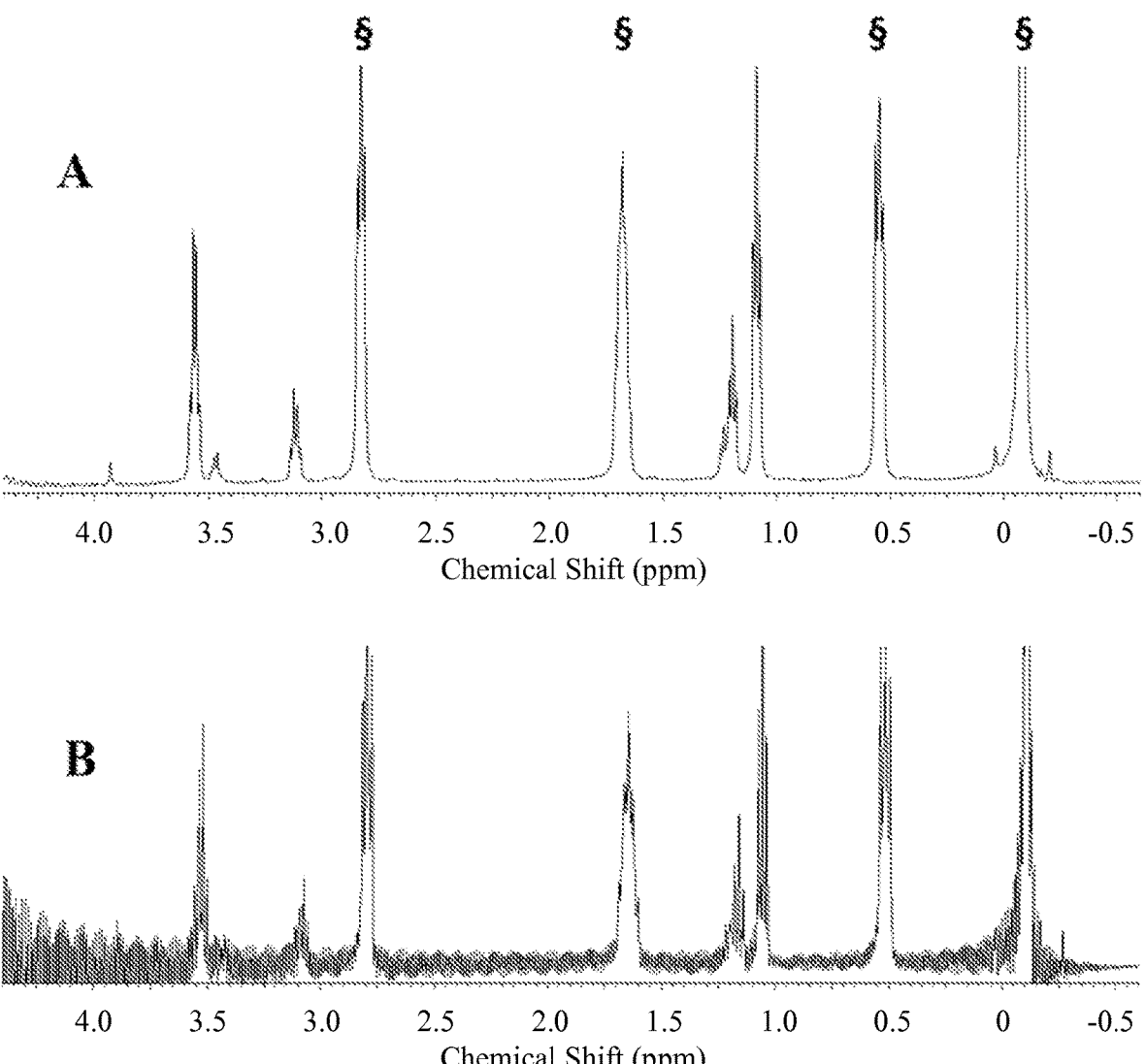
FIG. 7. Diamagnetic region $^1$H NMR spectra of 10 mM $[Co(TCMC)]^{2+}$, 100 mM NaCl, 0.40 mM $Na_2HPO_4$, 25 mM $K_2CO_3$ in $D_2O$, pD 7.5 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions FIG. 8. Diamagnetic region $^1$H NMR spectra of 10 mM $[Co(CCRM)]^{2+}$, 100 mM NaCl, 0.40 mM $Na_2HPO_4$, 25 mM $K_2CO_3$ in $D_2O$, pD 7.9 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.
Figure 8:
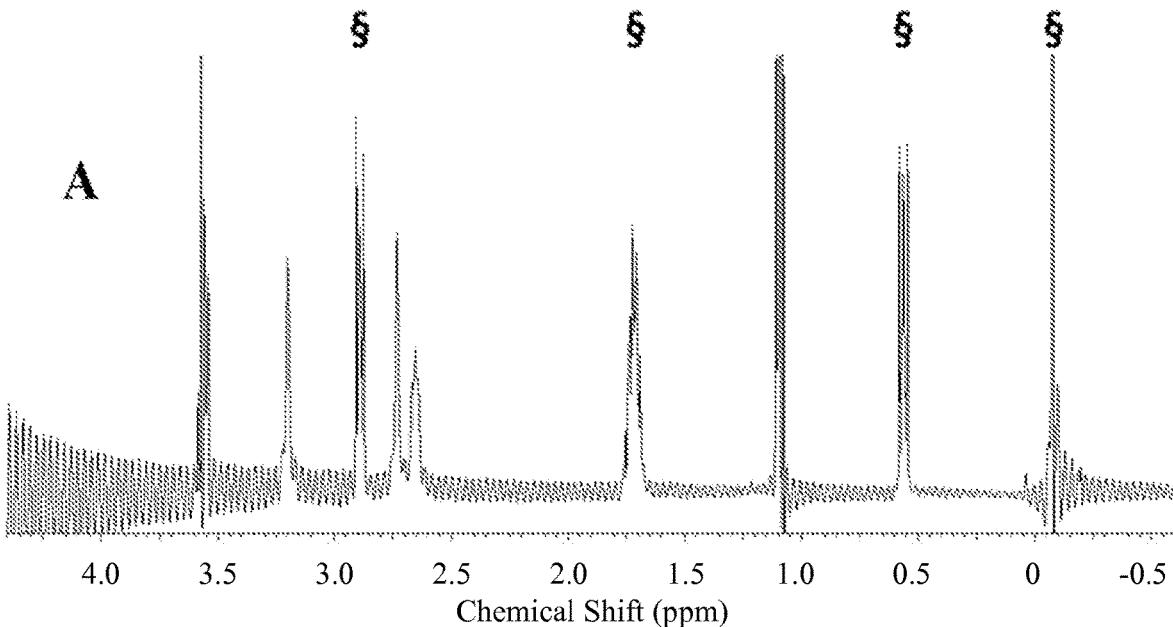
Figure 8:
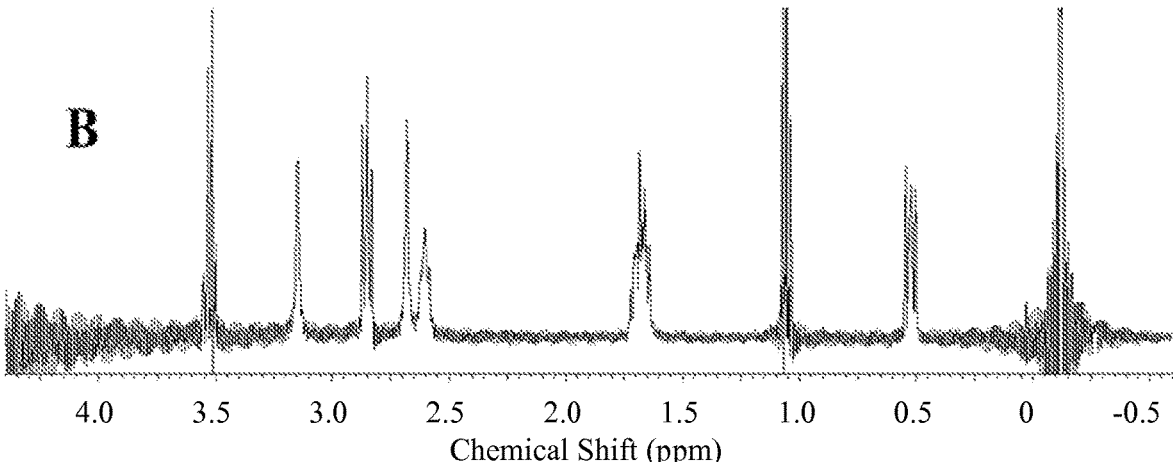
Figure 9:
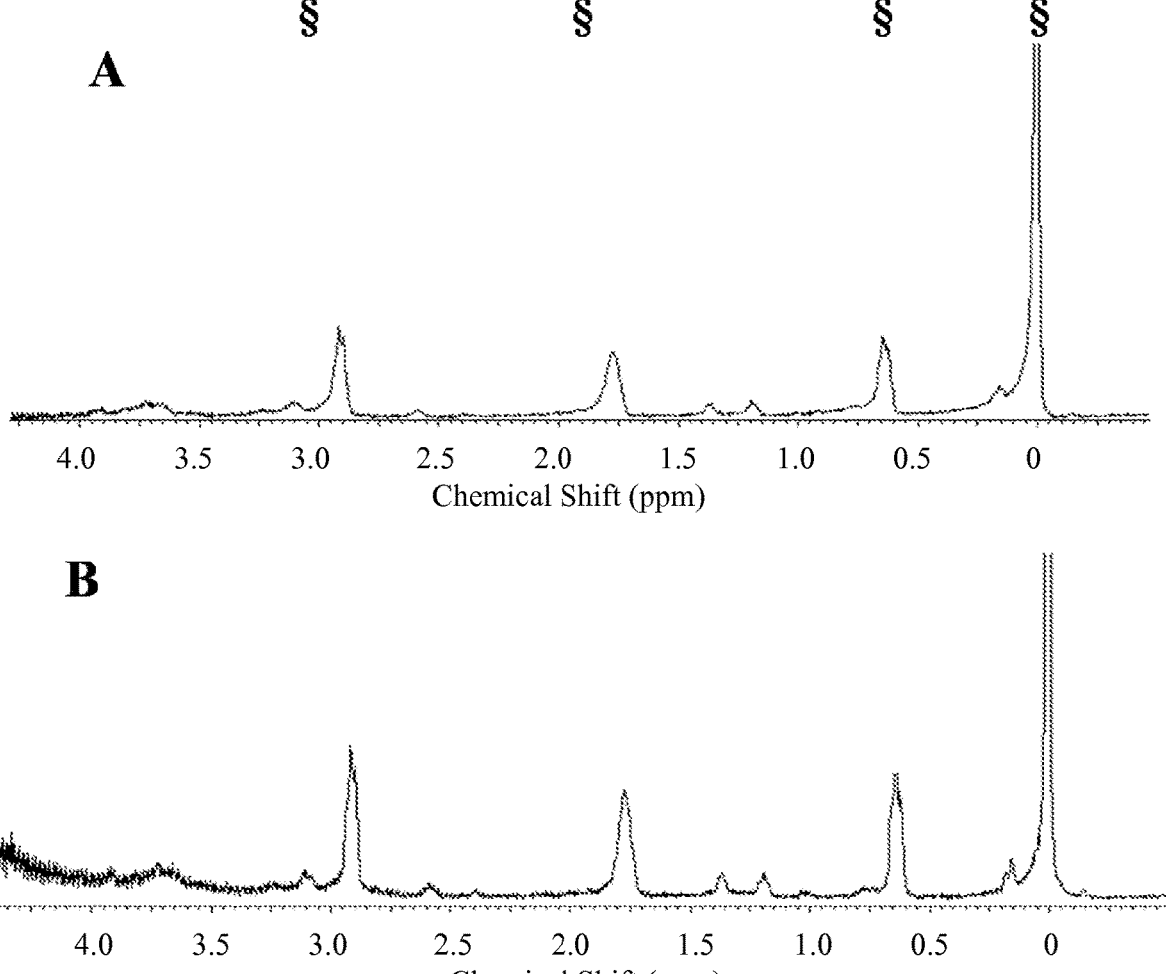
FIG. 9. Diamagnetic region $^1$H NMR spectra of 10 mM $[Co(NOPE)]^{2+}$, 100 mM NaCl, 0.40 mM $Na_2HPO_4$, 25 mM $K_2CO_3$ in D2O, pD 7.5 at 37° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.
Figure 10:
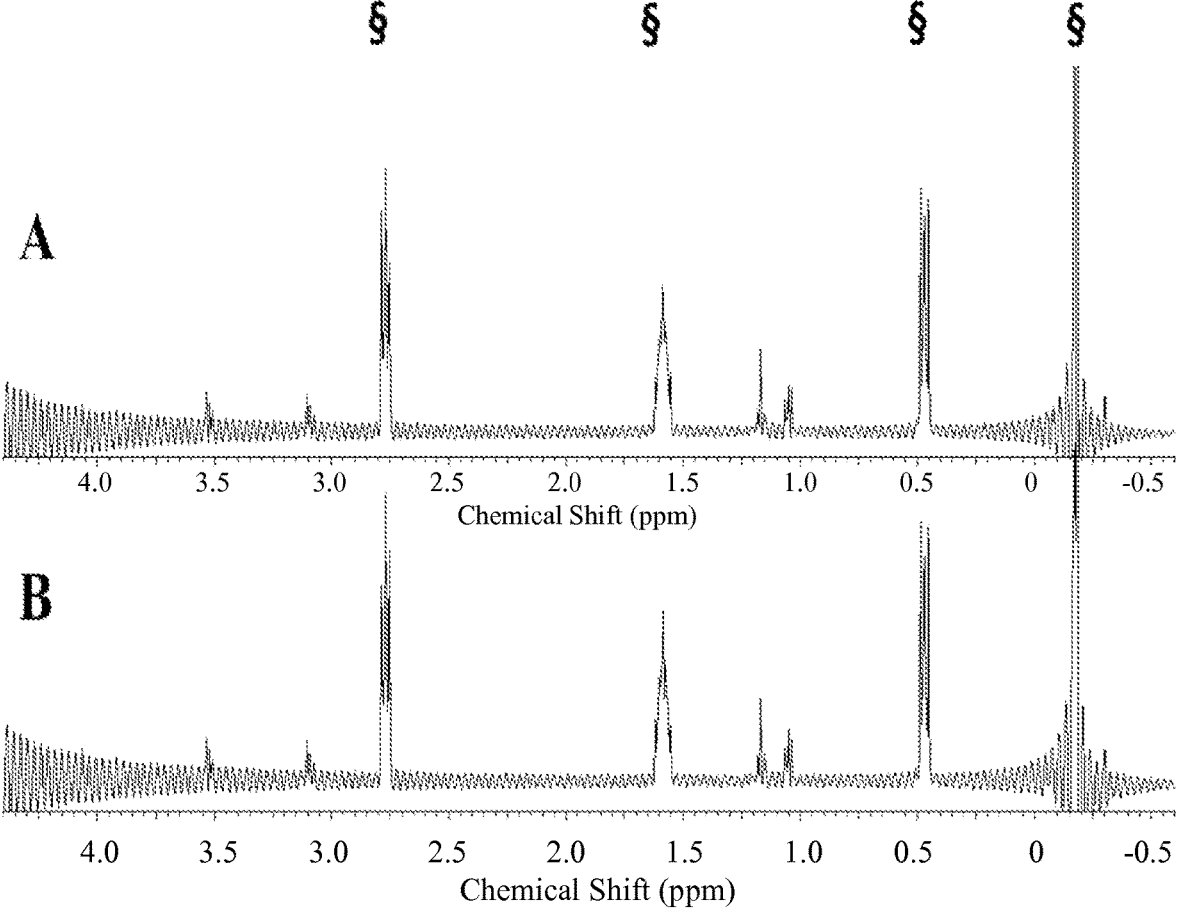
FIG. 10. Diamagnetic region $^1$H NMR spectra of 10 mM $[Co(TCMT)]^{2+}$, 100 mM NaCl, in $D_2O$, pD 3.7 at 25° C. (A) at 1 hr (B) at 12 hrs after incubation at 37° C. Contains 5 mM 3-(trimethylsilyl)-1-propanesulfonic acid standard, indicated by §. This data shows that the complex doesn't dissociate under these conditions.

Cyclic voltammograms were obtained using a Princeton Applied Research Model 263A Potentiostat/Galvanostat and PowerSuite software program. CHI 104 Glassy Carbon Disk working electrode from CH Instruments, Inc. (Austin, Tex.) was used. Cyclic Voltammetry. Cyclic voltammetry experiments showed a reversible oxidation for 1.7 mM [Co(TPT)]$^{2+}$ at 1.00 M KCl under argon at 25° C. (FIG. 6). The external ferrocyanide standard with $E_o$ (Fe(III)/Fe(II))=303±10 mV vs. NHE contained 1.0 mM K$_4$Fe(CN)$_6$ and 1.00 M KCl under argon. The redox potential of the complex calculated based on a NHE reference using eq. 6:

$$E°(\text{vs. NHE}) = E°(\text{vs. Ag/AgCl}) + 167 \text{ mV}, \quad \text{eq. 6}$$

Determination of Magnetic Moment.

The effective magnetic moment was calculated by using a previously known method. In a typical experiment, oxygen-free solution of 8-20 mM [Co(TPT)]$^{2+}$ in deuterium oxide, pD 7.0, containing 5% tert-butanol by volume was placed in an NMR tube, while a reference solution of 5% tert-butanol (v/v) in deuterium oxide, pD 7.0, was placed into NMR tube insert. All solutions of [Co(TPT)]$^{2+}$ were purged with argon and kept in the absence of air. The effective magnetic moment ($\mu_{eff}$) was calculated at 298 K (T) using the following equations 7-8. In these equations the mass susceptibility of solute ($\chi_g$) was calculated by obtaining the observed frequency shift of the reference ($\Delta f$) in Hz, the spectrometer frequency (f) in Hz, the mass of the substance per cm$^3$ of the solution (m), and the mass susceptibility of deuterium oxide ($\chi_o$=−0.6466×10$^{-6}$ cm$^3$/g). The last term in eq. SI is neglected due to the minimal contribution to mass susceptibility of solute. The molar susceptibility ($\chi_m$) is the product of $\chi_g$ multiplied by the molecular weight of the [Co(TPT)]Cl$_2$ complex. Reported value of the effective magnetic moment was obtained by averaging of three independent experiments.

$$\chi_g = (-3\Delta f)/(4\pi f m) + \chi_0 + [\chi_0(d_0 - d_s)]/m \quad \text{eq. 7}$$

$$\mu_{eff} = 2.84(\chi_m T)^{1/2} \quad \text{eq. 8}$$

Dissociation of the [Co(TPT)]$^{2+}$ Complex.

$^1$H NMR spectra (37° C.) were collected periodically over 24 hours using samples containing biologically relevant anions, which were incubated at 37° C. under an argon atmosphere. Solutions contained 8 mM [Co(TPT)]$^{2+}$ complex, 100 mM NaCl, 0.40 mM Na$_2$HPO$_4$, 25 mM K$_2$CO$_3$, and 10 mM 3-(trimethylsilyl)propionic acid sodium salt (TMSP) as an internal $^1$H NMR standard in deuterium oxide, pD 7.5. The $^1$H NMR spectra were obtained after 0.5 hour, 12 hours, 18 hours, and 24 hours of incubation at 37° C. Integration of the aromatic protons with chemical shifts δ=14.4 and 82.6 ppm (37° C.) was compared to integrated intensities of methyl protons of TMSP for the quantification of [Co(TPT)]$^{2+}$ dissociation. Integrated resonance intensities of diamagnetic protons of [Co(TPT)]$^{3+}$ were taken into account when the total concentration of complex was calculated.

CEST Experiments.

In general, CEST data was acquired with a pre-saturation pulse power (B$_1$) of 1093 Hz applied for 3 seconds. Most of the CEST data was obtained at 37° C. Data were acquired in 1 ppm increments and were plotted as normalized water intensity against frequency offset to produce a CEST spectrum. Samples containing 8 mM metal complex were prepared from freshly prepared [Co(TPT)]$^{2+}$, or from [Co(TPT)]$^{3+}$ with subsequent addition of reducing aliquots of sodium dithionite. Solutions also contained 20-40 mM of appropriate buffers of desired pH and 100-200 mM NaCl. An NMR tube insert filled with DMSO-d$_6$ was used to lock the signal on NMR spectrometer. The pH dependence of CEST was measured in the range of pH 5.4-8.1 using 40 mM MES, HEPES, or CHES with 200 mM NaCl. All CEST samples were purged with argon for 15 minutes prior to the addition of [Co(TPT)]Cl$_2$, and they were kept under inert atmosphere during the course of the experiments.

Exchange Rate Constants.

The exchange rate constants were calculated by using a previously reported procedure. The magnetization of the on-resonance (M$_z$) and off-resonance (M$_o$) were acquired at different pre-saturation pulse powers between 350-1090 Hz applied for 4 seconds. To calculate the exchange rate constant (k$_b$), the x-intercept (−1/k$_b^2$) was obtained from the plot of M$_z$/(M$_o$−M$_z$) against 1/ω$_1^2$ (ω$_1$ in rad/s). Samples contained 16 mM [Co(TPT)]Cl$_2$, 200 mM NaCl, and 40 mM MES or HEPES at pH 6.4-7.5. Measurements were carried out at 37° C.

PARACEST Imaging.

CEST images were acquired on a 4.7 Tesla preclinical MR scanner using a 35 mm radiofrequency coil and the ParaVision 3.0.2 research platform (Bruker Biospin, Billerica, Mass.). A pair of gradient-echo MR images were acquired at either 37° C. with a pre-saturation pulse train comprised of five 1 second Gauss pulses (12 μT, 200 μs interpulse delay) applied symmetrically about the bulk water resonance (+/−135 ppm). Other pertinent acquisition parameters include: echo time/repetition time=2.1/5010 ms, flip angle=90 deg, acquisition matrix=160×160, slice thickness=2 mm, field of view=32×32 mm, averages=1.

To determine the CEST effect, each image was normalized to the signal intensity of the buffer and salt-only phantom and the normalized image intensity of each phantom was sampled using commercially available software (Analyze 7.0, AnalyzeDirect Inc., Overland Park, Kans.). The percent loss of signal due to PARACEST exchange was calculated using the following equation:

$$\% \text{ CEST} = 1 - SI_{on}/SI_{off}, \quad \text{eq. 9}$$

where SI$_{on}$ and SI$_{off}$ are the image intensities of each sample acquired with on-resonance and off-resonance pre-saturation pulses, respectively. To create the CEST image (FIG. 46), raw k-space data was zero-filled to a 512×512 matrix, reconstructed to spatial domain, filtered with a spatial low-pass filter (kernel size: 11×11) to improve signal-to-noise, and then normalized by image intensity of the buffer and salt-only phantom. The % CEST effect was calculated pixel-by-pixel using the normalized on/off resonance image pair in MATLAB (MathWorks, Natick, Mass.). Phantoms in the CEST image were isolated using binary masking techniques, and a "hot-iron" pseudocolor lookup table was applied to enhance perceptual contrast between samples.

$T_1/T_2$ Relaxivity.

Samples of 2 mM, 4 mM, and 8 mM of [Co(TPT)]Cl$_2$ in 100 mM NaCl and 20 mM HEPES, pH 7.0, were used for $T_1/T_2$ relaxivity measurements. $T_1/T_2$ relaxivity values were determined on a 4.7 Tesla MRI system. $T_1$ relaxation rates of serial dilutions were measured using an inversion-recovery TrueFISP acquisition with the following parameters: TE/TR=1.5/3.0 ms, flip angle=30°, inv. repetition time=10 s, segments=8, frames=100. $T_2$ relaxation rates were measured using a multi-echo, Carr-Purcell-Meiboom-Gill (CPMG) spin-echo sequence with a fixed TR of 3000 ms and TE times ranging from 20-1200 ms in 20 ms increments (60 echoes). The relaxation rate of each sample calculated using non-linear regression analysis routines developed in MAT-LAB and relaxivities were then calculated by linear regression (concentration vs. relaxation rate). Results are shown in FIG. 46.

Materials.

All solvents and reagents were reagent grade, and they were used as received without additional purification. 1,4,7-Triazacyclononane (TACN) was purchased from TCI America (Portland, Oreg.), and 3-(chloromethyl)-1H-pyrazole hydrochloride was purchased from Accela ChemBio Inc. (San Diego, Calif.). N,N-Diisopropylethylamine (DIPEA), 1,8-diazabicycloundec-7-ene (DBU), and L-ascorbic acid were obtained from Sigma-Aldrich (St. Louis, Mo.). Cobalt(II) chloride hexahydrate, sodium dithionite, and sodium peroxydisulfate were received from Alfa Aesar (Ward Hill, Mass.). Basic alumina (50-200 μm) was purchased from Dynamic Adsorbents Inc. (Norcross, Ga.).

Synthesis of 1,4,7-tris(pyrazol-3-ylmethyl)-1,4,7-triazacyclononane (TPT) (FIG. 71). 3-(Chloro-methyl)-1H-pyrazole hydrochloride (0.58 g, 3.8 mmol, 3 equiv.) was added in one portion to argon-purged solution of TACN (0.16 g, 1.3 mmol) and 1.4 mL of DIPEA (1.1 g, 8.2 mmol, 6.5 equiv.) in 65 mL of acetonitrile (ACN) heated at 70° C. After stirring at 70° C. for 45 minutes, a portion of DBU (0.77 g, 5.1 mmol, 4 equiv in 0.75 mL) was added to the reaction mixture. The reaction mixture was further stirred at 60° C. under argon for 8 hours. Solvent (ACN) was removed in vacuo, producing a yellow solid. The solid was redissolved in a minimal volume of methanol, and diethyl ether was added drop-wise until a white cloudy precipitate was formed. This precipitate turned into oil after placing the sample at −20° C. for 3 hours. The supernatant was isolated upon decantation, and the solvent was removed in vacuo to produce a yellowish residue. This residue was subject to column chromatography using ca. 100 mL of basic Al$_2$O$_3$ packed with 2% methanol in methylene chloride. The product was eluted by a solvent gradient containing 2% to 15% of methanol in methylene chloride. Yield: 0.24 g, 51%. $^1$H NMR, 500 MHz (CDCl$_3$, ppm): δ=7.52 d (3H, Ar, J=2 Hz), 6.11 d (3H, Ar, J=2 Hz), 3.76 s (6H, 3×CH$_2$), 3.48 s (3×NH), 2.67 m (12H, 6×CH$_2$). $^{13}$C NMR, 75 MHz (CD$_3$OD, ppm): δ=146.92, 134.78, 105.92, 54.56, 54.11. ESI-MS (m/z): [M+H]$^+$, calculated: 370.2. found: 370.3.

Synthesis of [Co(TPT)]$^{2+}$ (FIG. 71). In a representative procedure, TPT (40 mg, 0.11 mmol) was placed in the tube with 1.1 mL of acetonitrile. After purging the solvent with argon, CoCl$_2$(H$_2$O)$_6$ (25 mg, 0.11 mmol) was added. The reaction mixture was again purged with argon while stirring. This reaction mixture was sonicated for 10 minutes followed by stirring for 20 minutes several times. A sky-blue flaky precipitate of [Co(TPT)]Cl$_2$ was formed promptly upon sonication, while the dark-blue crystalline CoCl$_2$(H$_2$O)$_6$ disappeared. After sonication for a total period of 60 minutes, the reaction mixture was stirred under argon at room temperature After 8 hours the reaction mixture was centrifuged, and the blue supernatant solution was decanted. The sky-blue solid was washed with 200 μL of acetonitrile. The mixture was centrifuged, and the slightly blue supernatant was decanted affording analytically pure [Co(TPT)]Cl$_2$. Yield: 36 mg, 0.07 mmol, 67%. $^1$H NMR of the product in argon-purged D$_2$O, pD 5.2, indicated that >95% of complex was present in the paramagnetic Co(II) state, while additional diamagnetic signals corresponded to <5% of complex in Co(III) form. $^1$H NMR, 500 MHz (D$_2$O, pD 5.2, ppm) at 25° C.: δ=210.06 s br. (3H), 195.64 s br. (3H), 133.80 s br. (3H), 100.13 s br. (3H), 82.61 s (3H, Ar), 14.39 s (3H, Ar), −22.32 s br. (3H), −102.86 s br. (3H). This product was further characterized in both Co(II) and Co(III) forms.

Synthesis of [Co(TPT)]$^{3+}$. The Co(III) complex was prepared by oxidation of the Co(II) complex. In a typical preparation, [Co(TPT)]Cl$_2$ (15 mg, 30 μM) was dissolved in 0.8 mL of a solution containing 100 mM NaCl in D$_2$O. The initial pD of 4.5 was adjusted to neutral by addition of 4% NaOD solution in D$_2$O. Upon stirring under air the color of the solution turned tea-red. A pD of 6.8-7.2 of the solution was maintained by adding aliquots of 4% NaOD in D$_2$O every 15 minutes for 4 hours. The reaction mixture was stirred under air for 8 hours, and the pD was adjusted to neutral several times over the course of the reaction. The completion of oxidation was confirmed by $^1$H NMR in D$_2$O, pD 7.0. The solvent was removed by lyophilization, producing a red powder. $^1$H NMR, 500 MHz (D$_2$O, pD 7.0, ppm): δ=7.66 d (3H, Ar, J=2 Hz), 6.46 d (3H, Ar, J=2 Hz), 4.03 dt (6H, NCH$_2$Ar), 3.88 ddd (3H, NCH$^{ax}$HCH$_2$, axial), 3.41 dd (3H, NCH$^{eq}$HCH$_2$, equatorial), 2.88 dd (3H, NC H$^{eq}$HCH$_2$, equatorial), 2.30 ddd (3H, NCH$^{ax}$HCH$_2$, axial). Assignments of ring protons are based on comparison to reported complexes. $^{13}$C NMR, 75 MHz (D$_2$O, ppm): δ=154.84, 141.17, 105.84, 63.94, 63.15, 62.58. ESI-MS (m/z): [M-2H$^+$]$^+$, calculated: 426.2. found: 426.2 (100%); [2*(M-3H$^+$)+H$^+$]$^+$, calculated: 851.3. found: 851.2 (85%); [3*(M-3H$^+$)+H$^+$]$^+$, calculated: 1276.5. found: 1276.2 (65%).

Synthesis of dinitrocobalt(III) sarcophagene. One equivalent of cobalt (III) tris(ethylene diamine) (1.2 g, 3 mmol) was stirred in water and the temperature of the solution was adjusted to approximately 4 degrees Celsius. Nitromethane (4 equivalents, 12 mmol) and formaldehyde (10 equivalents, 30 mmol) were added to this solution. Subsequently, a chilled (approximately 4 degrees Celsius) solution of sodium hydroxide (NaOH, 4 M, 1 mL per mmol Cobalt starting material) was added to the reaction mixture. After addition was complete, the temperature of the solution was allowed to rise to room temperature and this solution was stirred for 90 minutes. After 90 minutes, hydrochloric acid (6.0 M, 2.0 mL) was added to quench the reaction. The resulting solution was cooled on ice for two hours. The resulting orange solid was isolated by vacuum filtration and washed with ethanol.

Synthesis of diaminocobalt(III) sarcophagene [(Co (SAR)]$^{3+}$. The dinitrocobalt(III) sarcophagene (2.0 g, 3.7 mmol) was dissolved in deoxygenated water under inert conditions. Zinc dust (approximately 10 equivalents per dinitrocobalt (III) sarcophagene) was added and the solution was stirred under inert atmosphere conditions for 5 minutes. After this, hydrochloric acid (6.0 M, 15 mL) was added and the solution was stirred for one hour under an inert atmosphere. After one hour, the nitrogen gas was turned off and 1.0 mL of 30% hydrogen peroxide was added to the solution. The solution was then heated on a water bath (75 degrees Celsius) for 15 minutes. After heating, the product was purified on a cation exchange column. The resulting solid was yellow in color.

Synthesis of cobalt(III) sepulchrate. Cobalt (III) trisethylenediamine (0.9 g) was dissolved in water (20 mL) with 12 equivalents lithium carbonate. To this solution was slowly added formaldehyde and ammonia (50 mL each) and the solution was stirred over the course of an hour. The resulting solution was filtered, the solid was discarded and the red filtrate was retained. To the red filtrate, was added a solution of sodium diethyldithiocarbamate (2.5 g in 50 mL water) and stirred for half an hour. The red solid was collected via vacuum filtration. The precipitate was washed with methylene chloride:hexane (20:80) three times (50 mL). The solid was suspended in acetonitrile (10 mL) and hydrochloric acid (12 M) was added dropwise until the solid changed from red to yellow. The solution was gently heated for 5-10 minutes, and the resulting yellow solid was collected.

Synthesis of 1,7-bis(benzyloxycarbonyl)-1,4,7,10-tetraazacyclododecane (bis-CBZ-Cyclen). Cyclen was dissolved in water (2.5 g in 18 mL) and the pH was adjusted to 3 by adding HCl (5 mL of 6M) followed by the addition of 15 mL of dioxane. Benzyl chloroformate (6.4 g) was dissolved in dioxane. This solution was added to the reaction mixture over approximately 20 hours while the solution pH was maintained at 2-3 by addition of NaOH. Upon completion of the reaction, the solvents were removed by evaporation and the resulting solid was extracted with diethylether to give an oil. The remaining residue was dissolved in basic solution and extracted with diethylether. The combined extracts gave additional product to give a total yield of 80%.

Synthesis of 1,4,7,10-tetraazacyclododecane-1,4-bis(acetic acid) (BAC). To a solution of bis-CBZ-Cyclen (2 g) dissolved in dry acetonitrile was added t-butyl bromoacetate (2 equivalents) in acetonitrile along with two equivalents of potassium carbonate and catalytic amount of 18-crown-6. The mixture was stirred at 60° C. for 14 hours. The solvent was removed by rotary evaporation. To the resulting residue was added a 1:1 mixture of diethylether and water. The compound partitioned to the organic layer and this layer was washed with water (2×), with base (2×), and water (2×) and then dried over $Na_2SO_4$. The solvent was removed from the crude product and was chromatographed on silica gel. The compound was eluted using methylene chloride containing 2% to 10% methanol. The CBZ protecting groups were removed by using a Parr hydrogenation apparatus. Typically 0.2 g of compound was dissolved in methanol (20 mL), 50 mg of 10% Pd/C was added, and the apparatus was charged with hydrogen gas to 40 psi for 24 hours. The catalyst was filtered off on Celite, and the methanol was removed under vacuum producing oil. Finally, the t-butyl esters were hydrolyzed by treatment of the oil with 6 M HCl in ethyl acetate for 4 hours at ambient temperature. The compound was recrystallized from methanol-ether mixture.

Synthesis of 1,4-bis(pyrazol-3-methyl)-1,4,7,10-tetraazacyclododecane (BPC). To a solution of bis-CBZ-Cyclen (2 g) dissolved in dry acetonitrile was added 3-(chloromethyl) pyrazole hydrochloride (2 equivalents) in acetonitrile and four equivalents of diisopropylethylamine. The mixture was stirred at 65° C. for 14 hours. The solvent was removed by rotary evaporation. To the resulting residue was added a 1:1 mixture of chloroform and water. The compound partitioned to the organic layer and this layer was washed with water (2×), and with brine (1×). The solvent was removed from the crude product and was recrystallized from isopropanol-hexanes mixture. The CBZ protecting groups were removed by using a Parr hydrogenation apparatus. Typically 0.2 g of compound was dissolved in methanol (20 mL), 50 mg of 10% Pd/C was added, and the apparatus was charged with hydrogen gas to 40 psi for 24 hours. The catalyst was filtered off on Celite, and the methanol was removed under vacuum. Product was additionally purified by recrystallization from isopropanol-hexanes mixture affording 45% yield.

Synthesis of 1,4-bis(benzimidazol-2ylmethyl)-1,4,7,10-tetraazacyclododecane (BBzC). To a solution of bis-CBZ-Cyclen (2 g) dissolved in dry acetonitrile was added 2-(chloromethyl)benzimidazole (2 equivalents) in acetonitrile and two equivalents of diisopropylethylamine. The mixture was stirred at 65° C. for 14 hours. The solvent was removed by rotary evaporation. To the resulting residue was added a 1:1 mixture of chloroform and water. The compound partitioned to the organic layer and this layer was washed with water (2×), and with brine (1×). The solvent was removed from the crude product and was recrystallized from isopropanol-hexanes mixture. The CBZ protecting groups were removed by using a Parr hydrogenation apparatus. Typically 0.2 g of compound was dissolved in methanol (20 mL), 50 mg of 10% Pd/C was added, and the apparatus was charged with hydrogen gas to 40 psi for 24 hours. The catalyst was filtered off on Celite, and the methanol was removed under vacuum. Product was additionally purified by recrystallization from methanol-diethyl ether mixture affording 40% yield.

Synthesis of 1,4-tetrakis(pyrazol-3-methyl)-1,4,7,10-tetraazacyclododecane (TPC). To a solution of Cyclen (1 g) in dry acetonitrile was added four equivalents of 3-(chloromethyl)pyrazole hydrochloride and eight equivalents of diisopropylethylamine. The mixture was stirred at 65° C. for 6 hours. The solvent was removed by rotary evaporation. The crude product was purified by column chromatography using basic alumina Methanol (1% to 12%) in dichloromethane was used as an eluent. Fractions with pure product were combined, solvent removed in vacuo giving 38% yield.

Synthesis of 1,4-tris(N-methyl-imidazol-2ylmethyl)-1,4,7-triaazacyclononane (TMIT). To a solution of TACN (0.5 g) in dry acetonitrile was added 1-methyl-2-chloromethyl imidazole and six equivalents of diisopropylethylamine. The mixture was stirred at 65° C. for 12 hours. The solvent was removed by rotary evaporation. The crude product was purified by column chromatography using basic alumina Methanol (2% to 8%) in dichloromethane was used as an eluent. Fractions with pure product were combined, solvent removed in vacuo giving 25% yield.

Synthesis of Co(II) complexes of BZT, BPC, TPC, BBZC. In a general procedure, the ligand was placed in a tube with 1 mL of acetonitrile. After purging the solvent with argon, $CoCl_2(H_2O)_6$ was added. The reaction mixture was again purged with argon while stirring. This reaction mixture was sonicated for 10 minutes followed by stirring for 20 minutes several times followed by stirring overnight in under argon atmosphere. The complexes were isolated upon centrifugation of the tubes and decantation of the supernatant. The Co(II) complex of BAC was prepared in aqueous solution.

Synthesis of Fe(II) complexes of BZT, BPC, TPC, TMIT. In a general procedure, the ligand was placed in a tube with 1 mL of acetonitrile. After purging the solvent with argon, an equivalent of $Fe(CF_3SO_3)_2$ was added. The reaction mixture was again purged with argon while stirring. This reaction mixture was sonicated for 10 minutes followed by stirring for 20 minutes several times followed by stirring overnight in under argon atmosphere. The complexes were isolated upon centrifugation of the tubes and decantation of the supernatant.

Example 4

This example describes synthesis of macrocyclic compounds and cobalt complexes thereof.

The ligand 2,2'-(1,7-dioxa-4,10-diazacyclododecane-4,10-diyl)diacetamide (NODA) was synthesized by adding 92 mg (0.53 mmol) of 1,7-dioxa-4,10-diazacyclododecane, along with 171 mg (1.24 mmol) to a solution of ethanol (1.1 mL). 1.62 mL of triethylamine (1.43 mol) was added and the solution was refluxed for 4 hours at 80° Celsius. The product was allowed to cool to room temperature, and a precipitate formed. The precipitate was dissolved in 80:20 EtOH/H$_2$O solution, heated to 50° C. then allowed to cool slowly and stored in a freezer overnight. The liquid was decanted to give a white powder which was dried overnight under vacuum. 108 mg (70.1% yield) of product was obtained. ESI-MS m/z: 289.3 (100%), 290.3, (10%) [M+H$^+$]; 311.3 (40%), 312.3 (<10%) [M+Na$^+$]. $^1$H NMR (500 MHz, D$_2$O): 3.51 (t, 8H, ring OCH$_2$), 3.13 (s, 4H, pendent CH$_2$), 2.69 (s, 8H, ring NCH$_2$).

The cobalt (II) complex of 2,2'-(1,7-dioxa-4,10-diazacyclododecane-4,10-diyl)diacetamide chloride ([Co(NODA)]Cl$_2$) was synthesized by adding 43.8 mg of 2,2'-(1,7-dioxa-4,10-diazacyclododecane-4,10-diyl)diacetamide (NODA) and 35.7 mg of CoCl$_2$ hexahydrate to a round bottom flask with 3 mL of ethanol. The mixture was stirred for 2 hours at room temperature under argon gas. A reddish purple solid was isolated. ESI-MS m/z: 173.7 (100%) [M$^{2+}$/2], 346.3 (50%) [M$^{2+}$-H$^+$], 382.2 (40%)[M$^{2+}$+Cl$^-$]. $^1$H NMR (500 MHz, D$_2$O): 108, 90, 70, 37, 33 ppm.

Synthesis of 7,13-di(prop-2-yn-1-yl)-1,4,10-trioxa-7,13-diazacyclopentadecane. To a round bottom flask was added 4,10-diaza-15-crown-5-ether (0.1544 g, 0.707 mmol), propargyl bromide (147 µL, 1.56 mmol), and anhydrous potassium carbonate (293 mg, 2.12 mmol) in dimethylformamide (15 mL) and the solution was heated to 60° C. for 3 hours. The solvent was removed under vacuum. The resulting oil was dissolved in chloroform, filtered, then extracted to give a yellow/orange oil. Yield: 83%+. ESI-MS: m/z=295.3 [M–H$^+$], 317.3 [M-Na$^+$].

Synthesis of (((1,4,10-trioxa-7,13-diazacyclopentadecane-7,13-diyl)bis(methylene))bis(1H-1,2,3-triazole-4,1-diyl))bis(methylene) bis(2,2-dimethylpropanoate). In a round bottom flask, 7,13-di(prop-2-yn-1-yl)-1,4,10-trioxa-7,13-diazacyclopentadecane (0.1721 g, 0.585 mmol) and azidomethyl pivalate (203 µL, 1.29 mmol) were stirred at room temperature in a methanol/water (3:1) mixture under argon gas. To this solution was added copper sulfate-pentahydrate (14.6 mg, 0.0585 mmol) and sodium ascorbate (23.2 mg, 0.117 mmol). The solution was stirred overnight and the solvent was removed under vacuum. The resulting oil was dissolved in chloroform, filtered and the filter was washed with cold methanol. Solvent was then removed under vacuum. Column chromatography of the crude mixture on basic alumina with a chloroform methanol gradient gave a light yellow oil. Yield: 70%+. ESI-MS: m/z=609.4 [M–H$^+$], 631.4 [M-Na$^+$].

Synthesis of 7,13-bis((1H-1,2,3-triazol-4-yl)methyl)-1,4,10-trioxa-7,13-diazacyclopentadecane. In a round bottom flask, (((1,4,10-trioxa-7,13-diazacyclopentadecane-7,13-diyl)bis(methylene))bis(1H-1,2,3-triazole-4,1-diyl))bis(methylene) bis(2,2-dimethylpropanoate) (0.248 g, 0.408 mmol) and sodium hydroxide (35.9 mg, 0.898 mmol) were stirred at room temperature in a methanol/water (1:1) mixture for 10 minutes. The solution was neutralized with hydrochloric acid (32.7 mg, 0.898 mmol) and the solvent removed under vacuum. The residue was dissolved in chloroform and filtered and then the solvent was then removed under vacuum. The product was purified by column chromatography on basic alumina with a chloroform/methanol gradient to give a clear oil. Yield: 37%+. ESI-MS: m/z=381.3 [M–H$^+$], 403.3 [M-Na$^+$].

Synthesis of Co$^{II}$(TOPE). In a round bottom flask, TOPE (57.8 mg, 0.152 mmol) and cobalt(II) nitrate hexahydrate (44.2 mg, 0.152 mmol) were stirred at room temperature in ethanol (5 mL) for 1 hour. The solvent removed under vacuum to give a purple oil. ESI-MS: m/z=438.3 [M], 219.8 [M/2].

The preceding descriptions provide specific examples of the present disclosure. Those skilled in the art will recognize that routine modifications to these embodiments can be made which are intended to be within the scope of the disclosure.

The invention claimed is:

1. A macrocyclic compound having a macrocyclic core having the following structure:

wherein R is a pendant group independently chosen from H,

-continued and at least one pendant group is not H;

wherein R is a pendant group independently chosen from H,

-continued and at least one pendant group is not H;

wherein R is a pendant group independently chosen from H,

-continued and at least one pendant group is not H;

wherein R is a pendant group independently chosen from H, and at least one pendant group is not H;

wherein, optionally, one or more of the —CH$_2$— moieties of the macrocyclic core are substituted with an alkyl group or a pendant group independently chosen from:

-continued wherein a Co(II) cation is complexed to the macrocyclic core and/or at least one pendant group substituent of the macrocyclic compound;

or $$\text{(I)}$$

wherein R is a pendant group independently chosen from H, and at least one pendant group is not H;

and at least one pendant group is not H;

wherein R is a pendant group independently chosen from H, wherein R is a pendant group independently chosen from H, and at least one pendant group is not H;

$$\text{(IV)}$$

wherein R is a pendant group independently chosen from H, and at least one pendant group is not H;
wherein, optionally, one or more of the —CH$_2$— moieties of the macrocyclic core are substituted with an alkyl group or a pendant group independently chosen from:

wherein an Fe(II) cation is complexed to the macrocyclic core and/or at least one pendant group substituent of the macrocyclic compound, wherein $R_1$ is H, $C_1$ to $C_{12}$ alkyl groups of linear or branched structure, PEG group, thioether group, or $CH_2CO_2R'$, wherein R' is a $C_1$ to $C_{12}$ alkyl group of linear or branched structure, $R_2$ is H, $C_1$ to $C_{12}$ alkyl groups of linear or branched structure, benzyl groups, PEG group, thioether group, $CH_2CO_2R$, or $OCH_3$, $R_3$ is H, $C_1$ to $C_{12}$ alkyl groups of linear or branched structure, PEG group, thioether group, or $CH_2CO_2R'$, wherein R' is a $C_1$ to $C_{12}$ alkyl group of linear or branched structure, $R_7$ and $R_8$ are independently an amine group, a nitro group, or a halide, and wherein the macrocyclic compound exhibits reversible oxidation to Co(III) or Fe(III), respectively, with the proviso:

i) the macrocyclic core does not have the following structure:

ii) the macrocyclic core does not have the following structure:

[Structure of cyclen with four acetamide arms]

and iii) if macrocyclic core has the following structure:

[Structure of cyclen with two pyrazolylmethyl arms]

then Co(II) is chelated to the macrocyclic core.

2. The macrocyclic compound of claim 1, wherein the macrocyclic compound has at least one exchangeable proton or associated water molecule.

3. The macrocyclic compound of claim 1, wherein the macrocyclic compound is one of a plurality of the macrocyclic compounds tethered together via a polymer, dendrimer, protein, or peptide.

4. The macrocyclic compound of claim 1, wherein the macrocyclic compound has one of the following structures:

[M(TPT)]$^{2+}$
M = Co

[Co(Bn-TTT)]$^{2+}$

[M(BPC)]$^{2+}$
M = Co

, or

[M(TPC)]$^{2+}$
M = Co

5. A composition comprising a compound of claim 1 and a pharmaceutically acceptable carrier.

6. A method to obtain an image of at least a portion of a cell, organ, vasculature, or tissue comprising the steps of:
   contacting the cell, organ, vasculature, or tissue with a compound of claim 1, and
   imaging at least a portion of the cell, organ, vasculature, or tissue to obtain an image of the portion of a cell, organ, vasculature, or tissue,
   wherein the image is obtained by using magnetic resonance.

7. The method of claim 6, wherein the cell, organ, vasculature, or tissue is part of an individual.

8. The method of claim 6, wherein the image is obtained using magnetic resonance imaging (MM).

9. The method of claim 6, wherein the image is obtained using chemical exchange saturation transfer (CEST).

10. The method of claim 6, wherein the image is obtained using paramagnetic chemical exchange saturation transfer (paraCEST).

11. The method of claim 6, wherein the image is obtained using magnetic resonance spectroscopy imaging (MRSI).

12. The method of claim 6, wherein the cell, organ, vasculature, or tissue is contacted with the compound and the image is indicative of the redox status of the cell, organ, vasculature, or tissue.

13. The method of claim 7, wherein the compound is administered to the individual.

* * * * *

UNITED STATES PATENT AND TRADEMARK OFFICE
CERTIFICATE OF CORRECTION

PATENT NO. : 10,960,088 B2
APPLICATION NO. : 15/021626
DATED : March 30, 2021
INVENTOR(S) : Janet R. Morrow et al.

Page 1 of 2

It is certified that error appears in the above-identified patent and that said Letters Patent is hereby corrected as shown below:

In the Claims

Column 74, Line 2, in Claim 1, the fourth structure should read:

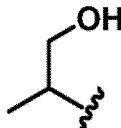

Column 75, Lines 24-34, in Claim 1, the structures should read:

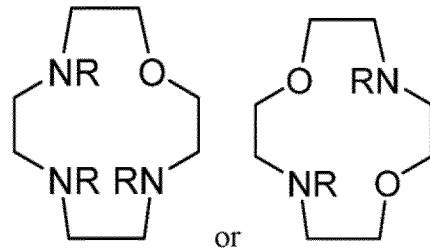

Column 75, Lines 36-45, Claim 1, the fourth structure should read:

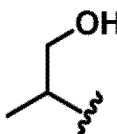

Column 76, Lines 10-16, Claim 1, the third structure should read:

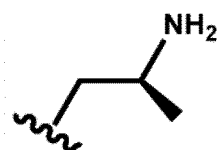

Signed and Sealed this
Second Day of May, 2023

*Katherine Kelly Vidal*

Katherine Kelly Vidal
*Director of the United States Patent and Trademark Office*

CERTIFICATE OF CORRECTION (continued)
U.S. Pat. No. 10,960,088 B2

Column 80, Line 15, through Column 81, Line 44, in Claim 1, the structures should read:

[chemical structures]

Column 82, Lines 40-47, in Claim 1, the structures should read:

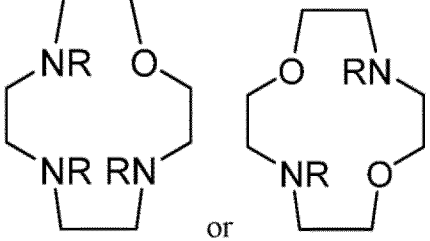

Column 83, Lines 29-34, in Claim 1, the second structure should read:

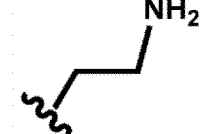

Column 89, Lines 3-4, Claim 8 should read:
8. The method of claim 6, wherein the image is obtained using magnetic resonance imaging (MRI).